United States Patent
Matsushita

(10) Patent No.: US 10,806,925 B2
(45) Date of Patent: Oct. 20, 2020

(54) MUSCLE ELECTROSTIMULATION DEVICE

(71) Applicant: MTG CO., LTD., Nagoya-shi, Aichi (JP)

(72) Inventor: Tsuyoshi Matsushita, Nagoya (JP)

(73) Assignee: MTG CO., LTD., Nagoya (JP)

( * ) Notice: Subject to any disclaimer, the term of this patent is extended or adjusted under 35 U.S.C. 154(b) by 173 days.

(21) Appl. No.: 15/553,155

(22) PCT Filed: Jun. 22, 2015

(86) PCT No.: PCT/JP2015/067929
§ 371 (c)(1),
(2) Date: Aug. 23, 2017

(87) PCT Pub. No.: WO2016/135996
PCT Pub. Date: Sep. 1, 2016

(65) Prior Publication Data
US 2018/0296831 A1  Oct. 18, 2018

(30) Foreign Application Priority Data

Feb. 27, 2015  (JP) .................................. 2015-039009

(51) Int. Cl.
*A61N 1/18* (2006.01)
*A61N 1/36* (2006.01)
(Continued)

(52) U.S. Cl.
CPC ....... *A61N 1/36003* (2013.01); *A61N 1/0452* (2013.01); *A61N 1/3603* (2017.08)

(58) Field of Classification Search
CPC ... A61N 1/36; A61N 1/32; A61N 1/34; A61N 1/36003; A61N 1/36021; A61N 1/37211; A61N 1/0456; A61N 1/0452; A61N 1/375
(Continued)

(56) References Cited

U.S. PATENT DOCUMENTS

| 5,423,874 A | 6/1995 | D'Alerta |
| 5,562,717 A | 10/1996 | Tippey et al. |

(Continued)

FOREIGN PATENT DOCUMENTS

| AU | 1998300 A | 8/2000 |
| CN | 101146573 A | 3/2008 |

(Continued)

OTHER PUBLICATIONS

Dec. 18, 2018 Office Action issued in Russian Patent Application No. 2017132855.
(Continued)

*Primary Examiner* — Carl H Layno
*Assistant Examiner* — Jon Eric C Morales
(74) *Attorney, Agent, or Firm* — Oliff PLC

(57) ABSTRACT

A muscle electrostimulation device includes: a main body; a power source stored in the main body; an electrode unit that receives power from the power source; a controller that controls the supply of power to the electrode unit; and an operation unit that changes a control mode of the controller. The electrode unit includes a first and a second electrode group. The first group extends from the main body to be disposed on a right hand side of a person with respect to a center line of the main body. The second group extends from the main body to be disposed on a left hand side of the person with respect to the center line when the device is attached to the abdomen. The first and the second electrode group can be electronically connected via the person and include four or more electrodes in total.

20 Claims, 49 Drawing Sheets

(51) Int. Cl.
*A61N 1/04* (2006.01)
*A61N 1/08* (2006.01)

(58) Field of Classification Search
USPC .............................................. 607/46, 2, 59
See application file for complete search history.

(56) References Cited

U.S. PATENT DOCUMENTS

| | | | |
|---|---|---|---|
| 6,445,955 B1* | 9/2002 | Michelson | A61N 1/36003 607/2 |
| 6,728,577 B2 | 4/2004 | Minogue et al. | |
| 6,760,629 B2 | 7/2004 | Minogue et al. | |
| 6,885,896 B2 | 4/2005 | Minogue et al. | |
| 7,069,089 B2 | 6/2006 | Minogue et al. | |
| 7,072,721 B1 | 7/2006 | Trent | |
| 7,747,327 B2 | 6/2010 | Minogue et al. | |
| 8,938,303 B1 | 1/2015 | Matsen | |
| 2002/0058972 A1 | 5/2002 | Minogue et al. | |
| 2002/0091420 A1 | 7/2002 | Minogue et al. | |
| 2002/0103513 A1* | 8/2002 | Minogue | A61N 1/321 607/46 |
| 2002/0128686 A1 | 9/2002 | Minogue et al. | |
| 2002/0128693 A1 | 9/2002 | Minogue et al. | |
| 2002/0133195 A1 | 9/2002 | Minogue et al. | |
| 2003/0050673 A1 | 3/2003 | Yamazaki et al. | |
| 2003/0065368 A1 | 4/2003 | Van Der Hoeven | |
| 2003/0153958 A1 | 8/2003 | Yamazaki et al. | |
| 2006/0206168 A1 | 9/2006 | Minogue et al. | |
| 2008/0161883 A1 | 7/2008 | Conor | |
| 2010/0234919 A1 | 9/2010 | Minogue et al. | |
| 2012/0116477 A1 | 5/2012 | Crowe et al. | |
| 2014/0128939 A1 | 5/2014 | Embrey et al. | |
| 2014/0249601 A1 | 9/2014 | Bachinski et al. | |
| 2015/0020287 A1 | 1/2015 | Liu | |
| 2015/0142080 A1 | 5/2015 | Maxwell | |
| 2017/0036019 A1 | 2/2017 | Matsushita | |

FOREIGN PATENT DOCUMENTS

| | | |
|---|---|---|
| CN | 201640564 U | 11/2010 |
| CN | 202069771 U | 12/2011 |
| CN | 102470246 A | 5/2012 |
| CN | 202665969 U | 1/2013 |
| CN | 202961520 U | 6/2013 |
| CN | 104287102 A | 1/2015 |
| DE | 202 00 685 U1 | 3/2002 |
| DE | 10 2007 057 808 A1 | 6/2009 |
| EP | 1 266 672 A1 | 12/2002 |
| JP | S52-17589 U | 2/1977 |
| JP | H07-136286 A | 5/1995 |
| JP | H08-501946 A | 3/1996 |
| JP | H09-182805 A | 7/1997 |
| JP | H10-57506 A | 3/1998 |
| JP | 2001-293097 A | 10/2001 |
| JP | 2002-345979 A | 12/2002 |
| JP | 2003-19216 A | 1/2003 |
| JP | 2006-271689 A | 10/2006 |
| JP | 2008-125694 A | 6/2008 |
| JP | 2008-264088 A | 11/2008 |
| JP | 2009-142624 A | 7/2009 |
| JP | 3158303 U | 3/2010 |
| RU | 2 173 567 C2 | 9/2001 |
| RU | 45 629 U1 | 5/2005 |
| WO | 2006/113802 A2 | 10/2006 |
| WO | 2013/106644 A1 | 7/2013 |
| WO | 2013/171445 A1 | 11/2013 |

OTHER PUBLICATIONS

Aug. 29, 2017 International Preliminary Report on Patentability issued in International Patent Application No. PCT/JP2015/067929.
Jun. 18, 2018 Written Opinion issued in Singaporean Patent Application No. 11201706459U.
Jun. 16, 2015 Search Report issued in International Patent Application No. PCT/JP2015/058230.
Aug. 11, 2015 Search Report issued in International Patent Application No. PCT/JP2015/067929.
Mar. 27, 2018 Office Action issued in Japanese Patent Application No. 2017-159511.
Nov. 14, 2017 Notification of Reasons for Refusal issued in Japanese Patent Application No. 2017-159511.
Jan. 21, 2019 Extended Search Report issued in European Patent Application No. 15883286.5.
Oct. 1, 2019 Examination Report issued in Australia Patent Application No. 2015384447.
Jun. 25, 2019 Notice of Reasons for Refusal issued in Japanese Patent Application No. JP 2017-501829.
Jan. 30, 2020 Office Action issued in Taiwanese Patent Application No. 105105969.
Feb. 4, 2020 Office Action issued in European Patent Application No. 15883286.5.
Apr. 14, 2020 Office Action issued in Chinese Patent Application No. 201710883986.5.
May 25, 2020 Office Action issued in Chinese Patent Application No. 201580076749.7.
Aug. 23, 2018 Reconsideration Report by Examiner before Appeal issued in Japanese Patent Application No. 2017-159511.
May 15, 2018 Decision of Refual issued in Japanese Patent Application No. 2017-211946.
Nov. 28, 2017 Notice of Reason for Refusal issued in Japanese Patent Application No. 2017-211946.
Jan. 30, 2018 Notice of Reason for Refusal issued in Japanese Patent Application No. 2017-211946.
Apr. 3, 2018 Notice of Reason for Refusal issued in Japanese Patent Application No. 2017-211946.
Jul. 3, 2020 Office Action issued in Chinese Patent Application No. 201710883986.5.

* cited by examiner

FIG. 7a  Basic waveform B1 (2 Hz)
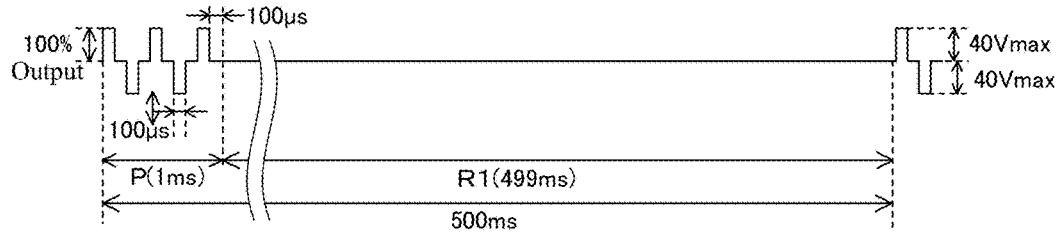
FIG. 7b  Basic waveform B2 (4 Hz)
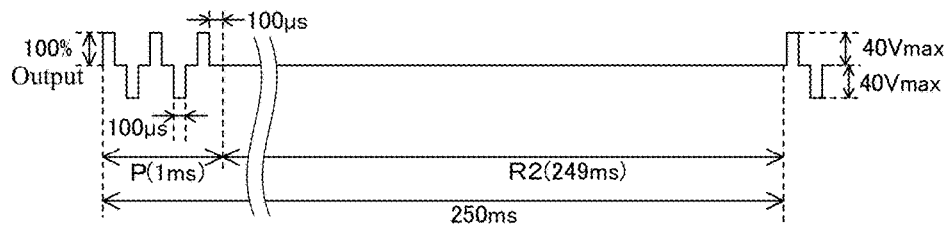
FIG. 7c  Basic waveform B3 (8 Hz)
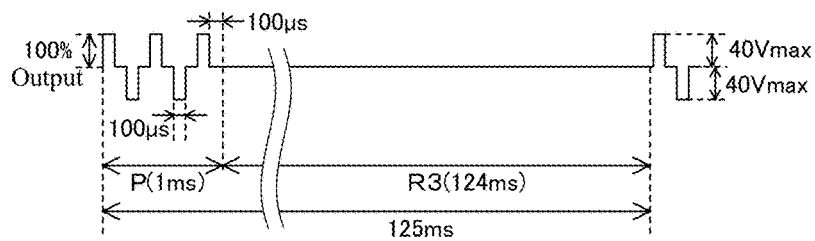
FIG. 7d  Basic waveform B4 (16 Hz)
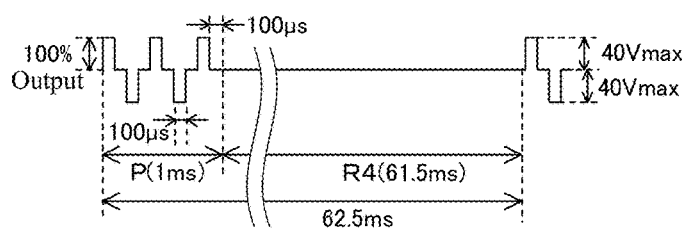
FIG. 7e  Basic waveform B5 (20 Hz)
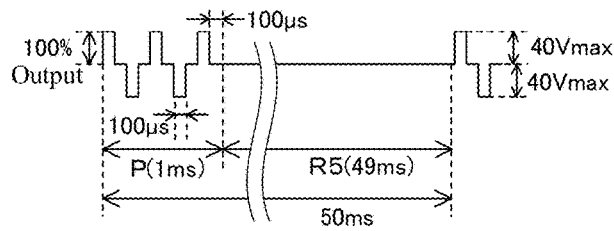

FIG. 13a  First burst wave (2 Hz)
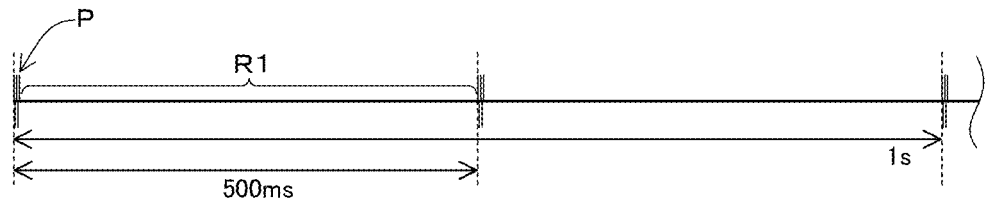
FIG. 13b  Second burst wave (4 Hz)
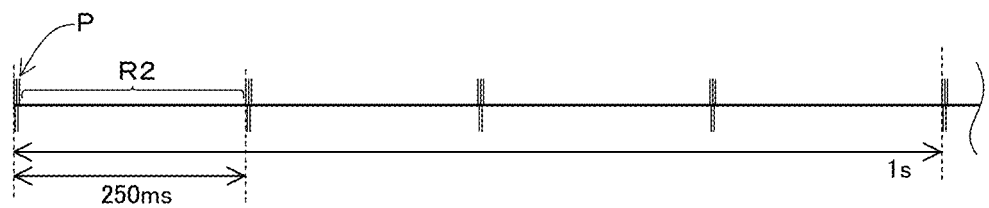
FIG. 13c  Third burst wave (8 Hz)
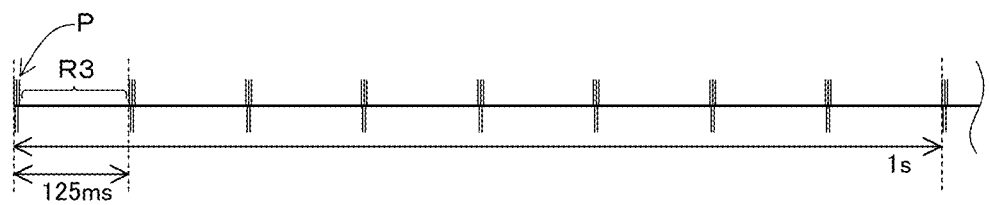
FIG. 13d  Fourth burst wave (16 Hz)
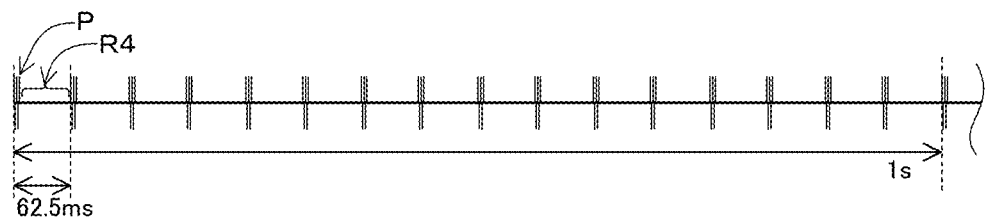
FIG. 13e  Fifth burst wave (20 Hz)
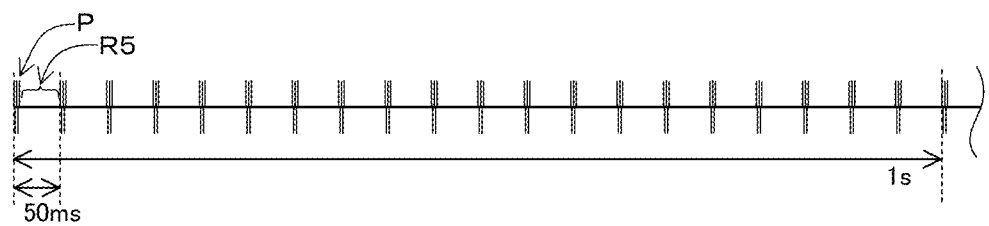

Basic waveforms B1 to B5

$$\begin{cases} \text{Basic waveform B1 (2Hz, 500ms)} & = \text{P(1ms)} + \text{R1 (499ms)} \\ \text{Basic waveform B2 (4Hz, 250ms)} & = \text{P(1ms)} + \text{R2 (249ms)} \\ \text{Basic waveform B3 (8Hz, 125ms)} & = \text{P(1ms)} + \text{R3 (124ms)} \\ \text{Basic waveform B4 (16Hz, 62.5ms)} & = \text{P(1ms)} + \text{R4 (61.5ms)} \\ \text{Basic waveform B5 (20Hz, 50ms)} & = \text{P(1ms)} + \text{R5 (49ms)} \end{cases}$$

MUSCLE ELECTROSTIMULATION DEVICE

TECHNICAL FIELD

The present invention relates to a muscle electrostimulation device.

BACKGROUND ART

A muscle electrostimulation device that uses an electric pulse to stimulate muscles is disclosed in Patent Document 1, the device including: a main body containing a power source; and a pair of electrodes elongated from the main body, wherein the pair of electrodes are attached to a human body to apply the electric pulse to the human body to stimulate the muscles.

PRIOR ART DOCUMENT

Patent Document

Patent Document 1: JP-U-3158303

SUMMARY OF THE INVENTION

Problem to be Solved by the Invention

However, the configuration disclosed in Patent Document 1 includes only one pair of electrodes that stimulates the muscles. Therefore, there is room for improvement in order to effectively stimulate the muscles, such as abdominal muscles, spread in a wide range at the center of the abdomen.

The present invention has been made in view of these circumstances, and an object of the present invention is to provide a muscle electrostimulation device that can effectively stimulate abdominal muscles.

Means for Solving the Problem

One aspect of the present invention resides in a muscle electrostimulation device including: a main body; a power source stored in the main body; an electrode unit that receives power from the power source; a controller that controls supply of power to the electrode unit; and an operation unit configured to be capable of changing a control mode of the controller, the device being configured to bring the electrode unit into contact with an abdomen of a person to apply electrostimulation to the abdomen, wherein the electrode unit includes: a first electrode group extended from the main body so as to be disposed in a right direction of the person with respect to a center line parallel to a height direction of the person and passing through a center of the main body when the device is attached to a middle of the abdomen; and a second electrode group extended from the main body so as to be disposed in a left direction of the person with respect to the center line, the first electrode group and the second electrode group are configured to be electronically connected via the human body, and the first electrode group and the second electrode group include four or more electrodes in total.

Effects of the Invention

The abdominal muscles of a person include two rectus abdominis muscles extending in a height direction. Tendinous intersections divide the two rectus abdominis muscles in a direction intersecting the height direction, and three or four compartments are formed in each rectus abdominis muscle. In the muscle electrostimulation device, the first electrode group and the second electrode group of the electrode unit include four or more electrodes in total. When the muscle electrostimulation device is attached to the abdomen of the person, the first electrode group is disposed on the right hand side of the person with respect to the center line of the main body, and the second electrode group is disposed on the left hand side of the person with respect to the center line of the main body. Therefore, the electrodes can be easily attached according to four or more compartments of the rectus abdominis muscles in the muscle electrostimulation device. Therefore, in the compartments corresponding to the electrodes, electrostimulation can be easily applied to motor points (places on the skin where nerves connected to muscles can be easily energized) via the electrodes. As a result, the electrostimulation can be effectively applied to the muscle of each compartment. This can attain advantageous effects of muscle movement (contraction and relaxation) of the rectus abdominis muscles as well as promotion of a blood flow based on the movement of the muscles, increase in the rectus abdominis muscles, and promotion of metabolism.

When the muscle electrostimulation device is attached to the abdomen, the electrodes included in the first electrode group and the electrode included in the second electrode group are lined up in the lateral direction of the person across the main body. Therefore, equivalent electrostimulation can be obtained on the left and the right of the main body, and well-balanced stimulation can be applied to the abdominal muscles.

Since the power source is stored in the main body in the muscle electrostimulation device, the power does not have to be supplied from the outside, and the device can be wireless. Therefore, the usability is excellent, and the device can be used at a location without an external power source.

The first electrode group and the second electrode group are formed to extend from the main body and are provided integrally with the main body. Therefore, the first electrode group and the second electrode group are attached to the abdomen while a specific positional relationship between the groups with respect to the main body is maintained. Accordingly, the electrodes can be easily attached according to the four or more compartments of the rectus abdominis muscles just by attaching the device to the abdomen of the person such that the main body is disposed a little above the umbilicus of the person and such that the center line of the main body is parallel to the central axis of the person. Therefore, the usability is excellent in the muscle electrostimulation device.

As described, according to the present invention, a muscle electrostimulation device that can effectively stimulate abdominal muscles can be provided.

BRIEF DESCRIPTION OF THE DRAWINGS

FIG. 7 is a diagram showing basic waveforms output from the muscle electrostimulation device in Embodiment 1.

FIG. 13 is a diagram showing burst waves output from the muscle electrostimulation device in Embodiment 2.

MODE FOR CARRYING OUT THE INVENTION

Figure 1:
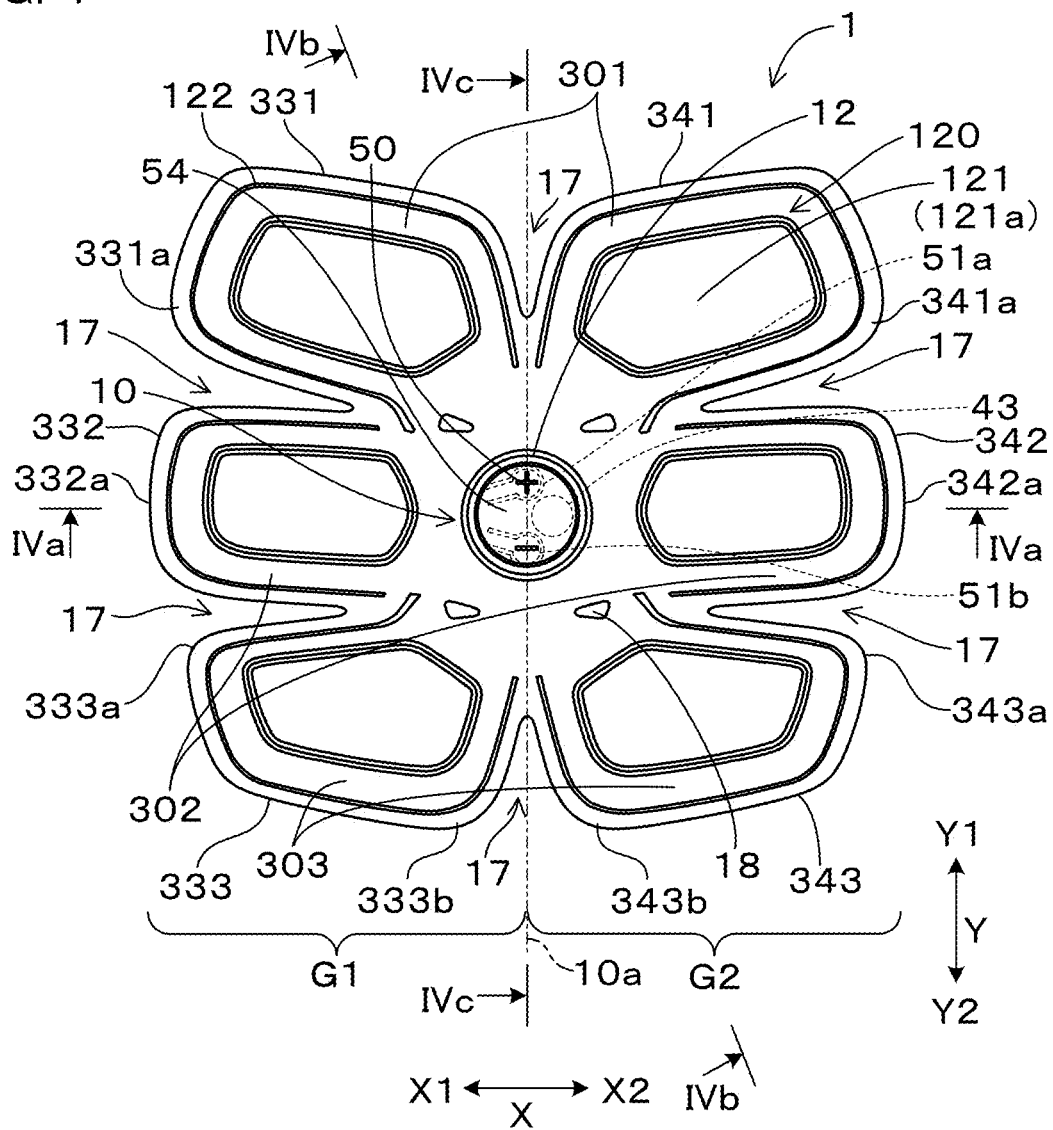
FIG. 1 is a front view of a muscle electrostimulation device in Embodiment 1.

The muscle electrostimulation device is used by attaching the device to the abdomen of the person such that the main body is disposed a little above the umbilicus of the person, and the center line of the main body is parallel to the central axis of the person. Even if the position of the main body upon the attachment is a position somewhat offset from a little above the umbilicus, the electrostimulation can be applied to the rectus abdominis as long as the electrodes are at positions corresponding to the rectus abdominis muscles. The muscle electrostimulation device can be independently attached to the abdomen of the person. A belt covering the abdomen may be wound around the muscle electrostimulation device, while the muscle electrostimulation device is attached to the abdomen. In this case, fall or drop of the muscle electrostimulation device can be surely prevented when the device is used.

It is preferable that the first electrode group and the second electrode group include the same number of the electrodes. In this case, deviation of the electric current flowing from the electrode unit via the human body can be prevented, and well-balanced electrostimulation can be applied to the muscles of the compartments corresponding to the electrodes in the rectus abdominis muscles.

It is preferable that the electrodes included in the first electrode group and the electrodes included in the second electrode group be disposed line-symmetrically with respect to the center line when the device is attached to the abdomen. In this case, when the muscle electrostimulation device is to be attached to the abdomen, the electrodes included in the first electrode group and the electrodes included in the second electrode group can be arranged along the pair of left and right rectus abdominis muscles just by attaching the device to the abdomen of the person such that the center line of the main body is parallel to the central axis of the person. Therefore, well-balanced electrostimulation can be applied to the muscles of the compartments corresponding to the electrodes in the rectus abdominis muscles.

It is preferable that the first electrode group include a plurality of electrodes arranged in the height direction when the device is attached to the abdomen, and the second electrode group include a plurality of electrodes arranged in the height direction when the device is attached to the abdomen. In this case, well-balanced electrostimulation can be applied from the electrodes to the muscles of the compartments divided in the height direction of the person in the pair of left and right rectus abdominis muscles just by attaching the device to the abdomen of the person such that the center line of the main body is parallel to the central axis of the person.

It is preferable that each of the first electrode group and the second electrode group include three electrodes. In this case, the electrodes are arranged according to six compartments in the abdomen in which the rectus abdominis muscles are divided into six or more parts, and the electrostimulation can be more effectively applied to the muscles of the compartments.

It is preferable that, in the height direction of the person when the device is attached to the abdomen, the first electrode group and the second electrode group be configured to form: an upper electrode pair at uppermost positions; a lower electrode pair at lowermost positions; and a central electrode pair at positions between the upper electrode pair and the lower electrode pair, and the central electrode pair project in its extending direction from the main body more than the upper electrode pair and the lower electrode pair. In this case, the electrodes can be more accurately arranged according to six compartments of the rectus abdominis muscles in the abdomen in which the rectus abdominis muscles are partitioned into six or more parts, and the electrostimulation can be more effectively applied to the muscles of the compartments.

It is preferable that the upper electrode pair project in the extending direction from the main body more than the lower electrode pair. In this case, the electrodes can be more accurately arranged according to six compartments just by attaching the device to the abdomen of the person such that the center line of the main body is parallel to the central axis of the person in the abdomen in which the rectus abdominis muscles are partitioned into six or more parts, and the electrostimulation can be more effectively applied to the muscles of the compartments.

It is preferable that notches cut toward the main body be formed between the electrodes adjacent to each other in the first electrode group and the second electrode group. In this case, the electrode unit can be easily deformed according to the movement of the abdomen of the person during the use, and this prevents the electrode unit from falling from the abdomen during the use and prevents the muscle electrostimulation device from dropping off from the abdomen. The notches can reduce accumulation of sweat or moisture between the muscle electrostimulation device and the abdomen. This also prevents the electrode unit from falling from the abdomen during the use and prevents the muscle electrostimulation device from dropping off from the abdomen.

EMBODIMENT

Embodiment 1

A muscle electrostimulation device according to an embodiment of this example will be described with reference to FIGS. 1 to 12.

A muscle electrostimulation device 1 of this embodiment includes a main body 10, a power source 20, an electrode unit 30, a controller 40, and an operation unit 50 as shown in FIGS. 1 to 4 and 6.

The power source 20 is stored in the main body 10 as shown in FIG. 4.

Figure 6:
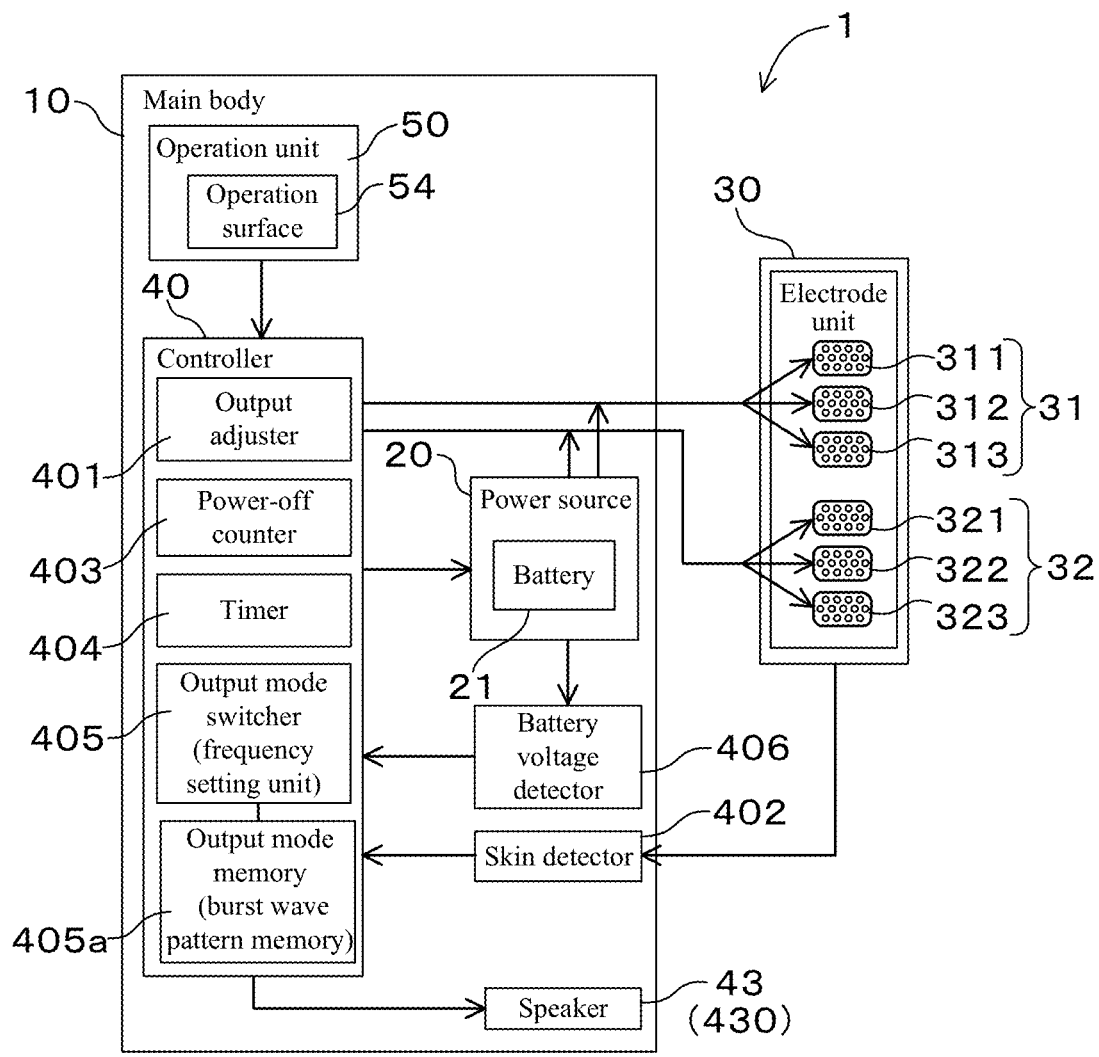
FIG. 6 is a block diagram showing a configuration of the muscle electrostimulation device in Embodiment 1.

The electrode unit 30 is configured to receive power from the power source 20 as shown in FIG. 6.

The controller 40 controls the supply of power to the electrode unit 30.

The operation unit 50 is configured to be capable of changing a control mode of the controller 40.

The electrode unit 30 is brought into contact with an abdomen 3 of a person 2, and the muscle electrostimulation device 1 applies electrostimulation to the abdomen 3.

Figure 2:
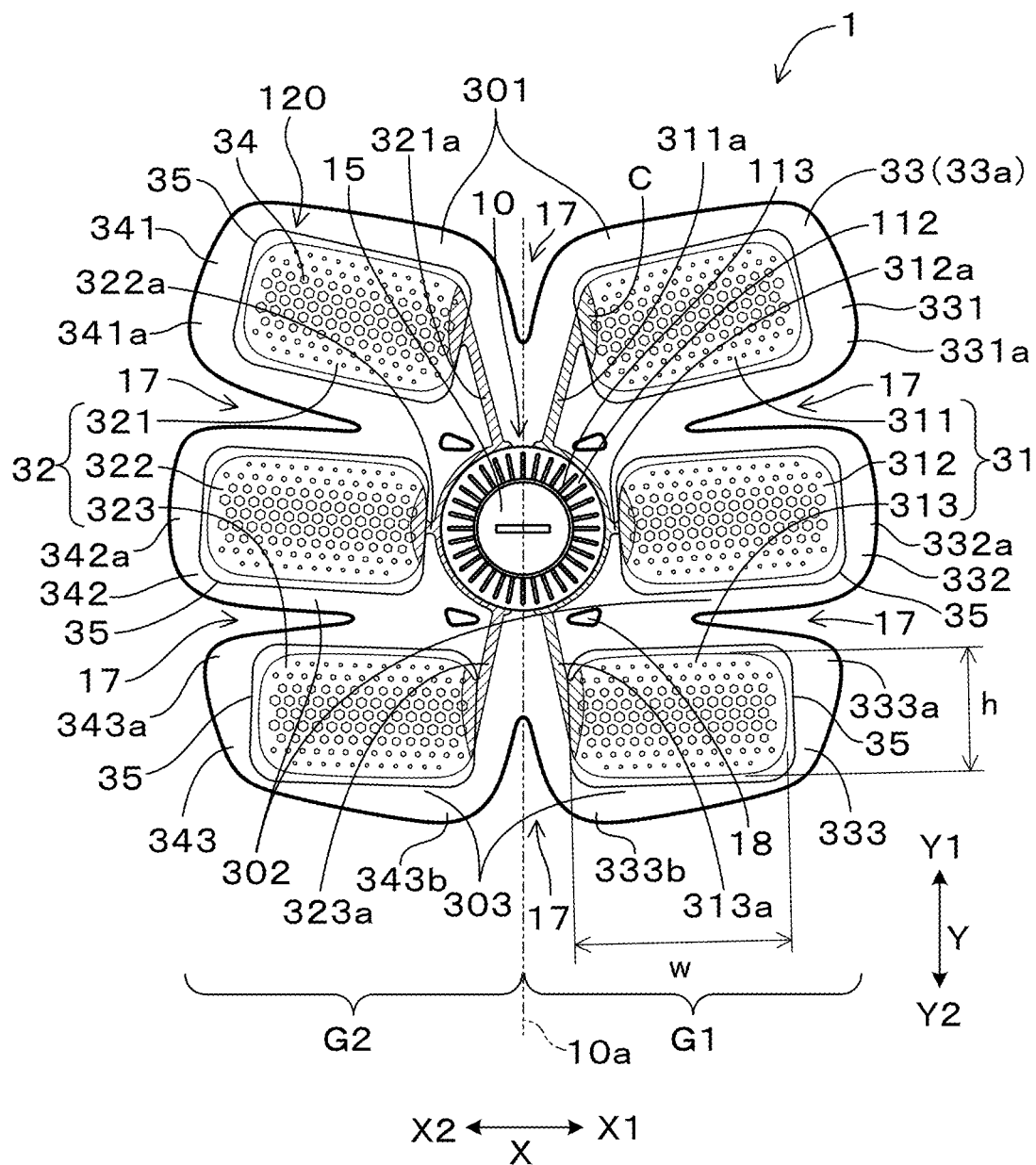
FIG. 2 is a rear view of the muscle electrostimulation device in Embodiment 1.

As shown in FIG. 2, the electrode unit 30 includes a first electrode group 31 and a second electrode group 32.

Figure 5:
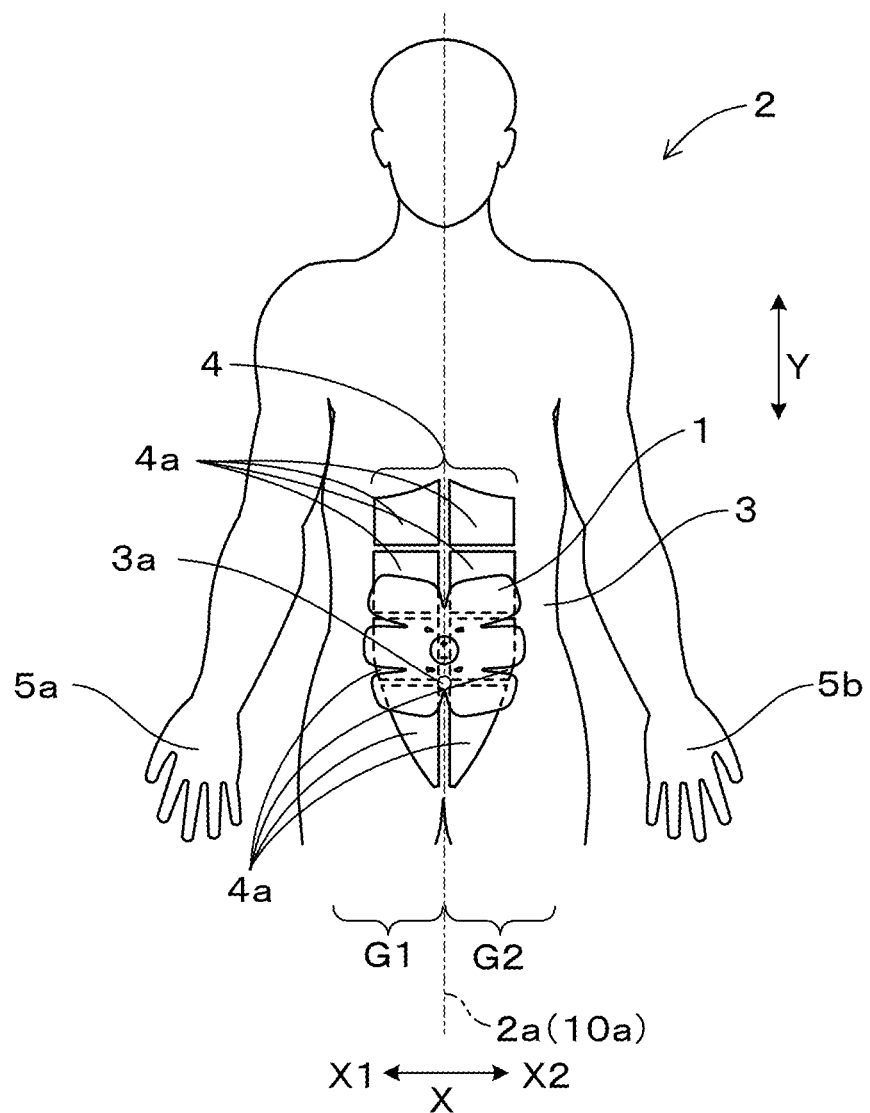
FIG. 5 is a schematic diagram illustrating a usage mode of the muscle electrostimulation device in Embodiment 1.

As shown in FIG. 5, the first electrode group 31 extends from the main body 10 such that the first electrode group 31 is disposed on a right hand side X1 of the person 2 with respect to a center line 10a parallel to a height direction Y of the person 2 and passing through the center of the main body 10 when the device is attached to the middle of the abdomen 3.

As shown in FIG. 5, the second electrode group 32 extends from the main body 10 such that the second electrode group 32 is disposed on a left hand side X2 of the person 2 with respect to the center line 10a when the device is attached to the middle of the abdomen 3.

The first electrode group 31 and the second electrode group 32 can be electronically connected via the person 2.

The first electrode group 31 and the second electrode group 32 include four or more (six in Embodiment 1) electrodes in total.

The muscle electrostimulation device 1 of this embodiment is attached such that a front surface (i.e. an outer surface 121a of an electrode support 121 described later) and a rear surface on the opposite side (i.e. a rear surface 33a that is a surface on the side provided with the electrode unit 30 in a substrate 33 described later) face the abdomen 3 of the person 2. As shown in FIG. 5, the muscle electrostimulation device 1 of this embodiment is attached to the abdomen 3 of the person 2 and used. In this embodiment, a longitudinal direction of the height of the person 2 is referred to as the height direction Y. A direction toward the head in the height direction Y is referred to as an upper side Y1, and a direction toward the legs is referred to as a lower side Y2. Facing the front side of the person 2, a direction toward a right hand side 5a of the person 2 from a central axis 2a of the person 2 parallel to the height direction Y and passing through an umbilicus 3a is referred to as the right direction X1, and a direction toward a left hand side 5b of the person 2 from the central axis 2a is referred to as the left direction X2. The right direction X1 and the left direction X1 are integrally referred to as a lateral direction X.

Hereinafter, the muscle electrostimulation device 1 will be described in detail.

Figure 3:
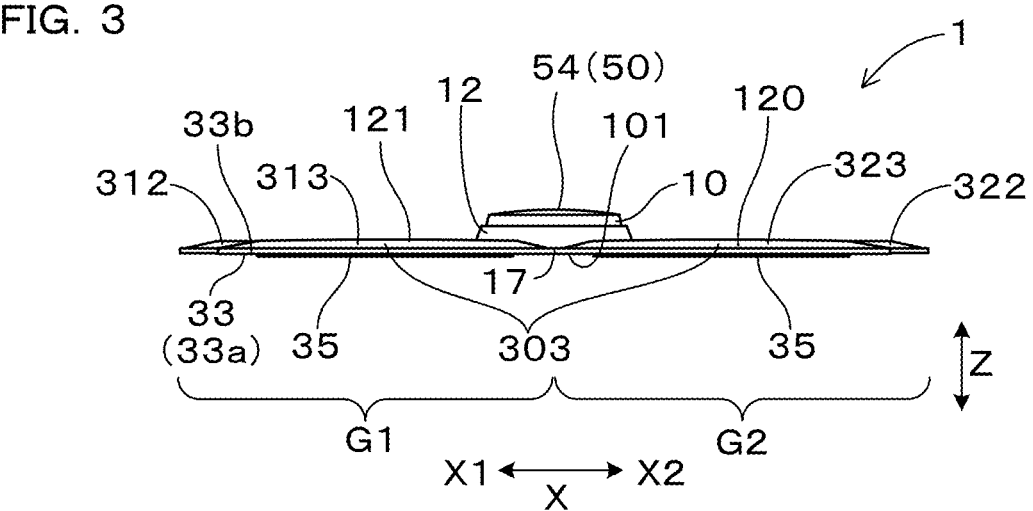
FIG. 3 is a side view of the muscle electrostimulation device in Embodiment 1.

As shown in FIG. 1, the main body 10 is provided at the center of the muscle electrostimulation device 1. As shown in FIGS. 1 and 3, the main body 10 has a substantially disc shape. As shown in FIG. 4, the main body 10 includes: a case 11 for storing the power source 20 and the controller 40 described later; and a shell forming body 12 attached to the case 11 and forming a shell of the muscle electrostimulation device 1.

Figure 4A:
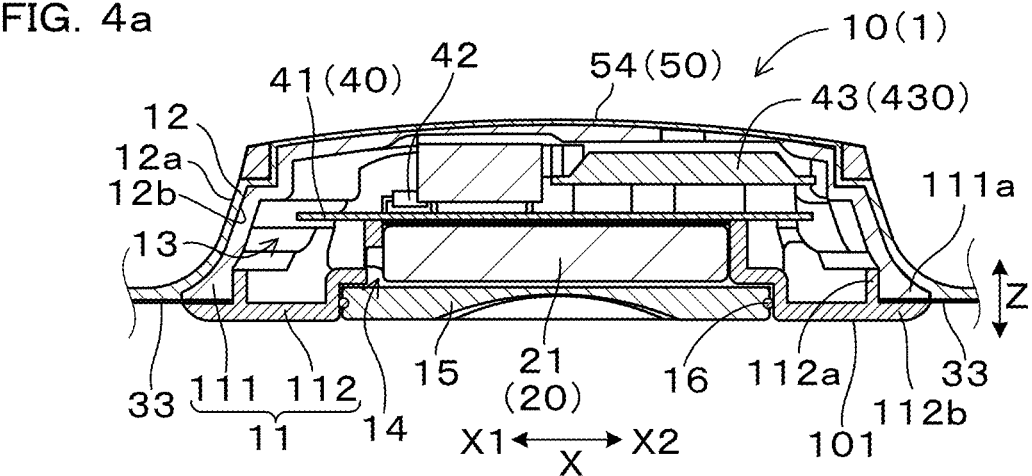
FIG. 4a is a partially enlarged sectional view taken along line IVa-IVa in FIG. 1.
Figure 4B:
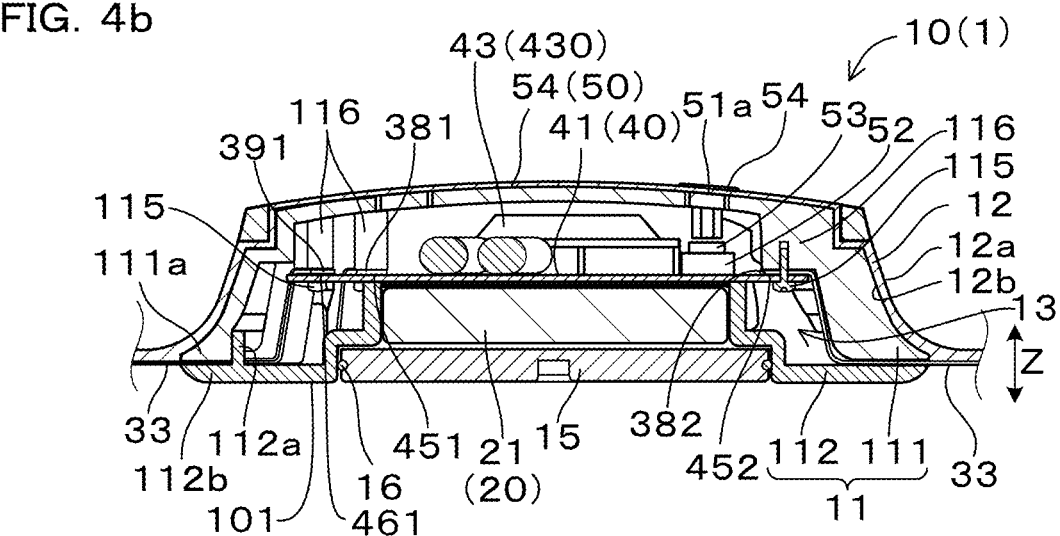
FIG. 4b is a partially enlarged sectional view taken along line IVb-IVb in FIG. 1.
Figure 4C:
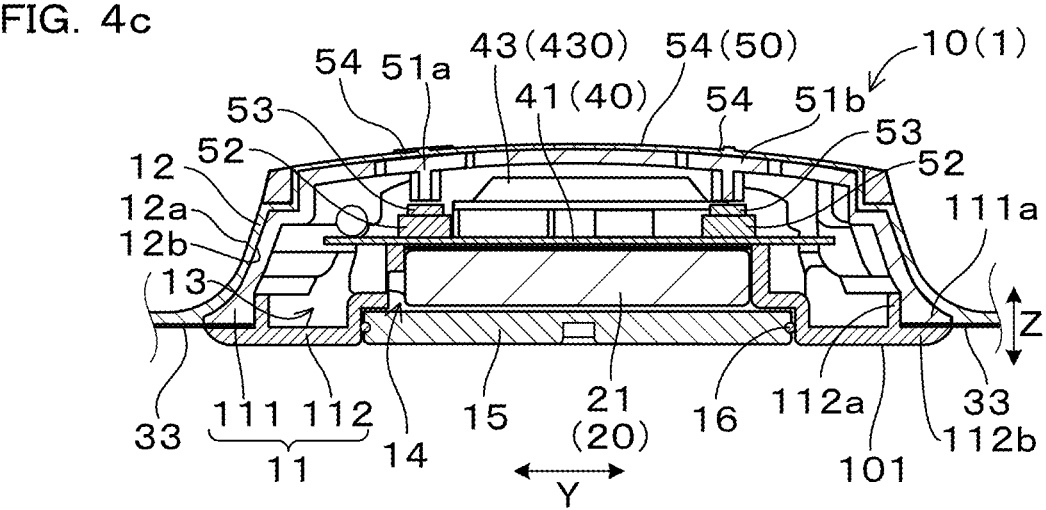
FIG. 4c is a partially enlarged sectional view taken along line IVc-IVc in FIG. 1.

As shown in FIGS. 4a, 4b, and 4c, the shell forming body 12 includes: a surface 12b on a side provided with the substrate 33 described later; and an outer surface 12a on the opposite side. The shell forming body 12 is made of an elastomer and is made of black silicone in this embodiment. As described later, the electrode support 121 extends from the shell forming body 12 so as to cover a front surface 33b of the substrate 33. Accordingly, an extending portion 120 including the electrode support 121 and the substrate 33 is formed around the main body 10. As shown in FIG. 1, a colored area 122 in a linear shape substantially along the peripheries of electrodes 311 to 313 and 321 to 323 described later is formed on the outer surface 121a of the electrode support 121. In this embodiment, the colored portion 122 is colored in orange.

As shown in FIGS. 4a, 4b, and 4c, the case 11 includes: a first case 111 in a concave shape; and a second case 112 attached to the first case 111 and forming a container 13 for storing the controller 40 between the second case 112 and the first case 111. Both the first case 111 and the second case 112 are made of ABS. A rib 112a provided to stand along the periphery of the second case 112 is fitted with the inside of a peripheral portion 111a of the first case 111, and the second case 112 is connected to the first case 111.

As shown in FIGS. 1, 4b, and 4c, a first cantilever 51a and a second cantilever 51b forming part of the operation unit 50 described later are formed on the first case 111. The first cantilever 51a and the second cantilever 51b are formed in a cantilever beam shape by removing part of the wall of the first case 111. The first cantilever 51a and the second cantilever 51b are arranged in this order from the upper side to the lower side in the height direction Y.

As shown in FIGS. 1, 4b, and 4c, both cantilevers 51a and 51b are covered by the shell forming body 12. In the shell forming body 12, a symbol "+" is formed to protrude immediately above the first cantilever 51a, and a symbol "−" is formed to protrude immediately above the second cantilever 51b, thereby forming an operation surface 54 forming part of the operation unit 50 described later. As a result of the arrangement of both the cantilevers 51a and 51b, "+" is the upper side in the height direction Y, and "−" is the lower side in the height direction Y, thereby allowing the user to perform ergonomically easy operation.

As shown in FIGS. 4a, 4b, and 4c, a control board 41 forming the controller 40 (see FIG. 6) is stored in the container 13 formed between the first case 111 and the second case 112. The control board 41 is a printed board, and a wiring pattern not shown, electronic components 42, and the like are provided on the control board 41 to form a control circuit. As shown in FIG. 4b, the control board 41 is fixed to the first case 111 via four bosses 116 and screws 115 formed to protrude on an inner surface of the first case 111. In FIG. 4b, three of the four bosses 116 are described. A small surface-mounted speaker 43 is electrically connected to the control board 41. Drive voltages of the electronic components 42 and the speaker 43 are both 3.0 V. Although not shown, a booster circuit that increases an output voltage of a battery 21 is mounted on the control board 41. Accordingly, the power of the battery 21 is increased to a predetermined voltage (for example, 40 V) and supplied to the electrode unit 30.

As shown in FIGS. 4b and 4c, switch mechanisms 52 forming the operation unit 50 are also stored in the container 13. The switch mechanisms 52 are electrically connected to the controller 40. The switch mechanisms 52 are tactile switches and include switch sections 53 that can be pressed. The switch mechanisms 52 are electrically connected to the controller 40. The switch mechanisms 52 are arranged immediately below the first cantilever 51a and the second cantilever 51b formed on the first case 111. Accordingly, when the first cantilever 51a is pressed from the outside via the operation surface 54 of the shell forming body 12 covering the first case 111, the first cantilever 51a in the cantilever beam shape is bent to press the switch section 53 of the switch mechanism 52. When the press on the operation surface 54 is released, the resilience of the first cantilever 51a in the cantilever beam shape causes the first cantilever 51a to return to the original position. Likewise, the press and the release of the press are performed in the second cantilever 51b.

As shown in FIGS. 4a, 4b, and 4c, a battery holder 14 for holding the battery 21 included in the power source 20 is formed on the second case 112. Accordingly, the power source 20 is embedded in the main body 10. The battery 21 can be replaced and can be, for example, a coin battery or a button battery. In this embodiment, a small and thin coin battery (lithium-ion battery CR2032, nominal voltage 3.0 V) is adopted as the battery 21. Instead of the battery 21, a battery with a nominal voltage of 3.0 V to 5.0 V can be adopted.

A lid 15 for preventing the battery 21 from dropping off is detachably attached to the battery holder 14 holding the battery 21. The lid 15 has a disc shape one size larger than the battery 21, and an O-ring 16 for sealing between the lid 15 and the second case 112 is fitted around the periphery of the lid 15. The battery 21 is electrically connected to the controller 40 via a lead not shown. As shown in FIG. 2, a plurality of linear grooves 113 radially extending from the periphery of the lid 15 are formed on the second case 112 at regular intervals.

As shown in FIGS. 4a, 4b, and 4c, a flange 112b projecting outside of the rib 112a is formed on the second case 112. The sheet-shaped substrate 33 is sandwiched between the flange 112b and the peripheral portion 111a of the first case 111 via a double-sided waterproof seal not shown. The substrate 33 is made of PET. As shown in FIG. 2, the substrate 33 extends in a sheet shape from the main body 10. As shown in FIGS. 1 and 3, the front surface 33b of the substrate 33 that is a surface on the side where the operation surface 54 is exposed is covered by the electrode support 121 extended from the shell forming body 12. The rear surface 33a opposite to the front surface 33b in the substrate 33 spreads over the entire back side opposite to the surface (front surface) closer to the shell forming body 12 in the muscle electrostimulation device 1. The substrate 33 and the electrode support 121 are joined by an adhesive tape and a silicone adhesion treating agent manufactured by 3M company not shown.

As shown in FIGS. 2 and 6, the electrode unit 30 includes the first electrode group 31 and the second electrode group 32. As shown in FIG. 5, the first electrode group 31 extends from the main body 10 so as to be disposed in the right direction X1 on the right hand side 5a of the person 2 with respect to the center line 10a when the device is attached to the abdomen 3. As shown in FIG. 5, the second electrode group 32 extends from the main body 10 so as to be disposed in the left direction X2 on the left hand side 5b of the person 2 with respect to the center line 10a when the device is attached to the abdomen 3. The first electrode group 31 includes the first right electrode 311 as a first electrode, the second right electrode 312 as a second electrode, and the third right electrode 313 as a third electrode, and the second electrode group 32 includes the first left electrode 321 as a first electrode, the second left electrode 322 as a second electrode, and the third left electrode 323 as a third electrode.

Each of the electrodes 311 to 313 and 321 to 323 is formed in a substantially rectangular shape with rounded corners. A longitudinal direction of each of the electrodes 311 to 313 and 321 to 323 (for example, direction indicated by symbol w in the third right electrode 313 as shown in FIG. 2) is substantially along the lateral direction X. In this embodiment, the electrodes 311 to 313 and 321 to 323 all have the same shape. As for the shape of the electrodes 311 to 313 and 321 to 323, h/w can be, for example, 0.40 to 0.95, preferably, 0.50 to 0.80, wherein w is the length in the longitudinal direction, and h is the length in short transverse direction, and in this embodiment, h/w is 0.55.

As shown in FIG. 2, a plurality of hexagonal-shaped portions 34 that form no electrode and have predetermined sizes are formed at predetermined intervals inside of each of the electrodes 311 to 313 and 321 to 323. Leads 311a, 312a, and 323a for connection to the controller 40 are drawn from the main body 10 and formed on the right electrodes 311, 312, and 313, respectively. Likewise, leads 311a, 312a, and 323a for connection to the controller 40 are drawn from the main body 10 and formed on the left electrodes 321, 322, and 323, respectively. The leads 311a to 313a and 321a to 323a are silicone-coated to prevent electric conduction to the outside. Portions of the electrodes 311 to 313 and 321 to 323 connected to the leads 311a to 313a and 321a to 323a and adjacent areas of the portions (hatched areas indicated by symbol C in FIG. 2) are also silicone-coated to prevent electric conduction to the outside. The right electrodes 311 to 313 are connected in parallel to each other, and the left electrodes 321 to 323 are also connected in parallel to each other.

As shown in FIG. 2, the electrode unit 30 is formed on the rear surface 33a of the substrate 33. Accordingly, the electrode unit 30 is formed integrally with the main body 10. The electrode unit 30 is formed by printing a conductive ink containing a silver paste on the rear surface 33a of the substrate 33. The first electrode group 31 and the second electrode group 32 include four or more electrodes in total. In this embodiment, the first electrode group 31 and the second electrode group 32 include the same number of the electrodes 311 to 313 and 321 to 323, respectively, and the number of electrodes is three each. More specifically, the first electrode group 31 includes the first right electrode 311, the second right electrode 312, and the third right electrode 313. The plurality of second electrode groups 32 include the first left electrode 321, the second left electrode 322, and the third left electrode 323. In the substrate 33, portions where the first right electrode 311, the second right electrode 312, and the third right electrode 313 are formed are referred to as a first right electrode base part 331, a second right electrode base part 332, and a third right electrode base part 333, respectively, and portions where the first left electrode 321, the second left electrode 322, and the third left electrode 323 are formed are referred to as a first left electrode base part 341, a second left electrode base part 342, and a third left electrode base part 343, respectively.

A gel pad 35 ("ST-gel (registered trademark)" manufactured by Sekisui Plastics Co., Ltd., model No. SR-RA240/100) is pasted over each of the electrodes 311 to 313 and 321 to 323. The gel pads 35 are electroconductive, and the electrodes 311 to 313 and 321 to 323 can energize the abdomen 3 (see FIG. 5) via the gel pads 35. The gel pads 35 are strongly adhesive, and the muscle electrostimulation device 1 is attached to the abdomen 3 via the gel pads 35.

As shown in FIG. 2, the gel pads 35 have a shape one size larger than the electrodes 311 to 313 and 321 to 323, and the gel pads 35 separately cover the electrodes 311 to 313 and 321 to 323. The gel pads 35 are replaceable and can be appropriately replaced when, for example, the gel pads 35 deteriorate in adhesive force along with the use, are damaged, or become dirty. The used gel pads 35 may be replaced with new pads every predetermined time period (for example, every month or two months).

As shown in FIG. 2, the first right electrode 311, the second right electrode 312, and the third right electrode 313 extend from the main body 10 so as to be disposed on the right hand side X1 (first area G1) of the person 2 with respect to the center line 10a parallel to the height direction Y of the person 2 (see FIG. 5) and passing through the center of the main body 10. The first right electrode 311, the second right electrode 312, and the third right electrode 313 are arranged in this order from the upper side to the lower side in the height direction Y.

On the contrary, the first left electrode 321, the second left electrode 322, and the third left electrode 323 extend from the main body 10 so as to be disposed in the direction X2 (second area G2) on the left hand side 5b of the person 2 with respect to the center line 10a. The first left electrode 321, the second left electrode 322, and the third left electrode 323 are arranged in this order from the upper side to the lower side in the height direction Y.

As shown in FIG. 2, the first electrode group 31 and the second electrode group 32 are disposed line-symmetrically with respect to the center line 10a when the device is attached to the abdomen 3 (see FIG. 5). More specifically, when the device is attached to the abdomen 3, the first right electrode 311 and the first left electrode 321 are disposed line-symmetrically, the second right electrode 312 and the second left electrode 322 are disposed line-symmetrically, and the third right electrode 313 and the third left electrode 323 are disposed line-symmetrically with respect to the center line 10a.

As shown in FIG. 2, when the device is attached to the abdomen 3 (see FIG. 5), the first electrode group 31 and the second electrode group 32 are configured to form: an upper electrode pair 301 including the first right electrode 311 and the first left electrode 321 at uppermost positions of the first electrode group 31 and the second electrode group 32, respectively, in the height direction Y; a lower electrode pair 303 including the third right electrode 313 and the third left electrode 323 at lowermost positions; and a central electrode pair 302 including a pair of the second right electrode 312 and the second left electrode 322 disposed between the upper electrode pair 301 and the lower electrode pair 303. Accordingly, the upper electrode pair 301, the central electrode pair 302, and the lower electrode pair 303 are arranged in this order from the upper side to the lower side in the height direction Y.

The central electrode pair 302 protrudes in the extending direction from the main body 10 (lateral direction X) more than the upper electrode pair 301 and the lower electrode pair 303. More specifically, when the device is attached to the abdomen 3, the second right electrode 312 included in the central electrode pair 302 projects in the right direction X1 more than the first right electrode 311 included in the upper electrode pair 301 and the third right electrode 313 included in the lower electrode pair 303. Likewise, the second left electrode 322 included in the central electrode pair 302 projects in the left direction X2 more than the first left electrode 321 included in the upper electrode pair 301 and the third left electrode 323 included in the lower electrode pair 303.

As shown in FIG. 2, the upper electrode pair 301 is inclined in a V-shape so as to be deviated upward in the extending direction. As described above, the electrodes 311 to 313 and 321 to 323 have the same size. On the contrary, the right electrode base parts 331 to 333 in the substrate 33 of the electrode unit 30 are larger than the right electrodes 311 to 313, and the left electrode base parts 341 to 343 are larger than the left electrodes 321 to 323.

As shown in FIG. 2, the upper electrode pair 301 projects in the extending direction from the main body 10 (lateral direction X) more than the lower electrode pair 302. More specifically, when the device is attached to the abdomen 3, the first right electrode 311 included in the upper electrode pair 301 projects in the right direction X1 more than the third right electrode 313 included in the lower electrode pair 303. Likewise, the first left electrode 321 included in the upper electrode pair 301 projects in the left direction X2 more than the third left electrode 323 included in the lower electrode pair 303.

As shown in FIG. 2, a lower peripheral portion 331a of the first right electrode base part 331 protrudes in the right direction X1, and a lower peripheral portion 341a of the first left electrode base part 341 protrudes in the left direction X2.

A central peripheral portion 332a of the second right electrode base part 332 protrudes a little in the right direction X1, and a central peripheral portion 342a of the second left electrode base part 342 protrudes a little in the left direction X2.

An upper peripheral portion 333a of the third right electrode base part 333 protrudes in the right direction X1, and a lower peripheral portion 333b of the third right electrode base part 333 protrudes in a lower direction (downward in the Y direction). An upper peripheral portion 343a of the third left electrode base part 343 protrudes in the left direction X2, and a lower peripheral portion 343b of the third left electrode base part 343 protrudes in the lower direction.

The configuration of the base parts 331 to 333 and 341 to 343 in the substrate 33 as described above allows visually recognizing that the sizes of the upper electrode pair 301, the central electrode pair 302, and the lower electrode pair 303 are different when the muscle electrostimulation device 1 is viewed from the front side as shown in FIG. 1 and allows visually recognizing that the shape resembles the shape of compartments 4a (see FIG. 5) of rectus abdominis muscles 4 in the abdomen 3. This can give the user the impression that the muscle electrostimulation device 1 is suitable for the stimulation of the compartments 4a of the rectus abdominis muscles 4 and can expect an advantageous effect of increasing the motivation of the user in using the muscle electrostimulation device 1. Furthermore, the recognition of the shape allows the user to imagine shaped abdomen and six-pack abdominal muscles. This can exert an advantageous effect of visualization training for building the shaped abdomen 3 with six-pack abdominal muscles by using the muscle electrostimulation device 1 (improvement in athletic effects based on visualization training is widely known to the public).

As shown in FIG. 2, notches 17 cut toward the main body 10 are formed between the electrodes 311 to 313 and 321 to 323 adjacent to each other in the first electrode group 31 and the second electrode group 32. In this embodiment, the notches 17 are formed at six positions in total, between the first right electrode 311 and the second right electrode 312, between the second right electrode 312 and the third right electrode 313, between the third right electrode 313 and the third left electrode 323, between the third left electrode 323 and the second left electrode 322, between the second left electrode 322 and the first left electrode 321, and between the first left electrode 321 and the first right electrode 311. Furthermore, through holes 18 are formed at four positions around the main body 10.

Next, the configuration of the muscle electrostimulation device 1 of this embodiment will be described with reference to a block diagram.

As shown in FIG. 6, the muscle electrostimulation device 1 includes a skin detector 402 and a battery voltage detector 406, in addition to the power source 20, the controller 40, and the operation unit 50 inside of the main body 10.

The skin detector 402 detects whether the electrode unit 30 is in contact with the skin. More specifically, the skin detector 402 is electrically connected to the electrode unit 30 and detects a resistance value between the first electrode group 31 and the second electrode group 32. The skin detector 402 compares the detected value with a preset threshold and detects that the skin is in contact with the first electrode group 31 and the second electrode group 32 when the detected value is smaller than the threshold.

The battery voltage detector 406 detects a voltage of the battery 21 in the power source 20 and determines whether a detected battery voltage V of the battery 21 in the power source 20 is lower than a predetermined threshold Vm. In this embodiment, a nominal voltage V0 of the battery 21 is 3.0 V, and the threshold Vm is 2.1 V.

As shown in FIG. 6, the power source 20 is provided with the battery 21. The controller 40 is provided with an output adjuster 401, a power-off counter 403, a timer 404, an output mode switcher 405, and an output mode memory 405a. The output adjuster 401 adjusts an output voltage (output level) in the electrode unit 30. In this embodiment, a maximum output voltage is set to 40 V, and 100% output voltage is reduced by 2.0 V every time the output level is decreased by 1. The output levels include fifteen ranges of level 1 to level 15.

The power-off counter 403 measures an elapsed time from receipt of a count start signal. The timer 404 measures an elapsed time from receipt of an output start signal. The output mode switcher 405 switches the output mode in the electrode unit 30 to one of a first output mode, a second output mode, and a third output mode. The output mode memory 405a stores the first output mode, the second output mode, and the third output mode. Basic waveforms as burst wave patterns including pulse group output suspension periods R1 to R5 are stored in advance in the first output mode, the second output mode, and the third output mode, and the output mode memory 405a configures a burst wave pattern memory. Note that the burst wave pattern memory 405a includes description of definition of waveforms of the burst waves on a program.

Next, the output modes in the electrode unit 30 will be described.

The output mode memory 405a stores five basic waveforms B1 to B5 shown in FIGS. 7a to e. The basic waveforms B1 to B5 include: a stimulation step P of 1 ms in total in which an electric signal including a bipolar wave with a pulse width of 100 µs is output five times at intervals of 100 µs; and stimulation stop steps R1 to R5 of predetermined time periods in which the electric signal is not output. The basic waveforms B1 to B5 are repeatedly output in a predetermined combination for a predetermined period, and a burst wave is output in which the stimulation step P is output at a predetermined cycle. In this embodiment, the voltage value of the electric signal in the stimulation step P is +40 V or −40 V at the maximum.

As shown in FIG. 7a, the basic waveform B1 (2 Hz) includes the stimulation step P of 1 ms and the stimulation stop step R1 of 499 ms. That is, the basic waveform B1 (2 Hz) is output in which the stimulation step P is output at a frequency of 2 Hz.

As shown in FIG. 7b, the basic waveform B2 (4 Hz) includes the stimulation step P of 1 ms and the stimulation stop step R2 of 249 ms. That is, the basic waveform B2 (4 Hz) is output in which the stimulation step P is output at a frequency of 4 Hz.

As shown in FIG. 7c, the basic waveform B3 (8 Hz) includes the stimulation step P of 1 ms and the stimulation stop step R3 of 124 ms. That is, the basic waveform B3 (8 Hz) is output in which the stimulation step P is output at a frequency of 8 Hz.

As shown in FIG. 7d, the basic waveform B4 (16 Hz) includes the stimulation step P of 1 ms and the stimulation stop step R4 of 61.5 ms. That is, the basic waveform B4 (16 Hz) is output in which the stimulation step P is output at a frequency of 16 Hz.

As shown in FIG. 7e, the basic waveform B5 (20 Hz) includes the stimulation step P of 1 ms and the stimulation stop step R4 of 49 ms. That is, the basic waveform B5 (20 Hz) is output in which the stimulation step P is output at a frequency of 20 Hz.

That is, the basic waveforms B1 to B5 include the common stimulation step P, and the length of the stimulation stop steps R1 to R5 are different. Accordingly, the frequencies of occurrence of the stimulation step P in the basic waveforms B1 to B5 are set at the respective predetermined cycles as described above.

The first to third output modes stored in the output mode memory 405a are formed by combining the basic waveforms B1 to B5 in predetermined formats. First, as shown in Table 1, the first output mode is a warm-up mode for sequentially performing the following first to fourth statuses. Conditions of the statuses are as follows.

Figure 8:
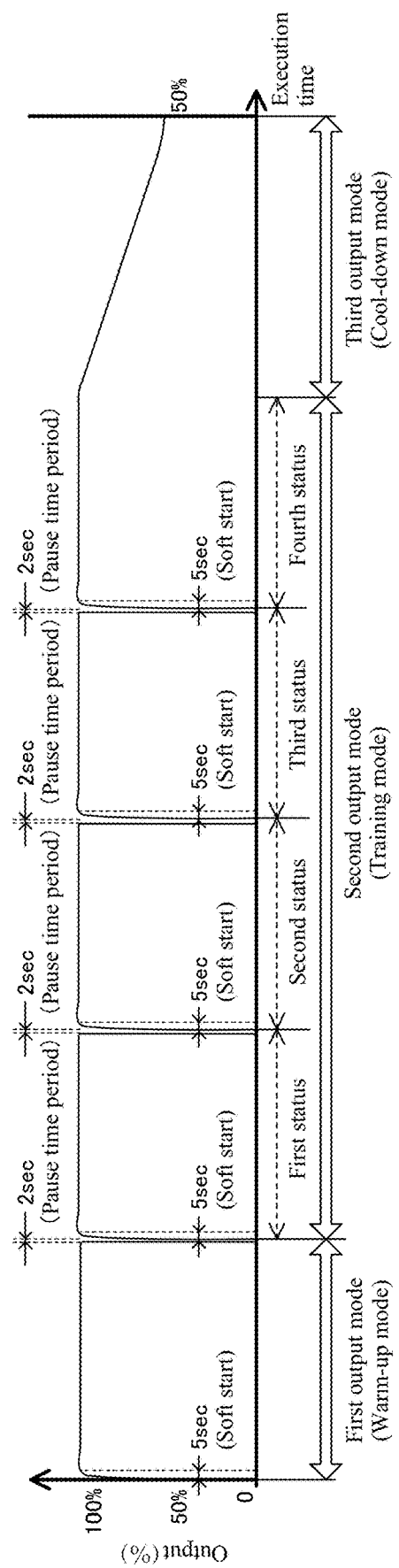
FIG. 8 is a diagram showing variation in voltage output from the muscle electrostimulation device in Embodiment 1.

(1) In the first status, 100% output is performed for twenty seconds through the basic waveform B1 (2 Hz). As shown in FIG. 8, what is called soft start is performed for the first five seconds in the first status, wherein the output voltage is gradually increased from 0% to 100%.

(2) In the second status, 100% output is performed for twenty seconds through the basic waveform B2 (4 Hz).

(3) In the third status, 100% output is performed for ten seconds through the basic waveform B3 (8 Hz).

(4) In the fourth status, 100% output is performed for ten seconds through the basic waveform B4 (16 Hz).

The duration period of the first output mode (i.e. total duration period of first to fourth statuses) is one minute. In the first output mode, the frequency of the basic waveform gradually increases from 2 Hz to 16 Hz, and the first output mode is called a warm-up mode.

[Table 1]

TABLE 1

| First Output Mode (Warm-Up Mode) | | | | |
|---|---|---|---|---|
| | Status | | | |
| | 1 | 2 | 3 | 4 |
| Frequency | 2 Hz | 4 Hz | 8 Hz | 16 Hz |
| Output Rate | 100% | 100% | 100% | 100% |
| Output Period | 20 sec | 20 sec | 10 sec | 10 sec |
| Duration Period | | 60 sec (=1 min) | | |

In the first output mode as a warm-up mode, the frequency of movement of the muscles increases with a gradual increase in the frequency of the burst wave from 2 Hz to 16 Hz, and the muscles and the body are gradually warmed up. This prevents a sudden increase in the blood pressure, a temporary lack of oxygen in the muscles, and the like. The gradual warming of the muscles increases the blood flow and increases the flexibility of the muscles. Accordingly, an advantageous effect of the stimulation of the muscles can be more easily obtained in the following training mode. The user can appropriately get used to the stimulation by performing the warm-up mode prior to the training mode, and the sensitivity improves.

Next, as shown in Table 2, the second output mode is a training mode for sequentially performing the following first to fourth statuses. Conditions of the statuses are as follows.

(1) In the first status, 100% output is performed for three seconds through the basic waveform B5 (20 Hz), and a state without output is maintained for two seconds. This is repeated for five minutes.

(2) In the second status, 100% output is performed for three seconds through the basic waveform B5 (20 Hz), and 100% output is performed for two seconds through the basic waveform B2 (4 Hz). This is repeated for five minutes.

(3) In the third status, 100% output is performed for four seconds through the basic waveform B5 (20 Hz), and 100% output is performed for two seconds through the basic waveform B2 (4 Hz). This is repeated for five minutes.

(4) In the fourth status, 100% output is performed for five seconds through the basic waveform B5 (20 Hz), and 100% output is performed for two seconds through the basic waveform B2 (4 Hz). This is repeated for five minutes.

As shown in FIG. 8, what is called soft start is performed for the first five seconds in each of the first to fourth statuses in the second output mode, wherein the output voltage is gradually increased from 0% to 100%.

The duration of the second output mode is twenty minutes. Since the basic waveform B5 at a frequency of 20 Hz is maintained for a predetermined time period, and the state without output or the basic waveform B2 at a frequency of 4 Hz is maintained for a predetermined time period in the second output mode, the second output mode is excellent in effectively stimulating the muscles. Therefore, the second output mode is called a training mode.

[Table 2]

TABLE 2

| | Second Output Mode (Training Mode) | | | | | | | |
|---|---|---|---|---|---|---|---|---|
| | Status | | | | | | | |
| | 1 | | 2 | | 3 | | 4 | |
| Frequency | 20 Hz | Without Output | 20 Hz | 4 Hz | 20 Hz | 4 Hz | 20 Hz | 4 Hz |
| Output Rate | 100% | 0% | 100% | 100% | 100% | 100% | 100% | 100% |
| Output Period | 3 sec | 2 sec | 3 sec | 2 sec | 4 sec | 2 sec | 5 sec | 2 sec |
| Duration Period | 300 sec (=5 min) | | 300 sec (=5 min) | | 300 sec (=5 min) | | 300 sec (=5 min) | |

Next, as shown in Table 3, the third output mode is a cool-down mode for sequentially performing the following first to fourth statuses. Conditions of the statuses are as follows.

(1) In the first status, output is performed for ten seconds through the basic waveform B4 (16 Hz).

(2) In the second status, output is performed for ten seconds through the basic waveform B3 (8 Hz).

(3) In the third status, output is performed for twenty seconds through the basic waveform B2 (4 Hz).

(4) In the fourth status, output is performed for twenty seconds through the basic waveform B1 (2 Hz).

In the third output mode, the output in each status is 100% at the start of the first status and is gradually reduced to 50% at the end of the fourth status as shown in FIG. 8.

The duration of the third output mode is one minute. In the third output mode, the frequency of the basic waveform is gradually reduced from 16 Hz to 2 Hz, and the third output mode is called a cool-down mode.

[Table 3]

TABLE 3

| | Third Output Mode (Cool-Down Mode) | | | |
|---|---|---|---|---|
| | Status | | | |
| | 1 | 2 | 3 | 4 |
| Frequency | 16 Hz | 8 Hz | 4 Hz | 2 Hz |
| Output Rate | | Gradual Reduction from 100% to 50% | | |
| Output Period | 10 sec | 10 sec | 20 sec | 20 sec |
| Duration Period | | 60 sec (=1 min) | | |

In the third output mode as a cool-down mode, the frequency of movement of the muscles is reduced with a gradual decrease in the frequency of the burst wave from 16 Hz to 2 Hz, and the warmed muscles and body are gradually cooled down. Fatigue substances generated in the muscles in the preceding training mode are actively discharged from the muscles to prevent the fatigue substances from excessively remaining in the muscles.

As described, the total time of the sequential execution of the first output mode (warm-up mode), the second output mode (training mode), and the third output mode (cool-down mode) is twenty two minutes. In this embodiment, a pause time period of two seconds is provided at each of four sections in total between the first output mode and the second output mode and between the statuses in the second output mode as shown in FIG. 8. Therefore, the total time of the entire process including the pause time periods is twenty two minutes and eight seconds.

Next, a usage mode in the muscle electrostimulation device 1 of this embodiment will be described in detail.

A main operation flow S100 shown in FIG. 9 will be described. In the main operation flow S100, "+" of the operation surface 54 is pressed for two seconds (S101). Accordingly, the power of the muscle electrostimulation device 1 is turned on to activate the muscle electrostimulation device 1, and the speaker 43 makes a notification sound ("beep") for notifying the activation (S102). Subsequently, the muscle electrostimulation device 1 is brought into an output standby state, the output level is set to 0, and the input into the operation unit 50 is invalidated (S103).

Next, the skin detector 402 detects whether the skin is in contact with the electrode unit 30 (S104). If the skin detector 402 detects that the skin is in contact with the electrode unit 30 (Yes in S104), the operation unit 50 is validated (S105). The output level is input through the operation unit 50 (S106). The output level is input from the operation surface 54 of the operation unit 50. The output level is incremented by 1 every time "+" of the operation surface 54 of the operation unit 50 is pressed, and the output level is decremented by 1 every time "−" of the operation surface 54 is pressed. When the output level is set, the controller 40 transmits an output start signal to the timer 404, and the timer 404 starts the measurement (S107). The output level can be operated at any time during the use (from the validation of the operation unit 50 to the power-off).

The output mode in the electrode unit 30 is set to the first output mode (warm-up mode) for one minute after the start (elapsed time 0) of the measurement by the timer 404 (S108). When the elapsed time reaches one minute, the output mode switcher 405 switches the output mode in the electrode unit 30 to the second output mode (training mode) and maintains the second output mode for twenty minutes until the elapsed time is twenty one minutes (S109). When the elapsed time reaches twenty one minutes, the output mode switcher 405 switches the output mode in the electrode unit 30 to the third output mode (cool-down mode) and maintains the third output mode for one minute until the elapsed time is twenty two minutes (S110). When the elapsed time reaches twenty two minutes, the measurement in the timer 404 is finished (S111). The muscle electrostimulation device 1 is then stopped (S112). In this way, S108 to S111 are performed to perform one set of the first output mode (warm-up mode), the second output mode (training mode), and the third output mode (cool-down mode), and the process ends. Note that the elapsed time does not include two seconds of each pause time period.

On the contrary, if the skin detector 402 determines that the skin is not in contact with the electrode unit 30 (No in S104), the speaker 43 makes a notification sound ("beep, beep, beep") for notifying the determination (S113). The power-off counter 403 then starts to measure the elapsed time (S114).

Next, the skin detector 402 detects whether the electrode unit 30 is in contact with the skin (S115). If the skin detector 402 detects that the skin is in contact with the electrode unit 30, the process returns to step S103 described above, and the state is brought into the output standby state (Yes in S115). On the contrary, if the skin detector 402 determines that the skin is not in contact with the electrode unit 30 (No in S115), whether the elapsed time in the power-off counter 403 exceeds two minutes is determined (S116). If it is determined that the elapsed time in the power-off counter 403 does not exceed two minutes (No in S116), the process returns to S115 again, and the skin detector 402 detects whether the skin is in contact with the electrode unit 30. On the contrary, if it is determined that the elapsed time in the power-off counter 403 exceeds two minutes in S116 (Yes in S116), the power of the muscle electrostimulation device 1 is turned off (S117).

Figure 10:
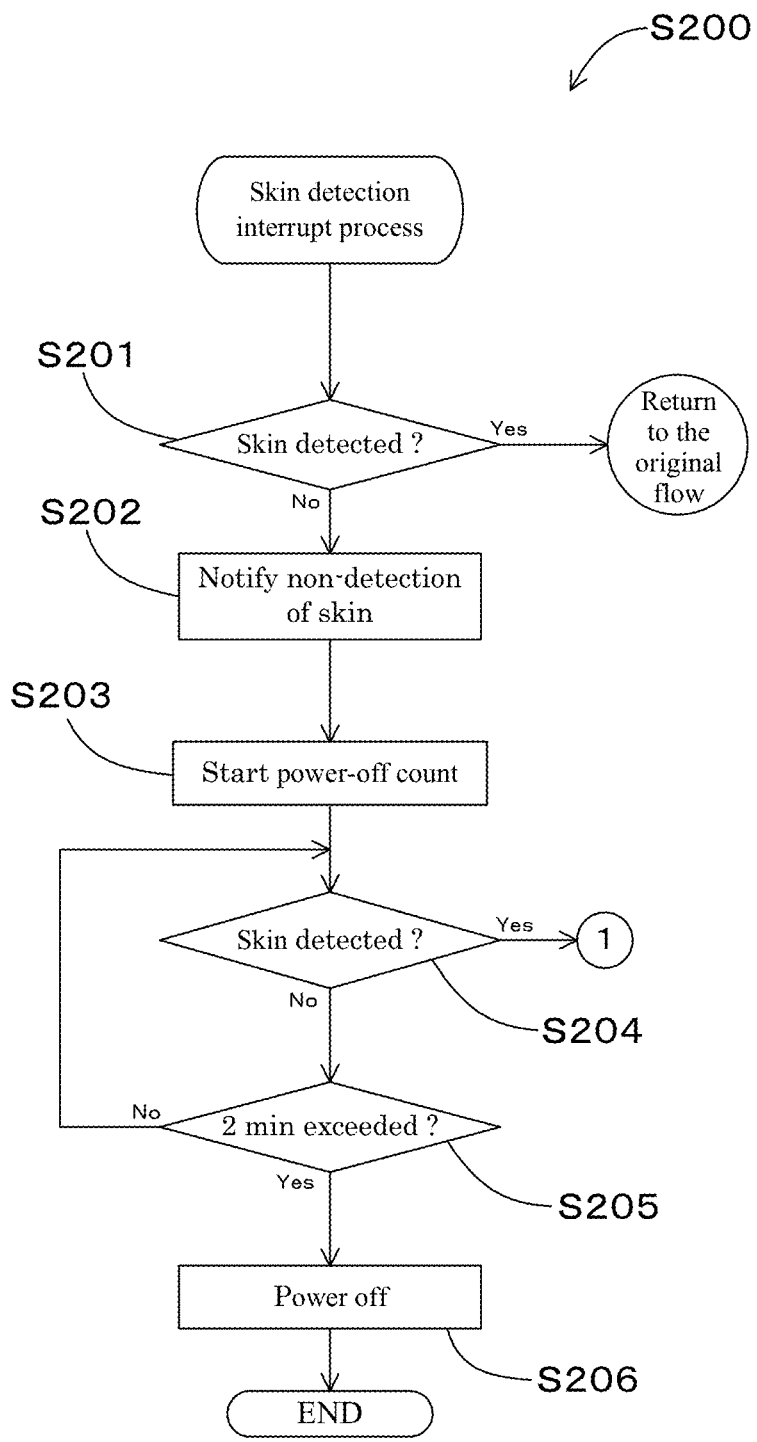
FIG. 10 is a flowchart illustrating a first interrupt process of the muscle electrostimulation device in Embodiment 1.

Next, interrupt processes that interrupt S105 to S110 in the main operation flow S100 and that are preferentially processed will be described. As shown in FIG. 10, a skin detection interrupt process S200 is executed as a first interrupt process. The skin detection interrupt process S200 is used as a function for automatically turning off the power source when the electrode drops off from the human body in the middle of usage. In the skin detection interrupt process S200, the skin detector 402 first detects whether the skin is in contact with the electrode unit 30 (S201). If the skin detector 402 detects that the skin is in contact with the electrode unit 30 (Yes in S201), the process returns to the original flow in the main operation flow S100. On the contrary, if the skin detector 402 determines that the skin is not in contact with the electrode unit 30 (No in S201), the speaker 43 makes a notification sound ("beep, beep, beep") for notifying the determination (S202). The power-off counter 403 then starts to measure the elapsed time (S203).

Next, the skin detector 402 detects whether the skin is in contact with the electrode unit 30 (S204). If the skin detector 402 detects that the skin is in contact with the electrode unit 30, the process returns to step S103 of the main operation flow S100 (Yes in S204). On the contrary, if the skin detector 402 determines that the skin is not in contact with the electrode unit 30 (No in S204), whether the elapsed time in the power-off counter 403 exceeds two minutes is determined (S205). If it is determined that the elapsed time in the power-off counter 403 does not exceed two minutes (No in S205), the process returns to S204 again, and the skin detector 402 detects whether the skin is in contact with the electrode unit 30. On the contrary, if it is determined in S205 that the elapsed time in the power-off counter 403 exceeds two minutes (Yes in S205), the power of the muscle electrostimulation device 1 is turned off (S206).

Figure 11:
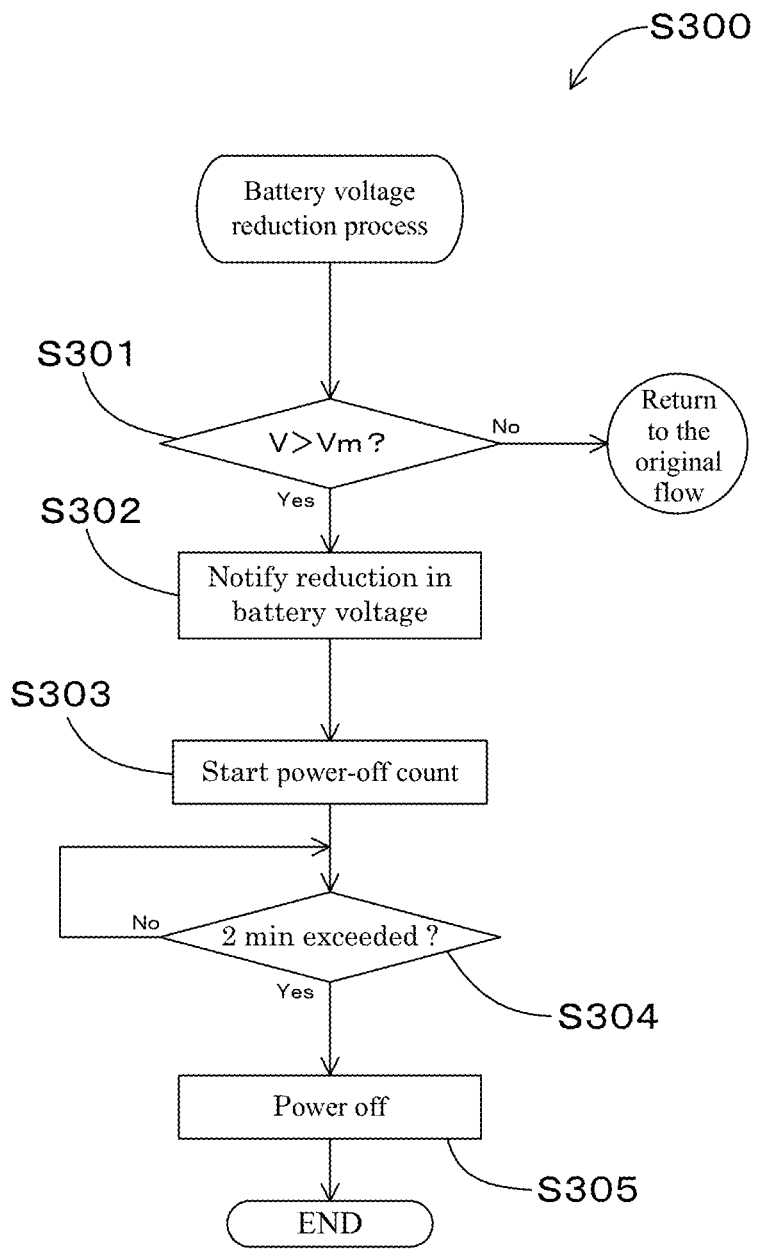
FIG. 11 is a flowchart illustrating a second interrupt process of the muscle electrostimulation device in Embodiment 1.

Next, as shown in FIG. 11, a battery voltage reduction process S300 as a second interrupt process that interrupts S105 to S110 in the main operation flow S100 and that is preferentially processed will be described. The battery voltage reduction process S300 is a function for automatically turning off the power source when the battery voltage of the battery 21 is reduced. Accordingly, when, for example, the battery needs to be replaced, the user can easily notice this. The battery voltage detector 406 first determines whether the detected battery voltage V of the battery 21 in the power source 20 is lower than the predetermined threshold Vm (S301). If the battery voltage detector 406 determines that the battery voltage V is not lower than the predetermined threshold Vm (No in S301), the process returns to the original flow in the main operation flow S100. On the contrary, if the battery voltage detector 406 determines that the battery voltage V is lower than the predetermined threshold Vm, the speaker 43 makes a notification sound ("beep, beep, beep") for notifying the determination (S302). The controller 40 then transmits a count start signal to the power-off counter 403, and the power-off counter 403 starts to measure the elapsed time (S303).

Next, whether the elapsed time in the power-off counter 403 exceeds two minutes is determined (S304). If it is determined that the elapsed time in the power-off counter 403 does not exceed two minutes (No in S304), the process returns to S304 again. If it is determined that the elapsed time in the power-off counter 403 exceeds two minutes (Yes in S304), the power of the muscle electrostimulation device 1 is turned off (S305).

Figure 12:
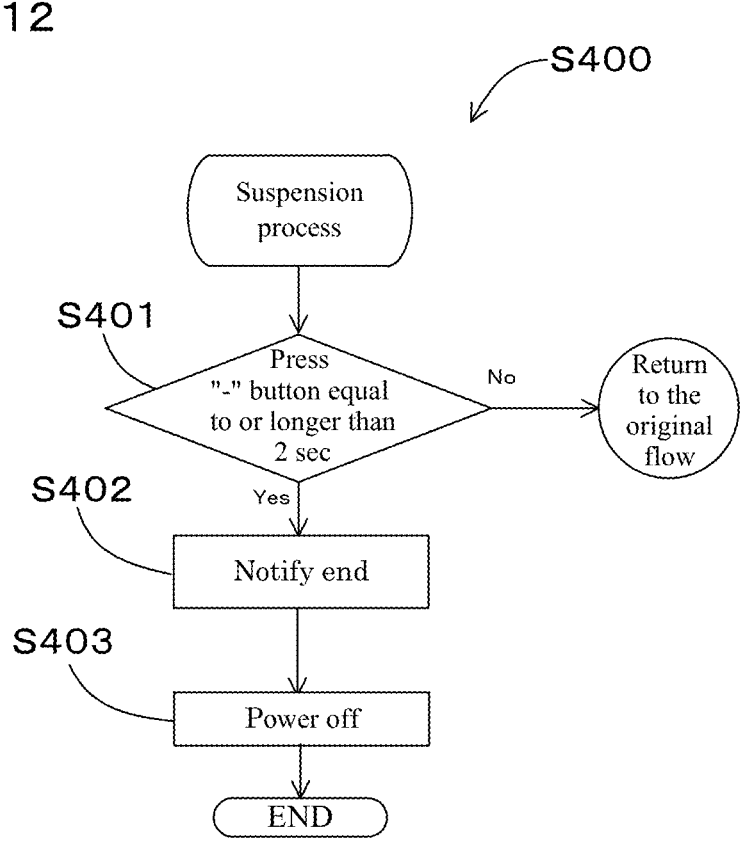
FIG. 12 is a flowchart illustrating a third interrupt process of the muscle electrostimulation device in Embodiment 1.

Next, as shown in FIG. 12, a suspension process S400 as a third interrupt process that interrupts S105 to S110 in the main operation flow S100 and that is preferentially processed will be described. The controller 50 first determines whether the time of the press of the "−" button of the operation surface 54 in the operation unit 50 is equal to or longer than two seconds (S401). If the controller 40 determines that the time of the press of the "−" button is not equal to or longer than two seconds (No in S401), the process returns to the original flow in the main operation flow S100. On the contrary, if the controller 40 determines that the time of the press of the "−" button is equal to or longer than two seconds (Yes in S401), the speaker 43 makes a notification sound ("beep") of notification for turning off the power source to end the muscle electrostimulation device 1 (S402). The power source is then turned off (S403).

Hereinafter, effects of the muscle electrostimulation device 1 of this embodiment will be described in detail.

According to the muscle electrostimulation device 1 of this embodiment, the first electrode group 31 and the second electrode group 32 of the electrode unit 30 include four or more electrodes 311 to 313 and 321 to 323 in total. Furthermore, when the muscle electrostimulation device 1 is attached to the abdomen 3 of the person 2, the first electrode group 31 is disposed on the right hand side X1 (first area S1) of the person 2 with respect to the center line 10a of the main body 10, and the second electrode group 32 is disposed on the left hand side X2 (second area S2) of the person 2 with respect to the center line 10a of the main body 10. Therefore, the electrodes 311 to 313 and 321 to 323 can be easily attached according to four or more compartments in the muscle electrostimulation device 1. Therefore, at the compartments corresponding to the electrodes 311 to 313 and 321 to 323, electrostimulation can be easily applied to motor points (places on the skin where nerves connected to muscles can be easily energized) via the electrodes 311 to 313 and 321 to 323. As a result, the electrostimulation can be effectively applied to the muscles of the compartments 4a. This can attain advantageous effects of muscle movement (contraction and relaxation) of the rectus abdominis muscles as well as promotion of a blood flow based on the movement of the muscles, increase in the rectus abdominis muscles, and promotion of metabolism.

Since the first electrode group 31 is arranged on the right hand side X1 (first area G1), and the second electrode group 32 is arranged on the left hand side X2 (second area G2), the first electrode group 31 and the second electrode group 32 are lined up in the lateral direction X of the person 2 across the main body 10 when the muscle electrostimulation device 1 is attached to the abdomen 3. Therefore, equivalent electrostimulation is applied to the left and the right of the main body 10, and well-balanced stimulation can be applied to the abdominal muscles (rectus abdominis muscles 4).

Since the power source 20 is stored in the main body 10, the power does not have to be supplied from the outside, and the muscle electrostimulation device 1 is wireless. Therefore, the usability is excellent, and the device can be used at a location without an external power source.

The first electrode group 31 and the second electrode group 32 are formed to extend from the main body 10 and are provided integrally with the main body 10. Therefore, the first electrode group 31 and the second electrode group 32 are attached to the abdomen 3 while a specific positional relationship with respect to the main body 10 is maintained. That is, the first right electrode 311 is disposed on the upper side in the right direction X1 of the main body 10 in this embodiment. The second right electrode 312 is disposed on the center in the right direction X1 of the main body 10. The third right electrode 313 is disposed on the lower side in the right direction X1 of the main body 10. the first left electrode 321 is disposed on the upper side in the left direction X2 of the main body 10. The second left electrode 322 is disposed on the center in the left direction X2 of the main body 10. The third left electrode 323 is disposed on the lower side in the left direction X2 of the main body 10. Accordingly, the first electrode group 31 and the second electrode group 32 can be easily attached according to four or more compartments 4a in the abdominal muscles (rectus abdominis muscles 4) just by attaching the device to the abdomen 3 of the person 2 such that the main body 10 is disposed a little above the umbilicus 3a of the person 2 and such that the center line 10a of the main body 10 is parallel to the central axis 2a of the person 2. Therefore, the usability is excellent in the muscle electrostimulation device 1.

In this embodiment, the first electrode group 31 and the second electrode group 32 include the same number of the electrodes 311 to 313 and 321 and 323. This can prevent deviation of the electric current flowing from the electrode unit 30 through the human body and can apply well-balanced electrostimulation to the muscles of the compartments 4a corresponding to the electrodes 311 to 313 and 321 to 323 in the rectus abdominis muscles 4.

In this embodiment, the right electrodes 311 to 313 included in the first electrode group 31 and the left electrodes 321 to 323 included in the second electrode group 32 are disposed line-symmetrically with respect to the center line 10a when the device is attached to the abdomen 3. Accordingly, when the muscle electrostimulation device 1 is attached to the abdomen 3, the right electrodes 311 to 313 included in the first electrode group 31 and the left electrodes 321 to 323 included in the second electrode group 32 can be arranged along the pair of left and right rectus abdominis muscles 4 just by attaching the device to the abdomen 3 of the person 2 such that the center line 10a of the main body 10 is parallel to the central axis 2a of the person 2. Therefore, well-balanced electrostimulation can be applied to the muscles of the compartments 4a corresponding to the electrodes 311 to 313 and 321 to 323 in the rectus abdominis muscles 4.

In this embodiment, the first electrode group 32 includes the plurality of right electrodes 311 to 313 arranged in the height direction Y when the device is attached to the abdomen 3, and the second electrode group 32 includes the plurality of left electrodes 321 to 323 arranged in the height direction Y when the device is attached to the abdomen 3. Accordingly, the electrodes 311 to 313 and 321 to 323 can apply well-balanced electrostimulation to the muscles of the compartments 4a divided in the height direction Y of the person 2 in the pair of left and right rectus abdominis muscles 4 just by attaching the device to the abdomen 3 of the person 2 such that the center line 10a of the main body 10 is parallel to the central axis 2a of the person 2.

In this embodiment, the first electrode group 31 and the second electrode group 32 include three electrodes 311 to 313 and 321 to 323, respectively. Accordingly, the electrostimulation can be more effectively applied to the muscles of the compartments 4a just by attaching the device to the abdomen 3 of the person 2 such that the center line 10a of the main body 10 is parallel to the central axis 2a of the person 2, because the electrodes 311, 312, 313, 321, 322, and 323 are arranged according to the six compartments 4a in the abdomen 3 in which the rectus abdominis muscles 4 are partitioned into six or more parts.

In this embodiment, in the height direction Y of the person 2 when the device is attached to the abdomen 3, the first electrode group 31 and the second electrode group 32 are configured to form: the upper electrode pair 301 at uppermost positions of the first electrode group 31 and the second electrode group 32; the lower electrode pair 303 at lowermost positions; and the central electrode pair 302 at positions between the upper electrode pair 301 and the lower electrode pair 303. The central electrode pair 302 projects in the extending direction (i.e. lateral direction X) from the main body 10 more than the upper electrode pair 301 and the lower electrode pair 303. Accordingly, the electrostimulation can be more effectively applied to the muscles of the compartments 4a just by attaching the device to the abdomen 3 of the person 2 such that the center line 10a of the main body 10 is parallel to the central axis 2a of the person 2, because the electrodes 311, 312, 313, 321, 322, and 323 can be more accurately arranged according to the six compartments 4a in the abdomen 3 in which the rectus abdominis muscles 4 are partitioned into six or more parts.

In this embodiment, the upper electrode pair 301 projects in the extending direction (i.e. lateral direction X) from the main body 10 more than the lower electrode pair 303. Accordingly, the electrodes 311, 312, 313, 321, 322, and 323 can be more accurately arranged according to the six compartments 4a just by attaching the device to the abdomen 3 of the person 2 such that the center line 10a of the main body 10 is parallel to the central axis 2a of the person 2 in the abdomen 3 in which the rectus abdominis muscles 4 are partitioned into six or more parts. Therefore, the electrostimulation can be more effectively applied to the muscles of the compartments 4a.

In this embodiment, the notches 17 cut toward the main body 10 are formed between the electrodes 311 to 313 and 321 to 323 adjacent to each other in the first electrode group 31 and the second electrode group 32. Accordingly, the electrode unit 30 can be easily deformed according to the movement of the abdomen 3 of the person 2 during the use, and this prevents the electrode unit 30 from falling from the abdomen 3 during the use and prevents the muscle electrostimulation device 1 from dropping off from the abdomen 3. The notches 17 can also reduce accumulation of sweat and moisture between the muscle electrostimulation device 1 and the abdomen 3. This also prevents the electrode unit 30 from falling from the abdomen 3 during the use and prevents the muscle electrostimulation device 1 from dropping off from the abdomen 3.

In this embodiment, all the electrodes 311 to 313 and 321 to 323 are formed in a substantially rectangular shape with rounded corners. The longitudinal direction of the electrodes 311 to 313 and 321 to 323 is substantially along the lateral direction X. Accordingly, since the electrodes 311 to 313 and 321 to 323 spread in the extending direction of the electrodes 311 to 313 and 321 to 323, the electrostimulation can be applied to a wider range, and the electrostimulation can be effectively applied to the rectus abdominis muscles spread into a relatively wide range.

In this embodiment, all the electrodes 311 to 313 and 321 to 323 have the same shape. This prevents deviation of the electric current flowing via the electrodes 311 to 313 and 321 to 323, and well-balanced electrostimulation can be applied to the rectus abdominis muscles 4.

In this embodiment, the grooves 113 are formed on the second case 112. The grooves 113 radially and linearly extend from the periphery of the lid 15, and the sweat between the main body 10 and the abdomen 3 can be guided to the outside of the main body 10. This can prevent accumulation of sweat and moisture between the main body 10 and the abdomen 3. Furthermore, the through holes 18 are formed around the main body 10. Therefore, the sweat guided to the outside of the main body 10 through the grooves 113 are easily discharged from between the muscle electrostimulation device 1 and the abdomen 3 via the through holes 18.

In this embodiment, the device includes: the main body 10; the plurality of electrode units 30 that output electrostimulation; the power source 20 that supplies power to the electrode units 30; the controller 40 that controls the supply of power by the power source 20; and the operation unit 50 configured to be capable of changing the control mode of the controller 40, and the power source 20 is embedded in the main body 10. Accordingly, the power supplied to the electrode units 30 does not have to be prepared outside, and the device can be easily used outdoors or places away from home where it is difficult to secure the power source. Since a cord or the like for connection to the power source is not necessary, the usability is improved, and the portability is excellent.

The electrode unit 30 in this embodiment includes the sheet-shaped substrate 33 elongated from the main body 10, the substrate 33 provided with: the plurality of electrodes 311 to 313 and 321 to 323; and the leads 311a to 313a and 321a to 323a for electrically connecting the electrodes 311 to 313 and 321 to 323 and the power source 30 via the controller 40. Accordingly, the electrode unit 30 is formed on the sheet-shaped substrate 30 elongated from the main body 10, and the main body 10 and the electrode unit 30 can be integrated. Therefore, a cord or the like for connecting the main body 10 and the electrode unit 30 is not necessary. Since the power source is embedded in the main body, and the main body and the electrode unit are integrated, excellent portability can be attained, thereby allowing to use the device in various environments. Since the power source 20, the main body 10, and the electrode unit 30 are integrated, the muscle electrostimulation device 1 can be easily attached to and removed from the human body 2, and particularly, the muscle electrostimulation device 1 can be easily removed even when the muscles are fatigued just after the use of the muscle electrostimulation device 1. Therefore, the muscle electrostimulation device 1 is more suitable for efficiently stimulating the muscles through electrostimulation in various environments.

In this embodiment, the replaceable battery 21 is provided on the power source 20. Accordingly, the power can be supplied just by replacing the battery 21, and the device can be easily used for a longer time than the battery capacity. Accordingly, a power source with an excessively large capacity does not have to be included, and the size of the device can be reduced.

The battery 21 can be a button battery or a coin battery, and in this embodiment, the battery 21 is a coin battery. Accordingly, the battery 21 is small, and this contributes to the reduction in the size of the muscle electrostimulation device 1. Since the weight can be reduced along with the reduction in the size of the muscle electrostimulation device 1, the electrode unit 30 is unlikely to be fallen or dropped off from the body of the user, and this improves the usability and improves the portability. The battery 21 is also thin, and this contributes to the reduction in the thickness of the muscle electrostimulation device 1. Since the muscle electrostimulation device 1 is thin, the user can wear clothes over the muscle electrostimulation device 1 while the device is attached. Therefore, the muscle electrostimulation device 1 can be used during commute to work or school, during housework or work, and in various other situations. The button battery has more stable discharge characteristics at a higher operating voltage compared to other dry batteries and the like, and stable operation of the muscle electrostimulation device 1 is possible for a relatively long time.

The nominal voltage of the battery 21 can be 3.0 to 5.0 V, and the battery 21 of 3.0 V is adopted in this embodiment. The drive voltages of the electronic components 42, the speaker 43, and the like included in the muscle electrostimulation device 1 are the same, and a step-down circuit or a booster circuit for driving the electronic components 42 and 43 does not have to be separately provided. This can contribute to the reduction in the size.

The power source 20 may contain a rechargeable battery instead of the replaceable battery 21. A power supply terminal connectable to an external power source may be provided as means for recharging the battery, or a noncontact power supply unit using electromagnetic induction may be provided. In this case, the battery can be repeatedly used, and expendable supplies can be reduced compared to when a nonchargeable battery is used.

In this embodiment, the substrate 33 provided with the electrode unit 30 is elongated from the main body 10, and the electrode support 121 elongated from the shell forming body 12 is bonded to integrally form the electrode unit 30 and the main body 10. Instead of this, the substrate 33 and the main body 10 may be separately formed, and the electrode support 121 and the shell forming body 12 may be separately formed to allow the main body 10 and the electrode unit 30 to be separated from each other when the device is not used. In this case, the electrode unit 30 can be separated from the main body 10 and replaced with an electrode unit in another format. The electrode unit 30 does not include electronic components, and the electrode unit 30 can be separated to easily clean the electrode unit 30.

In this embodiment, the second output mode (training mode) is executed based on the first to fourth statuses shown in Table 2 described above. Instead of this, a 2a status shown in Table 4 may be executed between the second status and the third status, and a 3a status shown in Table 4 may be executed between the third status and the fourth status as in the following Variation 1 in the first to fourth statuses equivalent to this embodiment.

[Table 4]

TABLE 4

Second Output Mode (Training Mode)

| | Status | | | | | | | | | | | | | |
|---|---|---|---|---|---|---|---|---|---|---|---|---|---|---|
| | 1 | | 2 | | 2a | | | 3 | | 3a | | | 4 | |
| Frequency | 20 Hz | Without Output | 20 Hz | 4 Hz | 4 Hz | 8 Hz | 16 Hz | 20 Hz | 4 Hz | 4 Hz | 8 Hz | 16 Hz | 20 Hz | 4 Hz |
| Output Rate | 100% | 0% | 100% | 100% | 100% | 100% | 100% | 100% | 100% | 100% | 100% | 100% | 100% | 100% |
| Output Period | 3 sec | 2 sec | 3 sec | 2 sec | 10 sec | 10 sec | 10 sec | 4 sec | 2 sec | 10 sec | 10 sec | 10 sec | 5 sec | 2 sec |
| Duration | 300 sec | | 300 sec | | 30 sec | | | 300 sec | | 30 sec | | | 300 sec | |
| Period | (=5 min) | | (=5 min) | | (=0.5 min) | | | (=5 min) | | (=0.5 min) | | | (=5 min) | |

As shown in Table 4, the 2a status and the 3a status are performed as follows.

(2a) In the 2a status, 100% output is performed for ten seconds through the basic waveform B2 (4 Hz), then 100% output is performed for ten seconds through the basic waveform B3 (8 Hz), and then 100% output is performed for ten seconds through the basic waveform B4 (16 Hz).

(3a) In the 3a status, 100% output is performed for ten seconds through the basic waveform B2 (4 Hz), then 100% output is performed for ten seconds through the basic waveform B3 (8 Hz), and then 100% output is performed for ten seconds through the basic waveform B4 (16 Hz).

In this variation, the 2a status and the 3a status are added to the second output mode (see Table 2) of this embodiment, and the total time of sequential execution of the first output mode (warm-up mode), the second output mode (training mode), and the third output mode (cool-down mode) shown in Table 4 is twenty three minutes. Note that the total time does not include two seconds of each pause time period.

The frequency of the basic waveform gradually increases from 4 Hz to 16 Hz in the 2a status, and the change in the frequency at the switch from the 2a status to the third status is smooth. Likewise, the change in the frequency at the switch from the 3a status to the fourth status is smooth. In this variation, the 2a status and the 3a status are added to this embodiment, and the pattern of electrostimulation in the second output mode (training mode) significantly changes. As a result, a reduction in sensitivity as the user gets used to the electrostimulation can be prevented, and the rectus abdominis muscles can be more effectively stimulated. The effects equivalent to this embodiment are also attained in this Variation 1 in which the second output mode (training mode) is set in this way.

In this embodiment, the leads 311a to 323a and part (hatched areas indicated by symbol C in FIG. 2) of the electrodes 311 to 313 and 321 to 323 connected to the leads 311a to 323a are silicone-coated. This can prevent a pain at the energization caused by concentration of electric charge in narrow areas of the leads 311a to 323a and 311a to 323a.

In another variation, the silicone-coated areas in the electrodes 311 to 313 and 321 to 323 may be expanded from the hatched areas indicated by symbol C, from the leads 311a to 313a and 321a to 323a to near the centers of the electrodes 311 to 313 and 321 to 323. In this case, the gel pads 35 with a shape equivalent to this embodiment can also be used. According to this, the areas substantially functioning as electrodes in the electrodes 311 to 313 and 321 to 313 are separated from each other, and the locations provided with the electrostimulation are easily spread in the lateral direction X. As a result, the user can easily recognize that the electrostimulation is applied to a wider range of the abdomen 3, and the sense of usage improves.

Since the shapes of the electrodes 311 to 313 and 321 to 323 (shapes of the entire electrodes including the silicone-coated areas) in the variation are similar to the shapes in this embodiment, the external forms of the shapes of the electrodes 311 to 313 and 321 to 323 can be used as guides for pasting the gel pads 35 to predetermined positions, and the gel pads 35 can be easily attached.

Although each of the six electrodes 311 to 313 and 321 to 323 corresponds to each of the compartments 4a of the rectus abdominis muscles 4 to allow applying electrostimulation to the six compartments 4a in this embodiment, the electrode unit 30 may include four electrodes, and the electrodes may be mounted across a plurality of compartments 4a instead of this. The electrode unit 30 may include eight electrodes, and each of the electrodes may correspond to each of the compartments 4a of the rectus abdominis muscles 4 to allow applying electrostimulation to eight compartments 4a.

As described, according to Embodiment 1, the muscle electrostimulation device 1 that can effectively stimulate the abdominal muscles (rectus abdominis muscles 4) can be provided.

Embodiment 2

The muscle electrostimulation device of Embodiment 2 in the present invention will be described.

Conventionally, it is widely known that muscles contract when an electric current is applied to muscle fibers. Particularly, this is utilized for the sake of building muscles in medical and sports fields. Specifically, a muscle stimulating method is used, in which the muscles are energized via electrodes attached to the human body to contract and relax the muscles based on electric signals. A low frequency signal is particularly effective as an electric signal for contracting the muscles. This is because the muscles start not to contract with an increase in the frequency of the electric signal.

However, a low frequency of the electrical signal tends to cause pain due to effects of electric resistance or the like on the surface of the skin of the person. On the contrary, a high frequency of the electric signal tends to reduce the effects of the electric resistance or the like and is unlikely to cause pain. Therefore, the user may feel pain on the skin depending on the electric pulse, and there is room for improvement in the sensitivity when the muscle electrostimulation device is used. On the contrary, the muscles cannot be efficiently stimulated just by reducing the voltage of the electric pulse or simply increasing the electric frequency in order to alleviate the pain of the user.

The muscle electrostimulation device 1 of Embodiment 2 is configured as follows in view of the problem. The same symbols are provided to the members equivalent to the members of the muscle electrostimulation device 1 in the preceding embodiment, and the description of the members and the description of the usage mode will not be repeated. When the drawings used in the description of this embodiment are the same as the drawings in the preceding embodiment, the drawings in the preceding embodiment will be used.

The muscle electrostimulation device 1 of Embodiment 2 is configured to apply electrostimulation to the muscles. The electrostimulation is performed by repeatedly outputting the burst waves (basic waveforms B1 to B5 shown in FIG. 7) including the pulse group output period P and the pulse group output suspension periods R1 to R5 as shown in FIG. 13.

Figure 14:
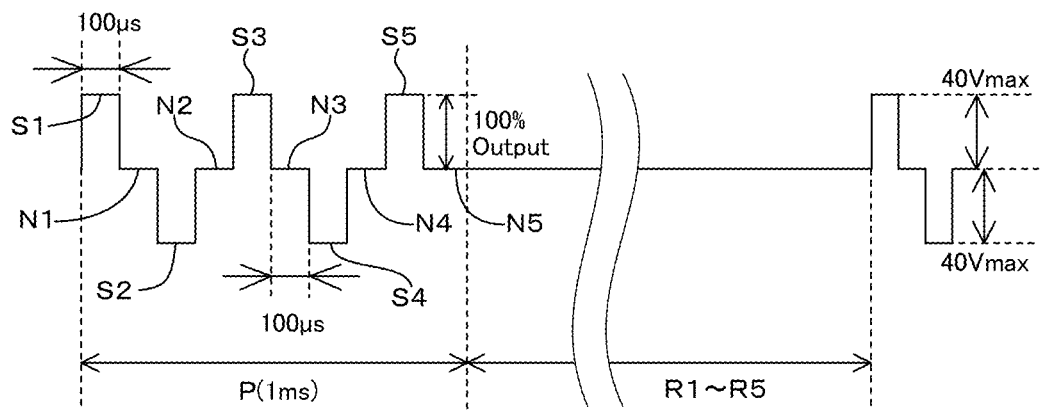
FIG. 14 is a diagram showing the basic waveforms stored in the muscle electrostimulation device in Embodiment 2.

As shown in FIG. 14, a plurality of rectangular wave pulse signals S1 to S5 are output with output stop times N1 to N5 being inserted between the signals in the pulse group output period P.

The pulse group output suspension periods R1 to R5 are longer than the output stop times N1 to N5, and the output of the pulse signals is stopped.

Next, output modes in the electrode unit 30 according to Embodiment 2 will be described.

First, the output mode memory 405a as a duration memory stores the five burst wave patterns (basic waveforms B1 to B5) shown in FIG. 7. The basic waveforms B1 to B5 include the pulse group output period P and the pulse group output suspension periods R1 to R5. That is, the basic waveforms B1 to B5 include the common pulse group output period P, and the lengths of the pulse group output suspension periods R1 to R5 are different.

As shown in FIG. 14, the plurality of rectangular wave pulse signals S1 to S5 are output with the output stop times N1 to N5 being inserted between the signals in the pulse group output period P. In this embodiment, five rectangular wave pulse signals S1 to S5 are output. That is, a first rectangular wave pulse signal S1, a first output stop time N1, a second rectangular wave pulse signal S2, a second output stop time N2, a third rectangular wave pulse signal S3, a third output stop time N3, a fourth rectangular wave pulse signal S4, a fourth output stop time N4, a fifth rectangular wave pulse signal S5, and a fifth output stop time N5 are sequentially executed in the pulse group output period P.

In Embodiment 2, the pulse widths and the pulse voltages of the rectangular wave pulse signals S1 to S5 are constant, and the durations of the output stop times N1 to N5 are also constant. In this embodiment, the pulse width of each of the rectangular wave pulse signals S1 to S5 is 100 µs, the pulse voltage is 40 V or −40 V during 100% output, and the duration of the output stop times N1 to N5 is 100 µs. Therefore, the duration of the pulse group output period P is 1 ms. The voltage polarities in the rectangular wave pulse signals S1 to S5 are alternately changed according to the output order. That is, the first rectangular wave pulse signal S1, the third rectangular wave pulse signal S3, and the fifth rectangular wave pulse signal S5 have a positive polarity, and the second rectangular wave pulse signal S2 and the fourth rectangular wave pulse signal S4 have a negative polarity.

As described, the pulse width of each of the rectangular wave pulse signals S1 to S5 and the duration of each of the output stop times N1 to N5 in the pulse group output period P are 100 µs. Therefore, the pulse cycle of each of the rectangular wave pulse signals S1 to S5 in the pulse group output period P is 200 µs, which is sufficiently short. Therefore, the user recognizes the rectangular wave pulse signals S1 to S5 as one electrostimulation. Note that the frequency of each of the rectangular wave pulse signals S1 to S5 in the pulse group output period P is 5,000 Hz.

In the basic waveforms B1 to B5, pulse signals are not output in the pulse group output suspension periods R1 to R5. The durations of the pulse group output suspension periods R1 to R5 are longer than the duration of the pulse group output period P. In this embodiment, the duration of the pulse group output period P is 1 ms, and the durations of the pulse group output suspension periods R1 to R5 are 499 ms, 249 ms, 124 ms, 61.5 ms, and 49 ms, respectively, as shown in FIG. 7. In this way, the pulse group output suspension periods R1 to R5 have durations significantly longer than the output stop time in the pulse group output period P.

Therefore, a first burst wave (2 Hz) includes the pulse group output period P of 1 ms and the pulse group output suspension period R1 of 499 ms as shown in FIG. 13. That is, the pulse group output period P is output at a frequency of 2 Hz in the first burst wave (2 Hz).

A second burst wave (4 Hz) includes the pulse group output period P of 1 ms and the pulse group output suspension period R2 of 249 ms. That is, the pulse group output period P is output at a frequency of 4 Hz in the second burst wave (4 Hz).

A third burst wave (8 Hz) includes the pulse group output period P of 1 ms and the pulse group output suspension period R3 of 124 ms. That is, the pulse group output period P is output at a frequency of 8 Hz in the third burst wave (8 Hz).

A fourth burst wave (16 Hz) includes the pulse group output period P of 1 ms and the pulse group output suspension period R4 of 61.5 ms. That is, the pulse group output period P is output at a frequency of 16 Hz in the fourth burst wave (16 Hz).

A fifth burst wave (20 Hz) includes the pulse group output period P of 1 ms and the pulse group output suspension period R5 of 49 ms. That is, the pulse group output period P is output at a frequency of 20 Hz in the fifth burst wave (20 Hz).

The basic waveforms B1 to B5 (see FIG. 7) are repeatedly output in a predetermined combination for a predetermined time period, and predetermined burst waves are output as shown in FIGS. 13a to e. As described, the user recognizes the plurality of rectangular wave pulse signals S1 to S5 in the pulse group output period P as one electrostimulation, and electrostimulation at a frequency of 2 Hz is output in the first burst wave in which the basic waveform B1 is repeated as shown in FIG. 8a.

Likewise, electrostimulation at a frequency of 4 Hz is output in the second burst wave in which the basic waveform B2 is repeated, electrostimulation at a frequency of 8 Hz is output in the third burst wave in which the basic waveform B3 is repeated, electrostimulation at a frequency of 16 Hz is output in the fourth burst wave in which the basic waveform B4 is repeated, and electrostimulation at a frequency of 20 Hz is output in the fifth burst wave in which the basic waveform B5 is repeated.

The first to third output modes stored in the output mode memory 405a as a duration memory is configured by appropriately selecting the basic waveforms B1 to B5 stored in the output mode memory 405a and combining the burst waves at predetermined frequencies.

In Embodiment 2, the first output mode (warm-up mode), the second output mode (training mode), and the third output mode (cool-down mode) are carried out as in the case of Embodiment 1.

That is, the conditions of the statuses in the first output mode are as follows as shown in Table 1 described above.

(1) In the first status, 100% output is performed for twenty seconds through the first burst wave (2 Hz). As shown in FIG. 8, what is called soft start is performed for the first five seconds in the first status, wherein the output voltage is gradually increased from 0% to 100%.

(2) In the second status, 100% output is performed for twenty seconds through the second burst wave (4 Hz).

(3) In the third status, 100% output is performed for ten seconds through the third burst wave (8 Hz).

(4) In the fourth status, 100% output is performed for ten seconds through the fourth burst wave (16 Hz).

The duration period of the first output mode (i.e. total duration period of first to fourth statuses) is one minute. In the first output mode, the frequency of the burst wave gradually increases from 2 Hz to 16 Hz.

Next, the conditions of the statuses in the second output mode are as follows as shown in Table 2 described above.

(1) In the first status, 100% output is performed for three seconds through the fifth burst wave (20 Hz), and a state without output is maintained for two seconds. This is repeated for five minutes.

(2) In the second status, 100% output is performed for three seconds through the fifth burst wave (20 Hz), and 100% output is performed for two seconds through the second burst wave (4 Hz). This is repeated for five minutes.

(3) In the third status, 100% output is performed for four seconds through the fifth burst wave (20 Hz), and 100% output is performed for two seconds through the second burst wave (4 Hz). This is repeated for five minutes.

(4) In the fourth status, 100% output is performed for five seconds through the fifth burst wave (20 Hz), and 100% output is performed for two seconds through the second burst wave (4 Hz). This is repeated for five minutes.

As shown in FIG. 8, what is called soft start is performed for the first five seconds in each of the first to fourth statuses in the second output mode, wherein the output voltage is gradually increased from 0% to 100%.

The duration of the second output mode is twenty minutes. Since the fifth burst wave at a frequency of 20 Hz is maintained for a predetermined time period, and the state without output or the second burst wave at a frequency of 4 Hz is maintained for a predetermined time period in the second output mode, the second output mode is excellent in effectively stimulating the muscles.

Next, as shown in Table 3 described above, the third output mode is a cool-down mode for sequentially performing the following first to fourth statuses. Conditions of the statuses are as follows.

(1) In the first status, output is performed for ten seconds through the fourth burst wave (16 Hz).

(2) In the second status, output is performed for ten seconds through the third burst wave (8 Hz).

(3) In the third status, output is performed for twenty seconds through the second burst wave (4 Hz).

(4) In the fourth status, output is performed for twenty seconds through the first burst wave (2 Hz).

Figure 9:
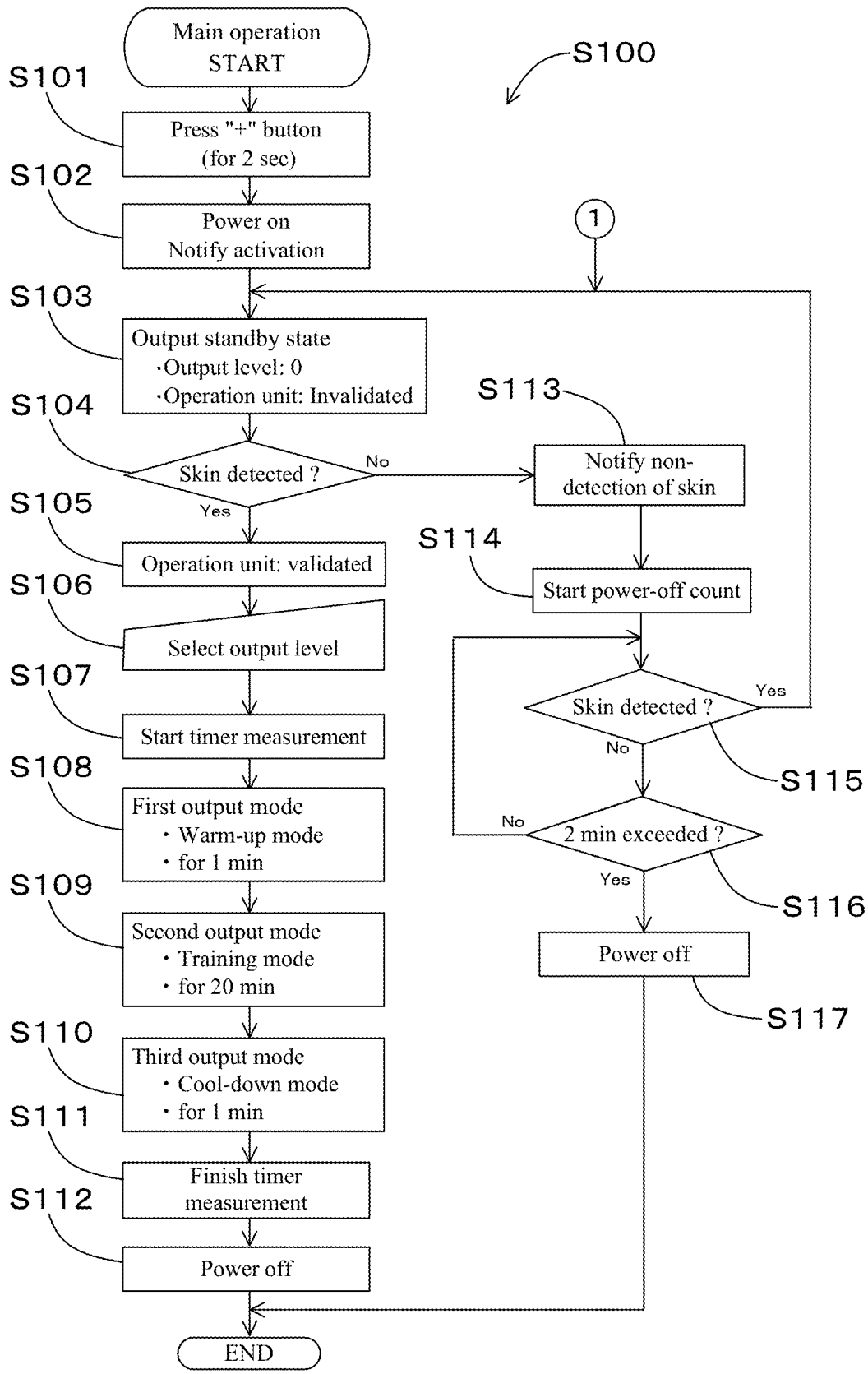
FIG. 9 is a flowchart illustrating a main operation of the muscle electrostimulation device in Embodiment 1.

In the third output mode, the output in each status is 100% at the start of the first status and is gradually reduced to 50% at the end of the fourth status as shown in FIG. 9.

The duration of the third output mode is one minute. In the third output mode, the frequency of the burst wave is gradually reduced from 16 Hz to 2 Hz.

As described, the total time of the sequential execution of the first output mode (warm-up mode), the second output mode (training mode), and the third output mode (cool-down mode) is twenty two minutes. In this embodiment, a pause time period of two seconds is provided at each of four positions in total between the first output mode and the second output mode and between the statuses in the second output mode as shown in FIG. 9. Therefore, the total time of the entire process including the pause time periods is twenty two minutes and eight seconds.

Hereinafter, effects of the muscle electrostimulation device 1 of Embodiment 2 will be described in detail.

In the muscle electrostimulation device 1 of this embodiment, the plurality of rectangular wave pulse signals S1 to S5 are output with the output stop times N1 to N5 being inserted between the signals in the pulse group output period P in the first to fifth burst waves forming the electrostimulation. Therefore, the rectangular wave pulse signals S1 to S5 are divided into a plurality of parts in the pulse group output period P. Accordingly, compared to when the rectangular wave pulse signals S1 to S5 are continuously output without the division in the pulse group output period P, the pulse width of each of the rectangular wave pulse signals S1 to S5 can be reduced while the same total output time of the rectangular wave pulse signals S1 to S5 is maintained. As a result, the pain of the user can be alleviated, while the electrostimulation output from the muscle electrostimulation device 1 and flowing in the muscles or the nerves connected to the muscles is maintained, and the sensitivity in using the muscle electrostimulation device 1 can be improved.

Although the pulse group output period P is configured by outputting the plurality of rectangular wave pulse signals S1 to S5 with the output stop times N1 to N5 being inserted between the signals in the burst waves (basic waveforms B1 to B5), the time period P for outputting the pulse is the same as in a burst wave including a pulse output time period for continuously outputting the pulse for the same time period as the pulse group output period P. Therefore, sensitivity close to the sensitivity of the burst waves including the pulse output time period without the insertion of the output stop times can also be obtained in the burst waves including the pulse group output period P with the output stop times N1 to N5 being inserted.

The plurality of rectangular wave pulse signals S1 to S5 are output with the output stop times N1 to N5 being inserted between the signals in the pulse group output period P, and the duration of the pulse group output period P is a sum of the pulse widths of the plurality of rectangular wave pulse signals S1 to S5 and all the output stop times N1 to N5. Therefore, compared to when the rectangular wave pulse signals S1 to S5 are continuously output without the division during the duration of the pulse group output period P, the actual pulse signal output time is reduced by the output stop times N1 to N5 while the same duration of the pulse group output period P is maintained, and the power consumption can be reduced. This contributes to the reduction in the size of the device because the device can be driven by a power source with a small capacity.

The burst waves forming the electrostimulation include the pulse group output period P and the pulse group output suspension periods R1 to R5, and the durations of the pulse group output suspension periods R1 to R5 are longer than the output stop times N1 to N5 in the pulse group output period P. The burst waves include the pulse group output suspension periods R1 to R5, and the frequencies of the burst waves can be easily set to desired values just by changing the durations of the pulse group output suspension periods R1 to R5 to predetermined lengths without changing the pulse group output period P. This facilitates controlling the output of the electrostimulation including the burst waves at frequencies suitable for contracting and relaxing the muscles, and the muscles can be efficiently stimulated.

In this embodiment, the pulse group output period P includes the rectangular wave pulse signals S1 to S5 with polarities different from each other. Accordingly, the deviation of the electric charge can be easily eliminated in one burst wave (basic waveforms B1 to B5), and the pain of the user can be further alleviated. As a result, the sensitivity and the usefulness in using the muscle electrostimulation device 1 can be further improved.

Furthermore, when the five rectangular wave pulse signals S1 to S5 output in a first pulse group output period P in the first burst wave are sequentially output in order of "positive, negative, positive, negative, positive" as in this example, the five rectangular wave pulse signals output in a second pulse group output period in the second burst wave occurring subsequent to the first burst wave can be output in order of "negative, positive, negative, positive, negative". In this case, the deviation of the electric charge in the first burst wave can be surely eliminated by the second burst wave, and the pain of the user can be further alleviated. Furthermore, the polarities of the plurality of rectangular wave pulse signals S1 to S5 output in the first pulse group output period P can be just inverted (potentials are inverted) for the second pulse group output period, and the control load can be alleviated compared to when the polarities of individual rectangular wave pulse signals in each pulse group output period are separately controlled.

Although the same pulse group output period P includes the rectangular wave pulse signals S1, S3 and S5 and the rectangular wave pulse signals S2 and S4 with polarities different from each other in this embodiment, the following is possible instead of this. The polarities of all the rectangular wave pulse signals S1 to S5 in the first pulse group output period P of the first burst wave may be positive, the polarities of all the rectangular wave pulse signals in the second pulse group output period of the second burst wave occurring with the pulse group output suspension periods R1 to R5 being inserted between the signals following the first burst wave may be negative, and the first burst wave and the second burst wave may be repeated. In this case, although the polarities of the rectangular wave pulse signals are the same in the individual pulse group output periods, the repeatedly output burst waves as a whole include the rectangular wave pulse signals with polarities different from each other. In this case, the deviation of the electric charge in the first burst wave can also be surely eliminated by the second burst wave, and the pain of the user can be further alleviated.

In this embodiment, the durations of the pulse group output suspension periods R1 to R5 are longer than the duration (1 ms) of the pulse group output period P. Accordingly, the intervals of the pulse group output periods P repeatedly output in the burst waves are sufficiently secured by the pulse group output suspension periods R1 to R5, and this allows the user to easily recognize the plurality of rectangular wave pulse signals S1 to S5 in the pulse group output periods P as one electrostimulation. As a result, low-frequency (2 to 20 Hz in this embodiment) burst waves can be easily output from the high-frequency (frequency of 5,000 Hz in this embodiment) rectangular wave pulse signals S1 to S5, and electrostimulation suitable for stimulating the muscles can be output.

In this embodiment, the device includes: the burst wave pattern memory (output mode memory 405a) storing in advance the plurality of burst wave patterns (basic waveforms B1 to B5) with frequencies different from each other, wherein the durations of the pulse group output periods P are the same, and the durations of the pulse group output suspension periods R1 to R5 are different; and the frequency setting unit (output mode switcher 405) that selects one of the plurality of burst wave patterns (basic waveforms B1 to B5) stored in the burst wave pattern memory (output mode memory 405a) to set the frequency of the burst wave in the electrostimulation. Accordingly, since the plurality of burst wave patterns (basic waveforms B1 to B5) at predetermined frequencies are stored in advance in the burst wave pattern memory (output mode memory 405a), the frequency setting unit (output mode switcher 405) can just select a predetermined pattern from the burst wave patterns stored in the burst wave pattern memory (output mode memory 405a) to change the frequency of the burst wave, and the frequency of the burst wave can be easily changed. Accordingly, the muscle electrostimulation device 1 is suitable for efficiently stimulating the muscles.

In this embodiment, the pulse widths of the rectangular pulse signals S1 to S5 and the output stop times N1 to N5 in the burst waves are constant. Accordingly, the electrostimulation applied to the muscles can be easily changed based on the frequencies of the burst waves. This facilitates adjusting the electrostimulation based on the frequencies of the burst waves and facilitates outputting the electrostimulation suitable for effectively stimulating the muscles.

In this embodiment, the electrode unit 30 includes three or more electrodes 311 to 313 and 321 to 323. As described above, since the pulse group output period P includes the output stop times N1 to N5, the power consumption is reduced, and sufficient electrostimulation can be applied even in this configuration including three or more electrodes 311 to 313 and 321 to 323. Accordingly, the electrostimulation can be applied to a wide range of muscles, and the muscles can be efficiently stimulated.

As described, according to Embodiment 2, the muscle electrostimulation device 1 can be provided, the device capable of attaining the effects equivalent to the effects in Embodiment 1, capable of improving the sensitivity when the device is used, and capable of efficiently stimulating the muscles.

Embodiment 3

The muscle electrostimulation device of Embodiment 3 in the present invention will be described.

JP-A-2009-142624 discloses a muscle electrostimulation device that uses an electric signal to stimulate muscles, the device outputting electrostimulation that repeats an output period and a non-output period, wherein a pulsed electric signal belonging to a frequency band of 4 to 20 Hz selected by the user is output for a predetermined time in the output period, and the electric signal is not output for a predetermined time in the non-output period. The device has an advantageous effect of promoting the blood flow, increasing the muscles, or promoting the metabolism.

However, according to the configuration disclosed in the publication, no electric signal is output in the non-output period even when fatigue substances are accumulated in the muscles due to contraction of the muscles caused by the electric signal in the output period in the output electrostimulation, and the fatigue substances may not be sufficiently discharged from the muscles in the non-output period. Therefore, the fatigue substances tend to accumulate in the muscles and an excessive burden tends to be imposed on the user when the device is used for a long time, and the sense of usage may be lost. Furthermore, the output electrostimulation just repeats the output period and the non-output period, and just a single output pattern of the electric signal in the output period is prepared for each output mode. Therefore, the mode of contraction of the muscles based on the output electrostimulation tends to be monotonous, and there is room for improvement in order for the user to actively and continuously use the device.

The muscle electrostimulation device 1 of Embodiment 3 is configured as follows in view of the problems. The same symbols are provided to the members equivalent to the members of the muscle electrostimulation device 1 in the preceding embodiments, and the description of the members and the description of the usage mode will not be repeated.

When the drawings used in the description of this embodiment are the same as the drawings in the preceding embodiments, the drawings in the preceding embodiments will be used.

The muscle electrostimulation device 1 of Embodiment 3 is configured to apply electrostimulation to the muscles.

The electrostimulation alternately repeats: a first output period (2-1, 3-1, 4-1 in Table 5 described later) for outputting a first electric signal (fifth burst wave shown in FIG. 13) causing at least one of incomplete tetanus and complete tetanus of muscles; and a second output period (2-2, 3-2, 4-2 in Table 5 described later) for outputting a second electric signal (second burst wave) causing muscle twitching.

As in the case of Embodiment 2, the first output mode (warm-up mode), the second output mode (training mode), and the third output mode (cool-down mode) are carried out in the muscle electrostimulation device 1 of Embodiment 3. Although the second output mode of this embodiment is substantially the same as in the cases of Embodiment 1 and Embodiment 2, each of the first to fourth statuses in the second output mode is divided into the first output period (1-1, 2-1, 3-1, 4-1) and the second output period (1-2, 2-2, 3-2, 4-2) for the convenience as shown in Table 5.

[Table 5]

TABLE 5

| | Second Output Mode (Training Mode) | | | | | | | |
|---|---|---|---|---|---|---|---|---|
| | Status | | | | | | | |
| | 1 | | 2 | | 3 | | 4 | |
| | 1-1 | 1-2 | 2-1 | 2-2 | 3-1 | 3-2 | 4-1 | 4-2 |
| Frequency | 20 Hz | Without Output | 20 Hz | 4 Hz | 20 Hz | 4 Hz | 20 Hz | 4 Hz |
| Output Rate | 100% | 0% | 100% | 100% | 100% | 100% | 100% | 100% |
| Output Period | 3 sec | 2 sec | 3 sec | 2 sec | 4 sec | 2 sec | 5 sec | 2 sec |
| Duration Period | 300 sec (=5 min) | | 300 sec (=5 min) | | 300 sec (=5 min) | | 300 sec (=5 min) | |

Next, the second output mode in Embodiment 3 is a training mode for sequentially performing the following first to fourth statuses as shown in Table 5. The second output mode is substantially the same as in the cases of Embodiment 1 and Embodiment 2, and the conditions of the statuses are as follows.

(1) In the first status, 100% output is performed for three seconds (1-1 in Table 2) through the fifth burst wave (20 Hz), and a state without output is maintained for two seconds (1-2 in Table 2). This is repeated for five minutes.

(2) In the second status, 100% output is performed for three seconds (2-1 in Table 2) through the fifth burst wave (20 Hz), and 100% output is performed for two seconds (2-2 in Table 2) through the second burst wave (4 Hz). This is repeated for five minutes.

(3) In the third status, 100% output is performed for four seconds (3-1 in Table 2) through the fifth burst wave (20 Hz), and 100% output is performed for two seconds (3-2 in Table 2) through the second burst wave (4 Hz). This is repeated for five minutes.

(4) In the fourth status, 100% output is performed for five seconds (4-1 in Table 2) through the fifth burst wave (20 Hz), and 100% output is performed for two seconds (4-2 in Table 2) through the second burst wave (4 Hz). This is repeated for five minutes.

In the second output mode, what is called soft start is performed for the first five seconds in each of the first to fourth statuses, wherein the output voltage is gradually increased from 0% to 100%.

In the second output mode shown in Table 5, the fifth burst wave (20 Hz) shown in FIG. 13e and the second burst wave (4 Hz) shown in FIG. 13b are repeatedly output in the second to fourth statuses as described above (see FIG. 13). The fifth burst wave (20 Hz) with a frequency in a range of 15 Hz or more and 30 Hz or less is an electric signal for causing incomplete tetanus of muscles. On the other hand, the second burst wave (4 Hz) with a frequency in a range of less than 15 Hz is an electric signal for causing muscle twitching. Therefore, electrostimulation that alternately repeats the first output period (2-1 in Table 2) and the second output period (2-2 in Table 2) is output in the second status of the second output mode, wherein the fifth burst wave (20 Hz) as a first electric signal for causing incomplete tetanus of muscles is output in the first output period, and the second burst wave (4 Hz) as a second electric signal for causing muscle twitching is output in the second output period. Likewise, electrostimulation that alternately repeats the first output period (3-1) and the second output period (3-2) is output in the third status of the second output mode, and electrostimulation that alternately repeats the first output period (4-1) and the second output period (4-2) is output in the fourth status. Although the fifth burst wave (20 Hz) is adopted as a first electric signal in this embodiment, the signal is not limited to this, and a burst wave with a frequency in a range of 15 Hz or more and 30 Hz or less can be adopted as a first electric signal.

The duration of the first output period is three seconds in the second status, four seconds in the third status, and five seconds in the fourth status in this embodiment as described above. The duration of the second output period is two seconds in all the second to fourth statuses. In this way, the duration of the first output period is longer than the duration of the second output period in this embodiment. The durations of the first output period and the second output period are not limited to these, and the duration of the entire electrostimulation, the duration of the output mode, and the like can be taken into account to appropriately set the durations.

As shown in FIGS. 13e and 14, the fifth burst wave (20 Hz) as a first electric signal includes a signal with a positive polarity and a signal with a negative polarity. Likewise, the second burst wave (4 Hz) as a second electric signal also includes a signal with a positive polarity and a signal with a negative polarity as shown in FIGS. 13b and 14.

Hereinafter, effects of the muscle electrostimulation device 1 of Embodiment 3 will be described in detail.

In the muscle electrostimulation device 1 of this embodiment, the output electrostimulation alternately repeats the first output period (2-1, 3-1, 4-1) and the second output period (2-2, 3-2, 4-2). The muscles subjected to the electrostimulation are first continuously contracted by the incomplete tetanus or the complete tetanus (incomplete tetanus in this embodiment) based on the fifth burst wave (20 Hz) as a first electric signal in the first output period (2-1, 3-1, 4-1), and the muscles can be effectively trained. Accordingly, the muscles can be built up. Along with this, fatigue substances are generated in the muscles. Subsequently, the blood circulation in the muscles is promoted by twitching based on the second burst wave (4 Hz) as a second electric signal in the second output period (2-2, 3-2, 4-2), and the fatigue substances generated in the first output period (2-1, 3-1, 4-1) are actively discharged from the muscles. After the fatigue substances are sufficiently discharged, the first output period (2-1, 3-1, 4-1) comes again, and the building of muscles by the incomplete tetanus or the complete tetanus and the promotion to discharge the fatigue substances based on the promotion of the blood circulation by twitching in the second output period (2-2, 3-2, 4-2) are sequentially performed. Accordingly, even when the muscle electrostimulation device 1 of this embodiment is continuously used, the fatigue substances are unlikely to accumulate in the muscles, and the muscles can be efficiently stimulated. Furthermore, since the burden of the user is alleviated, the sense of usage is excellent even when the device is used for a long time, and this can prompt the user for active and continuous usage.

In this embodiment, the fifth burst wave (20 Hz) as a first electric signal has a frequency in a range of 15 Hz or more and 30 Hz or less, and the second burst wave (4 Hz) as a second electric signal has a frequency in a range of less than 15 Hz. Accordingly, the fifth burst wave (20 Hz) as a first electric signal can cause the incomplete tetanus in the muscles in the first output period (2-1, 3-1, 4-1), and the second burst wave (4 Hz) as a second electric signal can stably cause the muscle twitching in the second output period (2-2, 3-2, 4-2). As a result, the muscles can be appropriately contracted without excessively contracting the muscles in the first output period (2-1, 3-1, 4-1). This can prevent sudden generation of fatigue substances in the muscles, and the muscles can be more efficiently stimulated. The fatigue substances generated in the first output period (2-1, 3-1, 4-1) are discharged from the muscles in the second output period (2-2, 3-2, 4-2), and the accumulation of the fatigue substances is prevented even when the device is continuously used.

Although the fifth burst wave (20 Hz) for causing the incomplete tetanus in the muscles is adopted as a first electric signal in this embodiment, the fourth burst wave (16 Hz) for causing the incomplete tetanus in the muscles may be similarly adopted instead of this. In this case, the effects equivalent to this embodiment are also attained.

Although the electric signal for causing the incomplete tetanus in the muscles is adopted as a first electric signal in the first output period (2-1, 3-1, 4-1), an electric signal for causing the complete tetanus in the muscles may be adopted as a first electric signal in the first output period (2-1, 3-1, 4-1). In this case, the effects equivalent to this embodiment are attained, except for the effects obtained when the first electric signal is an electric signal for causing the incomplete tetanus.

In this embodiment, each of the fifth burst wave (20 Hz) as a first electric signal and the second burst wave (4 Hz) as a second electric signal includes a signal with a positive polarity and a signal with a negative polarity, respectively. Accordingly, the deviation of the electric charge in the electrostimulation can be easily eliminated, and the pain of the user can be further alleviated. As a result, the sensitivity in the use of the muscle electrostimulation device 1 of this embodiment can be further improved.

In this embodiment, the duration of the first output period (2-1, 3-1, 4-1) is longer than the duration of the second output period (2-2, 3-2, 4-2). Accordingly, the first output period (2-1, 3-1, 4-1) is sufficiently secured in the output electrostimulation, and the advantageous effect of building the muscles is further increased.

In this embodiment, at least one of (both in this embodiment) the fifth burst wave (20 Hz) as a first electric signal and the second burst wave (4 Hz) as a second electric signal is formed by repeatedly outputting the burst waves (basic waveforms B1 to B5). In this embodiment, the burst waves (basic waveforms B1 to B5) include the rectangular wave pulse signals S1 to S5 as electric signals divided into a plurality of parts. The burst waves (basic waveforms B1 to B5) are recognized as one electric signal in the muscles. The durations (pulse widths) of divided individual electric signals P1 to P5 can be smaller than the duration of a continuous electric signal that is not divided, and the pain on the skin of the user can be alleviated. Therefore, the sensitivity of the user can be improved.

The output stop times N1 to N5 divide the electric signal of the pulse group output period P into the plurality of rectangular wave pulse signals S1 to S5, and the continuous energization time (i.e. pulse width) in the pulse group output period P is short. As described above, the positive polarity and the negative polarity alternately occur in the rectangular wave pulse signals S1 to S5 in the same pulse group output period P so that the deviation of the electric charge is cancelled out, and the rectangular wave pulse signals S1 to S5 with inverted phases come subsequent to the rectangular wave pulse signals S1 to S5 in the pulse group output period P. As a result, continuous energization time with the electric charge deviated to one of positive and negative is significantly short in the electrodes 311 to 323.

In the state in which the electric charge is deviated in the electrodes 311 to 323, the silver contained in the silver paste as a formation material of the electrodes 311 to 323 is easily discolored and darkened due to sulfurization caused by sulfur components such as sulfurous acid gas in the air. However, since the positive polarity and the negative polarity alternately occur in the rectangular wave pulse signals S1 to S5 to sequentially cancel out the deviation of the electric charge in this embodiment as described above, and the continuous energization time in which the electric charge is deviated to one of positive and negative is significantly short, the sulfurization can be prevented. This can effectively prevent discoloring and darkening of the electrodes 311 to 323. In addition, although the electrodes may be discolored and darkened by oxidation or chlorination of the silver contained in the silver paste, this can also be prevented likewise.

As described, according to this Embodiment 3, the muscle electrostimulation device 1 can be provided, the device capable of attaining the effects equivalent to the effects in Embodiment 1, capable of efficiently stimulating the muscles, capable of obtaining an excellent sense of usage even when the device is used for a long time, and capable of prompting the user for active and continuous usage.

Figure 15:
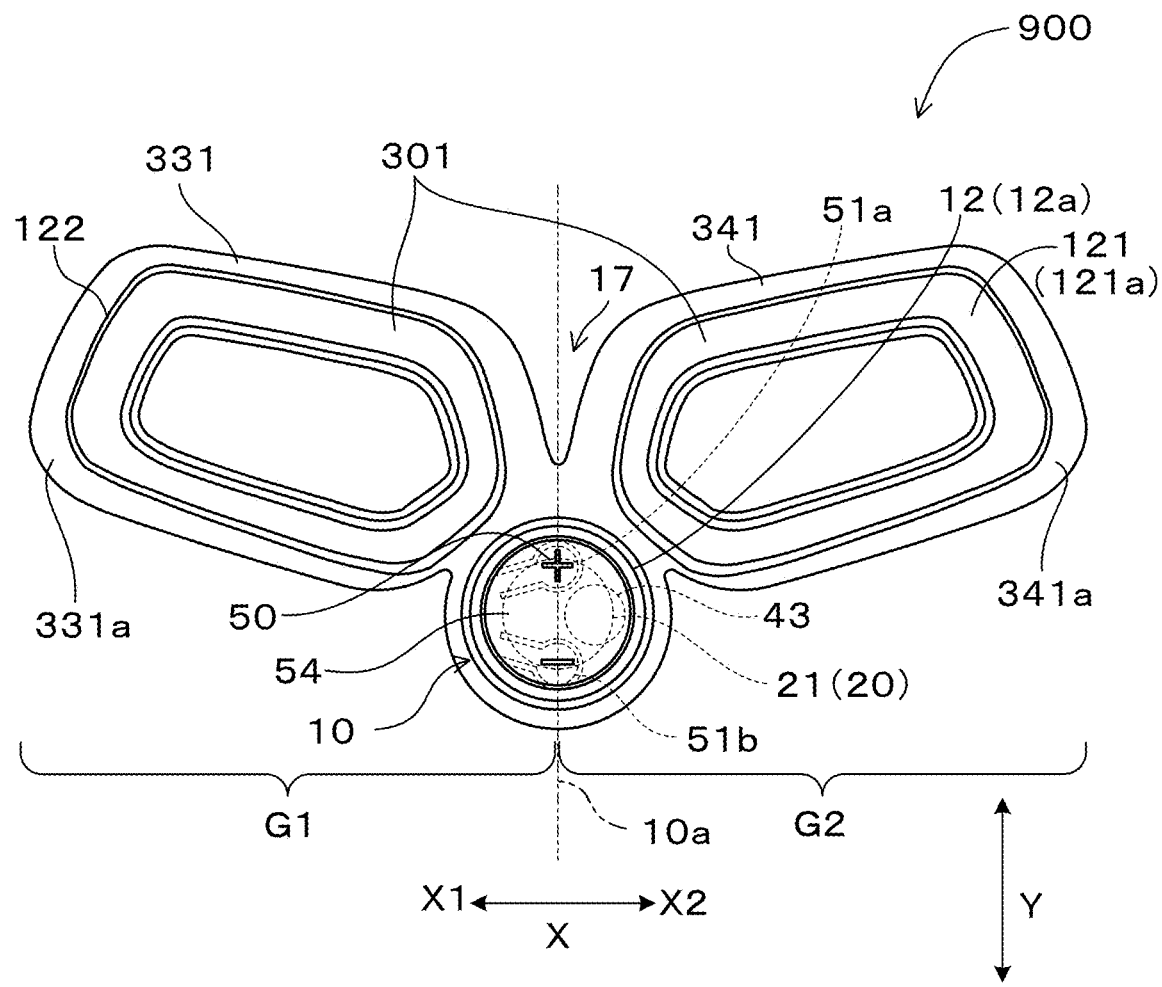
FIG. 15 is a front view of a muscle electrostimulation device in Reference Example 1.
Figure 16:
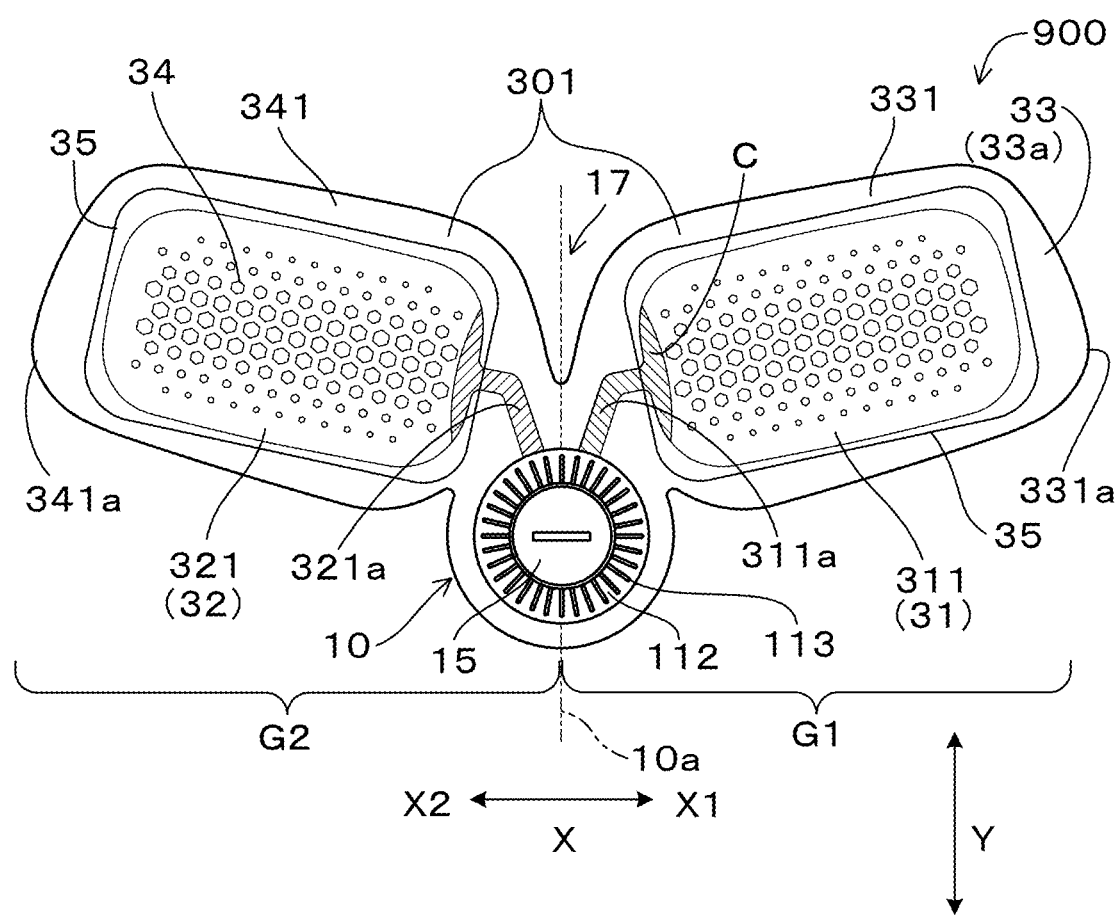
FIG. 16 is a rear view of the muscle electrostimulation device in Reference Example 1.

FIGS. 15 and 16 show Reference Example 1 provided with a muscle electrostimulation device 900 including two electrodes. Reference Example 1 includes two electrodes 311 and 321 configured in the same way, but one size larger than the electrodes 311 and 321 of Embodiments 1 to 3. In reference Example 1, the same symbols are provided to the constituent elements equivalent to the constituent elements of Embodiments 1 to 3, and the description will not be repeated.

In Reference Example 1, the effects equivalent to the effects in Embodiment 3 are also attained, except for the effects obtained when more than two electrodes are provided. According to the muscle electrostimulation device 900 of Reference Example 1, since the number of electrodes 311 and 321 is smaller than when the number of electrodes is six (see FIG. 2), the power consumption per electrode can be large, and the electrodes 311 and 321 are one size larger. Accordingly, the range that one electrode can apply electrostimulation is expanded, and muscles of a large part, such as an arm and a thigh, can be easily stimulated.

Embodiment 4

The muscle electrostimulation device of Embodiment 4 in the present invention will be described.

Since the muscle electrostimulation device disclosed in Patent Document 1 does not require an external power source, and the operation unit and the pair of electrodes are provided integrally with the main body, a cord or the like for connecting them is not provided. Therefore, while the pair of electrodes are attached to the human body, and the muscle electrostimulation device is attached to the human body, it is easy to wear clothes over the device, and the device can be easily used outdoors, for example.

However, when the user wears clothes while the muscle electrostimulation device disclosed in Patent Document 1 is attached to the body, the muscle electrostimulation device may be seen through the clothes. Particularly, when the outer surface of the muscle electrostimulation device has a large area in a bright color such as white, the muscle electrostimulation device can be more easily seen through the clothes. Therefore, there is a problem that the muscle electrostimulation device cannot be used without hesitation at a location, such as a place away from home, where the device may attract people's attention.

Furthermore, when the outer surface of the muscle electrostimulation device has a large area in a bright color such as white, the light is reflected and is unlikely to be absorbed compared to when the outer surface has a large area in a dark color such as black, and the muscle electrostimulation device is relatively unlikely to be warmed even when the light is received. Accordingly, there is room for improvement in warming the muscles to promote the blood circulation in order to increase the discharge effect of wastes in the muscles.

The muscle electrostimulation device 1 of Embodiment 4 is configured as follows in view of the problems. The same symbols are provided to the members equivalent to the members of the muscle electrostimulation device 1 in the preceding embodiments, and the description of the members and the description of the usage mode will not be repeated. When the drawings used in the description of this embodiment are the same as the drawings in the preceding embodiments, the drawings in the preceding embodiments will be used.

The muscle electrostimulation device 1 of Embodiment 4 includes the main body 10, the power source 20, the electrode unit 30, the controller 40, and the operation unit 50 as in the case of Embodiment 1 shown in FIGS. 1 to 4 and 6. The power source 20 is stored in the main body 10.

The electrode unit 30 receives power from the power source 20. The controller 40 controls the supply of power to the electrode unit 30. The operation unit 50 is configured to be capable of changing the control mode of the controller 40. The electrode unit 30 is brought into contact with the person 2, and the muscle electrostimulation device 1 applies electrostimulation to the human body 2 as shown in FIG. 5.

The electrode unit 30 is formed integrally with the main body 10 as in the case of Embodiment 1 shown in FIGS. 2 and 3.

When the electrode unit 30 is brought into contact with the human body 2 (see FIG. 5), 70% or more of the areas on the outer surfaces 12a and 121a opposite to the side facing the human body 2 has a dark color.

As shown in FIG. 4, the shell forming body 12 includes the surface 12b on the side provided with the substrate 33 described later and the outer surface 12a on the opposite side. The shell forming body 12 is made of an elastomer and is made of black silicone in this embodiment. The electrode support 121 extends from the shell forming body 12 so as to cover the front surface 33b of the substrate 33. As shown in FIG. 1, the colored area 122 in a linear shape substantially along the periphery of the electrodes 311 to 313 and 321 to 323 is formed on the outer surfaces 12a and 121a of the electrode support 121. In this embodiment, the colored area 122 is colored in orange. Although not shown, the outer surfaces 12a and 121a also include colored areas (other colored areas) displaying a product name, a brand name, or other characters or symbols. Areas other than the colored area 122 and the other colored areas are not colored on the outer surfaces 12a and 121a, and the formation material of the shell forming body 12 and the electrode support 121 are revealed. The proportion of the total of the colored area 122 and the other colored areas on the outer surfaces 12a and 121a is less than 30%. That is, in 70% or more of the areas on the outer surfaces 12a and 121a, the elastomer as a formation material of the shell forming body 12 and the electrode support 121 is revealed without being colored, and the areas have a dark color (black in this embodiment).

The colored area 122 is an area with a color different from the areas other than the colored area 122, and the colored area 122 can be formed by applying or printing an ink in a predetermined color on the area, for example. Instead of this, the colored area 122 may be formed by a member with a color different from the areas other than the colored area 122 to thereby form the colored area 122 without applying or printing the ink.

The dark color in this embodiment is a color with a lightness of 5.0 or less in a Munsell color system (JIS Z8721:1993) defined in the Japanese Industrial Standards. The areas in the dark color occupying 70% or more of the outer surfaces 12a and 121a have a lightness of 5.0 or less in the Munsell color system, and the lightness is preferably 4.0 or less, more preferably, 3.0 or less. The chroma of the areas in the dark color occupying 70% or more of the outer surface 12a and 121a is, for example, 3.0 or less, preferably, 2.0 or less, in the Munsell color system. The hue in the Munsell color system of the areas in the dark color occupying 70% or more of the outer surfaces 12a and 121a is not particularly limited, and the hue can be an arbitrary value. The lightness, the chroma, and the hue in the Munsell color system of the areas in the dark color can be measured by a colorimeter based on the Japanese Industrial Standards.

Figure 17A:
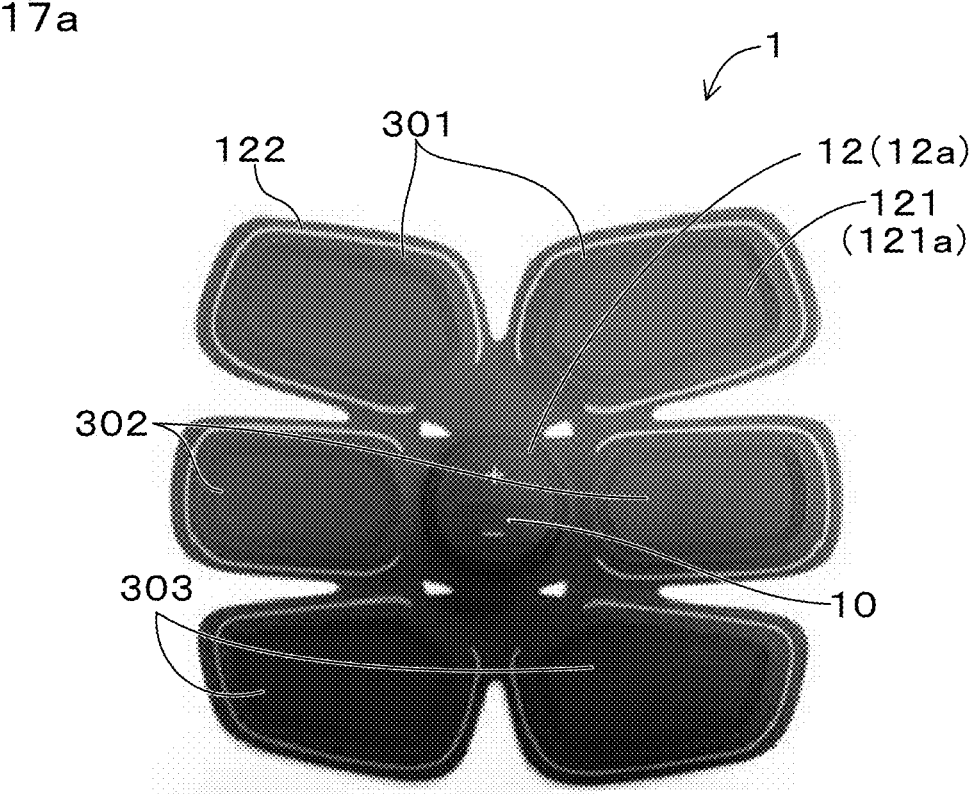
FIG. 17a is a diagram illustrating tint of a front side of the muscle electrostimulation device in Embodiment 4.
Figure 17B:
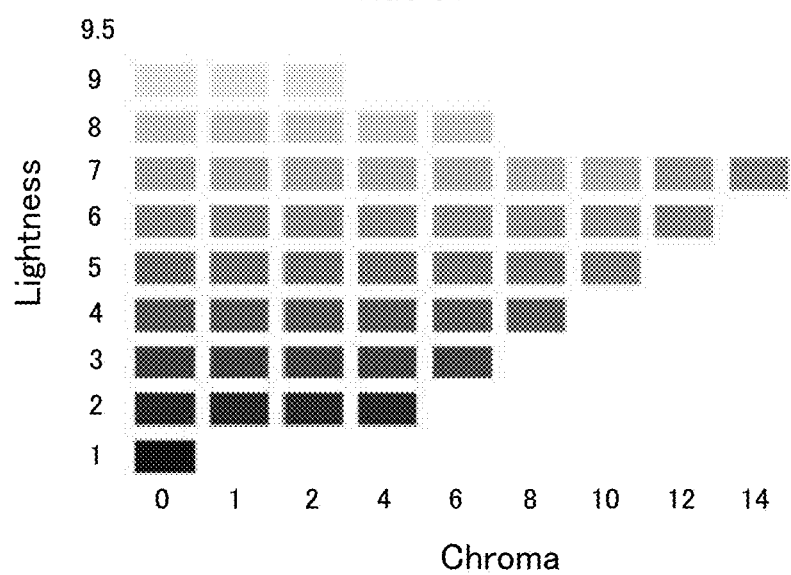
FIG. 17b is a diagram showing a relationship between lightness and chroma in hue 5YR of a Munsell color system.

In this embodiment, as shown in FIG. 17a, the lightness of the colored area 122 is 6.5 to 7.0, and the chroma is 12 to 13.5 in the Munsell color system (see FIG. 17b showing the relationship between the lightness and the chroma in hue 5YR) on the outer surfaces 12a and 121a. On the contrary, the lightness of the areas other than the colored area 122 and the other character areas is 1.0 to 2.0, and the chroma is 0. Although FIGS. 17a and 17b are actually colored, the drawings cannot be expressed in colors, and FIGS. 17a and 17b are expressed by a grayscale.

Note that the area in the dark color can be measured by using color systems other than the Munsell color system, such as CIE 1976 L*a*b (JIS Z8781-4:2013), L*C*h color system, Hunter Lab color system, and XYZ (Yxy) color system. The color systems can be mutually converted. Therefore, even when the area in the dark color is measured by the other color system, the lightness, the chroma, and the hue can be converted and expressed by the Munsell color system.

Hereinafter, effects of the muscle electrostimulation device 1 of Embodiment 4 will be described in detail.

Since the electrode unit 30 is formed integrally with the main body 10 according to the muscle electrostimulation device 1 of this embodiment, a cord or the like for connecting the electrode unit 30 and the main body 10 is not necessary, and the electrode unit 30 and the main body 10 are integrally attached to the human body when the device is used. Therefore, it is easy to wear clothes over the muscle electrostimulation device 1 while the device is attached. In the muscle electrostimulation device 1 of this embodiment, 70% or more of the areas of the outer surfaces 12a and 121a that can be visually recognized from the outside while the device is attached to the human body 2 has the dark color. Therefore, the light is unlikely to be reflected compared to the bright color such as white, and this prevents the muscle electrostimulation device 1 from being seen through the clothes. Accordingly, the muscle electrostimulation device 1 can be used without hesitation at a location, such as a place away from home, where the device may attract people's attention.

Since 70% or more of the areas on the outer surfaces 12a and 121a has the dark color according to the muscle electrostimulation device 1 of this embodiment, the light is easily absorbed compared to the bright color such as white, and the muscle electrostimulation device 1 is relatively easily warmed by receiving the light. Therefore, the muscle electrostimulation device 1 is relatively quickly warmed by directly receiving the light during the use or receiving the light transmitted through the clothes. Accordingly, when the muscles are not warmed, the muscle electrostimulation device 1 warms the muscles, and the blood circulation of the muscles is promoted. As a result, the wastes generated by the contraction of the muscles can be actively discharged from the muscles.

The electrode unit 30 in this embodiment includes the sheet-shaped substrate 33 elongated from the main body 10, the substrate 33 provided with: the plurality of electrodes 311 to 323; and the leads 311a to 313a and 321a to 323a for electrically connecting the electrodes 311 to 323 and the power source 20 via the controller 40. The outer surfaces 12a and 121a are formed by: the shell forming body 12 forming the shell of the main body 10; and the electrode support 121 extended from the shell forming body 12 and formed opposite to the side provided with the electrodes 311 to 323 in the substrate 33. Accordingly, the electrode unit 30 is formed on the sheet-shaped substrate 33 elongated from the main body 10, and the main body 10 and the electrode unit 30 can be integrated by a simple configuration and can be easily formed thin. Therefore, the device is not conspicuous through the clothes even when the user wears the clothes while the device is attached to the human body 2, and the device can be used without hesitation at a location where the device may attract people's attention. Since the device can be easily formed thin, the portability is also excellent.

In this embodiment, the shell forming body 12 and the electrode support 121 are made of an elastomer in a dark color. The elastomer as a formation material of the shell forming body 12 and the electrode support 121 is revealed on the outer surfaces 12a and 121a, and the outer surfaces 12a and 121a have a dark color. Accordingly, the outer surfaces 12a and 121a can have a dark color without special coloring, and the manufacturing cost can be reduced.

In this embodiment, the elastomer in a dark color forming the shell forming body 12 and the electrode support 121 is a silicone resin in a dark color. The shell of the muscle electrostimulation device 1 of this embodiment is formed by a silicone resin with a relatively low thermal conductivity. Therefore, since the shell forming body 12 and the electrode support 121 are easily warmed through the reception of light by the outer surfaces 12a and 121a in a dark color, and the shell forming body 12 and the electrode support 121 are formed by a silicone resin with a relatively low thermal conductivity, the shell forming body 12 and the electrode support 121 can be easily maintained in a warm state. Accordingly, the blood circulation in the muscles is further promoted, and the wastes generated in the muscles can be further actively discharged.

In this embodiment, the lightness of the areas in the dark color (areas other than the colored area 122 and the other colored areas on the outer surfaces 12a and 121a) in the Munsell color system is 5.0 or less. Since the absorbency of light in the areas in the dark color increases, and the muscle electrostimulation device 1 is easily warmed, the blood circulation in the muscles is further promoted. Therefore, the discharge effect of the wastes can be further promoted.

In this embodiment, the chroma of the areas in the dark color is 3.0 or less in the Munsell color system. Accordingly, the reflection of light in the areas in the dark color is prevented, and this further prevents the muscle electrostimulation device 1 from being seen through the clothes when the user wears the clothes over the muscle electrostimulation device 1 of this embodiment while the device is attached to the human body 2.

In this embodiment, the areas in the dark color are black. Accordingly, the values of both the lightness and the chroma in the Munsell color system are sufficiently low, and this further promotes the discharge effect of the wastes by warming of the muscle electrostimulation device 1 and further prevents the muscle electrostimulation device 1 of this embodiment from being seen through the clothes by preventing the reflection of light.

As described, according to Embodiment 4, the muscle electrostimulation device 1 can be provided, the device capable of attaining the effects equivalent to the effects in Embodiment 1, capable of making the device difficult to be seen through the clothes when the device is attached under the clothes, and capable of promoting the blood circulation in the muscles.

(Evaluation Test)

The following evaluation test is conducted to evaluate how much the muscle electrostimulation device 1 of the present invention can be seen through when the user wears clothes while using the device.

Figure 18A:
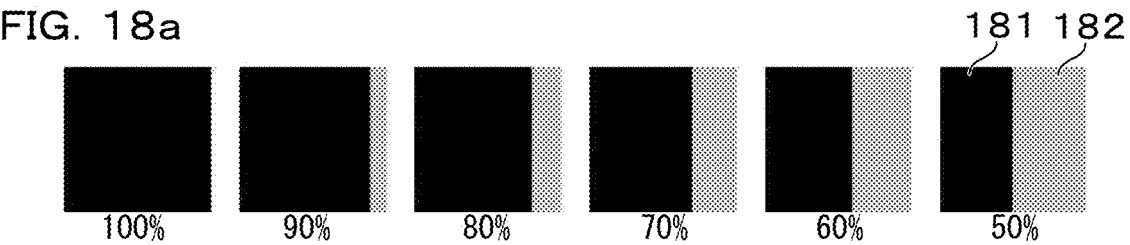
FIG. 18 is a diagram showing test patterns in an evaluation test.
Figure 18B:
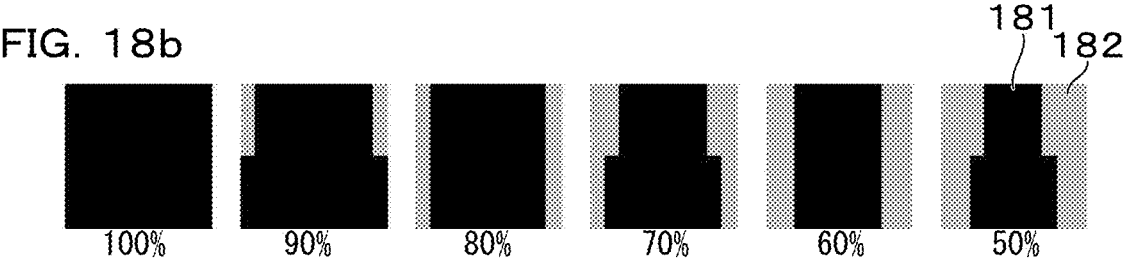
Figure 18C:
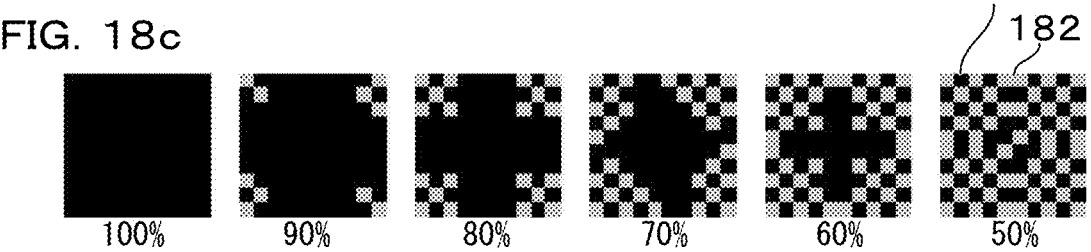
Figure 18D:
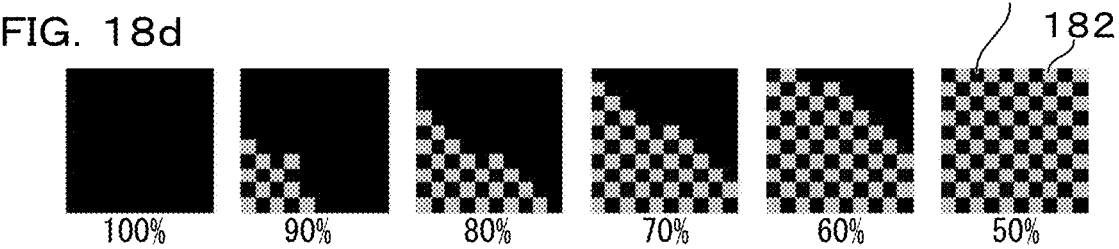
Figure 18E:
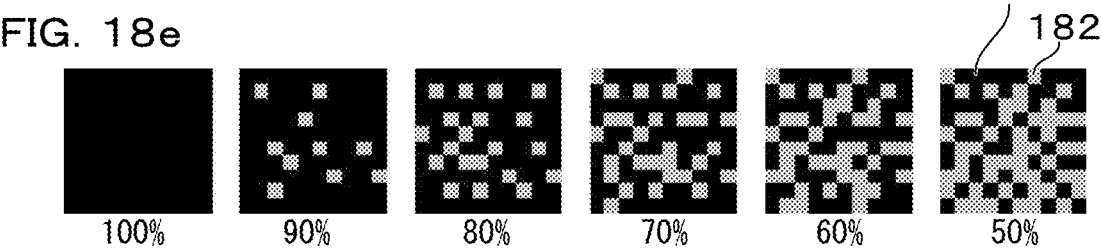

A test pattern 1 shown in FIG. 18a, a test pattern 2 shown in FIG. 18b, a test pattern 3 shown in FIG. 18c, a test pattern 4 shown in FIG. 18d, and a test pattern 5 shown in FIG. 18e are used as test targets in the evaluation test. The test patterns 1 to 5 are square pieces of paper with 3 cm sides, and predetermined patterns are displayed on the surfaces as shown in FIG. 18a to e, the predetermined patterns including a black section 181 in black that is an area in a dark color and a colored area 182 colored in orange that is another colored area. Specifically, the surface of each of the test patterns 1 to 5 is partitioned into ten grids in each of the vertical direction and the horizontal direction. The grids are black or orange, and the black section 181 and the colored area 182 are formed in predetermined shapes.

In this test example, the black section 181 occupies the entire area at 100% in all the test patterns 1 to 5 as shown in FIGS. 18a to e, and there is no colored area 182. The black section 181 occupies 90% at 90% in each of the test patterns 1 to 5, and the colored area 182 occupies 10%. The black section 181 occupies 80%, 70%, 60%, and 50% at 80%, 70%, 60%, and 50%, respectively, in each of the test patterns 1 to 5, respectively, and the colored areas 182 occupy 20%, 30%, 40%, and 50%, respectively. The black sections 181 and the colored areas 182 in the test patterns 1 to 5 are formed in different modes. Note that the colored area 182 is more scattered in the test patterns 3 to 5 than in the test patterns 1 and 2.

For the method of the evaluation test, the test patterns 1 to 5 placed on the palm are covered by a shirt under the light of a fluorescent lamp in a room, and whether the test patterns 1 to 5 can be seen through is visually evaluated. Five practitioners conducted the test (Asians, male and female). The shirt is a white plain men's shirt, and the material is cotton and polyester. As for the evaluation standards, ○ indicates that see-through of the test patterns 1 to 5 through the shirt is not noticeable, Δ indicates that see-through is not so noticeable, and x indicates that see-through is noticeable. Each practitioner has individually conducted the test. Table 5 shows evaluation results of the practitioners. In the evaluation by the practitioners, the test patterns 1 to 5 are added for each ratio of the black section 181, and Table 6 indicates the numbers of ○ and Δ and the ratios of the numbers to the parameter (25) and indicates the numbers of x and the ratios of the numbers to the parameter (25).

[Table 6]

TABLE 6

| Practitioner | Black Section | Test Pattern 1 | 2 | 3 | 4 | 5 |
|---|---|---|---|---|---|---|
| 1 | 100% | ○ | ○ | ○ | ○ | ○ |
|  | 90% | ○ | ○ | ○ | ○ | ○ |
|  | 80% | ○ | ○ | ○ | Δ | Δ |
|  | 70% | Δ | Δ | x | x | x |
|  | 60% | Δ | x | x | x | x |
|  | 50% | Δ | x | x | x | x |
| 2 | 100% | ○ | ○ | ○ | ○ | ○ |
|  | 90% | ○ | ○ | Δ | Δ | ○ |
|  | 80% | Δ | Δ | Δ | Δ | Δ |
|  | 70% | Δ | Δ | x | x | x |
|  | 60% | Δ | x | x | x | x |
|  | 50% | Δ | x | x | x | x |
| 3 | 100% | ○ | ○ | ○ | ○ | ○ |
|  | 90% | ○ | ○ | ○ | Δ | Δ |
|  | 80% | ○ | Δ | Δ | x | x |
|  | 70% | Δ | Δ | x | x | x |
|  | 60% | x | x | x | x | x |
|  | 50% | x | x | x | x | x |
| 4 | 100% | ○ | ○ | ○ | ○ | ○ |
|  | 90% | ○ | ○ | ○ | ○ | ○ |
|  | 80% | ○ | ○ | Δ | Δ | Δ |
|  | 70% | x | Δ | x | Δ | Δ |
|  | 60% | x | Δ | x | x | x |
|  | 50% | x | x | x | x | x |
| 5 | 100% | ○ | ○ | ○ | ○ | ○ |
|  | 90% | ○ | ○ | ○ | ○ | ○ |
|  | 80% | ○ | ○ | ○ | Δ | Δ |
|  | 70% | Δ | ○ | ○ | Δ | Δ |
|  | 60% | Δ | Δ | x | Δ | Δ |
|  | 50% | Δ | Δ | x | x | x |

[Table 7]

TABLE 7

| Black Section | Numbers of ○ and Δ (Ratio) | Numbers of x (Ratio) |
|---|---|---|
| 100% | 25 (100%) | 0 (0%) |
| 90% | 25 (100%) | 0 (0%) |
| 80% | 23 (92%) | 2 (8%) |
| 70% | 14 (56%) | 11 (44%) |
| 60% | 5 (20%) | 20 (80%) |
| 50% | 4 (16%) | 21 (84%) |

As shown in Table 6 and Table 7, all test patterns 1 to 5 indicate ○ for all practitioners when the proportion of the black section 181 is 100%, and the see-through of the test patterns 1 to 5 is not noticeable. All test patterns 1 to 5 indicate ○ or Δ for all practitioners when the proportion of the black section 181 is 90%, and the see-through of the test patterns 1 to 5 is not noticeable or not so noticeable. When the proportion of the black section 181 is 80%, the see-through of the test patterns 1 to 5 is not noticeable or not so noticeable at a high proportion of 92% among all the test patterns 1 to 5. When the proportion of the black section 181 is 70%, the see-through of the test patterns 1 to 5 is not noticeable or not so noticeable at a relatively high proportion of 56% that is more than a half among all the test patterns 1 to 5.

On the contrary, when the proportion of the black section 181 is 60%, the see-through of the test patterns 1 to 5 is not noticeable or not so noticeable at a low proportion of only 20% that is less than half among all the test patterns 1 to 5. Likewise, when the proportion of the black section 181 is 50%, the see-through of the test patterns 1 to 5 is not noticeable or not so noticeable at a low proportion of only 16% that is less than half among all the test patterns 1 to 5.

From the evaluation results, it can be recognized that the see-through of the test patterns 1 to 5 is not noticeable or not so noticeable when the proportion of the black section 181 is 70% or more in the test patterns 1 to 5. Therefore, as shown in FIG. 17, the muscle electrostimulation device 1 in which 70% or more areas on the outer surfaces 12a and 121a of the muscle electrostimulation device 1 have a dark color prevents the muscle electrostimulation device 1 from being seen through the clothes, and the device can be used without hesitation at a location, such as a place away from home, where the device may attract people's attention.

Embodiment 5

The muscle electrostimulation device of Embodiment 5 in the present invention will be described.

Patent Document 1 discloses a muscle electrostimulation device that uses an electrical signal to stimulate muscles, the device including: a main body containing a power source and including an operation unit; and a pair of electrodes elongated from the main body, wherein the pair of electrodes are attached to the human body to apply an electric pulse to the human body to stimulate the muscles. Gelatinous pads with adhesiveness and conductivity are pasted on the electrodes, allowing to use the adhesiveness of the pads to paste the electrodes and the main body on the human body and allowing to use the conductivity of the pads to electronically connect the electrodes and the human body.

The electrodes are easily fallen from the human body due to deterioration in the adhesive force of the pads when the muscle electrostimulation device disclosed in Patent Document 1 is repeatedly used, and this deteriorates the energization state of the electrodes and the human body or makes the pads dirty due to attachment of foreign matters to the pads. Therefore, the pads need to be replaced with new ones at an appropriate time. To replace the pads, new pads need to be attached to the electrodes after peeling off the old pads from the electrodes. If the new pads are not attached to appropriate positions, and the electrodes are exposed, the user may feel pain due to an excessive electric current caused by direct contact of the electrodes and the human body when the device is used. Therefore, when attaching the new pads to the electrodes, the user needs to attach the pads to appropriate positions while paying attention not to expose the electrodes, and the attachment work of the pads is burdensome.

The muscle electrostimulation device 1 of Embodiment 5 is configured as follows in view of the problems. The same symbols are provided to the members equivalent to the members of the muscle electrostimulation device 1 in the preceding embodiments, and the description of the members and the description of the usage mode will not be repeated. When the drawings used in the description of this embodiment are the same as the drawings in the preceding embodiments, the drawings in the preceding embodiments will be used.

The muscle electrostimulation device 1 of Embodiment 5 includes the main body 10, the power source 20, the electrode unit 30, the controller 40, the operation unit 50, and the pads 35 as in the case of Embodiment 1 shown in FIGS. 1 to 4 and 6. The power source 20 is stored in the main body 10. The electrode unit 30 receives power from the power source 20. The controller 40 controls the supply of power to the electrode unit 30. The operation unit 50 is configured to be capable of changing the control mode of the controller 40. The pads 35 are gelatinous, conductive, and adhesive and are attached to the electrode unit 30 in a replaceable manner. The muscle electrostimulation device 1 is configured to apply electrostimulation to the human body 2 (see FIG. 5) from the electrode unit 30 via the pads 35.

Figure 19A:
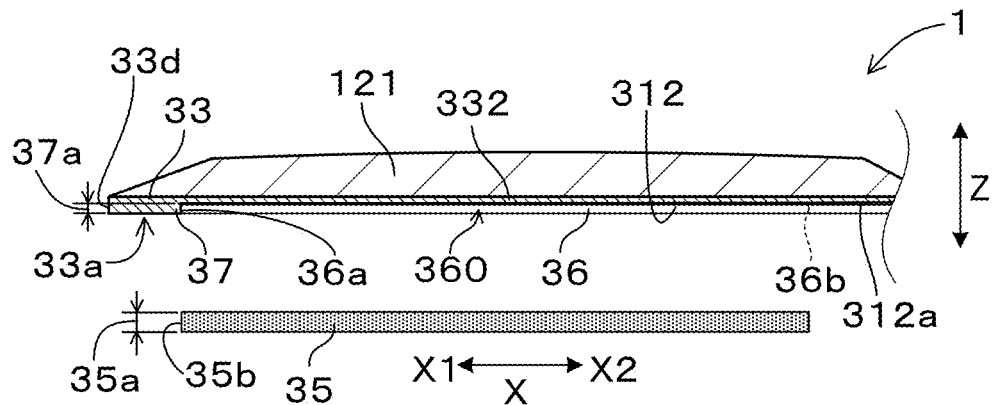
FIG. 19 is a partially enlarged sectional view corresponding to line IVa-IVa in FIG. 1 according to Embodiment 5.

The electrode unit 30 includes the sheet-shaped substrate 33 provided with the electrodes 311 to 323 (see FIG. 2). As shown in FIG. 19a, the substrate 33 is provided with: a pad attachment area 36 on which the pads 35 are attached so as to cover the electrode 312; and a peripheral projection 37 adjacent to at least part of a periphery 36a of the pad attachment area 36 and formed to protrude in a thickness direction Z of the pads 35. A length 37a of the peripheral projection 37 in the thickness direction Z is shorter than a thickness 35a of the pad 35.

Although the pad attachment area 36 and the peripheral projection 37 in the electrode 312 are described in FIG. 19a, the pad attachment area 36 and the peripheral projection 37 are similarly formed in the other electrodes 311 and 313 to 323.

As shown in FIGS. 2 and 19a, the pad attachment area 36 and the peripheral projection 37 are formed on the rear surface 33a of the substrate 33. As shown in FIG. 2, the pad attachment area 36 is formed on each of the electrodes 311 to 313 and 321 to 323, is substantially rectangular with rounded corners, and has a shape one size larger than the electrodes 311 to 313 and 321 to 323. The external forms of the pad attachment areas 36 are substantially the same shapes.

The peripheral projection 37 is adjacent to at least part of the periphery 36a of the pad attachment area 36 as shown in FIG. 2 and is formed to protrude in the thickness direction Z of the pad as shown in FIG. 19a. In this embodiment, the peripheral projections 37 are formed adjacent to the entire peripheries 36a of the pad attachment areas 36, except for peripheries 36b at parts covering connections of the electrodes 311 to 313 and 321 to 323 and the leads 311a to 313a and 321a to 323a.

In this embodiment, the peripheral projection 37 is formed from the periphery of the pad attachment area 36 to an edge 33d of the substrate 33 as shown in FIG. 19a. Accordingly, the pad attachment area 36 is formed in a shape recessed more than the peripheral projection 37 on the rear surface 33a of the substrate 33. In other words, part of the substrate 33 is depressed in the thickness direction Z to form a concave portion 360, the inner bottom surface of the concave portion 360 configures the pad attachment area 36, and the outside area of the concave portion 360 in the substrate 33 configures the peripheral projection 37 along with the inner circumferential surface (periphery 36a) of the concave portion 360.

Figure 19B:
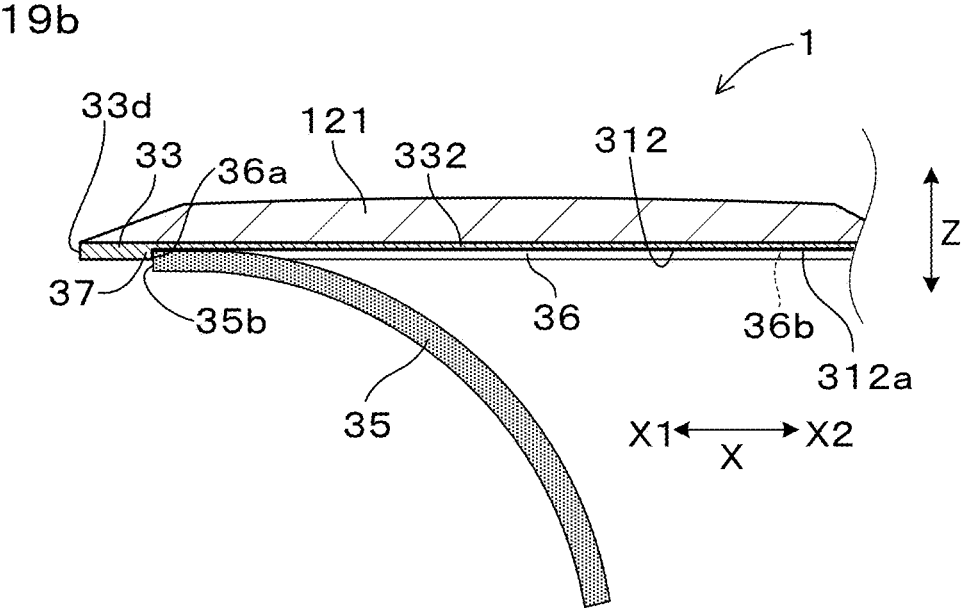
Figure 19C:
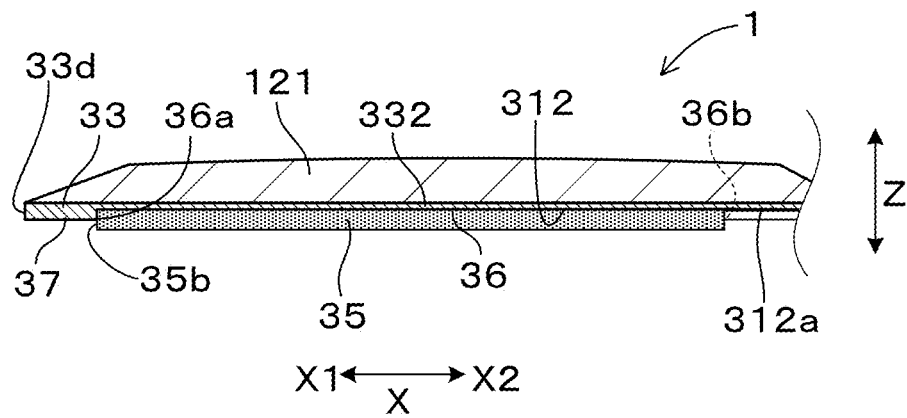

As shown in FIGS. 19b and 19c, the pad 35 is attached to the pad attachment area 36. The pad 35 has conductivity and adhesiveness and is gelatinous. The gel pad 35 used in this embodiment is "ST-gel (registered trademark)" manufactured by Sekisui Plastics Co., Ltd., model No. SR-RA240/100 as in Embodiment 1. The pad 35 has a sheet shape, has substantially the same shape as the pad attachment area 36, and has a substantially rectangular shape with rounded corners.

As shown in FIG. 19b, the edge of the pad 35 is put along the wall surface of the peripheral projection 37, and the pad 35 is placed on the pad attachment area 36 to attach the pad 35 to the pad attachment area 36. Accordingly, each pad 35 separately covers each of the electrodes 311 to 313 and 321 to 323. The pads 35 are conductive, and the electrodes 311 to 313 and 321 to 323 and the abdomen 3 (see FIG. 5) are configured to be electronically connected via the pads 35 when the device is used. The pads 35 are highly adhesive, and the muscle electrostimulation device 1 is attached to the abdomen 3 via the pads 35.

Although there is no clearance (gap) between the pad 35 and the peripheral projection 37 in this embodiment as shown in FIG. 19c, a clearance may be provided between the pad 35 and the peripheral projection 37 instead of this. That is, the external form of the pad 35 in plan view may be a little smaller than the shape of the periphery 36a of the pad attachment area 36 in plan view to thereby provide a gap on at least a part between a side surface 35b of the pad 35 and the peripheral projection 37. The clearance can be appropriately set in a range that does not expose each of the electrodes 311 to 323 when the pad 35 is attached to the pad attachment area 36.

When the clearance is provided, a finger or the like can be easily inserted between the end of the pad 35 attached to the pad attachment area 36 and the peripheral projection 37 in replacing the pad 35, and the pad can be easily peeled off. Since the clearance forms a space between the surface of the skin and the rear surface 33a of the substrate 33 when the device is used, the air permeability is increased, and this can reduce sweating and facilitates the discharge of the sweat.

Effects of the muscle electrostimulation device 1 of this embodiment will be described in detail.

According to the muscle electrostimulation device 1 of this embodiment, the peripheral projections 37 projecting in the thickness direction Z of the pads 35 are formed adjacent to the peripheries of the pad attachment areas 36. Accordingly, when the pads 35 are attached to the pad attachment areas 36, the pads 35 can be placed and attached to the pad attachment areas 36 while the edges of the pads 35 are put along the peripheral projections 37, and the displacement of the pads 35 can be prevented. Accordingly, the pads 35 are attached to appropriate positions without the user paying special attention to prevent the exposure of the electrode unit 30 (electrodes 311 to 323), and the exposure of the electrode unit 30 (electrodes 311 to 323) is prevented. As a result, the burden of the attachment work of the pads 35 is alleviated. Even if the adhesive force of the pads is weakened during the use, the displacement of the pads is prevented, and the exposure of the electrode unit 30 (electrodes 311 to 323) is prevented.

The electrode unit 30 (electrodes 311 to 323) may be exposed if the pads 35 are displaced or if pads smaller than the pad attachment areas 36 are used. However, in that case, the human body 2 (skin) comes into contact with the peripheral projections 37 formed to protrude adjacent to the peripheries of the pad attachment areas 36 when the device is used, and the human body 2 is unlikely to come into contact with the electrode unit 30 (electrodes 311 to 323) exposed in the pad attachment areas 36. Therefore, even if the electrode unit 30 (electrodes 311 to 323) is exposed, direct electronical connection of the human body 2 (skin) and the electrodes 311 to 323 is prevented. At least part of the side surfaces of the pads 35 attached in the pad attachment areas 36 is covered by the peripheral projections 37, and this can prevent trash and dust from sticking to the at least part of the side surfaces of the pads 35.

In this embodiment, the substrate 33 is elongated from the main body 10, and the plurality of leads 311a to 323a for electrically connecting the plurality of electrodes 311 to 323 and the power source 20 via the controller 40 are formed on the substrate 33. Accordingly, the main body 10 and the electrode unit 30 are integrally formed, and a cord or the like for connecting the electrode unit 30 and the power source 20 is not necessary. As a result, the usability of the muscle electrostimulation device 1 of this embodiment improves. The sheet-shaped substrate 33 is elongated from the main body 10, and the muscle electrostimulation device 1 of this embodiment can be formed thin. Accordingly, the portability of the muscle electrostimulation device 1 of this embodiment is excellent, and the muscle electrostimulation device 1 is inconspicuous even when the user wears clothes over the device while using the device. Therefore, the muscle electrostimulation device 1 can be used outdoors without hesitation.

In this embodiment, the peripheral projections 37 are formed adjacent to the entire peripheries 36a of the pad attachment areas 36, except for the peripheries 36b of the parts covering the connections of the electrode unit 30 and the leads 311a to 323a. Accordingly, substantially the entire edges of the pads 35 can be attached along the peripheral projections 37 when the pads 35 are attached to the pad attachment areas 36, and the displacement of the pads 35 can be further prevented. Therefore, the exposure of the electrodes 311 to 323 can be surely prevented without specially paying attention to the displacement of the pads 35, and the burden in attaching the pads 35 is further alleviated.

Note that the peripheral projections 37 are formed adjacent to the entire peripheries 36a of the pad attachment areas 36 except for the peripheries 36b, and cover members for covering the leads 311a to 313a and 321a to 323a may also be provided adjacent to the peripheries 36b. The cover members are made of, for example, the same material as the substrate 33. The cover members and the peripheral projections 37 may be adjacent to and surround the entire peripheries 36a of the pad attachment areas 36.

In this embodiment, the concave portion 360 depressed in the thickness direction Z is formed on part of the substrate 33, the inner bottom surface of the concave portion 360 configures the pad attachment area 36, and the outside area of the concave portion 360 in the substrate 33 configures the peripheral projection 37 along with the inner circumferential surface (periphery 36a) of the concave portion 360. Since both the pad attachment area 36 and the peripheral projection 37 can be formed just by forming the concave portion 360 on the substrate 33, the pad attachment area 36 and the peripheral projection 37 can be easily formed, and the workability in manufacturing the muscle electrostimulation device 1 is improved.

In this embodiment, part of the substrate 33 is depressed to form the concave portion 360 to form the peripheral projection 37 as described above. Instead of this, the rear surface 33a of the substrate 33 may be formed on substantially the same plane as the electrodes 311 to 323, and the peripheral projection 37 as a member separate from the substrate 22 may be provided on the rear surface 33a of the substrate 33 adjacent to at least part of the periphery 36a of the pad attachment area 36.

As described, according to Embodiment 5, the muscle electrostimulation device 1 can be provided, the device capable of attaining the effects equivalent to the effects in Embodiment 1 and capable of alleviating the burden in attaching the pads 35.

Figure 20:
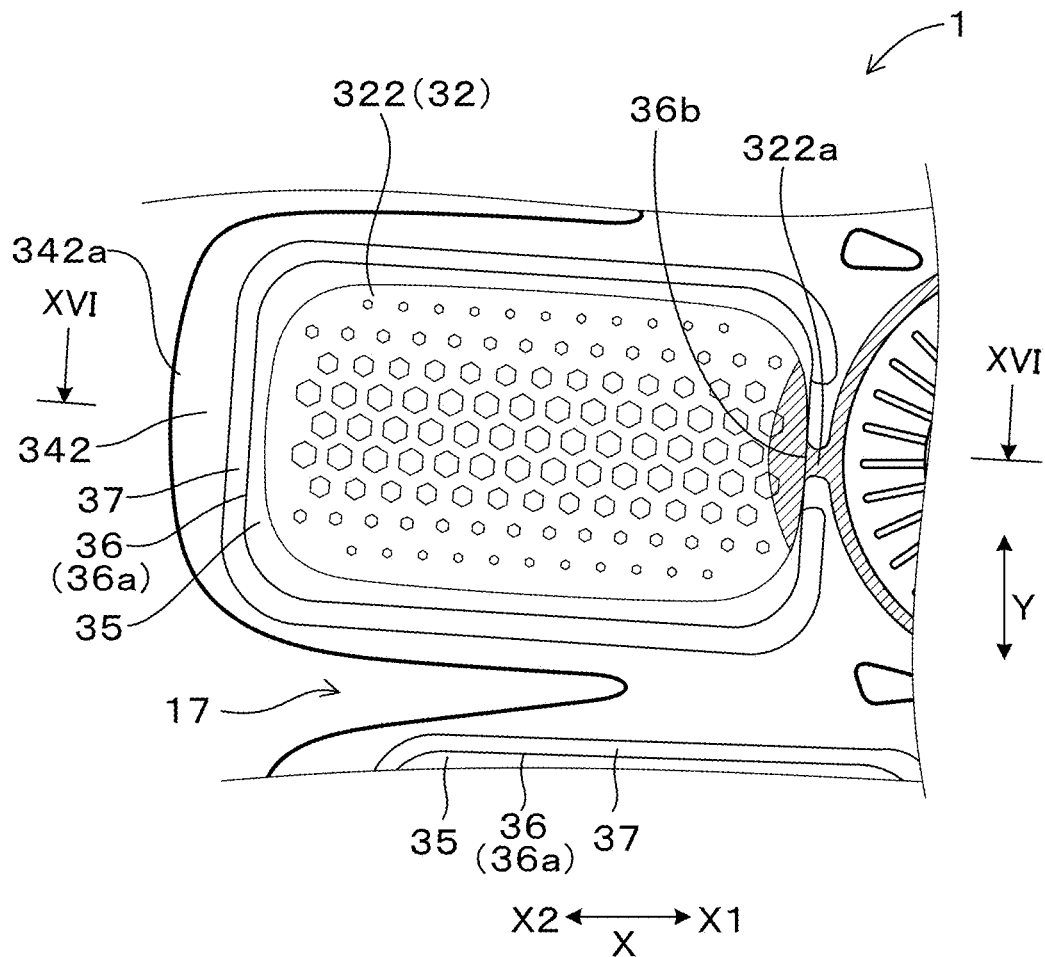
FIG. 20 is a partially enlarged rear view of the muscle electrostimulation device in Variation 2.
Figure 21:
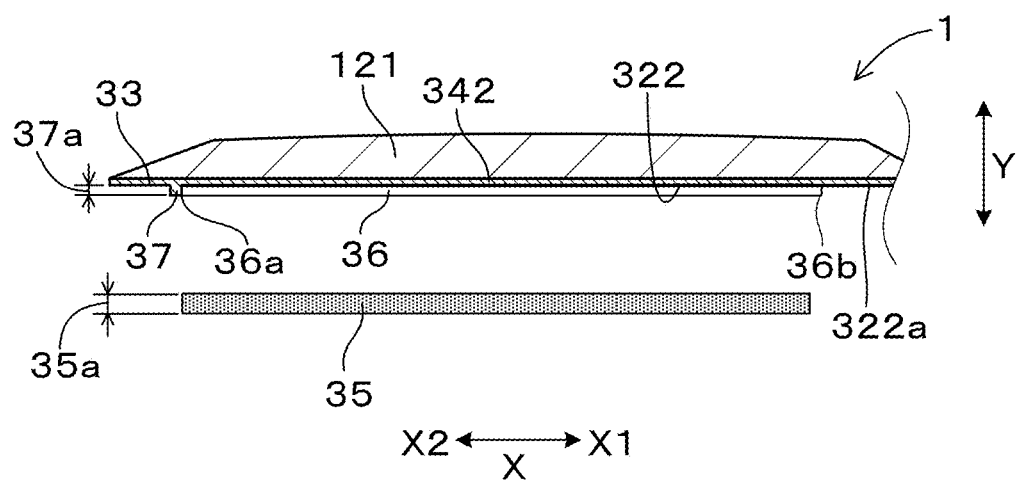
FIG. 21 is a sectional view taken along line XVI-XVI in FIG. 20.

Although the peripheral projection 37 is formed from the periphery of the pad attachment area 36 to the edge 33d of the substrate 33, and the pad attachment area 36 is formed to recess more than the peripheral projection 37 in this embodiment as shown in FIG. 19a, the following Variation 2 can be adopted instead of this. In Variation 2, the width of the peripheral projection 37 is narrower than the peripheral projection 37 in the case of Embodiment 5 (see FIG. 19a) as shown in FIGS. 20 and 21, and the peripheral projection 37 is formed in a rib shape adjacent to the periphery 36a of the pad attachment area 36 as shown in FIG. 21. Accordingly, since the contact area between the peripheral projection 37 and the skin is small when the device is used, the air permeability between the skin surface and the rear surface 33a of the substrate 33 improves, and the sweat can be easily discharged from between the skin surface and the rear surface 33a of the substrate 33 even when there is sweat. The effects equivalent to the case of Embodiment 5 are also attained in Variation 2.

Figure 22:
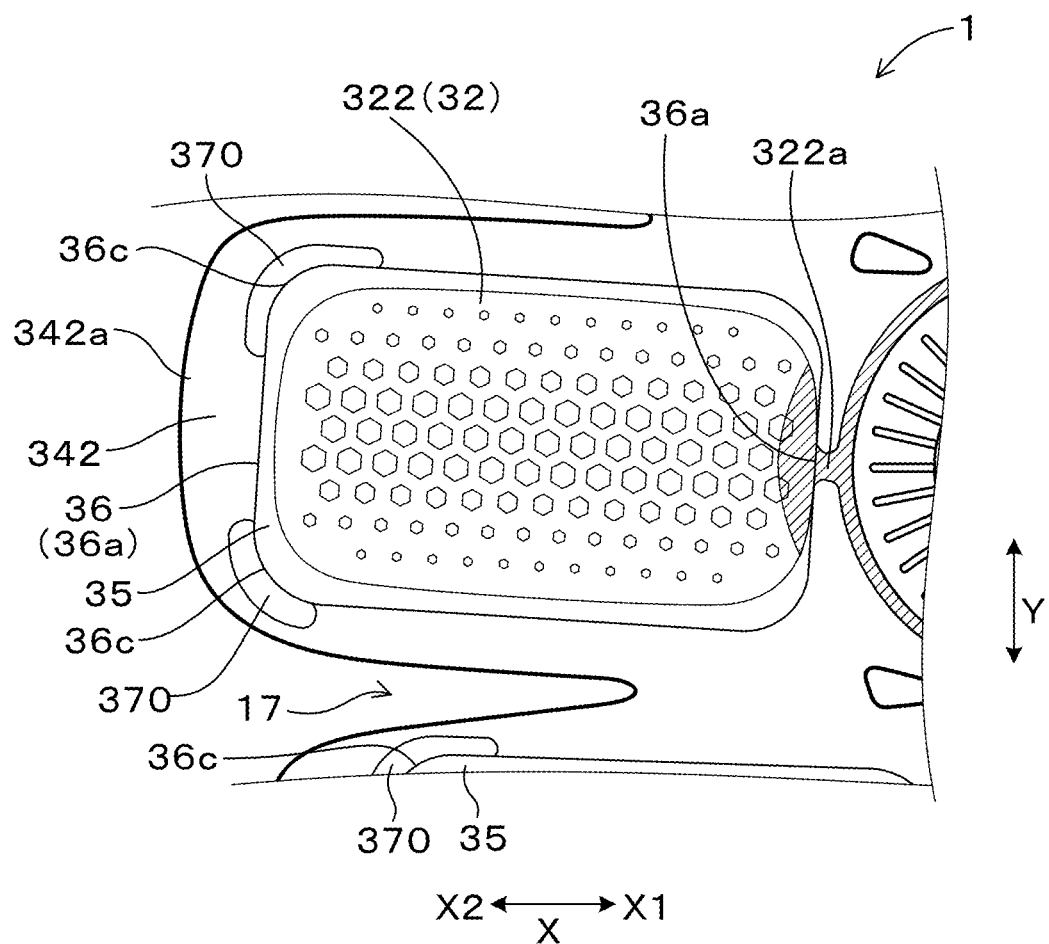
FIG. 22 is a partially enlarged rear view of the muscle electrostimulation device in Variation 3.

Although the peripheral projections 37 are provided adjacent to the entire peripheries 36a of the pad attachment areas 36 except for the peripheries 36b of the parts covering the connections of the electrodes 311 to 313 and 321 to 323 and the leads 311a to 313a and 321a to 323a in Variation 2, instead of this, peripheral projections 370 may be formed to protrude adjacent to peripheries 36c on both corners outside (left direction X2) of the pad attachment area 36 in the periphery 36a of the pad attachment area 36 of the electrode 322 as in Variation 3 shown for example in FIG. 22.

Although the pad attachment area 36 and the peripheral projection 37 in the electrode 322 of the second electrode group 32 are described in Variation 3 as show in FIG. 22, the pad attachment areas 36 and the peripheral projections 370 are also formed on the other electrodes 321 and 323 in the second electrode group as in the case of the electrode 322 although not shown. The pad attachment areas 36 and the peripheral projections 370 in the electrodes 311 to 313 of the first electrode group 31 are formed line-symmetrically to the pad attachment areas 36 and the peripheral projections 370 of the second electrode group 32 with the center line 10a serving as the axis of symmetry, although not shown.

In this case, since the area for forming the peripheral projections 370 is reduced, the area of contact with the skin surface can be reduced when the device is used, and the air permeability can be further increased. The peripheral projections 370 are unlikely to touch the skin, and traces of the peripheral projections 370 touching the skin are unlikely to remain after the use. Although the edges of the electrode base parts 331 to 333 and 341 to 343 are thin, the formation of the peripheral projections 370 makes the edges of the pad attachment portions 36 thick, and the rigidity increases. As a result, when the muscle electrostimulation device 1 attached to the human body is to be removed, the edges of the pad attachment portions 36 can be easily lifted, and the muscle electrostimulation device 1 can be easily removed. The effects equivalent to the case of Embodiment 5 are also attained in Variation 3, except for the effects obtained by providing the peripheral projections 37 adjacent to the entire peripheries except for the peripheries 36b of the parts covering the connections in Embodiment 5.

Embodiment 6

The muscle electrostimulation device of Embodiment 6 in the present invention will be described.

The muscle electrostimulation device disclosed in Patent Document 1 includes: a main body containing a power source and including an operation unit; and a pair of electrodes formed on a substrate elongated from the main body, wherein an electric pulse is applied from the electrodes to the human body to stimulate the muscles. The pair of electrodes are integrated by the sheet-shaped substrate provided with the main body. Gelatinous pads with adhesiveness and conductivity are pasted on the electrodes formed on the substrate, the adhesiveness of the pads is used to attach the electrodes and the main body to the human body, and the conductivity of the pads can be used to electronically connect the electrodes and the human body.

However, the electrodes may gradually fall off from the skin surface during the use when the adhesive force of the pads is deteriorated by repeated use of the muscle electrostimulation device disclosed in Patent Document 1. As the electrodes gradually fall off, the contact parts of the electrodes and the skin surface through the pads are gradually reduced, and the amount of current per unit area of the contact parts gradually increases. Therefore, when the electrodes are significantly fallen off, and the area of the contact parts is reduced, the amount of current per unit area of the contact parts becomes excessively large, and the user may feel pain.

The muscle electrostimulation device 1 of Embodiment 6 is configured as follows in view of the problem. The same symbols are provided to the members equivalent to the members of the muscle electrostimulation device 1 in the preceding embodiments, and the description will not be repeated. When the drawings used in the description of this embodiment are the same as the drawings in the preceding embodiments, the drawings in the preceding embodiments will be used.

The muscle electrostimulation device 1 of this embodiment includes the plurality of electrodes 311 to 313 and 321 to 323 formed on the substrate 33 and the plurality of gelatinous pads 35 with conductivity and adhesiveness as in the device shown in FIGS. 1 and 2 in Embodiment 1. The muscle electrostimulation device 1 is configured to apply electrostimulation to the human body 2 (see FIG. 5) from the electrodes 311 to 313 and 321 to 323 via the pads 35.

Pad attachment portions 361 to 363 and 371 to 373 for attaching the pads 35 so as to cover the electrodes 311 to 313 and 321 to 323 are formed on the substrate 33.

The plurality of electrodes 311 to 313 and 321 to 323 include electrodes 311 to 313 and 321 to 323 with areas of 10 to 65% of the areas of the pads 35 covering the electrodes 311 to 313 and 321 to 323.

The pads 35 may be detachably provided on the pad attachment portions 361 to 363 and 371 to 373. For example, when the adhesive force of the pads 35 is deteriorated, or when the pads 35 become dirty, the pads 35 may be able to be removed from the pad attachment portions 361 to 363 and 371 to 373 and attached again to the pad attachment portions 361 to 363 and 371 to 373 after the pads 35 are cleaned, or the pads 35 may be able to be removed from the pad attachment portions 361 to 363 and 371 to 373 to attach new pads 35 to the pad attachment portions 361 to 363 and 371 to 373. The pads 35 may not be provided on the pad attachment portions 361 to 363 and 371 to 373 in the distribution process of the muscle electrostimulation device 1, and the user may attach the pads 35 to the pad attachment portions 361 to 363 and 371 to 373 upon use or before use. On the contrary, the pads 35 may be fixed to the pad attachment portions 361 to 363 and 371 to 373 and unable to be removed, or replacement of the pads 35 may not be expected. Therefore, it is only necessary that the muscle electrostimulation device 1 is configured such that the pads 35 are attached to the pad attachment portions 361 to 363 and 371 to 373 at least when the device is used.

Figure 23:
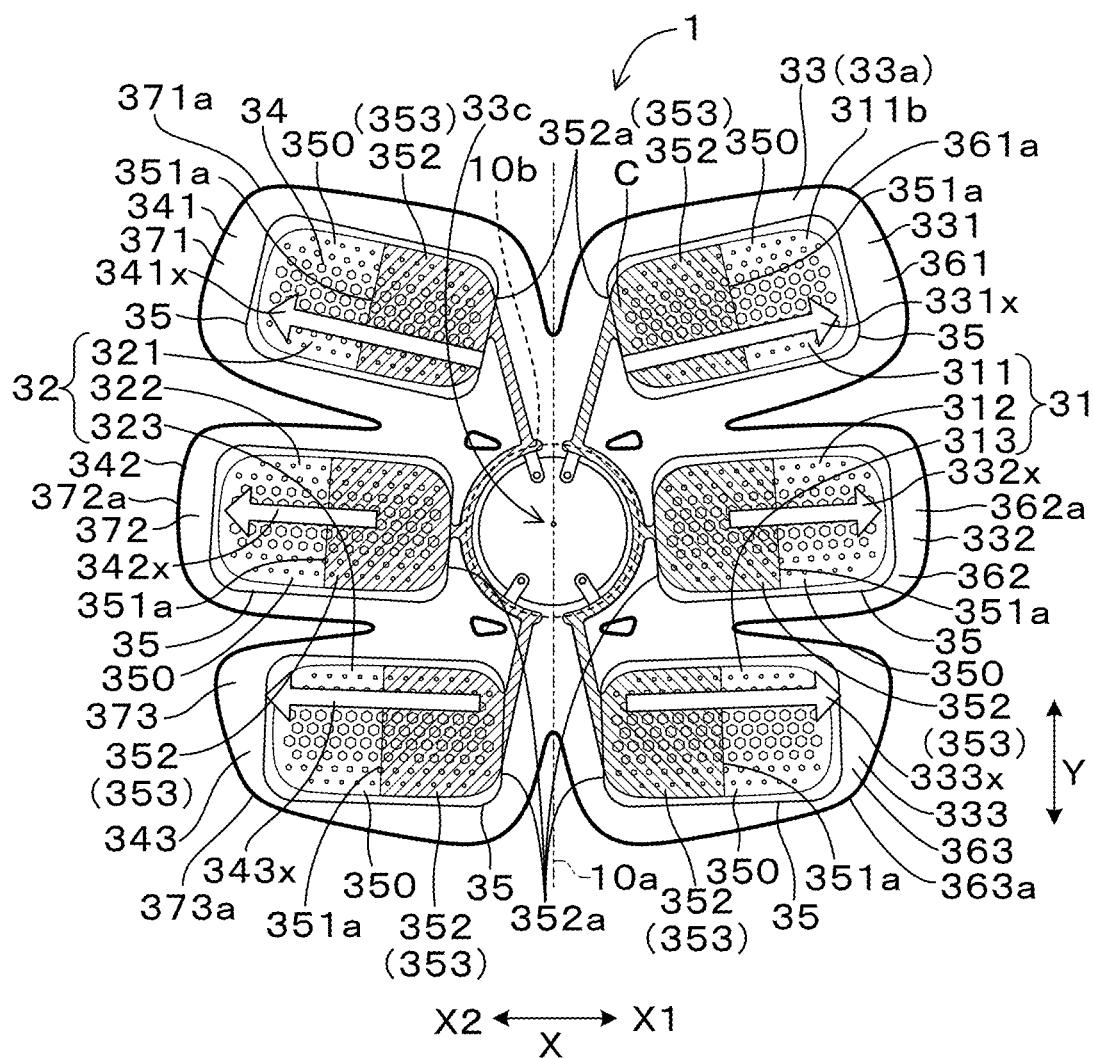
FIG. 23 is a rear view of the muscle electrostimulation device with a main body removed in Embodiment 6.

As shown in FIG. 23, the sheet-shaped substrate 33 joined to the main body 10 extends outward to form each of the electrode base parts 331 to 333 and 341 to 343 in this embodiment. The electrode base parts 331 to 333 extend in extending directions 331x to 333x, respectively, in the right direction X1 away from the center line 10a. Note that the extending directions 331x and 332x are a little upward in the Y direction, and the extending direction 333x is a little downward in the Y direction. The electrode base parts 341 to 343 extend in extending directions 341x to 343x, respectively, in the left direction X2 away from the center line 10a. Note that the extending directions 341x and 342x are a little upward in the Y direction, and the extending direction 343x is a little downward in the Y direction. The extending directions 331x to 333x and 341x to 343x of the electrode base parts 331 to 333 and 341 to 343 are not limited to these, and the directions can be appropriately determined by taking into account the arrangement and the like of the electrodes 311 to 323.

Figure 24:
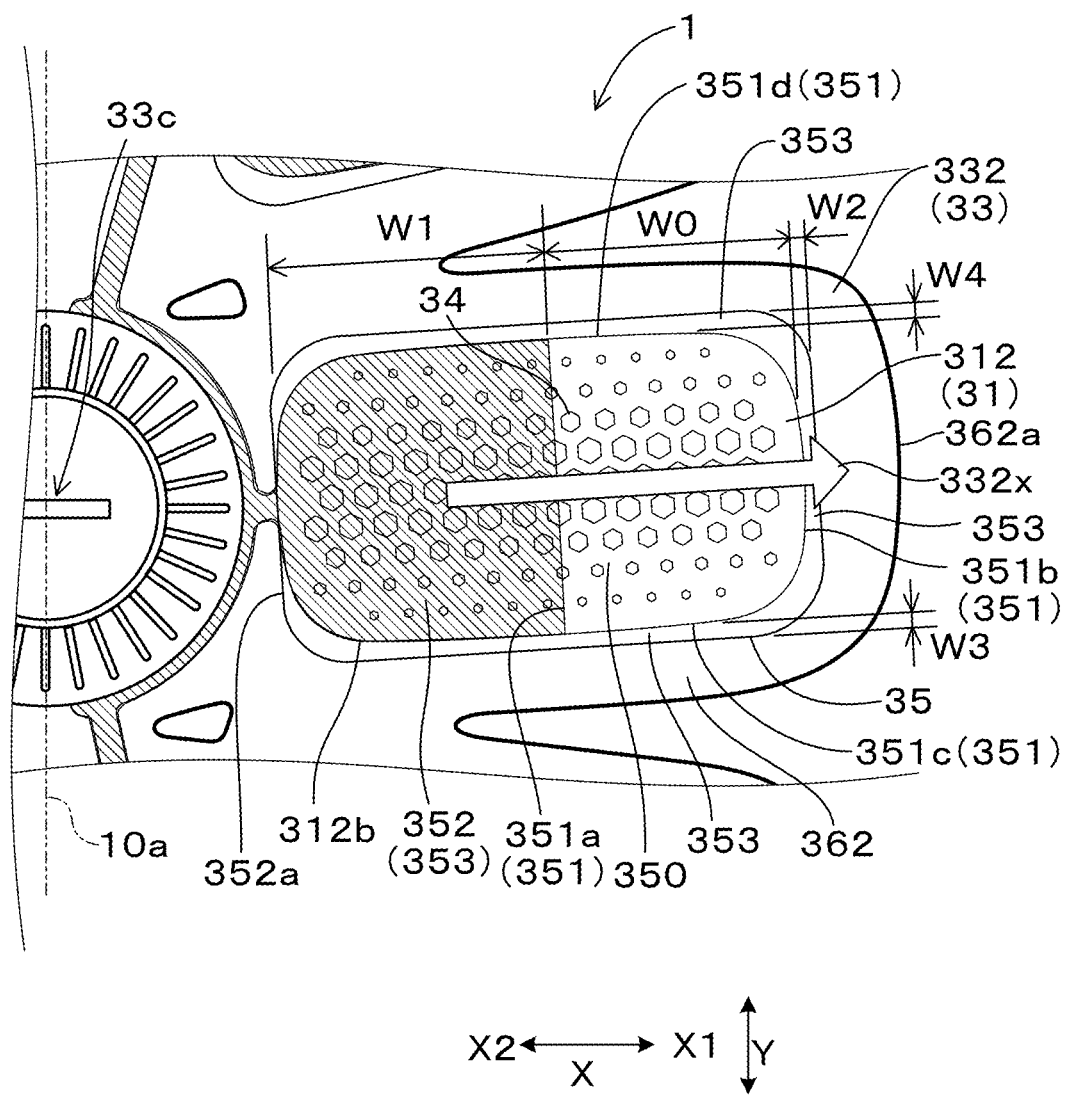
FIG. 24 is a partially enlarged rear view of the muscle electrostimulation device in Embodiment 5.

As shown in FIGS. 23 and 24, the external forms of the pads 35 are larger than the external forms of the electrodes 311 to 313 and 321 to 323, and the areas of the pads 35 are larger than the areas of the electrodes 311 to 313 and 321 to 323. The pads 35 are attached to the pad attachment portions 361 to 363 and 371 to 373. The pad attachment portions 361 to 363 and 371 to 373 are portions including areas for attaching the pads 35, and in this embodiment, the external forms of the electrode base parts 331 to 333 and 341 to 343 are one size larger than the external forms of the pads 35 to set the entire back side 33a of the electrode base parts 331 to 333 and 341 to 343 as the pad attachment portions 361 to 363 and 371 to 373.

As shown in FIG. 23, on the pad attachment portions 361 to 363 and 371 to 373, the electrodes 311 to 313 and 321 to 323 are disposed closer to ends on one side (ends 361a to 363a and 371a to 373a in this embodiment) in the pad attachment portions 361 to 363 and 371 to 373. In the pad attachment portion 361, the end 361a is an end farthest from a center 33c of the substrate 33 as viewed from the front side of the substrate 33 as shown in FIG. 23. Likewise, the ends 362a, 363a, and 371a to 373a are ends farthest from the center 33c of the substrate 33 as viewed from the front side of the substrate 33 in the pad attachment portions 362, 363, and 371 to 373, respectively.

The pads 35 are attached to the pad attachment portions 361 to 363 and 371 to 373 and cover the entire areas of the electrodes 311 to 313 and 321 to 323, respectively. As shown in FIG. 24, the pad 35 includes an electrode covered section 350 covering the entire area of the electrode 312 and an electrode non-covered section 353 not covering the electrode 312. The electrode non-covered section 353 includes a pad extending portion 352 widely extended from a periphery 351a opposite to the extending direction 332x of the electrode base part 332 in a periphery 351 of the electrode covered section 350.

As shown in FIG. 24, an amount of extension (shortest distance between the periphery 351a and a periphery 352a opposite to the extending direction 332x in the pad extending portion 352) W1 of the pad extending portion 352 in the electrode non-covered section 353 is sufficiently larger than an amount of extension W2 from a periphery 351b in the extending direction 332x of the electrode base part 332 in the periphery 351 of the electrode covered section 350 and is sufficiently larger than amounts of extension W3 and W4 from peripheries 351c and 351d in a direction 332y orthogonal to the extending direction 332x and the thickness direction Z of the electrode base part 332 (see FIG. 25) in the electrode non-covered section 353 of the pad 35. Accordingly, the pad extending portion 352 widely extends opposite to the extending direction 332x of the electrode base part 332. The pads 35 covering the electrodes 311, 313, and 321 to 323 also include the electrode covered sections 350 and the electrode non-covered sections 353 including the pad extending portions 352 formed in the same way.

In this embodiment, the pads 35 have external forms a little larger than the external forms of silver paste print sections 311b to 323b and are attached so as to cover the entire areas of the silver paste print sections 311b to 323b. In this embodiment, the amount of extension W1 of the pad extending portion 352 is substantially the same as a length W0 of the extending direction 332x of the electrode 312 as shown in FIG. 24. Therefore, the area of the pad extending portion 352 is larger than the area of the electrode 312. The same applies to the other electrodes 311, 313, and 321 to 323.

Figure 25A:
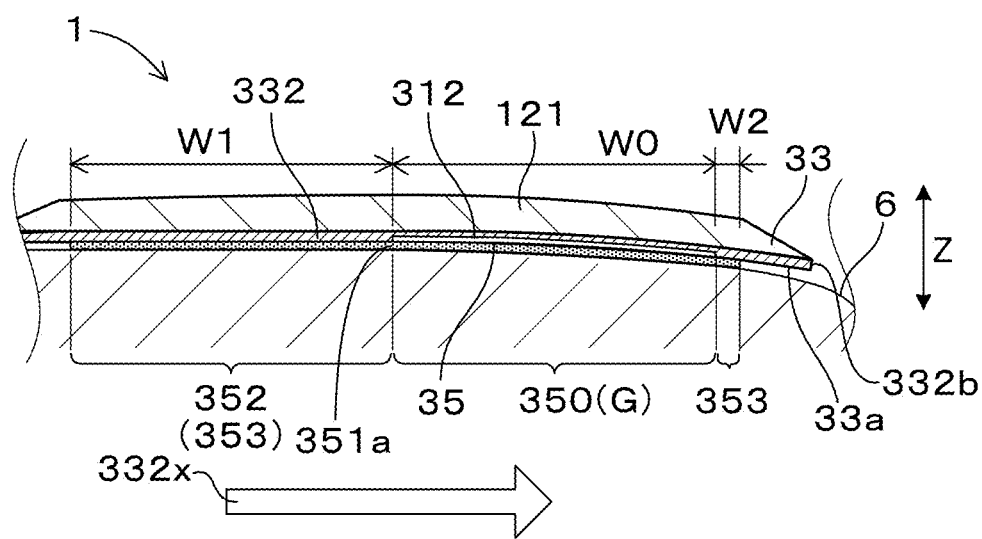
FIG. 25 is a schematic diagram illustrating a falling mode of an electrode in Embodiment 6.
Figure 25B:
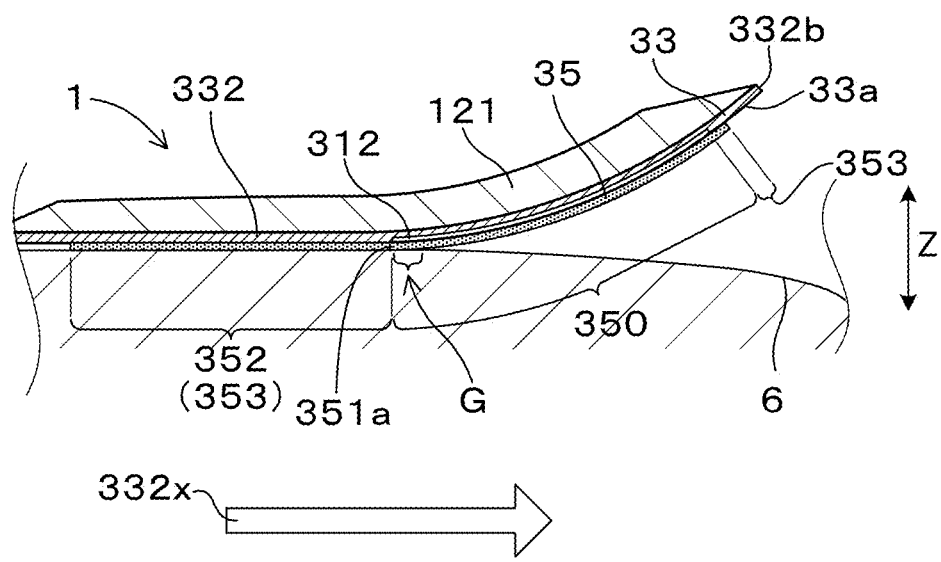

Next, a case in which the second right electrode 312 starts to fall off from a skin surface 6 during the use in the muscle electrostimulation device 1 of this embodiment as shown in FIGS. 25a and 25b will be described. As shown in FIG. 25a, the entire area of the pad 35 is adhered to the skin surface 6 in the normal state, and the entire area of the second right electrode 312 is in contact with the skin surface 6 via the pad 35. Therefore, a contact part G of the second right electrode 312 and the skin surface 6 via the pad 35 coincides with the entire area of the electrode covered section 350.

Here, the curvature of the skin surface 6 of the abdomen 3 gradually increases in a direction from the umbilicus 3a (see FIG. 5) to a flank 3b. In this embodiment, the direction from the umbilicus 3a to the flank 3b substantially coincides with the extending direction 332x of the electrode base part 332 as shown in FIGS. 25a and 25b, and the curvature of the skin surface 6 gradually increases toward the extending direction 332x.

When the adhesive force of the pad 35 is deteriorated by repeated use or the like, the second right electrode 312 may start to fall from the skin surface 6 as shown in FIG. 25b. More specifically, the pad 35 separates from the skin surface 6 at a periphery 332b of the electrode base part 332 of the substrate 33, i.e. at a tip of the electrode base part 332 in the extending direction 332x, and the second right electrode 312 starts to fall from the skin surface 6. The fall in the second right electrode 312 progresses in the direction opposite the extending direction 332x of the electrode base part 332. Along with the progression of the fall, the contact part G of the second right electrode 312 and the skin surface 6 via the pad 35 is gradually reduced. In the state shown in FIG. 25b, the contact part G is significantly small. However, although the electrode covered section 350 is just in contact with the skin surface 6 via the electrode covered section 350 at the significantly small contact part G in the pad 35, the pad extending portion 352 is in contact with the skin surface 6. Therefore, the electric current from the second right electrode 312 flows to the skin surface 6 via the electrode covered section 350 and the pad extending portion 352 at the significantly small contact part G. Accordingly, the electric current flowing from the second right electrode 312 to the skin surface 6 is not excessively concentrated even in this state, and the user is unlikely to feel pain. The same applies to the other electrodes 311, 313, and 321 to 323.

Effects of the muscle electrostimulation device 1 of Embodiment 6 will be described in detail.

The muscle electrostimulation device 1 includes the electrodes 311 to 323 with areas of 10 to 65% of the areas of the pads 35. The electrodes 311 to 323 are smaller than the areas of the pads 35, and the electrode covered sections 350 covering the electrodes 311 to 323 and the electrode non-covered sections 353 not covering the electrodes are formed on the pads 35 attached to the pad attachment portions 361 to 373. The electrode covered sections 350 are in contact with both the electrodes 311 to 323 and the skin surface 6, and the electric current actively flows from the electrodes 311 to 323 to the skin surface 6 touching the electrode covered sections 350. On the contrary, the electrode non-covered sections 353 are provided in areas without the formation of the electrodes 311 to 323 in the substrate 33, and the electric current does not actively flow.

When the electrode covered sections 350 start to separate due to deterioration in the adhesive force of the pads 35, the contact parts of the electrodes 311 to 323 and the skin surface 6 via the electrode covered sections 350 are gradually reduced, but the electrode non-covered sections 353 remain to be in contact with the skin surface 6. Therefore, since the energization area on the skin surface 6 is secured via the electrode non-covered sections 353 even if the contact parts become small, the concentration of power is reduced by preventing the amount of current per unit area on the skin surface 6 from becoming excessively large, and this can prevent the user's pain.

The areas of the pads 35 are sufficiently larger than the areas of the electrodes 311 to 323, and the electrodes 311 to 323 can be surely covered by the pads 35 even if there is a little displacement in attaching the pads 35. This improves the assembly workability and can prevent the electrodes 311 to 323 from being exposed from the pads 35 to come into direct contact with the skin surface. The exposure of the electrodes 311 to 323 from the pads 35 is prevented, and this can prevent the hand from coming into direct contact with the electrodes 311 to 323 when the muscle electrostimulation device 1 is removed from the human body 2 after the use or the like of the muscle electrostimulation device 1.

In this embodiment, the pad attachment portions 361 to 373 include the silver paste print sections 311b to 323b as attachment position display sections for displaying the attachment positions of the pads 35. This further facilitates attaching the pads 35 to appropriate positions and improves the assembly workability.

In this embodiment, the electrodes 311 to 323 are displaced closer to the ends 361a to 373a on one side in the pad attachment portions 361 to 373. Accordingly, since the electrode covered sections 350 covering the electrodes 311 to 323 in the pads 35 remain to be in contact with the skin surface 6 even when the pads 35 are fallen from anywhere other than the end 362a closer to the positions of the electrodes 311 to 323, the power is further unlikely to be concentrated, and this can easily prevent the user's pain.

In this embodiment, the ends 361a to 373a on one side form the ends 361a to 373a farthest from the center 33c of the substrate 33 in the pad attachment portions 361 to 373 as viewed from the front side of the substrate 33. Accordingly, the plurality of electrodes 311 to 323 are disposed closer to the ends 361a to 373a farthest from the center 33c of the substrate 33 in the pad attachment portions 361 to 373, and the distances between the electrodes 311 to 323 can be easily increased. Therefore, the electrostimulation output from the electrodes 311 to 323 easily reaches inner muscles in the human body 2, i.e. muscles at deep positions of the human body 2 from the skin surface 6. As a result, the muscles can be efficiently stimulated.

Although the electrodes 311 to 323 are disposed closer to the ends 361a to 373a in the pad attachment portions 361 to 373 in this embodiment as described above, the electrodes 311 to 323 may be disposed closer to the center 33c of the substrate 33 in the pad attachment portions 361 to 373 instead of this. In this case, when the pads 35 start to fall due to deterioration of the adhesive force of the pads 35, the electrode non-covered sections 353 tend to separate before the separation of the electrode covered sections 350. When the electrode non-covered sections 353 start to separate, the concentration of power is unlikely to occur because the electrode covered sections 350 remain to be in contact with the skin surface 6. Therefore, the user can easily notice the fall of the pads 35 (electrode non-covered sections 353) before feeling pain. As a result, the user is prompted to attach the pads 35 again before feeling pain.

In this embodiment, the plurality of electrodes 311 to 323 include the electrodes (electrodes 311 to 313) disposed on one of the sides divided by the center line 10a as a virtual center line passing through the center 33c of the substrate 33 and include the electrodes (electrodes 321 to 323) disposed on the other side. Accordingly, the electrodes 311 to 313 and the electrodes 321 to 323 are separately arranged across the virtual center line (center line 10a), and the electrostimulation output from the electrodes 311 to 323 can more easily reach the muscles at deep positions of the human body 2 from the skin surface 6. As a result, the muscles can be more efficiently stimulated.

In this embodiment, the substrate 33 includes the plurality of electrode base parts 331 to 333 and 341 to 343. Accordingly, the plurality of electrodes 311 to 323 formed on the plurality of electrode base parts 331 to 333 and 341 to 343, respectively, and the main body 10 are integrally formed, and the plurality of electrodes 311 to 323 can be attached all together upon use. Therefore, the burden of attaching the plurality of electrodes 311 to 323 is alleviated, and the usability improves. The pads 35 tend to fall in the directions opposite to the extending directions 331x to 343x of the electrode base parts 331 to 343 from the ends 332b of the electrode base parts 331 to 343. Therefore, when the pads 35 gradually fall from the skin surface 6 in the directions opposite to the extending directions 331x to 343x of the electrode base parts 331 to 343 from the ends 332b of the electrode base parts 331 to 343, the contact parts G of the electrodes 311 to 323, which come into contact via the electrode covered sections 350 covering the electrodes 311 to 323 in the pads 35, and the skin surface 6 are gradually reduced, but the pad extending portions 352 extending in the directions opposite to the extending directions 331x to 343x of the electrode base parts 331 to 343 from the electrode covered sections 350 in the pads 35 remain to be in contact with the skin surface 6. Therefore, since the energization area on the skin surface 6 is secured through the pad extending portions 352 even when the contact parts G become small, an excessive increase in the amount of current per unit area on the skin surface 6 is prevented, and this can prevent the user's pain.

Note that the extending directions (extending directions 331x to 343x) of the electrode base parts 361 to 373 in the substrate 33 can be appropriately determined based on the arrangement and the like of the electrodes 311 to 323. For example, the extending directions may be directions away from the center line 10a as a virtual center line passing through the center 33c of the substrate 33 and parallel to the main surface 33b of the substrate 33, or the extending directions may be directions toward arbitrary positions from relay portions provided to extend in directions away from the center line 10a in the substrate 33.

In this embodiment, the main body 10 is positioned at the center 33c of the substrate 33. Accordingly, since the muscle electrostimulation device 1 of this embodiment can be formed compactly, and the paths between the main body 10 and the electrodes 311 to 323 can be short, the electric current can be efficiently applied to the electrodes 311 to 323.

In this embodiment, part of the silver paste print sections 311b to 323b is silicone-coated, and the electrodes 311 to 323 are smaller than the silver paste print sections 311b to 323b. Accordingly, the areas of the electrodes 311 to 323 can be smaller than when the electrodes 311 to 323 are provided on the entire areas of the silver paste print sections 311b to 323b without the silicone coating. As a result, the power consumption of the entire device can be reduced. The pads 35 include the pad extending portions 352, and the sizes of the pads are secured. Since the reduction in the amount of current supplied to the electrodes 311 to 323 can be prevented, six electrodes 311 to 323 can be provided even when a coin battery is adopted as the battery 21 as in this embodiment.

Although the silicone-coated parts of the silver paste print sections 311b to 323b do not act as electrodes, the parts serve as guides for attaching the pads 35. That is, the silver paste print sections 311b to 323b form attachment position display sections that display positions for attaching the pads 35. When the pads 35 are attached so as to cover the entire silver paste print sections 311b to 323b as attachment position display sections, the pads 35 cover the entire areas of the electrodes 311 to 323, and sufficiently wide areas of the pad extending portions 352 can be secured.

As described, according to Embodiment 6, the muscle electrostimulation device 1 can be provided, the device capable of attaining the effects equivalent to the effects in Embodiment 1 and capable of preventing the user's pain when the pads 35 start to fall during the use.

Figure 26:
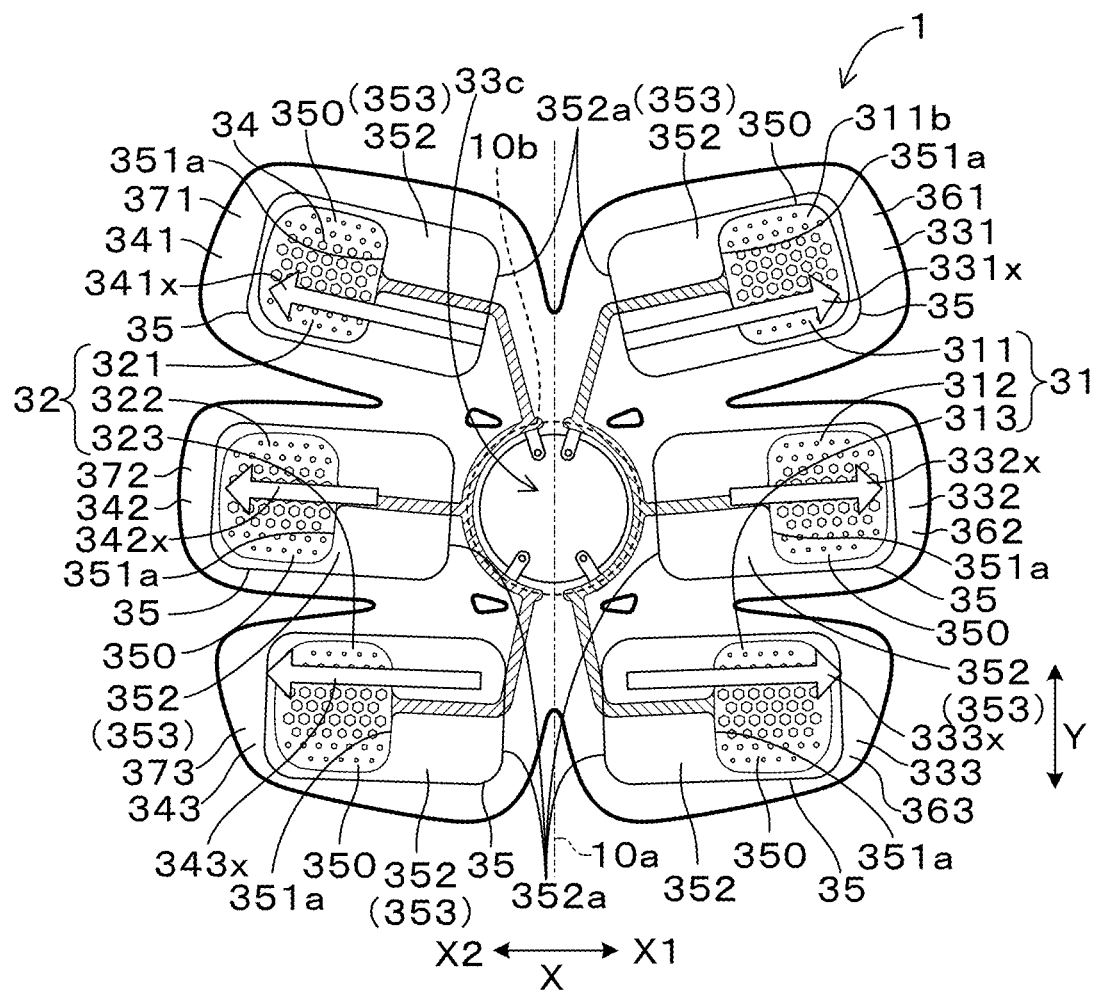
FIG. 26 is a rear view of the muscle electrostimulation device in Variation 4.

Although part of the silver paste print sections 311b to 323b is silicone-coated in this embodiment, instead of this, the shapes of the silver paste print sections 311b to 323b may be formed in advance to have shapes equivalent to the electrodes 311 to 323, and the electrodes 311 to 323 may be provided on substantially the entire areas of the silver paste print sections 311b to 323b as in Variation 4 shown in FIG. 26. Although the silver paste print sections 311b to 323b are not silicon-coated in this case, the leads are silicone-coated as in the case of Embodiment 1, and electric conduction to the outside is prevented. In this case, the effects equivalent to the effects in Embodiment 6 are also attained except that the silver paste print sections 311b to 323b function as guides for attaching the pads 35 in Embodiment 6.

Figure 27:
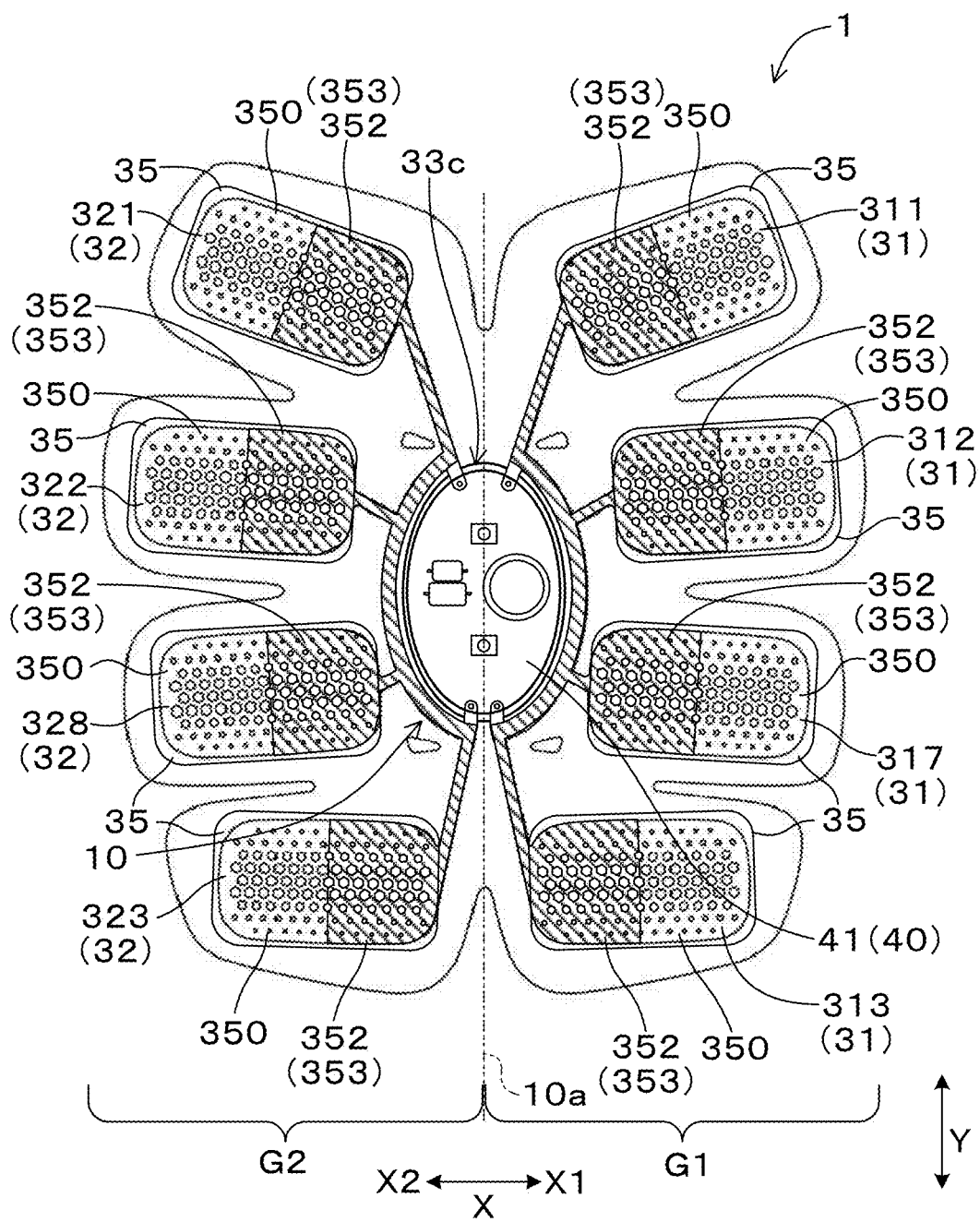
FIG. 27 is a rear view of the muscle electrostimulation device in Variation 5.

Although six electrodes 311 to 313 and 321 to 323 are provided in Embodiment 6, eight electrodes may be provided instead of this. For example, in Variation 5, the electrodes include a fourth right electrode 317 and a fourth left electrode 328 in addition to the electrodes 311 to 313 and 321 to 323 as shown in FIG. 27, and eight electrodes in total are provided. In Variation 5, the same symbols are provided to the elements equivalent to the elements in Embodiments 1 to 6, and the description will not be repeated.

In Variation 5, the fourth right electrode 317 is disposed between the second right electrode 312 and the third right electrode 313, and the fourth left electrode 328 is disposed between the second left electrode 322 and the third left electrode 323. The fourth right electrode 317 and the fourth left electrode 328 are also provided with the pads 35 as in the other electrodes 311 to 323, and the pad extending portions 352 are formed.

The effects equivalent to the effects in the case of Embodiment 6 are also attained in Variation 5. Since the pad extending portions 352 are provided, the reduction in the amount of current supplied to the electrodes 311 to 313, 317, 321 to 323, and 318 is prevented while the sizes of the pads 35 are secured, and eight electrodes can be included as in Variation 5.

Figure 28:
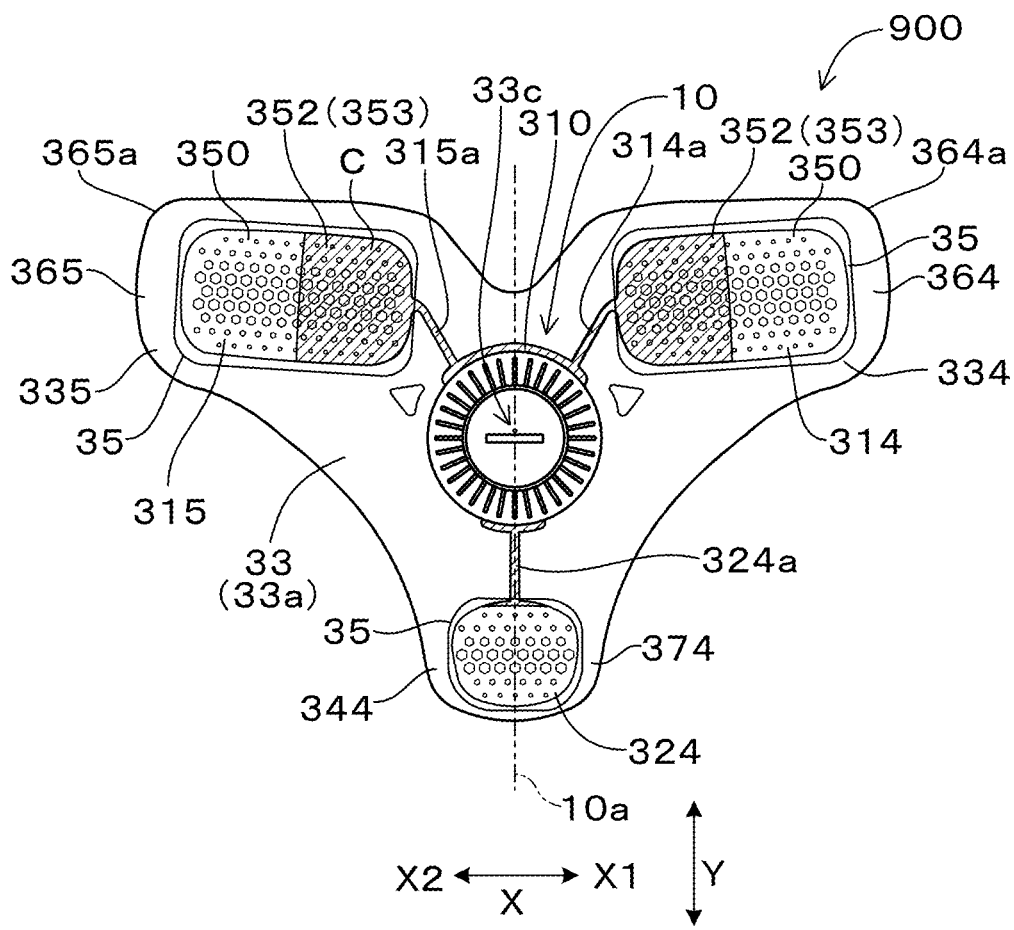
FIG. 28 is a rear view of the muscle electrostimulation device in Reference Example 2.

Although all the six electrodes 311 to 313 and 321 to 323 have areas in the range of 10 to 65% of the of the areas of the pads 35 in this embodiment, part of the plurality of electrodes included in the muscle electrostimulation device may have areas larger than 65% of the areas of the pads 35 instead of this. For example, the following Reference Example 2 can be adopted. That is, three electrodes 314, 315, and 324 are provided in Reference Example 2 as shown in FIG. 28. In Reference Example 2, the same symbols are provided to the elements equivalent to the elements in Embodiments 1 to 6, and the description will not be repeated.

In Reference Example 2, the substrate 33 has a substantially Y-shape as viewed from the front side as shown in FIG. 28. The main body 10 is formed at the center 33c of the substrate 33. The electrodes 314 and 315 are provided on a pair of electrode base parts 334 and 335, respectively, divided into two parts and extended upward in the Y direction of the substrate 33, and the electrode 324 is provided on an electrode base part 344 extending downward in the Y direction of the substrate 33.

The electrodes 314 and 315 have shapes equivalent to the electrodes 314 and 315 in Embodiment 6. However, a lead 314a of the electrode 314 and a lead 315a of the electrode 315 are linked via a linkage 310 printed by an ink containing a silver paste and provided with a coating, just like the leads 314a and 315a. The linkage 310 is connected to an output terminal (not shown) of the controller 40.

On the contrary, the electrode 324 includes a silver paste print section 324b formed on the back side 33a of the substrate 33. The silver paste print section 324b is not coated, and substantially the entire area of the silver paste print section 324b is the electrode 324. The silver paste print section 324b is smaller than the silver paste print sections 314b and 315b forming the electrodes 314 and 315. Therefore, the electrodes 314 and 315 and the electrode 324 have substantially the same area. The electrode 324 is connected to an output terminal (not shown) with the polarity opposite the output terminal connected with the linkage 310 among the output terminals of the controller 40, via the lead 324a printed by an ink containing a silver paste and provided with a coating.

As shown in FIG. 28, the pair of electrode base parts 334 and 335 extending upward in the Y direction of the substrate 33 form pad attachment portions 364 and 365, respectively, and the electrode base part 344 extending downward in the Y direction forms a pad attachment portion 374. The pads 35 are attached to the attachment portions 364, 365, and 374 so as to cover the electrodes 314, 315, and 324. The pad 35 attached to the electrode 324 has a shape according to the size of the silver paste print section 324b as a pad attachment position display section, and the pad 35 is smaller than the pads 35 covering the electrodes 314 and 315. The area of the electrode 324 is 85% of the area of the pad 35 covering the electrode 324. Note that the areas of the electrodes 314 and 315 are 45% of the areas of the pads 35 covering the electrodes 314 and 315 as in the case of Embodiment 6.

In this Reference Example 2, part (electrode 324) of the plurality of electrodes 314, 315, and 324 included in the muscle electrostimulation device 1 has an area larger than 65% of the area of the pad covering the electrode 324. However, the areas of the electrodes 314 and 315 are in the range of 10 to 65% of the areas of the pads covering the electrodes 314 and 315 as in Embodiment 6. Therefore, effects equivalent to the effects in the case of Embodiment 6 are attained by the electrodes 314 and 315 of Reference Example 2, except for the effects obtained by providing four or more electrodes in Embodiment 6.

Embodiment 7

The muscle electrostimulation device of Embodiment 7 in the present invention will be described.

The muscle electrostimulation device disclosed in Patent Document 1 just includes a pair of electrodes, and efficient electrostimulation of a plurality of muscles is difficult. Therefore, although the number of electrodes can be increased, the energization distances between the electrodes and the controller tend to vary if the number of electrodes is simply increased. Due to the variations in the energization distance, the electric resistance in the lead for electrically connecting the electrode and the controller tends to vary in each electrode, and the electrostimulation output from each electrode tends to vary. As a result, well-balanced electrostimulation of the muscles is difficult. On the contrary, if the leads are simply formed to have equivalent lengths to prevent the variations in the energization distance, the degree of freedom in arranging the electrodes is significantly reduced, and it is difficult to arrange the electrodes at positions suitable for applying electrostimulation to the muscles.

The muscle electrostimulation device 1 of Embodiment 7 is configured as follows in view of the problems. The same symbols are provided to the members equivalent to the members of the muscle electrostimulation device 1 in the preceding embodiments, and the description of the members and the description of the usage mode will not be repeated. When the drawings used in the description of this embodiment are the same as the drawings in the preceding embodiments, the drawings in the preceding embodiments will be used.

Figure 29:
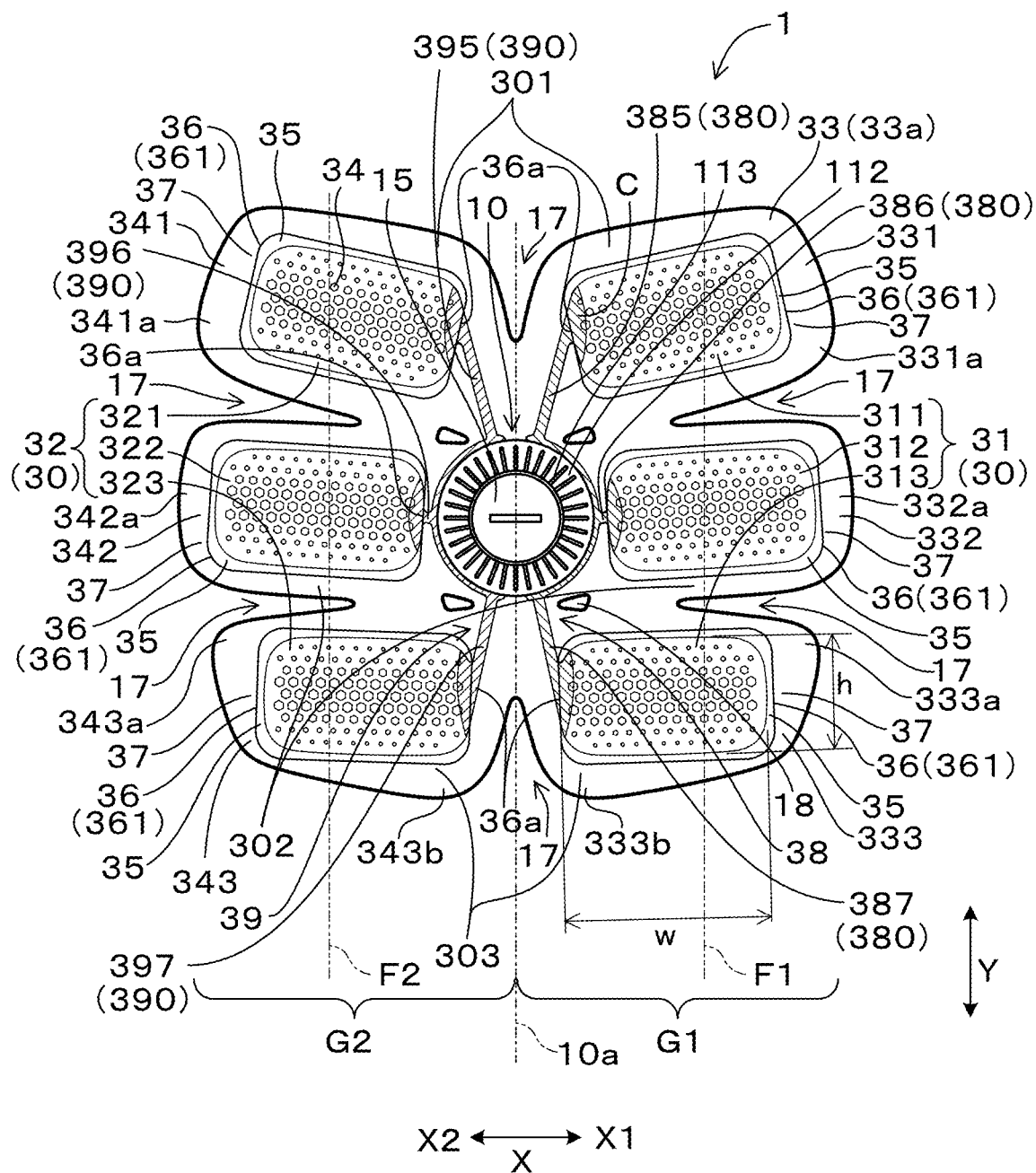
FIG. 29 is a rear view of the muscle electrostimulation device in Embodiment 7.

The muscle electrostimulation device 1 of Embodiment 7 includes the main body 10, the power source 20 (see FIG. 4), the electrode unit 30, the controller 40, and leads 38 and 39 as shown in FIG. 29. The power source 20 and the controller 40 are stored in the main body 10. The electrode unit 30 includes three or more electrodes 311 to 323 that receive power from the power source 20. The controller 40 controls the supply of power to the electrode unit 30. The leads 38 and 39 electrically connect the electrode unit 30 and the controller 40. The muscle electrostimulation device 1 is configured to apply electrostimulation to the human body 2 (see FIG. 5) from the electrode unit 30.

Figure 30:
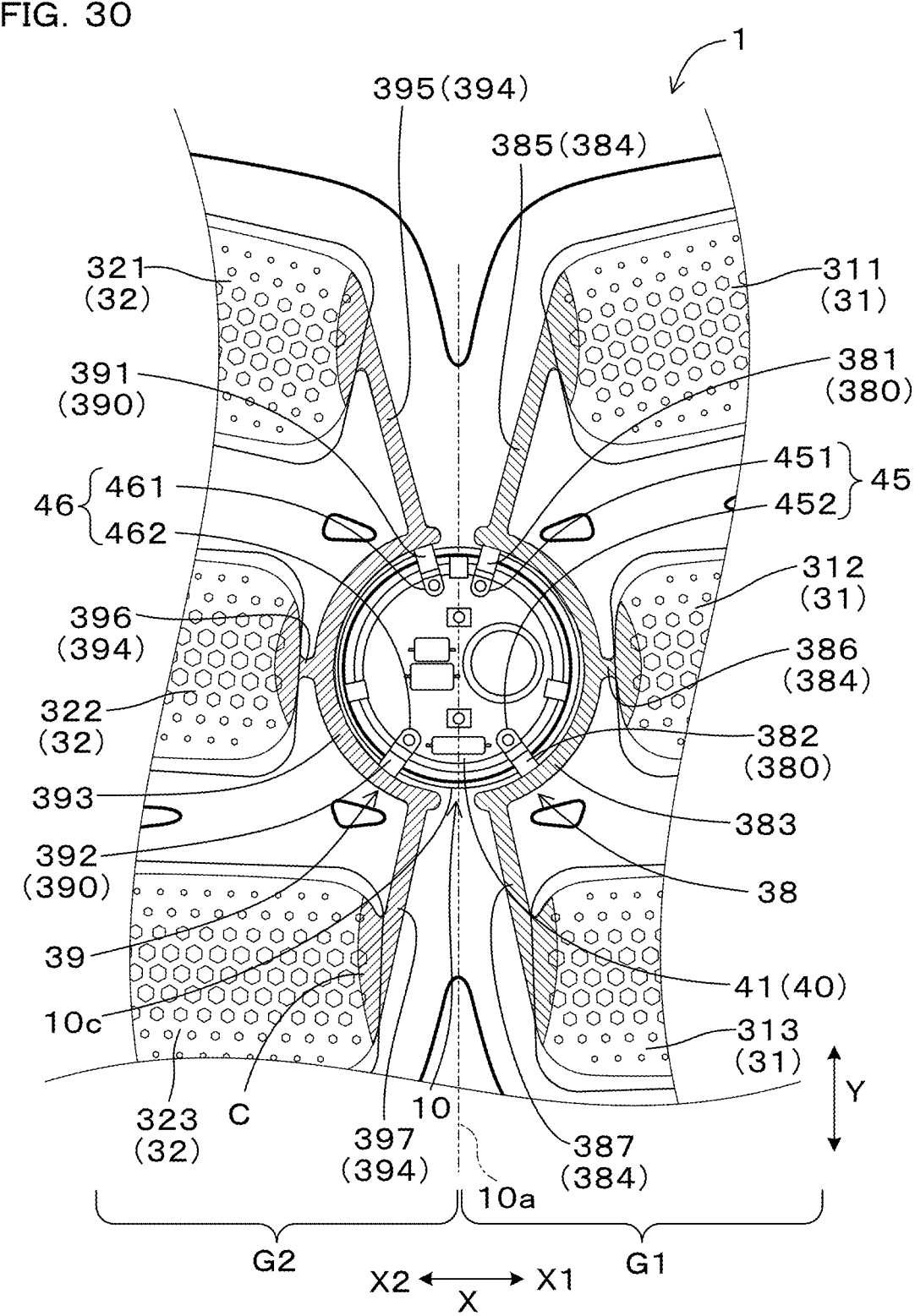
FIG. 30 is a partially enlarged back view with a second case removed in Embodiment 7.

As shown in FIGS. 29 and 30, the controller 40 includes a plurality of terminals 451 and 452 (461 and 462) provided with voltages of the same polarity.

The lead 38 (39) includes: a terminal connection 383 (393) for connecting the plurality of terminals 451 and 452 (461 and 462); and electrode connections 385 to 387 (395 to 397) for connecting the terminal connection 383 (393) and the electrodes 311 to 313 (321 to 323).

Figure 31:
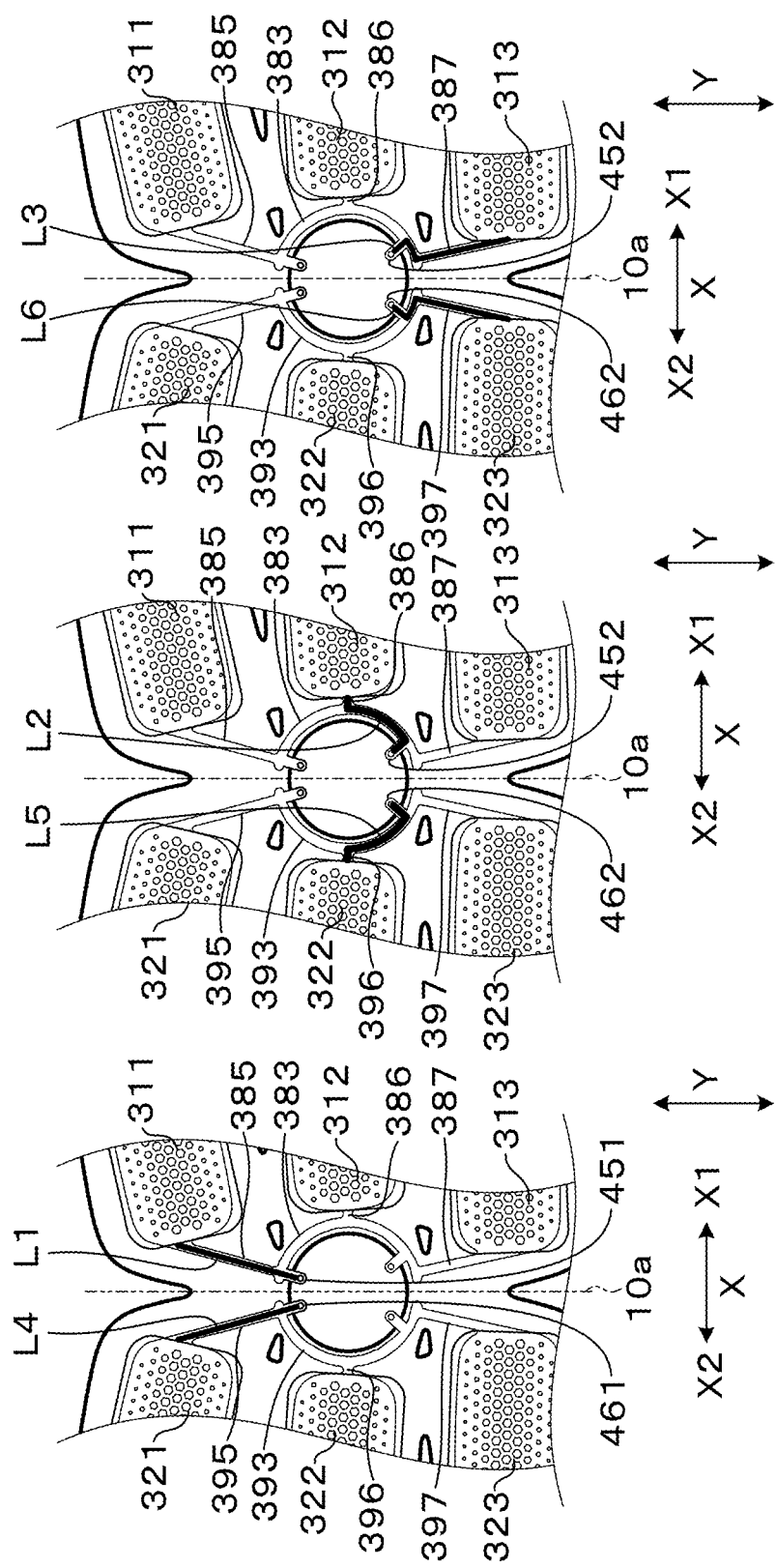
FIG. 31 is a schematic diagram illustrating shortest paths in Embodiment 7.

As shown in FIG. 31, differences between lengths of shortest paths L1 to L3 (L4 to L6) from the electrodes 311 to 313 (321 to 323) to the terminals 451 and 452 (461 and 462) and an average length of the shortest paths L1 to L3 (L4 to L6) are less than 20% of the average length.

In this embodiment, "the shortest paths L1 to L3 (L4 to L6) from the electrodes 311 to 313 (321 to 323) to the terminals 451 and 452 (461 and 462)" are defined as follows. First, a path electrically connected from one of the electrodes 311 to 313 (321 to 323) to one of the terminals 451 and 452 (461 and 462) is extracted in the lead 38 (39). A path virtual line connecting centers of positions of the extracted path in the width direction of the lead 38 (39) is depicted, and the length of the path virtual line is set as the length of the path. The lengths of the paths from one of the electrodes 311 to 313 (321 to 323) to the plurality of terminals 451 and 452 (461 and 462) are derived, and the paths with the shortest lengths are set as the shortest paths from the electrodes 311 to 313 (321 to 323) to the terminals 451 and 452 (461 and 462).

As shown in FIG. 30, the first lead 38 as a lead includes a first controller connection group 380, the first terminal connection 383, and a first electrode connection group 384. The first controller connection group 380 includes a plurality of controller connections (first controller connection 381, second controller connection 382) connected to the plurality of terminals (first terminal 451, second terminal 452) belonging to a first terminal group 45. The first controller connection 381 and the second controller connection 382 project toward the main body 10. As shown in FIG. 4b in Embodiment 1, the first controller connection 381 and the second controller connection 382 are bent in the thickness direction along the inner wall of the first case 111, and the tips are bent parallel to the control board 41. The tips of the first controller connection 381 and the second controller connection 382 are placed between the bosses 116 and the control board 41 as described above.

As shown in FIG. 30, the first terminal connection 383 as a terminal connection is formed to mutually electronically connect the plurality of controller connections (first controller connection 381, second controller connection 382) belonging to the first controller connection group 380. In this embodiment, the first terminal connection 383 has a substantially semicircular shape along a periphery 10b of the main body 10. The first controller connection 381 is provided on one end of the first terminal connection 383, and the second controller connection 382 is provided on the other end.

The first electrode connection group 384 includes the plurality of electrode connections (first electrode connection 385, second electrode connection 386, third electrode connection 387) that extend from the first terminal connection 383 toward the plurality of electrodes (first right electrode 311, second right electrode 312, third right electrode 313) belonging to the first electrode group 31 and that are connected to the plurality of electrodes 311 to 313. In this embodiment, the first electrode connection 385, the second electrode connection 386, and the third electrode connection 387 are formed in a linear shape.

Like the first lead 38, the second lead 39 as a lead includes a second controller connection group 390, the second terminal connection 393, and a second electrode connection group 394. The second controller connection group 390 includes a plurality of controller connections (third controller connection 391, fourth controller connection 392) connected to the plurality of terminals (third terminal 461, fourth terminal 462) belonging to the second terminal group 46. Like the first lead 38, the tips of the third controller connection 391 and the fourth controller connection 392 are placed between the bosses 116 and the control board 41.

As in the case of the first lead 38, the second terminal connection 393 as a terminal connection is formed to mutually electronically connect the plurality of controller connection (third controller connection 391, fourth controller connection 392) belonging to the second controller connection group 390. In this embodiment, as in the case of the first lead 38, the second terminal connection 393 has a substantially semicircular shape along the periphery 10b of the main body 10. The third controller connection 391 is provided on one end of the second terminal connection 393, and the fourth controller connection 392 is provided on the other end.

As in the case of the first lead 38, the second electrode connection group 394 includes the plurality of electrode connections (fourth electrode connection 395, fifth electrode connection 396, sixth electrode connection 397) that extend from the second terminal connection 393 toward the plurality of electrodes (first left electrode 321, second left electrode 322, third left electrode 323) belonging to the second electrode group 32 and that are connected to the plurality of electrodes 321 to 323. In this embodiment, the fourth electrode connection 395, the fifth electrode connection 396, and the sixth electrode connection 397 are formed in a linear shape.

As shown in FIGS. 31a to c, the first lead 38 (see FIG. 30) forms the first right path L1 as a first path, the second right path L2 as a second path, and the third right path L3 as a third path. The first right path L1 linearly extends from the first terminal 451 toward the first right electrode 311 and is connected to the first right electrode 311. The second right path L2 is connected to the second right electrode 312 from the first terminal 451 and the second terminal 452 via the first terminal connection 383. The third right path L3 is connected to the third right electrode 313 from the second terminal 452 via the first terminal connection 383. In the first lead 38, the paths L1 to L3 are shortest paths connected to the electrodes 311 to 313, respectively.

The lengths of the paths L1 to L3 in the first lead 38 are less than 20%, preferably, less than 18%, more preferably, less than 15%, of an average length obtained by averaging the lengths. In this embodiment, the lengths of the paths L1 to L3 are 40 mm, 35 mm, and 31 mm, respectively, and the average length obtained by averaging the lengths is 35.33 mm. The differences between the lengths of the paths L1 to L3 and the average length are 4.67 mm, 0.33 mm, and 4.33 mm, respectively, and are 13.21%, 0.93%, and 12.26% of the average length.

As shown in FIGS. 31a to c, the second lead 39 (see FIG. 30) forms the first left path L4 as a first path, the second left path L5 as a second path, and the third left path L6 as a third path. The first left path L4 linearly extends from the third terminal 461 toward the first left electrode 321 and is connected to the first left electrode 321. The second left path L5 is connected to the second left electrode 322 from the third terminal 461 and the fourth terminal 462 via the second terminal connection 393. The third left path L6 is connected to the third left electrode 323 from the fourth terminal 462 via the second terminal connection 393. In the second lead 39, the paths L4 to L6 are the shortest paths connected to the electrodes 321 to 323, respectively.

As in the first lead 38, the lengths of the paths L4 to L6 in the second lead 39 are less than 20%, preferably, less than 18%, more preferably, less than 15%, of the average length obtained by averaging the lengths. In this embodiment, the lengths of the paths L4 to L6 are 40 mm, 35 mm, and 31 mm, respectively, and the average length obtained by averaging the lengths is 35.33 mm. The differences between the lengths of the paths L4 to L6 and the average length are 4.67 mm, 0.33 mm, and 4.33 mm, respectively, and are 13.21%, 0.93%, and 12.26% of the average length.

As shown in FIG. 29, the first right electrode 311, the second right electrode 312, and the third right electrode 313 are arranged and disposed on a same virtual straight line F1. The first left electrode 321, the second left electrode 322, and the third left electrode 323 are also arranged and disposed on a same virtual straight line F2. In this embodiment, the virtual straight lines F1 and F2 are parallel to the center line 10a.

The effects of the muscle electrostimulation device 1 of Embodiment 7 will be described in detail.

In the muscle electrostimulation device 1, the differences between the lengths of the shortest paths L1 to L3 (L4 to L6) from the plurality of electrodes 311 to 313 (321 to 323) to the terminals 451 and 452 (461 and 462) and the average length of the shortest paths L1 to L3 (L4 to L6) are less than 20% of the average length. Therefore, the energization distances between the electrodes 311 to 313 (321 to 323) and the controller 40 are unlikely to vary, and the variations in the electric resistance among the electrodes at the lead 38 (39) for electrically connecting the electrodes 311 to 313 (321 to 323) and the controller 40 can be reduced. Therefore, the electrostimulation output from the electrodes 311 to 313 (321 to 323) is unlikely to vary, and well-balanced electrostimulation can be applied to the muscles.

The controller 40 includes the plurality of terminals 451 and 452 (461 and 462) provided with voltages of the same polarity. The lead 38 (39) is provided with the terminal connection 383 (393) connected to the plurality of terminals 451 and 452 (461 and 462) and the electrode connections 385 to 387 (395 to 397) for connecting the terminal connection 383 (393) and the electrodes 311 to 313 (321 to 323). Accordingly, the degree of freedom in arranging the electrodes 311 to 313 (321 to 323) can be increased, while the short shortest paths L1 to L3 (L4 to L6) via the lead 38 (39) are maintained. As a result, the electrodes 311 to 313 (321 to 323) can be arranged at positions suitable for applying electrostimulation to the muscles.

In this embodiment, the plurality of electrodes 311 to 313 (321 to 323) are arranged and disposed on the same virtual straight line F1 (F2). Accordingly, the electrodes 311 to 313 (321 to 323) can easily correspond to the plurality of compartments 4a arranged on the straight line as in the rectus abdominis muscles 4, and muscles, such as the rectus abdominis muscles 4, can be effectively stimulated.

In this embodiment, two terminals 451 and 452 (461 and 462) of the same polarity are provided. Accordingly, the manufacturing cost can be reduced, while the shortest paths L1 to L3 (L4 to L6) to the electrodes 311 to 313 (321 to 323) can be reduced using few components.

In this embodiment, the first electrode group 31 of the electrode unit 30 includes three electrodes 311 to 313, and the second electrode group 32 includes three electrodes 321 to 323. Accordingly, the electrodes 311 to 313 can correspond to three compartments 4a that are partitions of the rectus abdominis muscles 4 in the height direction Y, and the rectus abdominis muscles 4 can be more effectively stimulated.

In this embodiment, the plurality of terminals 451, 452, 461, and 462, the electrodes 311 to 312 and 321 to 323, and the leads 38 and 39 are respectively arranged in both of one of the areas (first area G1) and the other area (second area G2) divided into two parts by the center line 10a passing through the center of the main body 10. Voltages with different polarities are applied to the electrodes 311 to 312 arranged in one of the areas (first area G1) and the electrodes 321 to 323 arranged in the other area (second area G2). Accordingly, when the device is attached to the middle of the abdomen 3 such that the center line 10a is parallel to the height direction Y of the person 2, the electrodes 311 to 312 and 321 to 323 are easily disposed at positions corresponding to the left and right rectus abdominis muscles 4, and the muscle electrostimulation device 1 is suitable for stimulating the rectus abdominis muscles 4.

In this embodiment, the terminal connections (first terminal connection 383 and second terminal connection 393) are formed along the periphery 10b of the main body 10. Accordingly, the leads (first lead 38 and the second lead 39) can be easily shortened, and the electrostimulation can be efficiently output.

Although the plurality of controller connections 381, 382, 392, and 392 and the controller 40 are fastened and fixed via the screws 115 in this embodiment, the plurality of controller connections 381, 382, 391, and 392 may be placed between the first case 111 and the second case 112 and connected and fixed to the controller 40 by pressure instead of this.

As described, according to Embodiment 7, the muscle electrostimulation device 1 can be provided, the device capable of attaining the effects equivalent to the effects in Embodiment 1, capable of reducing the variations in the electrostimulation output from the electrodes 311 to 323, and capable of improving the degree of freedom in arranging the electrodes 311 to 323.

Although six electrodes 311 to 313 and 321 to 323 are provided in Embodiment 7, eight electrodes 311 to 314 and 321 to 324 may be provided as in Variation 6 shown in FIG. 17. In Variation 6, the same symbols are provided to the elements equivalent to the elements in Embodiments 1 to 7, and the description will not be repeated.

Figure 32:
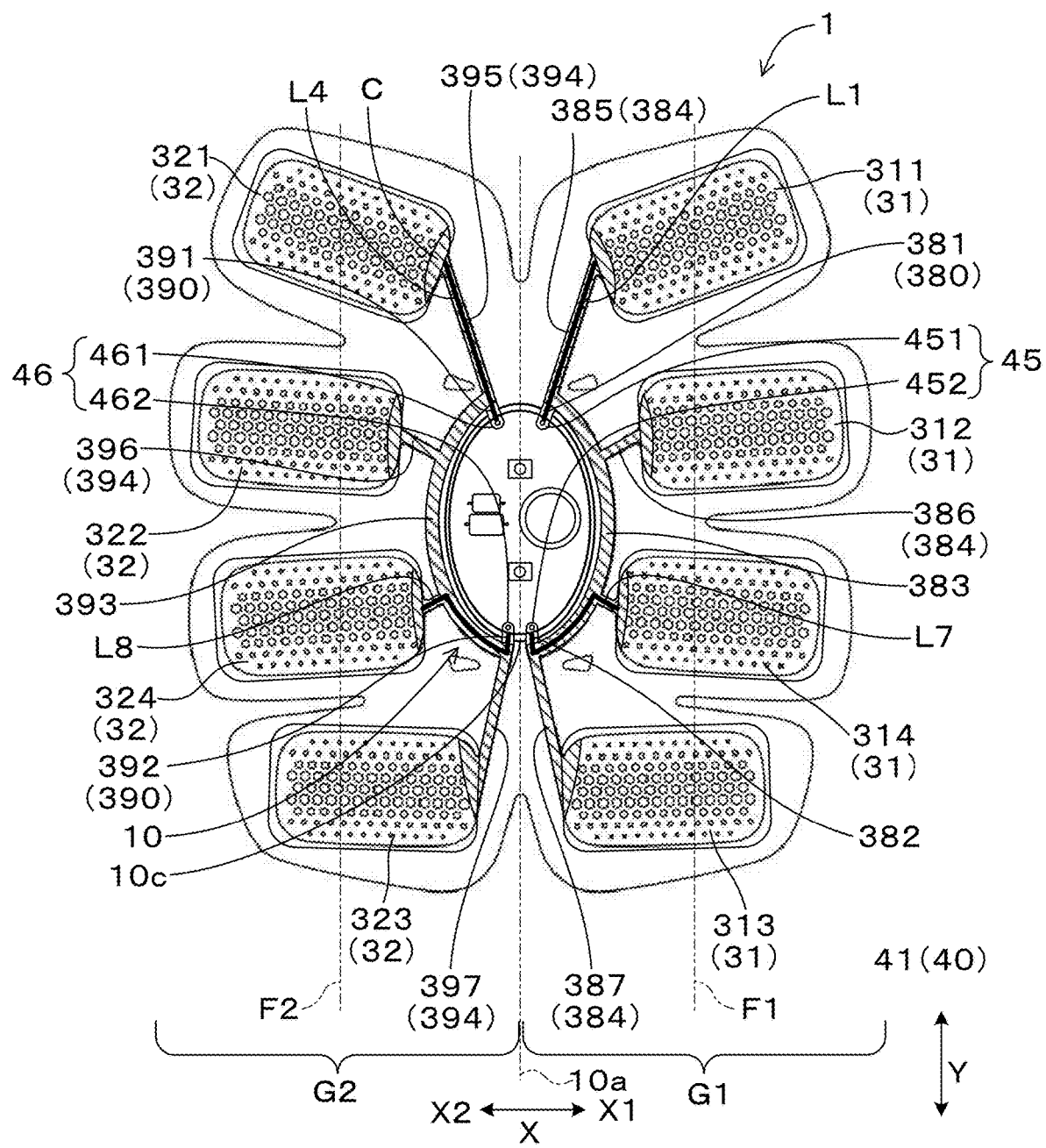
FIG. 32 is a rear view of the muscle electrostimulation device in Variation 6.

In Variation 6, the first electrode group 31 includes the fourth right electrode 314 as shown in FIG. 32, the fourth right electrode 314 positioned closer to the main body 10 than the third right electrode 313 and farther from the main body 10 than the second right electrode 312, positioned between the second right electrode 312 and the third right electrode 313, and circularly or linearly arranged along with the first right electrode 311, the second right electrode 312, and the third right electrode 313.

The second electrode group 32 includes the fourth left electrode 324 positioned closer to the main body 10 than the third left electrode 323 and farther from the main body 10 than the second left electrode 322, positioned between the second left electrode 322 and the third left electrode 323, and circularly or linearly arranged along with the first left electrode 321, the second left electrode 322, and the third left electrode 323.

The first lead 38 includes a right path L7 connected to the fourth right electrode 314 from the first terminal 451 and the second terminal 452 via the first terminal connection 383 and having substantially the same length as the first right path L1. Therefore, the difference between the length of the fourth right path L7 and the average length of the shortest paths is also less than 20% of the average length.

The second lead 39 includes a fourth left path L8 connected to the fourth left electrode 324 from the third terminal 461 and the fourth terminal 462 via the second terminal connection 393 and having substantially the same length as the first left path L4. Therefore, the difference between the length of the fourth left path L8 and the average length of the shortest paths is also less than 20% of the average length.

In Variation 6, the effects equivalent to the effects in Embodiment 7 are also attained.

In Variation 6, the first electrode group 31 and the second electrode group 32 in the electrode unit 30 include four electrodes 311 to 314 or 321 to 324 each. Accordingly, when the rectus abdominis muscles 4 are partitioned into four parts in the longitudinal direction (height direction Y), the electrodes can correspond to the compartments 4a, and the rectus abdominis muscles 4 can be more efficiently stimulated.

In Variation 6, the fourth right electrode 314 and the fourth left electrode 324 are disposed at symmetrical positions with respect to the center line 10a. Accordingly, the muscle electrostimulation device 1 is more suitable for stimulating the rectus abdominis muscles 4.

Embodiment 8

The muscle electrostimulation device of Embodiment 8 in the present invention will be described.

The main body and the electrodes are integrated in the muscle electrostimulation device disclosed in Patent Document 1, and the user can wear the device under the clothes. This allows the user to perform daily activities while wearing the device.

However, when the user continues to wear the conventional muscle electrostimulation device for a long time, there is a problem that the user feels uncomfortable due to sweat, moisture, or the like staying between the device and the skin. Therefore, it is difficult to use the conventional device in a format that the user performs daily activities while wearing the muscle electrostimulation device, and in many cases, the user wears the muscle electrostimulation device only when using the device.

On the contrary, the longer the time of the muscle stimulation, the higher the advantageous effect of building muscles by using the muscle electrostimulation device. Therefore, in the current situation in which the time of wearing the muscle electrostimulation device is limited, there is a limit to increasing the advantageous effect of building muscles. To further increase the advantageous effect of building muscles, a muscle electrostimulation device that allows the user to easily and continuously wear for a long time is desired.

The muscle electrostimulation device 1 of Embodiment 8 is configured as follows in view of the problems. The same symbols are provided to the members equivalent to the members of the muscle electrostimulation device 1 in the preceding embodiments, and the description of the members and the description of the usage mode will not be repeated. When the drawings used in the description of this embodiment are the same as the drawings in the preceding embodiments, the drawings in the preceding embodiments will be used.

The muscle electrostimulation device 1 of this embodiment includes two or more electrodes 311 to 313 and 321 to 323 (see FIG. 2) and can apply electrostimulation to the muscles via the electrodes 311 to 313 and 321 to 323. As shown in FIGS. 1 to 3 in Embodiment 1, the muscle electrostimulation device 1 includes: the main body 10 that supplies power to the electrodes 311 to 313 and 321 to 323; and the sheet-shaped extending portion 120 extending outward from the main body 10. The electrodes 311 to 313 and 321 to 323 are arranged on one of the surfaces of the extending portion 120.

Figure 33:
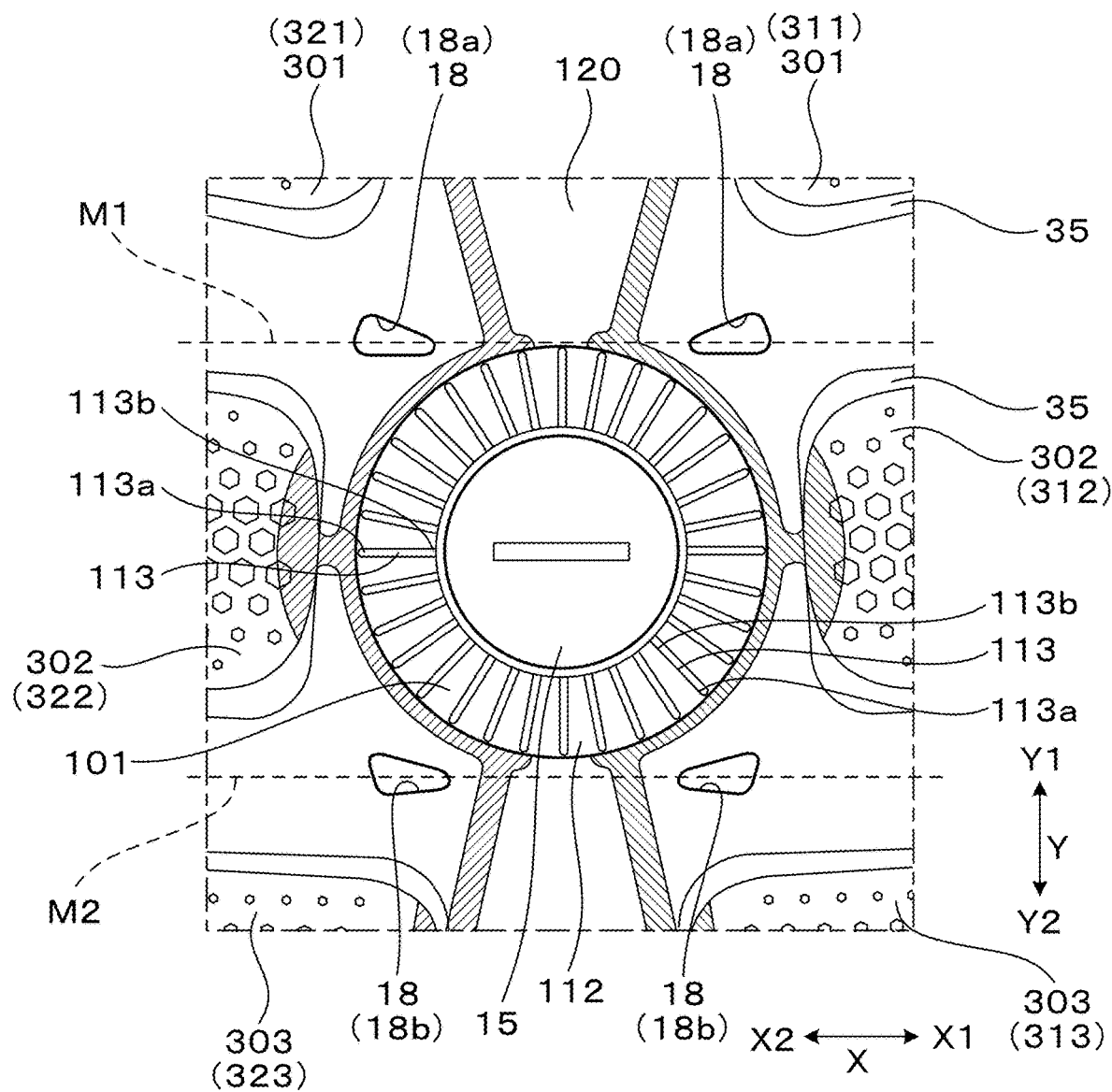
FIG. 33 is an enlarged view of main parts in the rear view of the muscle electrostimulation device in Embodiment 8.
Figure 34:
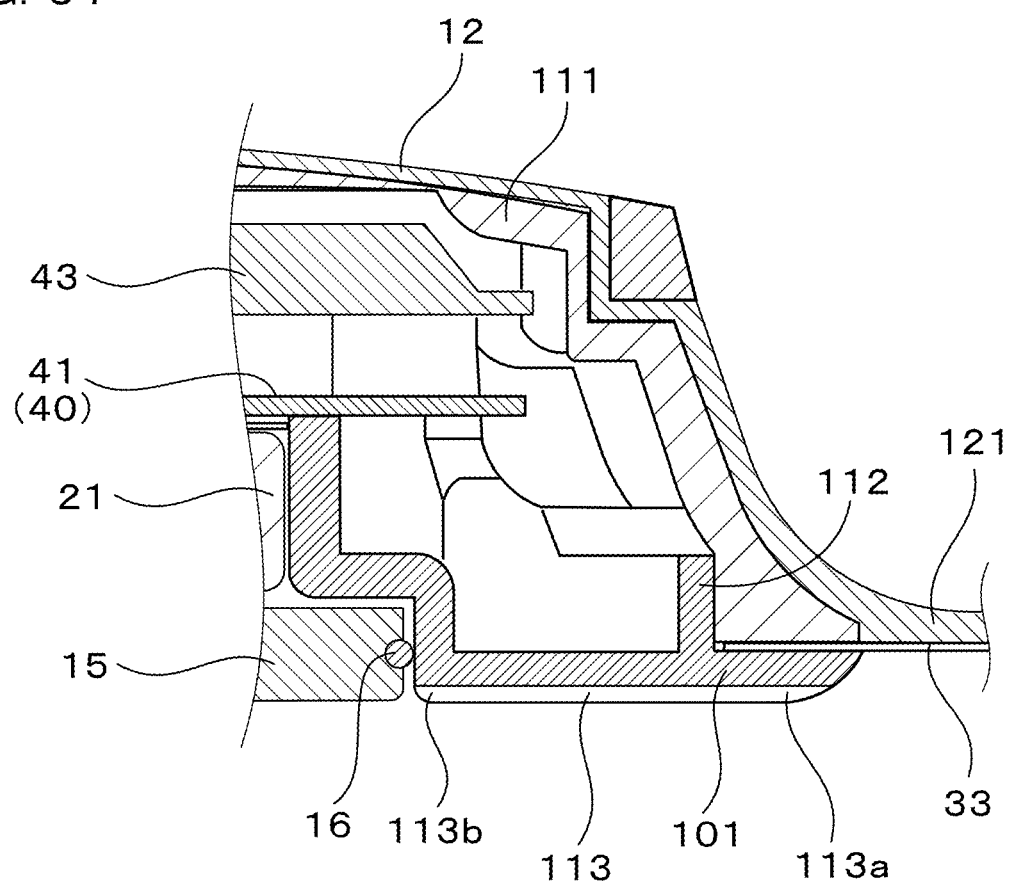
FIG. 34 is an enlarged view near a skin facing portion in a cross section corresponding to line IVa-IVa of FIG. 1 in Embodiment 8.

As shown in FIGS. 3 and 4a to 4c in Embodiment 1, the main body 10 includes a skin facing portion 101 that faces the human body when the muscle electrostimulation device 1 is used. As shown in FIGS. 33 and 34, the skin facing portion 101 includes a plurality of grooves 113 on the outer surface, in which at least ends 113a of the grooves 113 are arranged on or near a peripheral edge of the skin facing portion 101. The extending portion 120 includes the holes 18 penetrating in the thickness direction around the main body 10.

The skin facing portion 101 of the muscle electrostimulation device 1 in this embodiment includes the second case 112 and the lid 15 in the main body 10 as shown in FIGS. 4a to 4c and 33.

As shown in FIG. 33, the plurality of grooves 113 are arranged outside of the lid 15 in the skin facing portion 101, that is, on the outer surface of the second case 112. As shown in FIGS. 33 and 34, the grooves 113 of this embodiment radially extend from the center of the skin facing portion 101 in bottom view. The individual grooves 113 have a linear shape, and the ends 113a of the grooves 113 are arranged on the peripheral edge in the second case 112. Other ends 113b of the grooves 113 are arranged on edges in the second case 112 closer to the lid 15.

As shown in FIG. 2, the holes 18 are arranged at four places around the main body 10. More specifically, the holes 18 are arranged at four places outside of the leads 311a to 313a and 321a to 323a surrounding the main body 10. As shown in FIG. 33, holes 18a at two places among the holes 18 at four places are arranged on the upper side Y1 of the main body 10. Remaining holes 18b at two places among the holes 18 at four places are arranged on the lower side Y2 of the main body 10. The pair of holes 18a and the pair of holes 18b are lined up in the lateral direction X.

As shown in FIGS. 2 and 33, the pair of holes 18a arranged on the upper side Y1 are arranged such that a virtual straight line M1 formed by connecting the pair of holes 18a passes through the upper side Y1 of the main body 10 and passes between the first electrode pair 301 and the second electrode pair 302 described later. The pair of holes 18b arranged on the lower side Y2 are arranged such that a virtual straight line M2 formed by connecting the pair of holes 18b passes through the lower side Y2 of the main body 10 and passes between the second electrode pair 302 and the third electrode pair 303 described later.

The holes 18a and the holes 18b extend along the virtual straight line M1 and the virtual straight line M2, respectively.

The other components of the muscle electrostimulation device 1 in this embodiment are equivalent to the components in the muscle electrostimulation device 1 of Embodiment 1.

Hereinafter, effects of the muscle electrostimulation device 1 of this Embodiment will be described in detail.

The muscle electrostimulation device 1 includes the plurality of grooves 113 on the outer surface of the skin facing portion 101 (second case 112), wherein the ends 113a of the grooves 113 are arranged on the peripheral edge of the skin facing portion 101. The extending portion 120 includes the holes 18 penetrating in the thickness direction around the main body 10. Therefore, the muscle electrostimulation device 1 can naturally discharge, to the outside, sweat, moisture, or the like between the device and the human body when the user wears the device. Therefore, the muscle electrostimulation device 1 can alleviate the discomfort when the user wears the device for a long time, and the user can easily and continuously wear the device for a long time. The muscle electrostimulation device 1 can be used in a format that the user performs daily activities while wearing the muscle electrostimulation device 1.

The extending portion 120 includes two pairs of holes 18a and 18b. The holes 18 are arranged such that the virtual straight line L1 formed by connecting the holes 18a and the virtual straight line L2 formed by connecting the holes 18b pass through the positions deviated from the main body 10. Therefore, when the muscle electrostimulation device 1 is to be bent, it is unlikely that the main body 10 will obstruct the bending.

The muscle electrostimulation device 1 includes six electrodes 311 to 313 and 321 to 323 arranged in two rows. The holes 18 are arranged such that the virtual straight lines M1 and M2 extend in the arrangement direction (lateral direction X) of the right electrode group 31 as one of the rows of electrodes and the left electrode group 32 as the other row of electrodes. Therefore, falling or dropping of the muscle electrostimulation device 1 can be further prevented by wearing the muscle electrostimulation device 1 such that the virtual straight lines M1 and M2 are along the lateral direction X of the human body 2.

The muscle electrostimulation device 1 is arranged such that the virtual straight line L1 passes between the first electrode pair 301 and the second electrode pair 302 and such that the virtual straight line L2 passes between the second electrode pair 302 and the third electrode pair 303. Therefore, the muscle electrostimulation device 1 can attain advantageous effects of all of improvement in the durability of the electrodes 311 to 313 and 321 to 323, improvement in the property of following the bend of the body, and compatibility of the positions of the electrodes 311 to 313 and the 321 to 323 and the rectus abdominis muscles 4. Therefore, the user can particularly suitably wear the muscle electrostimulation device 1 around the abdomen 3.

As described, according to this embodiment, the muscle electrostimulation device 1 can be provided, the device capable of attaining the effects equivalent to the effects in Embodiment 1, capable of improving the sensitivity when the device is used, and capable of efficiently stimulating the muscles.

Figure 35:
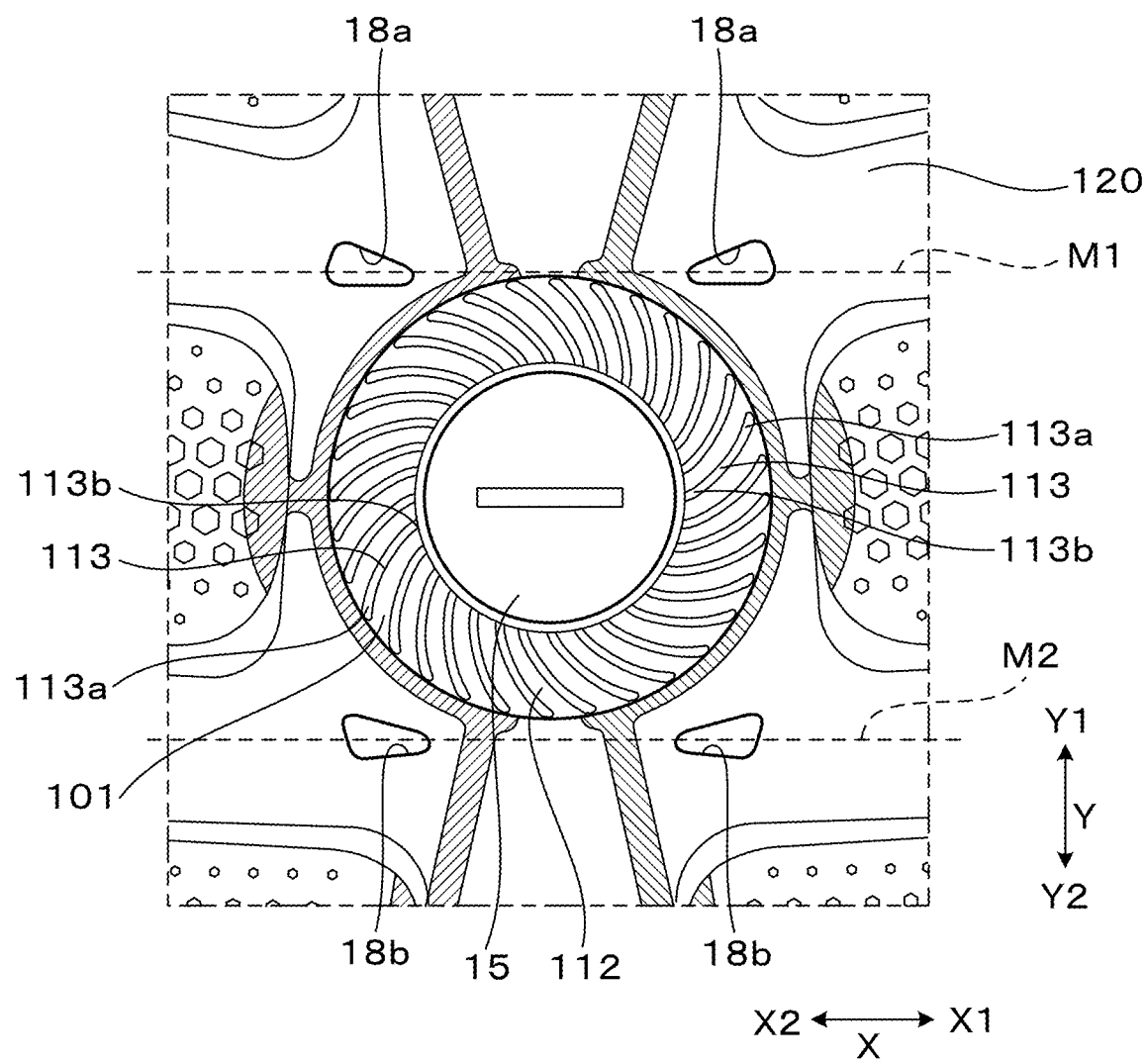
FIG. 35 is a partially enlarged rear view of the muscle electrostimulation device including curved and radially elongated grooves in Variation 7.

The shape, the number, and the positions of the grooves 113 are not limited to the mode of Embodiment 8 and can be changed to various modes. For example, the grooves 113 may have a shape curved in a spiral shape as in Variation 7 shown in FIG. 35.

Figure 36:
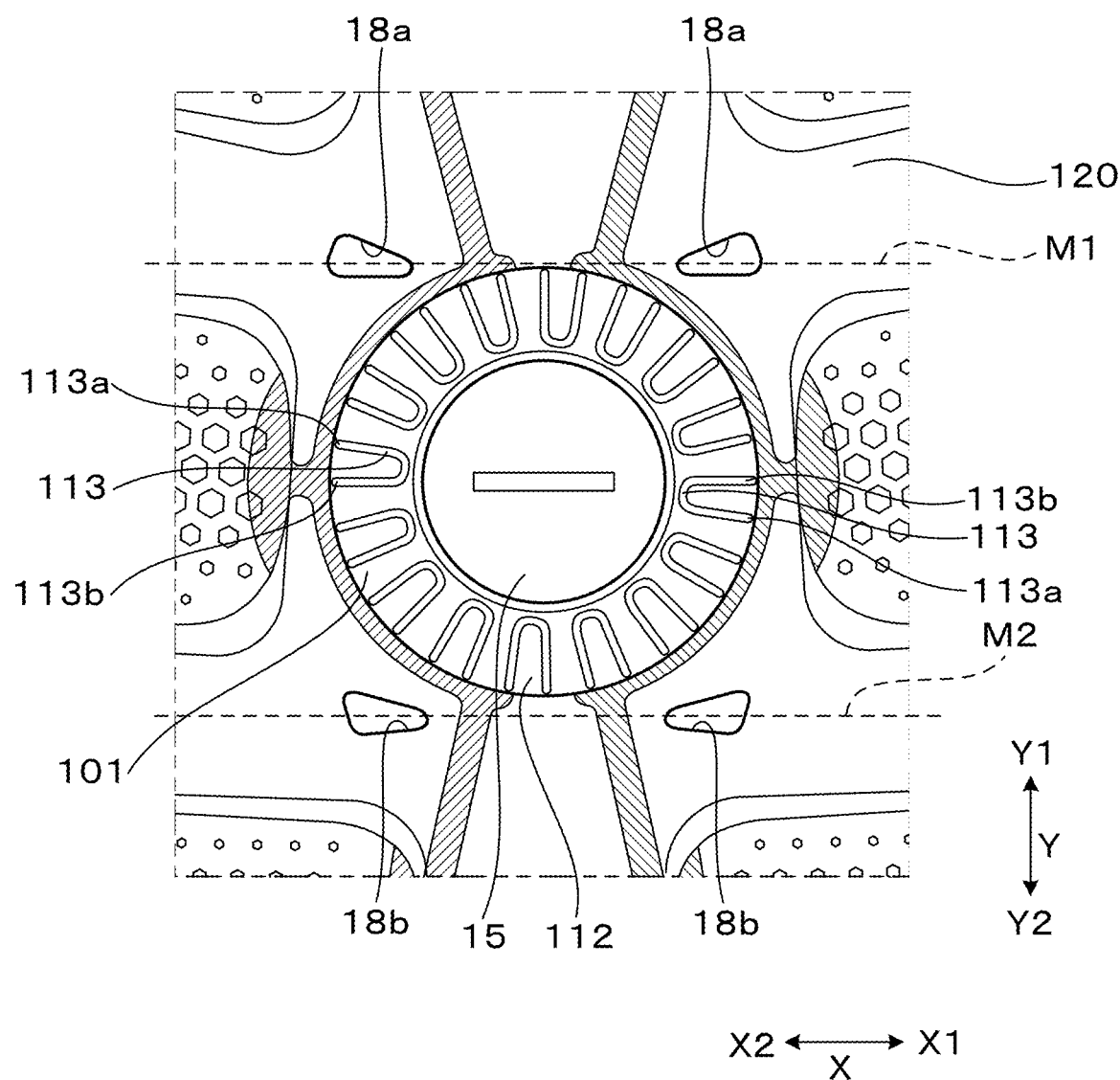
FIG. 36 is a partially enlarged rear view of the muscle electrostimulation device including the grooves with both ends arranged on a peripheral edge of the skin facing portion in Variation 8.

Furthermore, as in Variation 8 shown in FIG. 36, both ends 113a and 113b of the grooves 113 may be arranged on the peripheral edge of the skin facing portion 101, and the grooves 113 may have a substantially U-shape in plan view. The shape, the thickness, and the number of grooves 113 are not limited to Embodiments and Variations described above and can be changed to various modes.

Although not shown in the drawings, the shape, the number, and the positions of the holes 18 are not limited to the mode of Embodiment 8 and can be changed to various modes. For example, although the holes 18 are substantially oval in Embodiment 8, the shape of the holes 18 may be circular.

Figure 37:
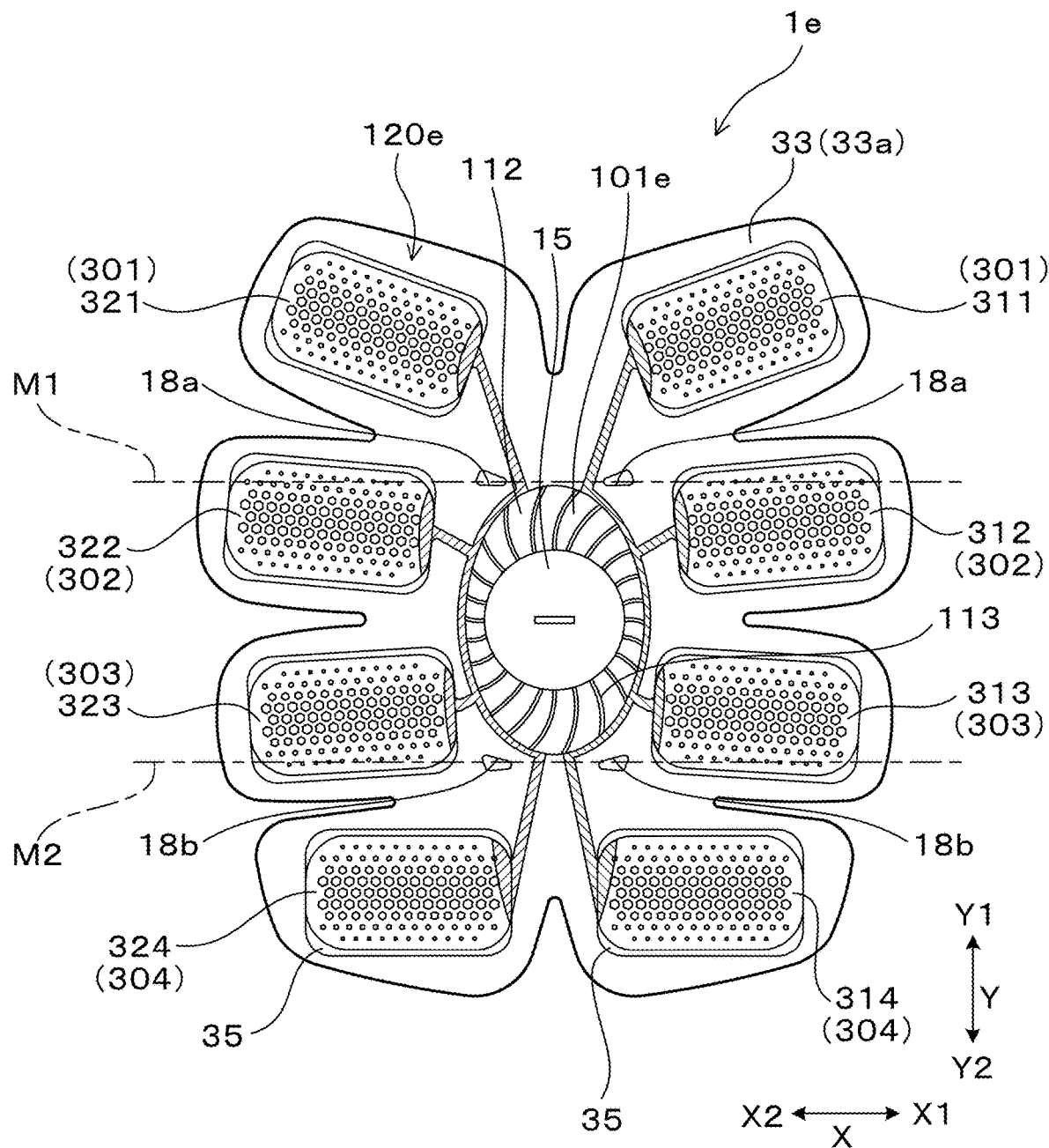
FIG. 37 is a rear view of a muscle electrostimulation device including a substantially elliptical skin facing portion in Variation 9.

Although the shape of the skin facing portion 101 in rear view is round in the example of the muscle electrostimulation device 1 illustrated in Embodiment 8, the following Variation 9 can be adopted instead of this. As shown in FIG. 37, a muscle electrostimulation device 1e of Variation 9 includes a main body 10e and an extending portion 120e extending outward from the main body 10e. Eight electrodes 311 to 314 and 321 to 324 are arranged in two rows on one of the surfaces of the extending portion 120e. The electrodes 311 to 314 and 321 to 324 configure four electrode pairs 301 to 304 arranged in the height direction Y. In this embodiment, for the convenience, the uppermost Y1 electrode pair of the four electrode pairs 301 to 304 is referred to as a first electrode pair 301, and the electrode pairs are referred to as a second electrode pair 302, a third electrode pair 303, and a fourth electrode pair 304 in order from the first electrode pair 301 toward the lower side Y2.

The main body 10e includes a skin facing portion 101e in a substantially elliptical shape in rear view. The skin facing portion 101e includes the second case 112 and the lid 15 as in Embodiment 1. The plurality of grooves 113 are arranged outside of the lid 15 in the skin facing portion 101.

Two pairs of holes 18 (18a, 18b) are arranged around the main body 10e. Of the holes 18, the pair of holes 18a arranged on the upper side Y1 are arranged such that the virtual straight line M1 formed by connecting the holes 18a passes through the upper side Y1 of the main body 10e. The pair of holes 18a are also arranged such that the virtual straight line M1 passes near the edge of the upper side Y1 in the second electrode pair 302.

The pair of holes 18b arranged on the lower side Y2 are arranged such that the virtual straight line M2 formed by connecting the holes 18b passes through the lower side Y2 of the main body 10e. The pair of holes 18b are also arranged such that the virtual straight line M2 passes near the edge of the lower side Y2 in the third electrode pair 303.

The other components are the same as in Embodiment 8. Among the symbols used in FIG. 37, the same symbols as in Embodiments 1 to 8 indicate the same constituent elements and the like as in Embodiments 1 to 8 unless otherwise particularly described.

Since the holes 18 and the grooves 113 are provided in Variation 9 as in Embodiment 8, the discomfort when the user wears the device for a long time can be alleviated, and the user can easily and continuously wear the device for a long time. The user can particularly suitably wear the muscle electrostimulation device 1e of Variation 9 around the abdomen as in Embodiment 8.

Embodiment 9

The muscle electrostimulation device of Embodiment 9 in the present invention will be described.

When the user continues to wear the muscle stimulation device of Patent Document 1 for a long time, sweat, moisture, and the like tend to stay between the device and the skin. Electronic components in the main body may be damaged when the sweat, moisture, and the like enter the main body, and it is desirable that this type of muscle stimulation device be a drip-proof type or have a higher waterproof performance. However, if the device has a waterproof structure, the main body is sealed, and the sound generated from the main body is less likely to be transmitted to the outside. Therefore, the conventional device has a problem that it is hard for the user to recognize that operation is accepted by the device, and the usability is poor.

The muscle electrostimulation device 1 of Embodiment 9 is configured as follows in view of the problem. The same symbols are provided to the members equivalent to the members of the muscle electrostimulation device 1 in the preceding embodiments, and the description of the members and the description of the usage mode will not be repeated. When the drawings used in the description of this embodiment are the same as the drawings in the preceding embodiments, the drawings in the preceding embodiments will be used.

The muscle electrostimulation device 1 of this embodiment includes the electrodes 311 to 313 and 321 to 323 and is configured to be capable of applying electrostimulation to the muscles via the electrodes 311 to 313 and 321 to 323 as in the device shown in FIG. 2 in Embodiment 1. As shown in FIGS. 1 to 3, the muscle electrostimulation device 1 includes: the main body 10 that supplies power to the electrodes 311 to 313 and 321 to 323; and the sheet-shaped extending portion 120 extending outward from the main body 10. The electrodes 311 to 313 and 321 to 323 are arranged on one of the surfaces of the extending portion 120.

Figure 38:
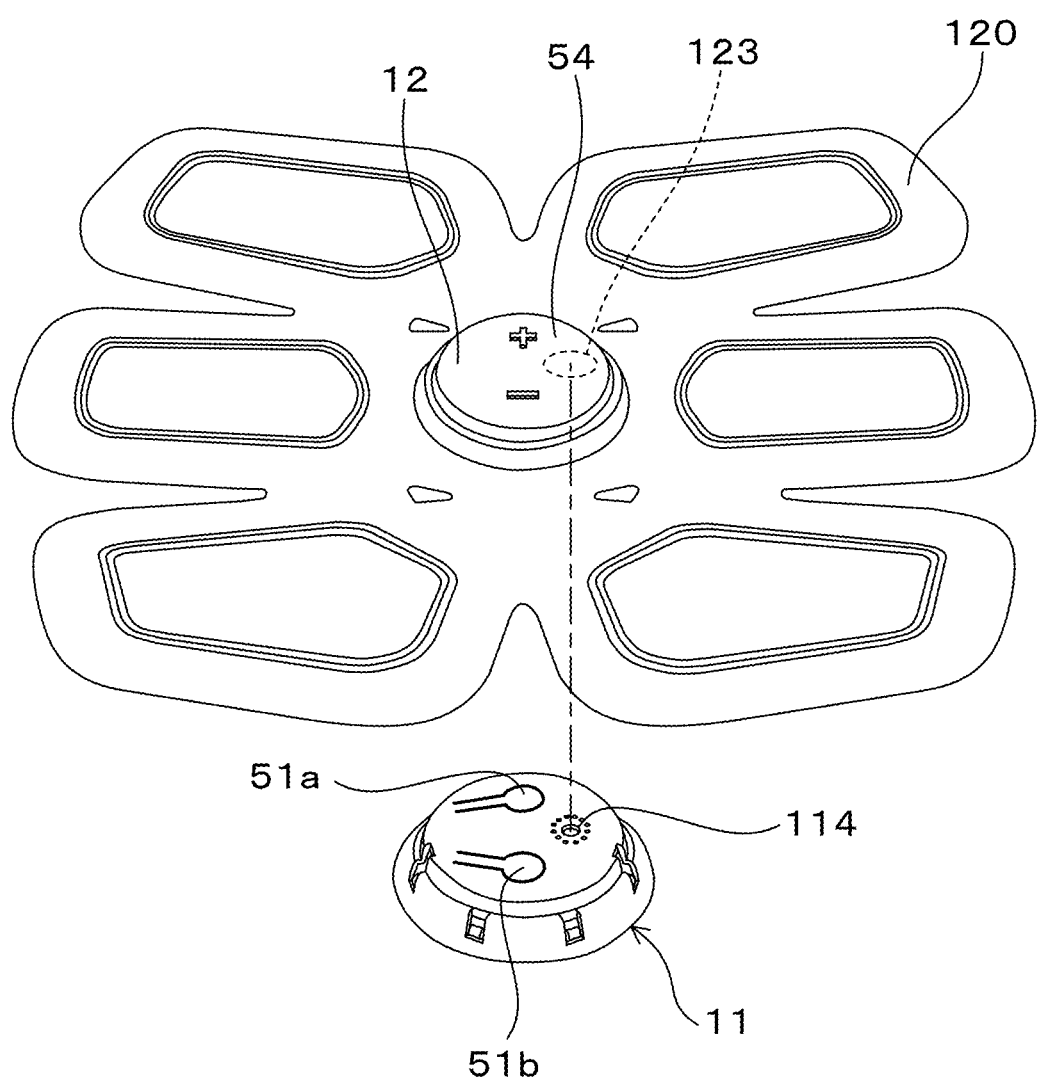
FIG. 38 is an exploded perspective view of the muscle electrostimulation device in Embodiment 9.
Figure 39:
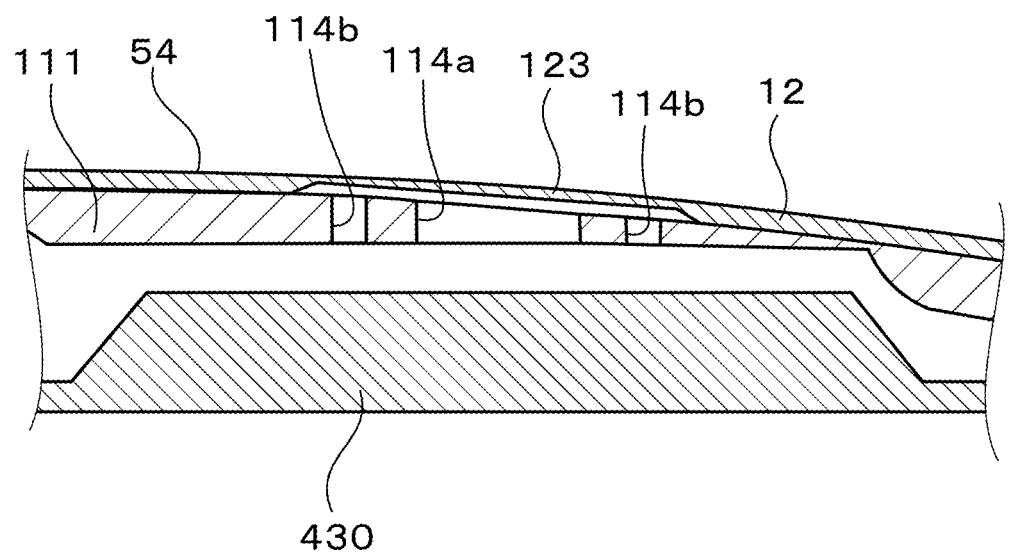
FIG. 39 is an enlarged view near a sounding body in the cross section corresponding to line IVa-IVa of FIG. 1 in Embodiment 9.

As shown in FIGS. 4a and 4b, the main body 10 includes the shell forming body 12 in which the operation surface 54 for changing the operation mode of the muscle electrostimulation device 1 is arranged on the outer surface. The main body 10 contains the sounding body 43 for producing sound when the operation mode is changed through the operation surface 54. As shown in FIGS. 38 and 39, the shell forming body 12 includes a thin body 123 thinner than the surroundings, at a position facing the sounding body 43.

As shown in FIGS. 1, 3, and 4a to 4c, the main body 10 of this embodiment includes the shell forming body 12 and the case 11 containing the sounding body 43. As shown in FIGS. 4a and 4b, the shell forming body 12 is substantially cup-shaped, and the operation surface 54 is arranged on the outer surface at the top of the shell forming body 12. The case 11 is housed in the shell forming body 12, and the second case 112 configuring part of the case 11 is exposed to the opening surface of the shell forming body 12. As shown in FIGS. 3 and 5, the user wears the muscle electrostimulation device 1 of this embodiment such that the second case 112 faces the human body 2, and the operation surface 54 faces the outer surface.

As shown in FIGS. 4a to 4c, a speaker 430 as the sounding body 43 is embedded in the case 11. The speaker 430 is arranged to face the operation surface 54, that is, the outer surface when the user wears the muscle electrostimulation device 1, and the speaker 430 faces the first case 111 configuring part of the case 11. Although the speaker 430 is adopted as the sounding body 43 in this embodiment, an electronic component that generates sound, such as a buzzer, can also be used in place of the speaker 430.

Figure 40:
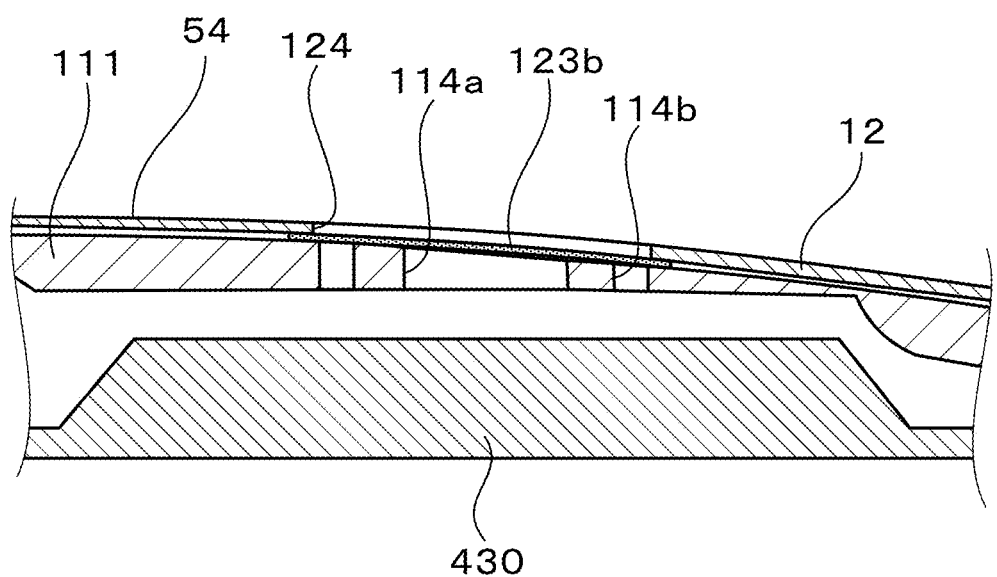
FIG. 40 is a partially enlarged sectional view showing main parts of the muscle electrostimulation device in which a thin body is a body separate from a shell forming body in Variation 10.

As shown in FIGS. 38, 39, and 40, a plurality of openings 114 (114a, 114b) are provided at positions facing the speaker 430 in the case 11. In this embodiment, an opening 114a is provided at a position corresponding to the center of the speaker 430, and a plurality of openings 114b with a smaller opening diameter are provided around the opening 114a.

As shown in FIGS. 38 and 39, the thin body 123 thinner than the surroundings is arranged at a position facing the opening 114 in the shell forming body 12. More specifically, the thin body 123 has a circular shape with the center at a position corresponding to the center of the opening 114a and is formed to face both the opening 114a and the openings 114b.

The thin body 123 of this embodiment is formed integrally with the shell forming body 12 and is arranged on the same plane as the outer surface of the shell forming body 12. That is, the thin body 123 is formed by depressing a part facing the first case 111 in the shell forming body 12 to form a concave shape.

The other components of the muscle electrostimulation device 1 in Embodiment 9 are equivalent to the components of the muscle electrostimulation device 1 in Embodiment 1.

Hereinafter, effects of the muscle electrostimulation device 1 of this embodiment will be described in detail.

The case 11 in the muscle electrostimulation device 1 houses the speaker 430 as the sounding body 43 and includes the openings 114 (114a, 114b) at the positions facing the speaker 430. The shell forming body 12 includes the thin body 123 at the position facing the opening 114. Therefore, the shell forming body 12 can efficiently transmit the sound generated from the speaker 430 to the outside of the main body 10 via the thin body 123 while securing the waterproof performance of the main body 10. Therefore, the muscle electrostimulation device 1 allows the user to easily recognize the generated sound upon the operation, compared to the conventional muscle electrostimulation device.

The thin body 123 is formed integrally with the shell forming body 12. Therefore, the number of components can be reduced compared to when the thin body 123 is a body separate from the shell forming body 12. Furthermore, work of joining the thin body 123 to the shell forming body 12 is not necessary in the process of creating the muscle electrostimulation device 1 in this case, and the productivity of the muscle electrostimulation device 1 can be further improved.

The thin body 123 is arranged on the same plane as the outer surface (operation surface 54) in the shell forming body 12. Therefore, dirt and the like are less likely to accumulate near the thin body 123, compared to when the thin body 123 is depressed inside of the outer surface of the shell forming body 12. Thus, the muscle electrostimulation device 1 can be easily maintained in a clean state. Furthermore, the design of the outer surface of the shell forming body 12 can be further improved.

The shell forming body 12 and the thin body 123 are formed by a silicone resin. Therefore, the sound generated from the speaker 430 can be efficiently transmitted to the outside. The waterproof performance of the main body 10 can be easily improved, and damage and the like of the thin body 123 can be prevented.

As described, the muscle electrostimulation device 1 of this embodiment allows the user to easily recognize whether the operation is accepted, and the usability can be further improved compared to the conventional muscle electrostimulation device. The muscle electrostimulation device 1 can more efficiently transmit the sound generated from the sounding body 43 to the outside, and the usability can be further improved even in a mode in which the user wears the device inside of the clothes, for example.

Although the thin body 123 is formed integrally with the shell forming body 12 in the example shown in Embodiment 9, the following Variation 10 can be adopted instead of this. In Variation 10, a thin body 123b is formed as a body separate from the shell forming body 12 as shown in FIG. 40. More specifically, the shell forming body 12 of Variation 4 includes a through hole 124 at a position corresponding to the center of the speaker 430. The thin body 123b is joined to an edge of the through hole 124. In Variation 10 shown in FIG. 40, the thin body 123b is joined to the edge closer to the case 11 in the thickness direction of the shell forming body 12. The other portions are the same as in Embodiment 9. In Variation 10, the same symbols are provided to the constituent elements equivalent to Embodiment 9, and the description will not be repeated.

In Variation 10, it is preferable to use a gas permeable material for the thin body 123b. For example, a porous film or the like made of a PTFE (polytetrafluoroethylene) resin can be suitably used for the material.

The type of the sound generated from the sounding body 43 is not particularly limited in the embodiment and the variation described above, and sound in various modes, such as a buzzer sound and an electronic sound, can be used. From the viewpoint of allowing the user to easily recognize the sound, it is preferable to use sound with a frequency of about 2000 to 5000 Hz at which a person tends to feel uncomfortable.

Although the sounding body 43 generates sound when "+" of the operation surface 54 is pressed to activate the muscle electrostimulation device 1 (FIG. 9, S101 and S102) and when "−" is pressed to end the muscle electrostimulation device 1 (FIG. 12, S401 and 402) in the examples illustrated in Embodiment 9 and Variation 10, the sound may be generated at other timing. For example, sound can be generated when the operation surface 54 is pressed to input the output level (FIG. 9, S106) after the activation of the muscle electrostimulation device 1.

Embodiment 10

The muscle electrostimulation device of Embodiment 10 in the present invention will be described.

When the user continues to wear the muscle stimulation device of Patent Document 1 for a long time, sweat, moisture, and the like tend to stay between the device and the skin. Electronic components in the main body may be damaged when the sweat, moisture, and the like enter the main body, and it is desirable that this type of muscle stimulation device be a drip-proof type or have a higher waterproof performance. However, if the device has a waterproof structure, the main body is sealed, and the sound generated from the main body is less likely to be transmitted to the outside. Therefore, the conventional device has a problem that it is hard for the user to recognize that operation is accepted by the device, and the usability is poor.

The muscle electrostimulation device 1 of Embodiment 10 is configured as follows in view of the problem. The same symbols are provided to the members equivalent to the members of the muscle electrostimulation device 1 in the preceding embodiments, and the description of the members and the description of the usage mode will not be repeated. When the drawings used in the description of this embodiment are the same as the drawings in the preceding embodiments, the drawings in the preceding embodiments will be used.

As in the device shown in FIGS. 1 to 3 in Embodiment 1, the muscle electrostimulation device 1 of this embodiment includes: the main body 10 that generates electrostimulation; the sheet-shaped extending portion 120 extending outward from the main body 10; and the electrodes 311 to 313 and 321 to 323 arranged on one of the surfaces of the extending portion 120, and the device is configured to be capable of applying electrostimulation to the muscles via the electrodes 311 to 323 and 321 to 323.

Figure 41A:
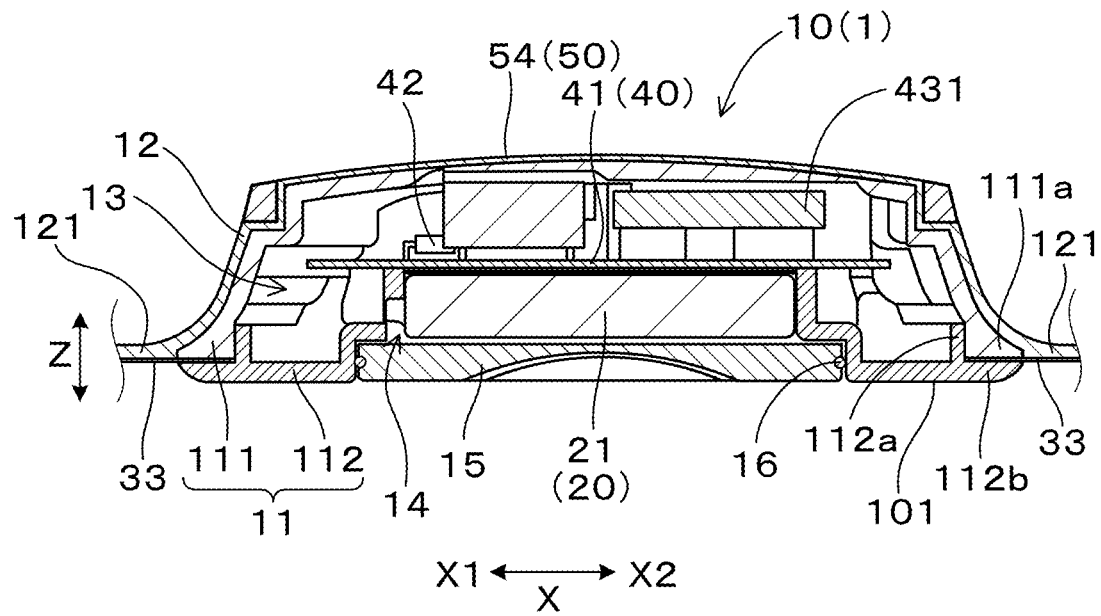
FIG. 41a is a partially enlarged sectional view corresponding to line IVa-IVa of FIG. 1 in embodiment 10.
Figure 41B:
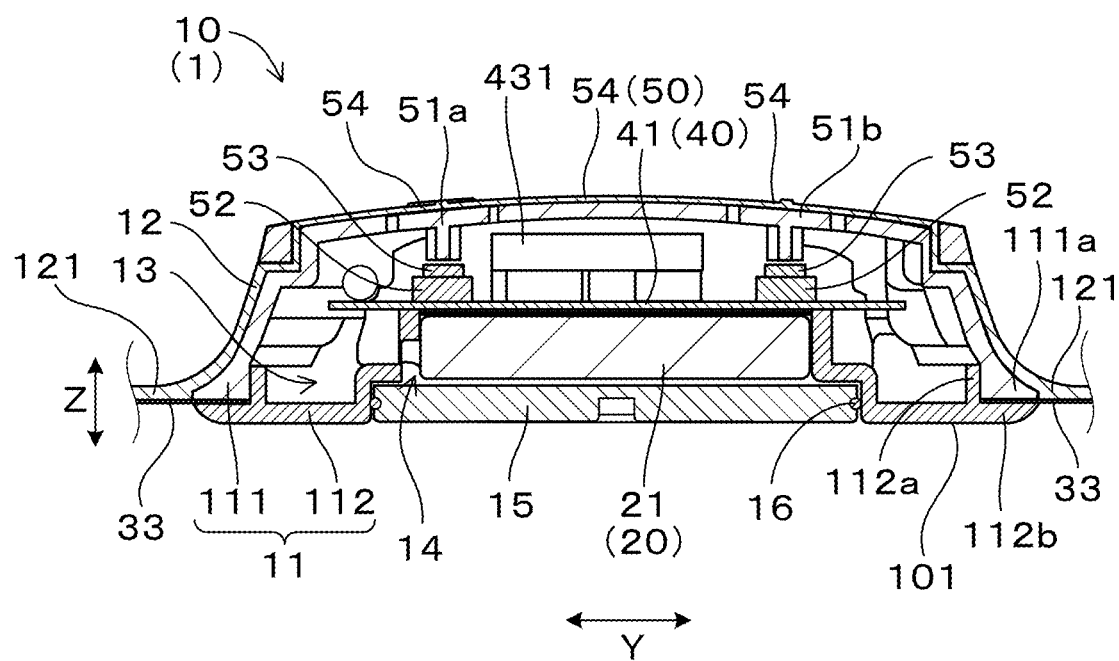
FIG. 41b is a partially enlarged sectional view corresponding to line IVc-IVc of FIG. 1.
Figure 42:
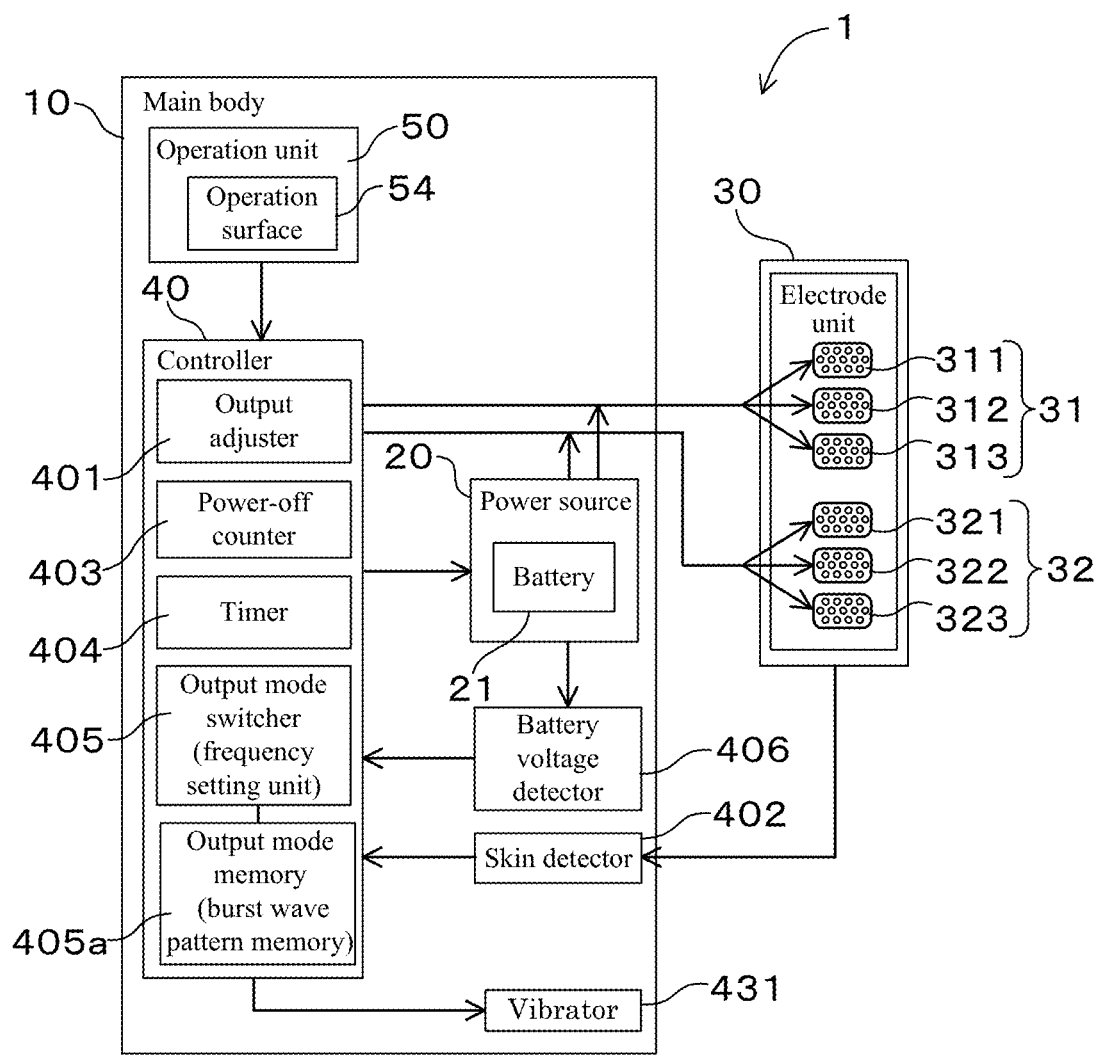
FIG. 42 is a block diagram showing a configuration of the muscle electrostimulation device in Embodiment 10.

As shown in FIGS. 41 and 42, a vibrator 431 is connected in the muscle electrostimulation device 1 of this embodiment instead of the speaker 43 in Embodiment 1. The vibrator 431 is embedded in the main body 10. The main body 10 includes, on the outer surface, the operation surface 54 for changing the supply mode of power in the controller 40.

The controller 40 is configured to vibrate the vibrator 431 when the supply mode of power to the electrode is changed. The shell forming body 12 covers at least part of the case 11.

The other components of the muscle electrostimulation device 1 in Embodiment 10 are equivalent to the components in the muscle electrostimulation device 1 of Embodiment 1.

Next, an operation flow of the muscle electrostimulation device 1 of this embodiment will be described in detail.

A main operation flow of the muscle electrostimulation device 1 of this embodiment is performed based on the main operation flow S100 shown in FIG. 9 as in the case of Embodiment 1. In the main operation flow S100, "+" of the operation surface 54 is pressed for two seconds (S101).

Accordingly, the power of the muscle electrostimulation device 1 is turned on, and the muscle electrostimulation device 1 is activated.

Figure 43A:
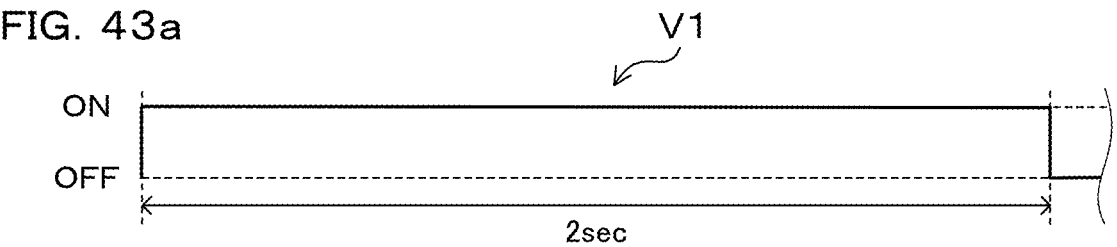
FIG. 43a is an explanatory view showing a power source operation pattern.

In this case, the controller 40 vibrates the vibrator 431 in a power source operation pattern V1 when the muscle electrostimulation device 1 is switched from the off-state to the on-state (S102, "notify activation"). An example of the power source operation pattern V1 includes a mode of vibrating the vibrator 431 for two seconds as shown in FIG. 43*a*. Subsequently, the muscle electrostimulation device 1 is brought into the output standby state, the output level is set to 0, and the input into the operation unit 50 is invalidated (S103).

Next, the skin detector 402 detects whether the skin is in contact with the electrode unit 30 (S104). If the skin detector 402 detects that the skin is in contact with the electrode unit 30 (Yes in S104), the operation unit 50 is validated (S105). The output level is input through the operation unit 50 (S106). The output level is input from the operation surface 54 of the operation unit 50. The output level is incremented by 1 every time "+" of the operation surface 54 of the operation unit 50 is pressed, and the output level is decremented by 1 every time "−" of the operation surface 54 is pressed.

In this case, the controller 40 vibrates the vibrator 431 in strength change patterns when the output level is changed (S106, "notify level change"). The strength change patterns of this embodiment include three types of vibration patterns including a strength increase pattern V2 shown in FIG. 43*b*, a strength reduction pattern V3 shown in FIG. 43*c*, and a limit notification pattern V4 shown in FIG. 43*d*.

Figure 43B:
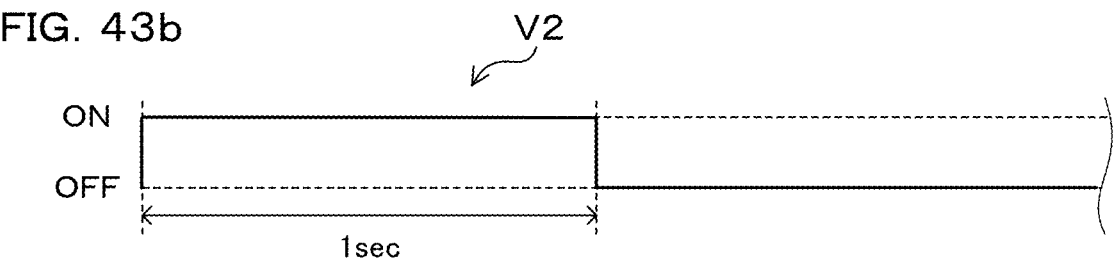
FIG. 43b is an explanatory view showing a strength increase pattern.

The strength increase pattern V2 is a vibration pattern generated when the output level is increased by pressing "+" of the operation surface 54. An example of the strength increase pattern V2 includes a mode of vibrating the vibrator 431 for one second as shown in FIG. 43*b*.

Figure 43C:
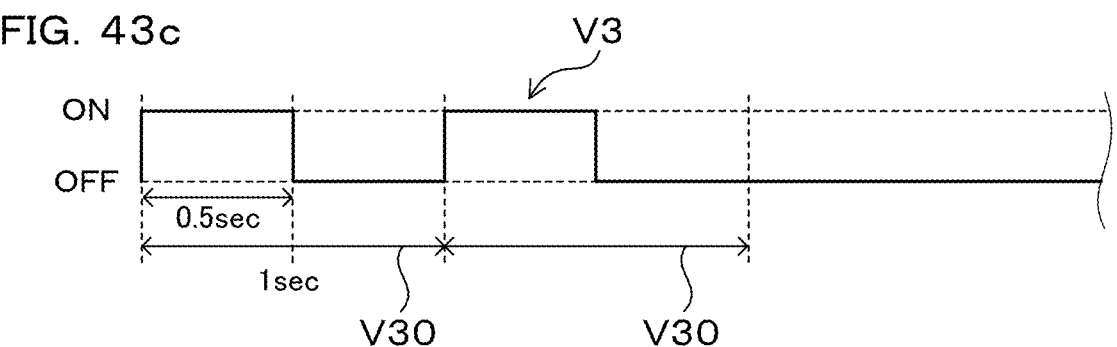
FIG. 43c is an explanatory view showing a strength reduction pattern.

The strength reduction pattern V3 is a vibration pattern generated when the output level is reduced by pressing "−". An example of the strength reduction pattern V3 includes a mode of repeating a basic waveform V30 twice, in which the vibrator 431 is vibrated for 0.5 seconds, and then the vibrator 431 is stopped for 0.5 seconds, as shown in FIG. 43*c*.

Figure 43D:
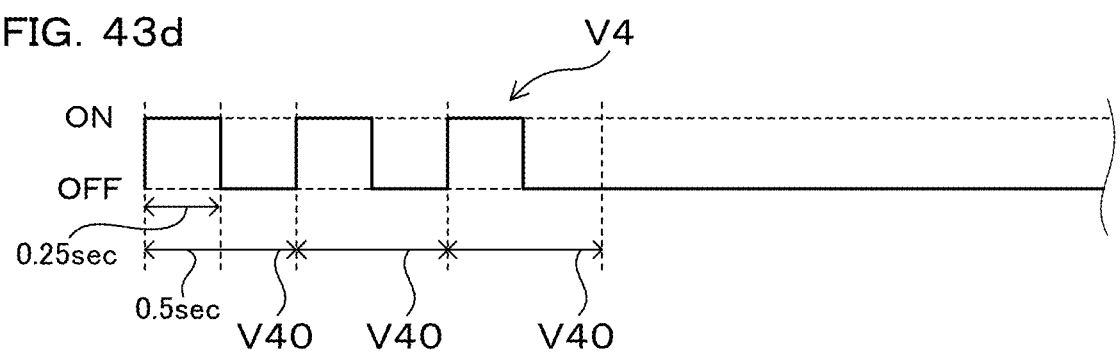
FIG. 43d is an explanatory view showing a limit notification pattern.

The limit notification pattern V4 is a vibration pattern generated when "+" is pressed with the output level in the maximum state or when "−" is pressed with the output level in the minimum state. An example of the limit notification pattern V4 includes a mode of repeating a basic waveform V40 three times, in which the vibrator 431 is vibrated for 0.25 seconds, and then the vibrator 431 is stopped for 0.25 seconds, as shown in FIG. 43*d*.

The operation flow from the step of inputting the output level via the operation unit 50 (S106) to the step of stopping the muscle electrostimulation device 1 (S112) is the same as in the case of Embodiment 1.

Figure 43E:
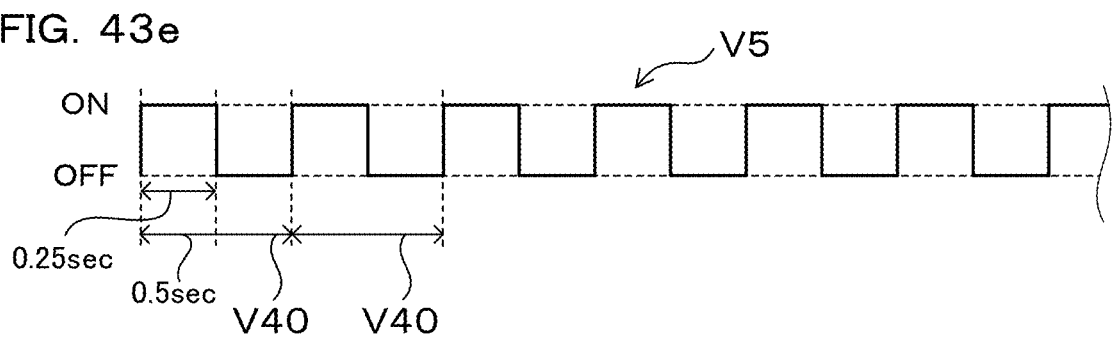
FIG. 43e is an explanatory view showing an error pattern of a vibrator in Embodiment 10.

On the contrary, if the skin detector 402 determines that the skin is not in contact with the electrode unit 30 (No in S104), the controller 40 generates an error pattern V5 (see FIG. 43*e*) for notifying the determination and vibrates the vibrator 431 (S113, "notify non-detection of skin"). An example of the error pattern V5 includes a mode of repeating the basic waveform V40, in which the vibrator 431 is vibrated for 0.25 seconds, and then the vibrator 431 is stopped for 0.25 seconds, as shown in FIG. 43*d*, until the skin detector 402 determines that the skin is in contact with the electrode unit 30.

The controller 40 further transmits a count start signal to the power-off counter 403, and the power-off counter 403 starts to measure the elapsed time (S114). The operation flow from the step of starting to measure the elapsed time (S114) to the step of stopping the muscle electrostimulation device 1 (S117) is the same as in the case of Embodiment 1.

Next, interrupt processes that interrupt S105 to S110 in the main operation flow S100 and that are preferentially processed will be described. The skin detection interrupt process S200 as a first interrupt process in the muscle electrostimulation device 1 of this embodiment is executed based on the skin detection interrupt process S200 shown in FIG. 10 as in the case of Embodiment 1.

The skin detection interrupt process S200 is used as a function for automatically turning off the power source when the electrode drops off from the human body in the middle of usage. In the skin detection interrupt process S200, the skin detector 402 first detects whether the skin is in contact with the electrode unit 30 as in the case of Embodiment 1 (S201). If the skin detector 402 detects that the skin is in contact with the electrode unit 30 (Yes in S201), the process returns to the original flow in the main operation flow S100.

On the contrary, if the skin detector 402 determines that the skin is not in contact with the electrode unit 30 (No in S201), the controller 40 generates the error pattern V5 (see FIG. 43*e*) as in S113 described above and vibrates the vibrator 431 (S202, "notify non-detection of skin"). The controller 40 transmits the count start signal to the power-off counter 403, and the power-off counter 403 starts to measure the elapsed time (S203).

From the next step in which the skin detector 402 detects whether the skin is in contact with the electrode unit 30 (S204) to the step in which the power of the muscle electrostimulation device 1 is turned off (S206) are the same as in the case of Embodiment 1.

Next, the battery voltage reduction process S300 as a second interrupt process that interrupts S105 to S110 in the main operation flow S100 (see FIG. 9) and that is preferentially processed will be described. The battery voltage reduction process S300 in the muscle electrostimulation device 1 in this embodiment is executed based on the battery voltage reduction process S300 shown in FIG. 11 as in the case of Embodiment 1.

As shown in FIG. 11, in the battery voltage reduction process S300, the battery voltage detector 406 first determines whether the detected battery voltage V of the battery 21 in the power source 20 is lower than the predetermined threshold Vm as in the case of Embodiment 1 (S301). If the battery voltage detector 406 determines that the battery voltage V is not lower than the predetermined threshold Vm (No in S301), the process returns to the original flow in the main operation flow S100.

On the contrary, if the battery voltage detector 406 determines that the battery voltage V is lower than the threshold Vm, the controller 40 generates the error pattern V5 (see FIG. 43*e*) and vibrates the vibrator 431 (S302, "notify reduction in battery voltage"). The controller 40 transmits the count start signal to the power-off counter 403, and the power-off counter 403 starts to measure the elapsed time (S303).

From the next step of determining whether the elapsed time exceeds two minutes in the power-off counter 403 (S304) to the step in which the power of the muscle electrostimulation device 1 is turned off (S305) are the same as in the case of Embodiment 1.

Next, the suspension process S400 as a third interrupt process that interrupts S105 to S110 in the main operation flow S100 (see FIG. 9) and that is preferentially processed will be described. The suspension process S400 in the muscle electrostimulation device 1 of this embodiment is executed based on the suspension process S400 shown in FIG. 12 as in the case of Embodiment 1.

As shown in FIG. 12, in the suspension process S400, the controller 40 first determines whether the time of the press of the "−" button of the operation surface 54 in the operation unit 50 is equal to or longer than two seconds (S401) as in the case of Embodiment 1. If the controller 40 determines that the time of the press of the "−" button is not equal to or longer than two seconds (No in S401), the process returns to the original flow in the main operation flow S100.

On the contrary, if the controller 40 determines that the time of the press of the "−" button is equal to or longer than two seconds (Yes in S401), the controller 40 vibrates the vibrator 431 in the power source operation pattern V1 when the muscle electrostimulation device 1 is switched from the on-state to the off-state (S402, "notify end"). An example of the power source operation pattern includes the mode shown in FIG. 43a. The power source is then turned off (S403).

Hereinafter, effects of the muscle electrostimulation device 1 of this embodiment will be described in detail.

The muscle electrostimulation device 1 of this embodiment includes the main body 10 containing the power source 20, the controller 40, and the vibrator 431 and including the operation surface 54 on the outer surface. The controller 40 is configured to vibrate the vibrator 431 when the supply mode of the power to the electrodes 311 to 313 and 321 to 323 is changed. Therefore, the muscle electrostimulation device 1 allows the user to easily recognize that the operation is accepted by the muscle electrostimulation device 1 through the vibration of the vibrator 431.

The muscle electrostimulation device 1 of this embodiment is configured to generate different vibration patterns according to the operation performed by the user as shown in FIGS. 9 to 12 and 43. Therefore, the user can more easily recognize the type of the operation accepted by the controller 40, and the usability of the muscle electrostimulation device 1 can be further improved. The muscle electrostimulation device 1 allows the user to easily recognize the type of the operation accepted by the controller 40 independently of the vision or hearing, and the device can also be suitably used in the mode of wearing the device under the clothes to use.

The main body 10 includes the skin facing portion 101 (second case 112) that faces the human body when the user wears the muscle electrostimulation device 1, and the skin facing portion 101 protrudes more than the surroundings. Therefore, the user can more easily sense the vibration while the user wears the muscle electrostimulation device 1. As a result, the usability of the muscle electrostimulation device 1 can be further improved.

Furthermore, the power source 20 is arranged near the skin facing portion 101 in the main body 10. Therefore, the body temperature of the user can prevent excessive reduction in the temperature of the power source 20 while the user wears the muscle electrostimulation device 1. As a result, the variations of power supplied from the power source 20 can be further reduced.

As described, according to Embodiment 10, the muscle electrostimulation device 1 with excellent usability is provided, the device attaining the effects equivalent to the effects in Embodiment 1.

Although the vibrator 431 is vibrated to notify acceptance of operation or occurrence of error in the example illustrated in Embodiment 10, the vibrator 431 can be vibrated at a timing other than a certain notification. For example, the vibrator 431 may be vibrated between the first status and the second status or between the second status and the third status in FIG. 8.

Since the electrostimulation by the muscle electrostimulation device 1 directly moves the muscles, the user may feel that the stimulated muscles are fatigued depending on the situation if the user continues to use the muscle electrostimulation device 1 for a long time. Therefore, for example, the vibrator 431 can be vibrated at a time of an interval between the first status and the second status, and an advantageous effect of relaxing the fatigued muscles can be expected. The vibration of the vibrator 431 can apply a type of stimulation different from the electrostimulation, and the ease of use of the muscle electrostimulation device 1 can be further improved.

Although the vibration pattern of the vibrator 431 is changed for each type of the operation in the example illustrated in Embodiment 10, other configurations can also be adopted. For example, the controller 40 may not include all the power source operation pattern V1, the strength increase pattern V2, the strength reduction pattern V3, and the limit notification pattern V4 and may not include some of the vibration patterns. Furthermore, the strength increase pattern can be the same vibration pattern as the strength reduction pattern, for example. The vibration patterns shown in FIG. 43 are examples, and the duration, the intervals, the number of repetitions, and the like of the vibration may be appropriately changed. That is, the vibrator 431 may be vibrated for a plurality of times in the power source operation pattern, for example.

Embodiment 11

The muscle electrostimulation device of Embodiment 11 in the present invention will be described.

In the configuration disclosed in Patent Document 1, gel pads in a predetermined size are attached to the electrodes. Therefore, changing the size or the conductivity of the gel pads according to the preference of each user is not easy.

The muscle electrostimulation device 1 of Embodiment 11 is configured as follows in view of the problem. The same symbols are provided to the members equivalent to the members of the muscle electrostimulation device 1 in the preceding embodiments, and the description of the members and the description of the usage mode will not be repeated. When the drawings used in the description of this embodiment are the same as the drawings in the preceding embodiments, the drawings in the preceding embodiments will be used.

In the muscle electrostimulation device 1 of Embodiment 11, a gel with conductivity and relatively low-viscosity adhesiveness are spread in a size (range) and thickness desired by the user so as to cover the electrodes 311 to 323, instead of attaching the gel pads 35 so as to cover the electrodes 311 to 323 in FIG. 2. An example of the gel includes a gel with sodium alginate as a main component, wherein the gel can be applied to cover the electrodes 311 to 323, and the gel has viscosity such that the gel does not easily runs off when the gel is applied.

The thickness of the gel applied to cover the electrodes 311 to 323 is not particularly limited, and the conductivity and the like of the gel can be taken into account to determine the thickness. For example, the thickness of the gel can be relatively thick to increase the electric resistance of the gel and reduce the conductivity so that the electrostimulation applied from the electrodes 311 to 323 becomes mild.

The other components of the muscle electrostimulation device 1 in Embodiment 11 are equivalent to the components of the muscle electrostimulation device 1 in Embodiment 1.

As described, according to Embodiment 11, the muscle stimulation electric device 1 can be provided, the device capable of attaining the effects equivalent to the effects in Embodiment 1 and capable of easily changing the size and the conductivity of the gel according to the preference of each user.

Embodiment 12

The muscle electrostimulation device of Embodiment 12 in the present invention will be described.

In the configuration disclosed in Patent Document 1, when the device is repeatedly used, dust may be attached to the gel pads attached to the electrodes, or the adhesive force may be deteriorated. In such a case, the gel pads are separately replaced with new gel pads.

However, the burden of the user increases when the gel pads are replaced with new gel pads every time in such a case. The gel pads are usually distributed in the market with protective sheets attached to both surfaces. Therefore, the user needs to peel off the protective sheets from the gel pads when the user replaces the gel pads, and the protective sheets become trash. The trash is generated every time the gel pads are replaced. The larger the number of electrodes and the number of used gel pads, the larger the burden and the amount of trash in the replacement.

The muscle electrostimulation device 1 of Embodiment 12 is configured as follows in view of the problem. The same symbols are provided to the members equivalent to the members of the muscle electrostimulation device 1 in the preceding embodiments, and the description of the members and the description of the usage mode will not be repeated. When the drawings used in the description of this embodiment are the same as the drawings in the preceding embodiments, the drawings in the preceding embodiments will be used.

Figure 44:
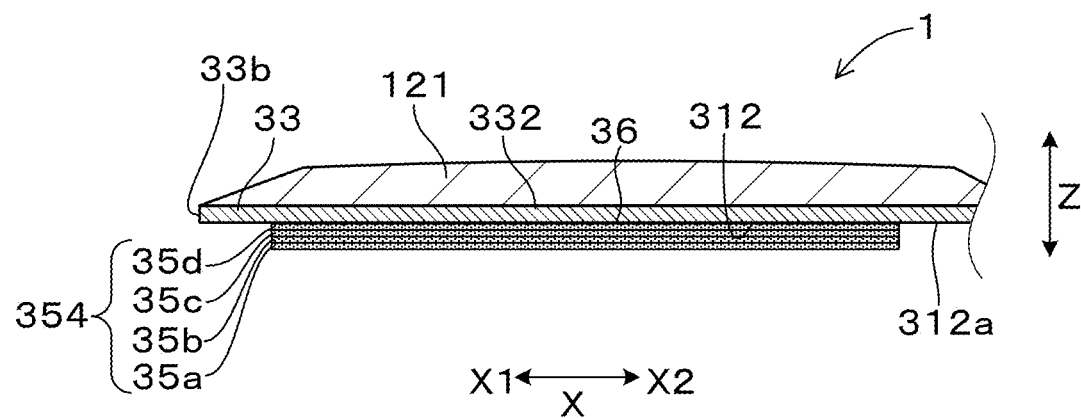
FIG. 44 is a partially enlarged sectional view corresponding to line IVa-IVa of FIG. 1 in Embodiment 12.

The muscle electrostimulation device 1 of Embodiment 12 is provided with laminated gel pads 354 formed by laminating a plurality of gel pads 35a to 35d as shown in FIG. 44, instead of the gel pads 35 attached to cover the electrodes 311 to 324 in FIG. 2. In this embodiment, the laminated gel pads 354 are formed by laminating four gel pads 35a to 35d. The laminated gel pads 354 can be peeled off in order from the gel pad 35a on the side opposite to the side attached to the electrodes 311 to 323.

When dust is attached to the gel pad 35a on the side opposite to the side attached to the electrodes 311 to 323, or the adhesive force is deteriorated in the laminated gel pads 354 after the repeated use of the muscle electrostimulation device 1 of this embodiment, the gel pad 35a can be peeled off to expose the gel pad 35b laminated below (closer to the electrodes 311 to 323) the gel pad 35a. Since the gel pad 35b has been covered by the peeled gel pad 35a, dust is not attached, and the adhesive force is not reduced. Therefore, the gel pad 35a can be peeled off to remove the dust from the laminated gel pads 354 and recover the adhesive force.

As a result, the burden of replacing the gel pads 35 can be eliminated, and the trash, such as the protective sheets, can be reduced during the distribution, compared to when the gel pads 35 are replaced with new gel pads 35. Even when the number of electrodes is large, the burden of replacing the gel pads 35 and the amount of trash generated in association with the replacement can be reduced by using the laminated gel pads 354 for the electrodes 311 to 323. The effects equivalent to the effects in Embodiment 1 are also attained in this embodiment.

Embodiment 13

The muscle electrostimulation device of Embodiment 13 in the present invention will be described.

In the configuration disclosed in Patent Document 1, the gel pad is attached to each electrode. The gel pads are replaced with new ones when dust is attached to the gel pads or when the adhesive force is deteriorated after repeated use. However, the larger the number of electrodes, the greater the burden of work of attaching the gel pads one by one in replacing the gel pads.

The muscle electrostimulation device 1 of Embodiment 13 is configured as follows in view of the problem. The configuration of the muscle electrostimulation device 1 of Embodiment 13 is equivalent to the configuration of the muscle electrostimulation device 1 of Embodiment 1. When the drawings used in the description of this embodiment are the same as the drawings in the preceding embodiments, the drawings in the preceding embodiments will be used.

Figure 45:
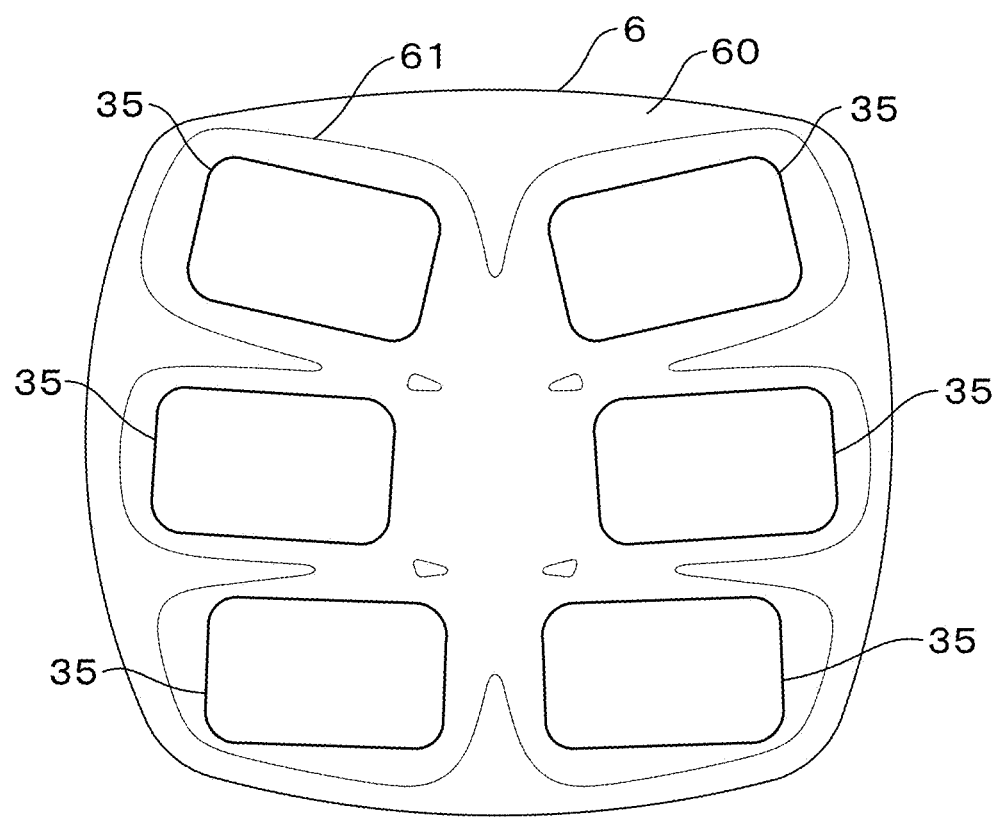
FIG. 45 is a front view of a mat with gel pads attached in Embodiment 14.

In the muscle electrostimulation device 1 of Embodiment 13, a mat 6 provided with a plurality of new gel pads 35 for replacement is used in replacing the gel pads 35 as shown in FIG. 45. The mat 6 has a sheet shape and has a pseudo-rectangular external form a little larger than the external form of the muscle electrostimulation device 1. An external form 61 of the muscle electrostimulation device 1 and shapes 618 of the holes 18 are printed on a paste surface 60 that is a surface in the mat 6 provided with the gel pads 35. In the external form 61 of the paste surface 60, the gel pads 35 are attached to positions equivalent to the positions provided with the gel pads 35 in the muscle electrostimulation device 1. In this embodiment, six gel pads 35 are attached to the paste surface 60. Note that a protective sheet (not shown) covering the plurality of gel pads 35 all together is attached to the mat 6 provided with the gel pads 35 during the distribution.

To replace the gel pads 35, all the gel pads 35 are first removed from the muscle electrostimulation device 1. The protective sheet (not shown) is then removed from the mat 6 provided with the gel pads 35. Subsequently, the paste surface 60 of the mat 6 is arranged to face the surface closer to the skin facing portion 101 (see FIG. 3) of the muscle electrostimulation device 1, and the paste surface 60 is brought into contact with the surface closer to the skin facing portion 101 while the external form 61 of the paste surface 60 and the periphery of the muscle electrostimulation device 1 are put together, thereby attaching the gel pads 35 to the surface closer to the skin facing portion 101 of the muscle electrostimulation device 1. The mat 6 is slowly peeled off so that the gel pads 35 are not peeled off from the muscle electrostimulation device 1. Accordingly, the gel pads 35 are attached to the positions for attaching the gel pads 35 in the muscle electrostimulation device 1. A surface treatment may be applied to the paste surface 60 to facilitate peeling of the gel pads 35.

As described, the mat 6 provided with the gel pads 35 can be used to attach the plurality of gel pads 35 to predetermined positions of the muscle electrostimulation device 1 all together. Therefore, the burden of replacing the gel pads 35 is significantly reduced compared to when the gel pads 35 are attached one by one. Furthermore, only one protective sheet becomes trash when the gel pads 35 are replaced, and the amount of trash can be reduced.

As described, according to Embodiment 13, the muscle electrostimulation device 1 can be provided, the device capable of attaining the effects equivalent to the effects in Embodiment 1, capable of significantly reducing the burden in attaching the pads 35, and capable of reducing the amount of trash in replacing the gel pads.

Embodiment 14

The muscle electrostimulation device of Embodiment 14 in the present invention will be described.

The muscle electrostimulation device 1 of Embodiment 14 includes gel pads 35 with a cosmetic component, instead of the gel pads 35 in Embodiment 1. Examples of the cosmetic component of the gel pads 35 include capsaicin effective in promoting metabolism, various vitamins effective in maintaining the elasticity, luster, smoothness, and the like of the skin, and various components effective in increasing the water retention of the skin. The gel pads 35 may include a plurality of cosmetic components.

The cosmetic component included in the gel pads 35 may be contained in advance in the gel pads 35, or the user may permeate or apply the cosmetic component to the gel pads 35 during or before use.

The other components of the muscle electrostimulation device 1 in this embodiment are equivalent to the components of the muscle electrostimulation device 1 in Embodiment 1.

As described, according to Embodiment 14, the muscle electrostimulation device 1 can be provided, the device capable of attaining the effects equivalent to the effects in Embodiment 1 and capable of attaining the cosmetic effect of skin through the cosmetic component included in the gel pads 35.

Embodiment 15

The muscle electrostimulation device of Embodiment 15 in the present invention will be described.

Although the device is attached to the human body and used in the configuration disclosed in Patent Document 1, the configuration is not particularly suitable for stimulating a predetermined part because the part of the human body for attaching the device is not particularly limited, and there is a room for improvement in effectively stimulating the rectus abdominis muscles.

The muscle electrostimulation device 1 of Embodiment 15 is configured as follows in view of the problem. The same symbols are provided to the members equivalent to the members of the muscle electrostimulation device 1 in the preceding embodiments, and the description of the members and the description of the usage mode will not be repeated. When the drawings used in the description of this embodiment are the same as the drawings in the preceding embodiments, the drawings in the preceding embodiments will be used.

Figure 46:
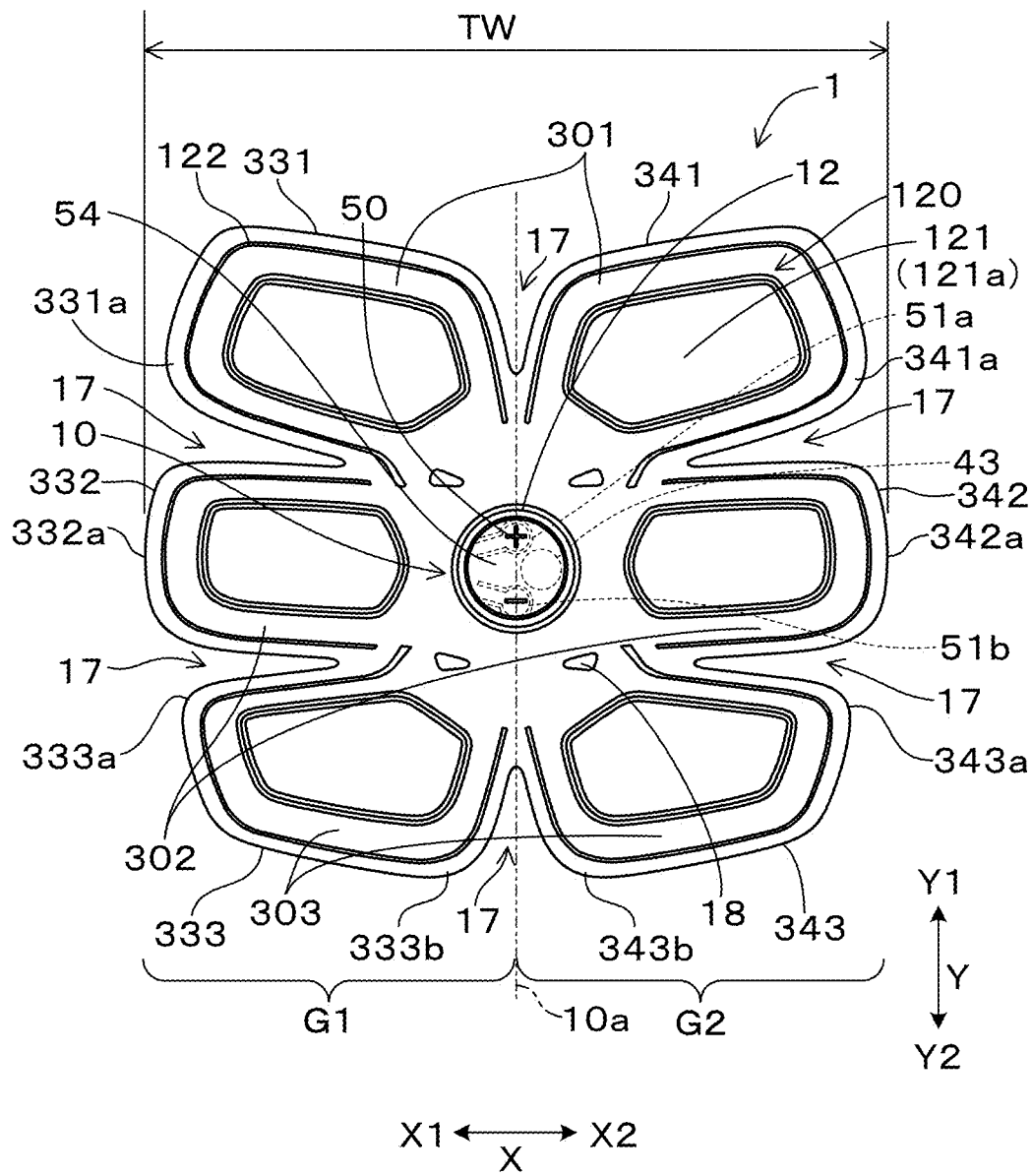
FIG. 46 is a front view of the muscle electrostimulation device in Embodiment 15.

In the muscle electrostimulation device 1 of Embodiment 15, a width (length in the lateral direction X) TW of the muscle electrostimulation device 1 is within a range (first range) of 175.00 to 237.5 mm, more preferably, in a range (second range) of 187.50 to 225.0 mm, and is 198.00 mm in this embodiment as shown in FIG. 46. The configuration of the muscle electrostimulation device 1 in this embodiment is equivalent to the configuration of the muscle electrostimulation device 1 in Embodiment 1.

When the length of ¼ of the abdominal circumference is calculated as the width of the rectus abdominis muscles 4 based on the statistics of abdominal circumference (around umbilicus) of adults disclosed in "Ministry of Health, Labour and Welfare, 2010 National Health and Nutrition Survey, Part 2, Physical Status Survey Results", the width of the rectus abdominis muscles 4 is in the first range in 61.4% of adults. The median of the width of the rectus abdominis muscles 4 in the statistics is in the second range.

Therefore, the width TW of the muscle electrostimulation device 1 of Embodiment 15 is in the first range (175.00 to 237.5 mm), and the muscle electrostimulation device 1 of Embodiment 15 has a size suitable for the rectus abdominis muscles 4 of adults. Furthermore, the width TW of the muscle electrostimulation device 1 of Embodiment 15 is in the second range (187.50 to 225.0 mm), and the muscle electrostimulation device 1 of Embodiment 15 has a size more suitable for the rectus abdominis muscles 4 of adults. Therefore, the electrodes 311 to 323 can be easily attached to positions near the rectus abdominis muscles 4 in the muscle electrostimulation device 1 of Embodiment 15, and the electrostimulation can be easily and effectively applied to the rectus abdominis muscles 4.

As described, according to Embodiment 15, the effects equivalent to the effects in Embodiment 1 can be attained, and the muscle electrostimulation device 1 suitable for stimulating the rectus abdominis muscles 4 can be provided.

Embodiment 16

The muscle electrostimulation device of Embodiment 16 in the present invention will be described.

Conventionally, there is a muscle electrostimulation device including a plurality of electrodes and capable of applying electrostimulation to a plurality of places at the same time. However, the device does not have a configuration for allowing the user to sense and recognize which electrode is applying electrostimulation and which part of the body is subjected to the electrostimulation.

The muscle electrostimulation device 1 of Embodiment 16 is configured as follows in view of the problem. The same symbols are provided to the members equivalent to the members of the muscle electrostimulation device 1 in the preceding embodiments, and the description of the members and the description of the usage mode will not be repeated. When the drawings used in the description of this embodiment are the same as the drawings in the preceding embodiments, the drawings in the preceding embodiments will be used.

Figure 47:
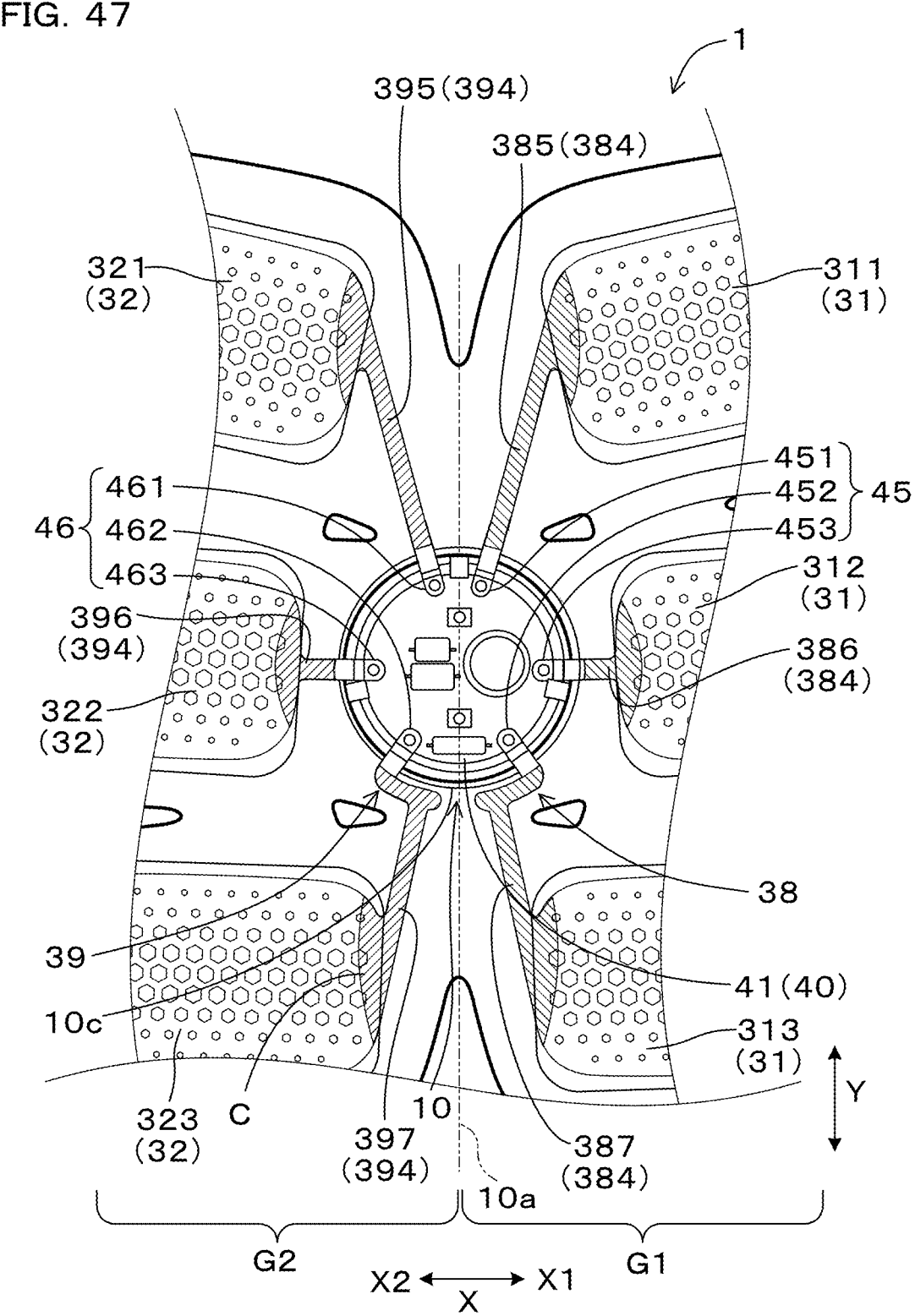
FIG. 47 is a partially enlarged back view with the second case removed in Embodiment 16.
Figure 48:
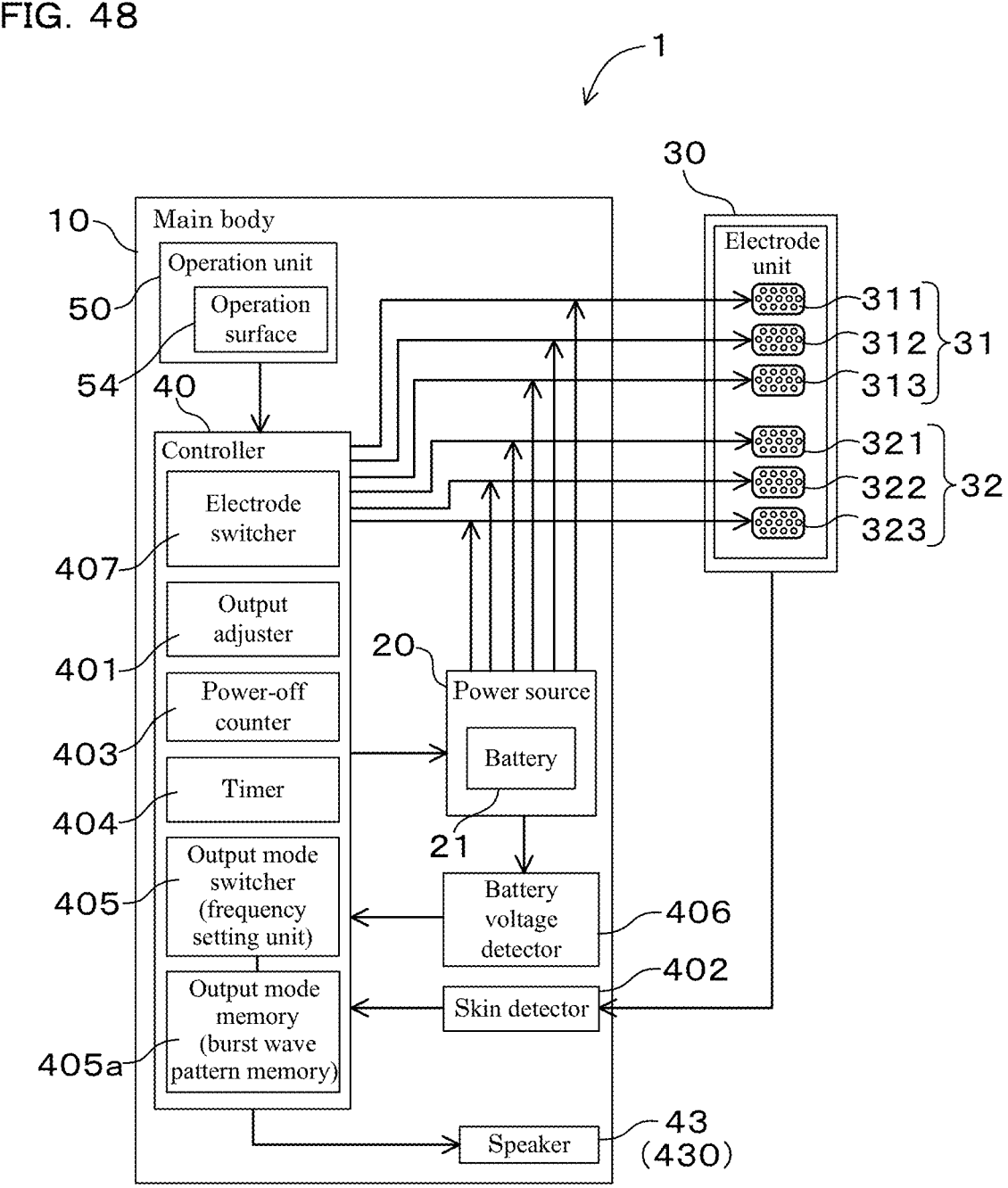
FIG. 48 is a block diagram showing a configuration of the muscle electrostimulation device in Embodiment 16.

The muscle electrostimulation device 1 of Embodiment 16 does not include the terminal connection 383 (393) (see FIG. 30) of Embodiment 1 as shown in FIG. 47. In the control board 41 including the controller 40, the first terminal group 45 includes a fifth terminal 453 in addition to the first terminal 451 and the second terminal 452, and the second terminal group 46 includes a sixth terminal 463 in addition to the third terminal 461 and the fourth terminal 462.

The first electrode connection 385 is directly connected to the first terminal 451, the third electrode connection 387 is directly connected to the second terminal 452, and the second electrode connection 386 is directly connected to the fifth terminal 453. Likewise, the fourth electrode connection 395 is directly connected to the third terminal 461, the sixth electrode connection 397 is directly connected to the fourth terminal 462, and the fifth electrode connection 396 is directly connected to the sixth terminal 463.

The controller 40 includes an electrode switcher 407. The electrode switcher 407 controls the electric current flowing in the electrodes 311 to 323 to switch the output state of the electrostimulation. The operation of the electrode switcher 407 is controlled through an electrode selector switch (not shown) provided on the operation surface 54.

The other components of the muscle electrostimulation device 1 in this embodiment are equivalent to the components of the muscle electrostimulation device 1 in Embodiment 1.

In the muscle electrostimulation device 1 of Embodiment 16, the electrode selector switch can switch a state of outputting electrostimulation from the electrodes 311 to 323 and a state of not outputting the electrostimulation, for each of the upper electrode pair 301, the central electrode pair 302, and the lower electrode pair 303, for example. Accordingly, the user can operate the electrode selector switch to more easily sense and recognize which of the electrodes 311 to 323 is applying electrostimulation and which part is subjected to the electrostimulation.

The electrode selector switch can increase the amount of current to other electrodes by, for example, preventing the flow of current or reducing the amount of current flowing in part of the electrodes 311 to 323. Accordingly, the power can be concentrated on desired electrodes 311 to 323, and the electrodes 311 to 323 can output electrostimulation stronger than the other electrodes 311 to 323.

The electrode selector switch can, for example, change the frequency of the electrostimulation output from the electrodes 311 to 323. Accordingly, for example, the frequency of the output electrostimulation can be shifted in the electrode pair of the right first electrode 311 and the third left electrode 323 disposed on the diagonal line and in the electrode pair of the right third electrode 313 and the first left electrode 321 disposed on the diagonal line to thereby use an interference wave to apply stimulation to a position of intersection (i.e. center 33c of substrate 33) between a virtual line connecting the right first electrode 311 and the third left electrode 323 disposed on the diagonal line and a virtual line connecting the right third electrode 313 and the first left electrode 321 disposed on the diagonal line. The frequency of the stimulation based on the interference wave can be set to a predetermined frequency between 4 and 20 Hz. Therefore, the stimulation based on the interference wave may be output in an output mode similar to each output mode in Embodiment 1.

As described, according to Embodiment 16, the muscle electrostimulation device 1 can be provided, the device capable of attaining the effects equivalent to the effects in Embodiment 1 and capable of allowing the user to easily sense and recognize which of the electrodes 311 to 323 is applying electrostimulation and which part of the body is subjected to the electrostimulation.

Embodiment 17

The muscle electrostimulation device of Embodiment 17 in the present invention will be described.

In the configuration disclosed in Patent Document 1, the electrostimulation is output in a predetermined output mode. However, when the same output mode is maintained for a long time, the body of the user gets used to the electrostimulation, thereby reducing the sensitivity and reducing the advantageous effects of the electrostimulation.

The muscle electrostimulation device 1 of Embodiment 17 is configured as follows in view of the problem. The same symbols are provided to the members equivalent to the members of the muscle electrostimulation device 1 in the preceding embodiments, and the description of the members and the description of the usage mode will not be repeated. When the drawings used in the description of this embodiment are the same as the drawings in the preceding embodiments, the drawings in the preceding embodiments will be used.

In the muscle electrostimulation device 1 of Embodiment 17, the output adjuster 401 of the controller 40 makes an adjustment to output the electrostimulation in another mode when the electrostimulation in the same mode is output for a predetermined time period. For example, when the electrostimulation through the fifth burst wave shown in FIG. 13 is output for a predetermined time, a switch can be made to output the electrostimulation through the second burst wave shown in FIG. 13 for a predetermined time.

The other components of the muscle electrostimulation device 1 in this embodiment are equivalent to the components of the muscle electrostimulation device 1 in Embodiment 1.

As described, according to Embodiment 17, the muscle electrostimulation device 1 can be provided, the device capable of attaining the effects equivalent to the effects in Embodiment 1 and capable of preventing the reduction in the sensitivity and the reduction in the advantageous effects of the electrostimulation when the body of the user gets used to the electrostimulation.

Embodiment 18

The muscle electrostimulation device of Embodiment 18 in the present invention will be described.

Although the electrostimulation is applied to the muscles via the skin surface of the person in the configuration disclosed in Patent Document 1, the ease of flow of the electric current in the person changes according to the amount of water in the skin of the person or the amount of fat, and the electrostimulation may not sufficiently reach the muscles depending on the amount of water or the amount of fat. The amount of water and the amount of fat vary from person to person, and there is a problem that the advantageous effects may vary from person to person even if the same muscle electrostimulation device is used.

The muscle electrostimulation device 1 of Embodiment 18 is configured as follows in view of the problem. The same symbols are provided to the members equivalent to the members of the muscle electrostimulation device 1 in the preceding embodiments, and the description of the members and the description of the usage mode will not be repeated. When the drawings used in the description of this embodiment are the same as the drawings in the preceding embodiments, the drawings in the preceding embodiments will be used.

Figure 49:
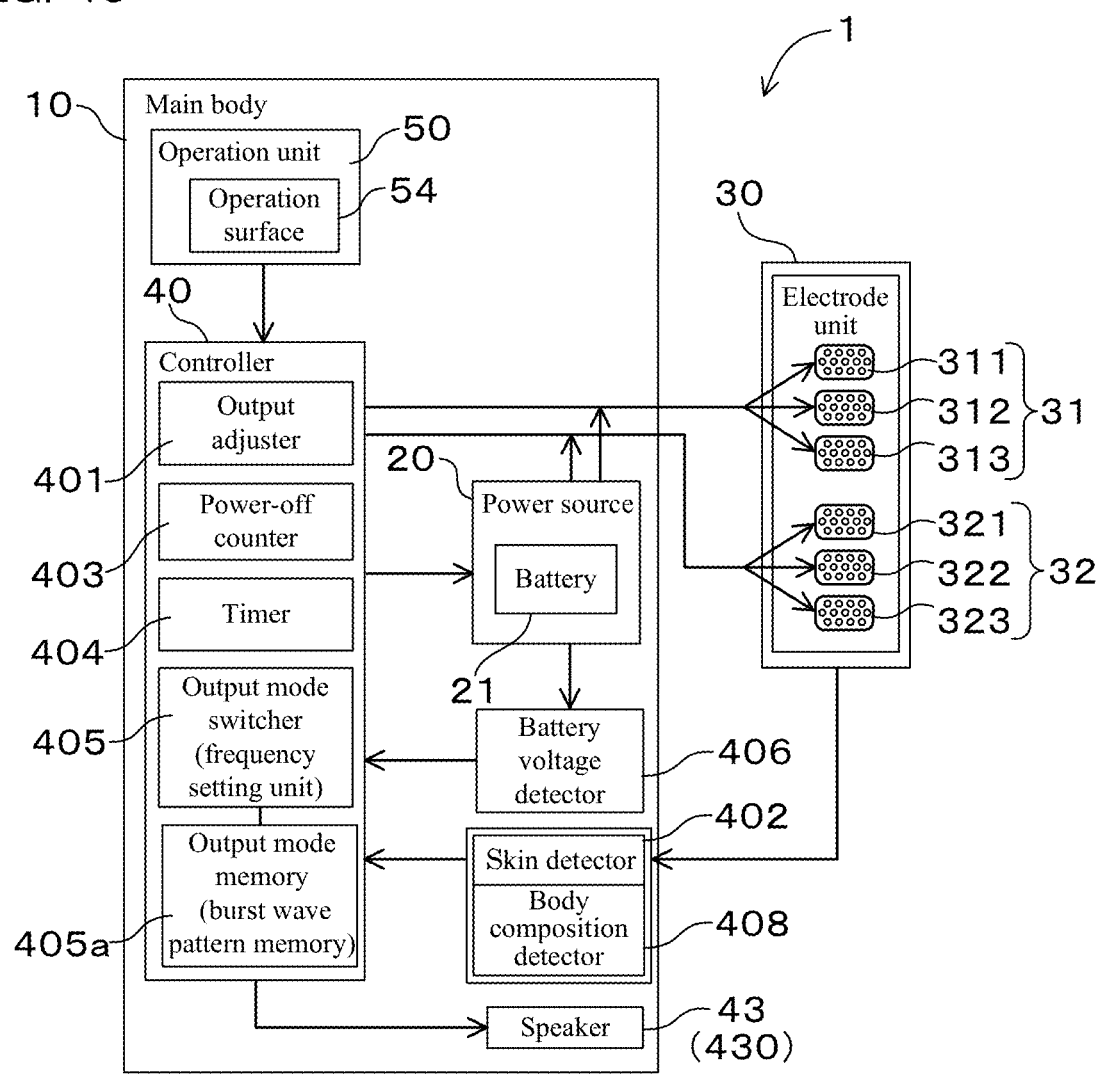
FIG. 49 is a block diagram showing a configuration of the muscle electrostimulation device in Embodiment 17.

In the muscle electrostimulation device 1 of Embodiment 18, the main body 10 includes a body composition detector 408 that detects electric resistance between the electrodes 311 to 323 to detect the amount of water of the skin and the amount of fat as shown in FIG. 49. By detecting resistance values between the electrodes 311 to 323 in step S104 shown in FIG. 9, the skin detector 402 detects whether the electrode unit 30 is in contact with the skin, and the body composition detector 408 detects the amount of water of the skin and the amount of fat. The output adjuster 401 of the controller 40 then sets the output level (output voltage value) according to the amount of water and the amount of fat. Specifically, in accordance with the amount of water and the amount of fat, the output level is set higher than a reference state if the flow of the electric current is not smooth compared to the reference state, and the output level is set lower than the reference state if the flow of the electric current is smooth compared to the reference state. Accordingly, the electrostimulation equivalent to the reference state can be applied even when the amount of water or the amount of fat is different from the reference state. Accordingly, this reduces the differences in the advantageous effects of the electrostimulation by the muscle electrostimulation device 1 of this embodiment caused by the individual differences in the amount of water and the amount of fat.

The body composition detector 408 may detect body compositions other than the amount of water and the amount of fat and may set the output level based on the values of the detected body compositions.

As described, according to Embodiment 18, the muscle electrostimulation device 1 can be provided, the device capable of attaining the effects equivalent to the effects in Embodiment 1 and capable of reducing the differences in the advantageous effects of the applied electrostimulation caused by the individual differences in the body compositions.

Embodiment 19

The muscle electrostimulation device of Embodiment 19 in the present invention will be described.

In the configuration disclosed in Patent Document 1, the user cannot acquire various pieces of information, such as various pieces of use history information in the muscle electrostimulation device, the output mode in use, the frequency of the electrostimulation being output, and the remaining battery.

The muscle electrostimulation device 1 of Embodiment 19 is configured as follows in view of the problem. The same symbols are provided to the members equivalent to the members of the muscle electrostimulation device 1 in the preceding embodiments, and the description of the members and the description of the usage mode will not be repeated. When the drawings used in the description of this embodiment are the same as the drawings in the preceding embodiments, the drawings in the preceding embodiments will be used.

The main body 10 (see FIG. 1) of the muscle electrostimulation device 1 in Embodiment 19 includes communication means capable of wirelessly communicating with an information terminal, such as a mobile terminal and a personal computer. The main body 10 of the muscle electrostimulation device 1 further includes storage means for storing various pieces of use history information and the like. The operation surface 54 includes a communication means operation unit (not shown) that turns on and off the communication means and that operates the communication. The communication means operation unit allows the muscle electrostimulation device 1 of Embodiment 19 to wirelessly transmit and receive information to and from the information terminal via the communication means.

Examples of the information transmitted to the information terminal include various pieces of use history information stored in the storage means, as well as the output mode in use, the frequency of the electrostimulation being output, and the remaining battery. The information to be transmitted can also be the values of various body compositions such as the amount of water and the amount of fat detected by the body composition detection 408 (see FIG. 49) of the muscle electrostimulation device 1, operation information of the operation surface 54 (such as whether the switch 53 is pressed and control information of the output state of the electrodes 311 to 323), or sound production information of the speaker 43. On the other hand, the information to be received from the information terminal can be setting information of the output mode, setting information of the frequency of the electrostimulation, operation information of the operation surface 54, or the like.

The type of the communication means is not particularly limited, and for example, Bluetooth (registered trademark), infrared light, an electromagnetic wave, or the like can be adopted. For example, the information can be transmitted and received to and from a portable information terminal, or what is called a smartphone, via Bluetooth (registered trademark). Dedicated software for transmitting and receiving the information can be installed in advance on the information terminal such as a smartphone. The information can be easily transmitted and received to and from the muscle electrostimulation device 1 of this embodiment via the software.

The other components of the muscle electrostimulation device 1 in this embodiment are equivalent to the components of the muscle electrostimulation device 1 in Embodiment 1.

According to the muscle electrostimulation device 1 of Embodiment 19, since various pieces of information in the muscle electrostimulation device 1 can be transmitted and received to and from the information terminal, the user can easily acquire the information and can perform operations such as changing the output mode and controlling the output state of the electrodes 311 to 323 in the muscle electrostimulation device 1 of Embodiment 19 from the information terminal via the communication means.

The muscle electrostimulation device 1 of Embodiment 19 may be configured and controlled to allow using a specific output mode that cannot be used in the initial state when information, such as the number of times of use stored in the storage means, reaches a predetermined threshold. In this case, the user is motivated to repeatedly use the muscle electrostimulation device 1 of Embodiment 19, and the user can enjoy using the muscle electrostimulation device 1. The user may be able to change the output mode to another desired output mode via the information terminal, such as so-called smartphone and PC (personal computer).

As described, according to Embodiment 19, the muscle electrostimulation device 1 can be provided, the device capable of attaining the effects equivalent to the effects in Embodiment 1, the device allowing the user to easily acquire the various pieces of information.

Embodiment 20

The muscle electrostimulation device of Embodiment 20 in the present invention will be described.

In the configuration disclosed in Patent Document 1, the muscle electrostimulation device can be attached to the person by using the adhesiveness of the gel pads covering the electrodes. However, dust may be attached to the gel pads when the device is repeatedly used, and the adhesiveness of the gel pads may be reduced. When the adhesiveness of the gel pads is reduced, the electrodes may fall from the skin surface during the use, resulting in suspension of the application of the electrostimulation or resulting in a fall of the muscle electrostimulation device.

The muscle electrostimulation device 1 of Embodiment 20 is configured as follows in view of the problem. The same symbols are provided to the members equivalent to the members of the muscle electrostimulation device 1 in the preceding embodiments, and the description of the members and the description of the usage mode will not be repeated.

When the drawings used in the description of this embodiment are the same as the drawings in the preceding embodiments, the drawings in the preceding embodiments will be used.

Figure 50A:
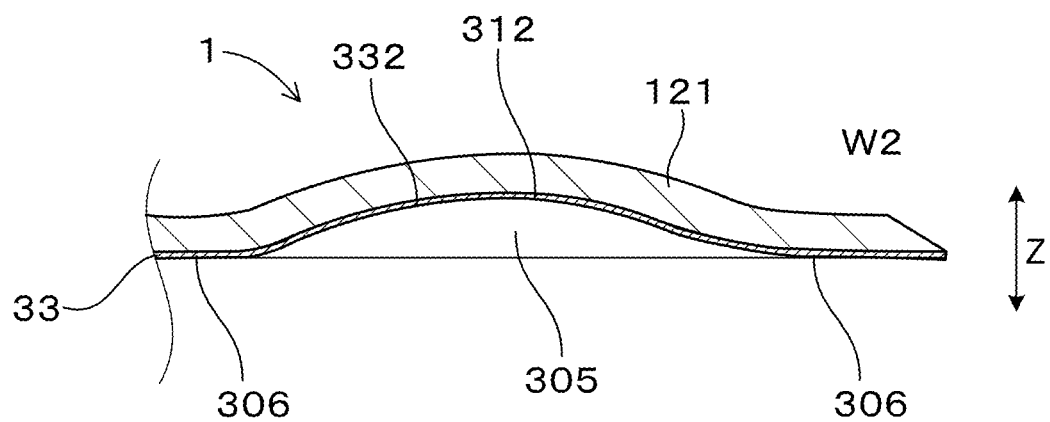
FIG. 50 is a schematic diagram illustrating an attachment mode of the electrode in Embodiment 17.
Figure 50B:
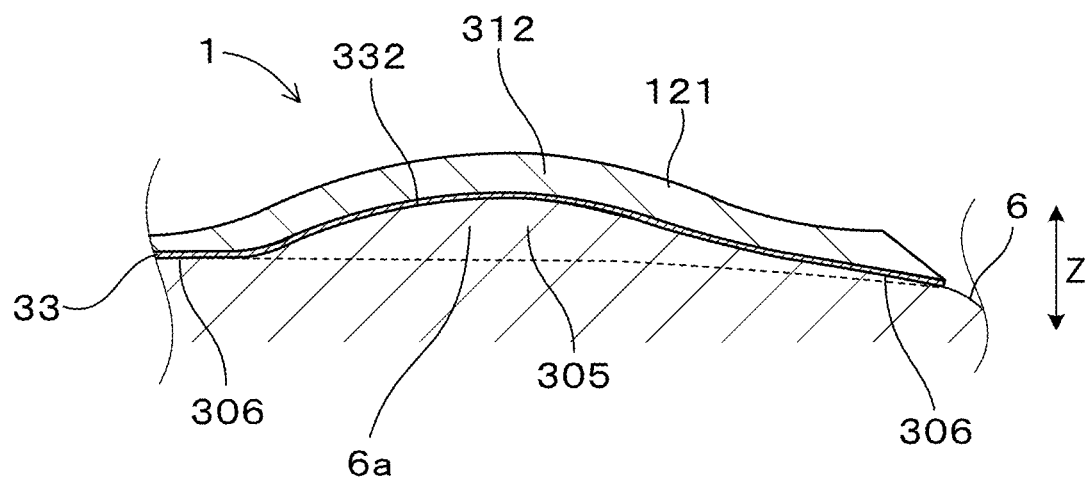

In the muscle electrostimulation device 1 of Embodiment 20, the gel pad 35 is not attached to the electrode 312 as shown in FIG. 50a. The center of the electrode support 121 supporting the electrode 312 is slowly curved in a cup shape to form a concave portion 305. An edge 306 of the concave portion 305 has a flat surface, and the electrode 312 is provided on the inner surface of the concave portion 305 via the substrate 33. To attach the muscle electrostimulation device 1, the electrode 312 is pressed against the skin surface 6, and the concave portion 305 and the edge 306 suck the skin surface 6 into the concave portion 305 to bring the skin surface 6 into contact with the electrode 312 as shown in FIG. 50b.

The other electrodes 311, 313, and 321 to 323 also have equivalent configurations. The other components of the muscle electrostimulation device 1 in this embodiment are equivalent to the components of the muscle electrostimulation device 1 in Embodiment 1.

According to the muscle electrostimulation device 1 of Embodiment 20, the electrode support 121 acts like a sucker to suck the skin surface 6 into the concave portion 305, thereby surely bringing the electrodes 311 to 323 into contact with the skin surface 6 and firmly attaching the muscle electrostimulation device 1 to the person 2. Therefore, the muscle electrostimulation device 1 can be attached to the person 2 without using the gel pads 35. Since the electrode support 121 acts like a sucker, a massage effect of the skin can also be obtained.

As described, according to Embodiment 20, the muscle electrostimulation device 1 can be provided, the device capable of attaining the effects equivalent to the effects in Embodiment 1, the device not causing a fall of the electrodes 311 to 323 or a drop of the muscle electrostimulation device 1 due to reduction in the adhesiveness of the gel pads 35 because the gel pads 35 do not have to be used.

Although the gel pads 35 are not used in this embodiment, the gel pads 35 may be used, and an adsorption portion (for example, sucker) that can be adsorbed to the skin surface may be provided on a portion or the like not provided with the electrodes in the substrate 33, so that the adsorption portion prevents a fall of the electrodes 311 to 323 and a drop of the muscle electrostimulation device 1 even if the adhesiveness of the gel pads 35 is reduced.

Embodiment 21

The muscle electrostimulation device of Embodiment 21 in the present invention will be described.

Although the electrodes are attached to the person via the gel pads in the configuration disclosed in Patent Document 1, the user may feel that the gel pads are cold and may feel uncomfortable.

The muscle electrostimulation device 1 of Embodiment 21 is configured as follows in view of the problem. The same symbols are provided to the members equivalent to the members of the muscle electrostimulation device 1 in the preceding embodiments, and the description of the members and the description of the usage mode will not be repeated. When the drawings used in the description of this embodiment are the same as the drawings in the preceding embodiments, the drawings in the preceding embodiments will be used.

In the muscle electrostimulation device 1 of Embodiment 21, the electrode support 121 (see FIG. 2) includes a heat generator although not shown. The heat generator is configured to generate heat by receiving power. A heat generator controller (not shown) included in the controller 40 controls the heat generation state of the heat generator.

The other components of the muscle electrostimulation device 1 in this embodiment are equivalent to the components of the muscle electrostimulation device 1 in Embodiment 1.

According to the muscle electrostimulation device 1 of Embodiment 21, when the power source of the muscle electrostimulation device 1 is turned on, the heat generator controller controls the power source to supply power to the heat generator, and the heat generator generates heat. This heats the gel pads 35 attached to the electrodes 311 to 323 provided on the electrode support 121 via the substrate 33. This prevents a situation that the user feels the gel pads are cold, and the discomfort of the user can be reduced. The heat generation of the heat generator during the use also heats the skin surface, and the blood circulation is promoted.

As described, according to Embodiment 21, the muscle electrostimulation device 1 can be provided, the device attaining the effects equivalent to the effects in Embodiment 1 and capable of alleviating the discomfort of the user feeling that the gel pads are cold.

Embodiment 22

The muscle electrostimulation device of Embodiment 23 in the present invention will be described.

Since the main body and the electrode unit are integrally formed in the configuration disclosed in Patent Document 1, the main body and the electrode unit cannot be separately replaced when the main body is broken or damaged or when the electrode unit is ruptured or disconnected, and the device needs to be replaced with a new muscle electrostimulation device. Therefore, the cost of the repair is high. When a program included in the main body is to be changed, the entire muscle electrostimulation device needs to be prepared, and the workability is poor.

The muscle electrostimulation device 1 of Embodiment 22 is configured as follows in view of the problem. The same symbols are provided to the members equivalent to the members of the muscle electrostimulation device 1 in the preceding embodiments, and the description of the members and the description of the usage mode will not be repeated. When the drawings used in the description of this embodiment are the same as the drawings in the preceding embodiments, the drawings in the preceding embodiments will be used.

In the muscle electrostimulation device 1 of Embodiment 22, the main body 10 and the electrode unit 30 are formed as different bodies although not shown although not shown. Therefore, the main body 10 and the electrode unit 30 can be individually and easily replaced when the main body 10 is broken or damaged or when the electrode unit 30 is ruptured or disconnected. When a program included in the main body 10 is to be changed, only the main body 10 needs to be removed and prepared, and the workability improves.

The muscle electrostimulation device 1 of Embodiment 22 includes, for example: a main body unit in which the power source 20, the controller 40, and the main body 10 storing the power source 20 and the controller 40 are integrally formed; an electrode unit in which the substrate 33 and the electrodes 311 to 323 are integrally formed; and a support unit that is a unit of the electrode support 121, wherein the units can be removed from each other.

The other components of the muscle electrostimulation device 1 in this embodiment are equivalent to the components of the muscle electrostimulation device 1 in Embodiment 1.

As described, according to Embodiment 22, the muscle electrostimulation device 1 can be provided, the device attaining the effects equivalent to the effects in Embodiment 1, the device facilitating the replacement of the main body 10, the electrode unit 30, and the like, the device improving the workability of the repair.

Embodiment 23

The muscle electrostimulation device of Embodiment 23 in the present invention will be described.

The main body and the electrode unit are integrally formed in the configuration disclosed in Patent Document 1, and the electrode unit cannot be replaced. Therefore, to use the electrodes according to the preference of the user, the used part, or the like, the muscle electrostimulation device needs to be prepared for each of the preference of the user, the used part, and the like.

The muscle electrostimulation device 1 of Embodiment 23 is configured as follows in view of the problem. The same symbols are provided to the members equivalent to the members of the muscle electrostimulation device 1 in the preceding embodiments, and the description of the members and the description of the usage mode will not be repeated. When the drawings used in the description of this embodiment are the same as the drawings in the preceding embodiments, the drawings in the preceding embodiments will be used.

In the muscle electrostimulation device 1 of Embodiment 23, the main body 10 and the electrode unit 30 are formed as different bodies although not shown. The power source 20 and the controller 40 included in the main body 10 and the electrode unit 30 are electrically connected via a detachable connector, and the main body 10 and the electrode unit 30 are mechanically connected. The type of the detachable connector is not limited, and for example, a snap connector can be adopted.

The other components of the muscle electrostimulation device 1 in this embodiment are equivalent to the components of the muscle electrostimulation device 1 in Embodiment 1.

According to the muscle electrostimulation device 1 of Embodiment 23, the main body 10 and the electrode unit 30 are connected via the detachable connector, and the electrode unit 30 can be removed from the main body 10. The electrode unit 30 can be replaced with an electrode unit including electrodes in a shape suitable for the preference of the user or the used part.

As described, according to Embodiment 23, the muscle electrostimulation device 1 can be provided, the device capable of attaining the effects equivalent to the effects in Embodiment 1 and capable of replacing the electrode unit with an electrode unit including electrodes in a shape suitable for the preference of the user or the used part.

Embodiment 24

The muscle electrostimulation device of Embodiment 24 in the present invention will be described.

In the configuration disclosed in Patent Document 1, the lid main body that supports the electrodes has a uniform thickness in the electrode unit. Therefore, there is a problem that it is difficult to peel off the electrode unit when the muscle electrostimulation device is to be removed from the person after the use.

The muscle electrostimulation device 1 of Embodiment 24 is configured as follows in view of the problem. The same symbols are provided to the members equivalent to the members of the muscle electrostimulation device 1 in the preceding embodiments, and the description of the members and the description of the usage mode will not be repeated. When the drawings used in the description of this embodiment are the same as the drawings in the preceding embodiments, the drawings in the preceding embodiments will be used.

Figure 51:
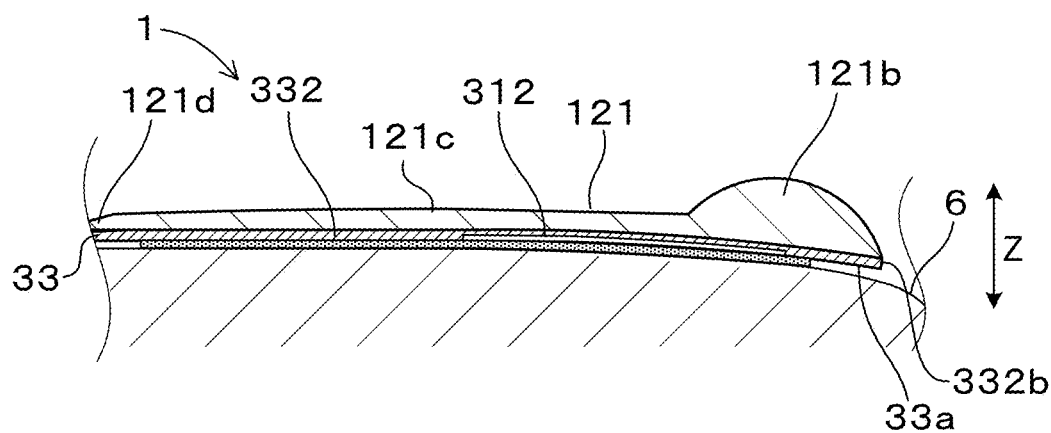
FIG. 51 is a schematic diagram illustrating an attachment mode of the electrode in Embodiment 24.

In the muscle electrostimulation device 1 of Embodiment 24, a peripheral portion (edge opposite to the main body 10) 121*b* of the electrode support 121 is formed thicker than a center portion 121*c* of the electrode support 121 and an inside portion (area closer to the main body 10) 121*d* of the electrode support 121 in the electrode 312 as shown in FIG. 51.

The other electrodes 311, 313, and 321 to 323 are also formed in the same way. The other components of the muscle electrostimulation device 1 in this embodiment are equivalent to the components of the muscle electrostimulation device 1 in Embodiment 1.

In the muscle electrostimulation device 1 of Embodiment 24, the peripheral portion 121*b* is thick, and a finger can be hooked to the peripheral portion 121*b* to easily peel off the electrodes 311 to 323 (electrode support 121) when the muscle electrostimulation device is to be removed from the person after the use. The center portion 121*c* and the inside portion 121*d* are thinner than the peripheral portion 121*b* and can be more easily curved according to the curve of the body compared to the peripheral portion 12*b*. As a result, the electrodes 311 to 323 are unlikely to be fallen from the skin surface 6 although the peripheral portion 121*b* is thick.

As described, according to Embodiment 24, the muscle electrostimulation device 1 can be provided, the device capable of attaining the effects equivalent to the effects in Embodiment 1, wherein the muscle electrostimulation device can be easily removed from the person after the use.

Embodiment 25

The muscle electrostimulation device of Embodiment 25 in the present invention will be described.

In the configuration disclosed on Patent Document 1, the lid main body that supports the electrodes has a uniform thickness in the electrode unit. Therefore, it is difficult to curve the lid main body according to the curve of the body, and the electrodes may be fallen from the skin surface during the use.

The muscle electrostimulation device 1 of Embodiment 25 is configured as follows in view of the problem. The same symbols are provided to the members equivalent to the members of the muscle electrostimulation device 1 in the preceding embodiments, and the description of the members and the description of the usage mode will not be repeated. When the drawings used in the description of this embodiment are the same as the drawings in the preceding embodiments, the drawings in the preceding embodiments will be used.

Figure 52:
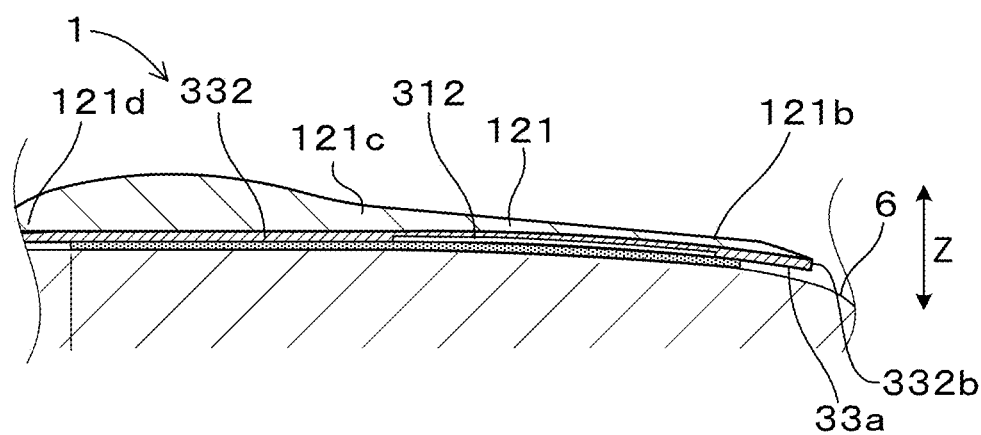
FIG. 52 is a schematic diagram illustrating an attachment mode of the electrode in Embodiment 25.

In the muscle electrostimulation device 1 of Embodiment 25, the peripheral portion (edge opposite to the main body 10) 121*b* of the electrode support 121 is formed thinner than the center portion 121*c* of the electrode support 121 and the inside portion (area closer to the main body 10) 121*d* of the electrode support 121 in the electrode 312 as shown in FIG. 52.

The other electrodes 311, 313, and 321 to 323 are also formed in the same way. The other components of the muscle electrostimulation device 1 in this embodiment are equivalent to the components of the muscle electrostimulation device 1 in Embodiment 1.

The peripheral portion 121*b* is thin in the muscle electrostimulation device 1 of Embodiment 25, and the electrodes 311 to 323 can be easily curved according to the curve of the skin surface 6. This can prevent the electrodes 311 to 323 from falling from the skin surface 6 during the use. Particularly, the center is flat, and the configuration is suitable for the rectus abdominis muscles 4 and the like in which the outside is curved.

As described, according to Embodiment 25, the muscle electrostimulation device 1 can be provided, the device capable of attaining the effects equivalent to the effects in Embodiment 1 and capable of preventing the electrodes 311 to 323 from falling from the skin surface 6 during the use.

Embodiment 26

The muscle electrostimulation device of Embodiment 26 in the present invention will be described.

In the configuration disclosed in Patent Document 1, a highly rigid coin battery is stored in the main body, and it is difficult to curve the main body along the body during the use. Therefore, there is a room for improvement in order to more surely curve the muscle electrostimulation device along the body to improve the adhesion between the muscle electrostimulation device and the skin surface.

The muscle electrostimulation device 1 of Embodiment 26 is configured as follows in view of the problem. The same symbols are provided to the members equivalent to the members of the muscle electrostimulation device 1 in the preceding embodiments, and the description of the members and the description of the usage mode will not be repeated. When the drawings used in the description of this embodiment are the same as the drawings in the preceding embodiments, the drawings in the preceding embodiments will be used.

The muscle electrostimulation device 1 of Embodiment 26 includes a flexible battery instead of the coin battery 21 although not shown. Examples of the flexible battery include a flexible aluminum battery and a lithium-ion secondary battery using metal fiber technology.

The other components of the muscle electrostimulation device 1 of this embodiment are equivalent to the components of the muscle electrostimulation device 1 in Embodiment 1.

The battery includes the flexible battery in the muscle electrostimulation device 1 of Embodiment 26, and the main body 10 containing the battery can be easily curved along the person 2 during the use. As a result, the muscle electrostimulation device 1 can be more surely curved along the body to improve the adhesion between the muscle electrostimulation device 1 and the skin surface 6.

As described, according to Embodiment 26, the muscle electrostimulation device 1 can be provided, the device capable of attaining the effects equivalent to the effects in Embodiment 1 and capable of improving the adhesion between the device and the skin surface.

Embodiment 27

The muscle electrostimulation device of Embodiment 27 in the present invention will be described.

In the configuration disclosed in Patent Document 1, the speaker can be embedded in the main body to generate sound upon operation or the like. The speaker is usually made of a highly rigid member, and if a highly rigid speaker is simply included, it is difficult to curve the main body along the body during the use. Therefore, there is a room for improvement in order to more surely curve the muscle electrostimulation device along the body to improve the adhesion between the muscle electrostimulation device and the skin surface.

The muscle electrostimulation device 1 of Embodiment 27 is configured as follows in view of the problem. The same symbols are provided to the members equivalent to the members of the muscle electrostimulation device 1 in the preceding embodiments, and the description of the members and the description of the usage mode will not be repeated. When the drawings used in the description of this embodiment are the same as the drawings in the preceding embodiments, the drawings in the preceding embodiments will be used.

The muscle electrostimulation device 1 of Embodiment 27 includes a flexible speaker instead of the speaker 43 although not shown. An example of the flexible speaker includes a film speaker.

The other components of the muscle electrostimulation device 1 in this embodiment are equivalent to the components of the muscle electrostimulation device 1 in Embodiment 1.

The muscle electrostimulation device 1 of Embodiment 27 includes the flexible speaker, and the main body 10 containing the battery can be easily curved along the person 2 during the use. As a result, the muscle electrostimulation device 1 can be more surely curved along the body to improve the adhesion between the muscle electrostimulation device 1 and the skin surface 6. When a film speaker is adopted instead of the speaker 43, the weight can be reduced.

As described, according to Embodiment 27, the muscle electrostimulation device 1 can be provided, the device capable of attaining the effects equivalent to the effects in Embodiment 1, wherein the adhesion between the device and the skin surface 6 is improved.

Embodiment 28

The muscle electrostimulation device of Embodiment 28 in the present invention will be described.

In the configuration disclosed in Patent Document 1, a rigid control board is stored in the main body, and it is difficult to curve the main body along the body during the use. Therefore, there is a room for improvement in order to more surely curve the muscle electrostimulation device along the body to improve the adhesion between the muscle electrostimulation device and the skin surface.

The muscle electrostimulation device 1 of Embodiment 28 is configured as follows in view of the problem. The same symbols are provided to the members equivalent to the members of the muscle electrostimulation device 1 in the preceding embodiments, and the description of the members and the description of the usage mode will not be repeated. When the drawings used in the description of this embodiment are the same as the drawings in the preceding embodiments, the drawings in the preceding embodiments will be used.

The muscle electrostimulation device 1 of Embodiment 28 includes a board with flexibility instead of the control board 41 although not shown. An example of the board with flexibility includes a flexible board.

The other components of the muscle electrostimulation device 1 in this embodiment are equivalent to the components of the muscle electrostimulation device 1 in Embodiment 1.

In the muscle electrostimulation device 1 of Embodiment 28, the controller 40 includes the flexible board, and the main body 10 containing the battery can be easily curved along the person 2 during the use. As a result, the muscle electrostimulation device 1 can be more surely curved along the body to improve the adhesion between the muscle electrostimulation device 1 and the skin surface 6.

As described, according to Embodiment 28, the muscle electrostimulation device 1 can be provided, the device capable of attaining the effects equivalent to the effects in Embodiment 1, wherein the adhesion between the device and the skin surface 6 is improved.

Embodiment 29

The muscle electrostimulation device of Embodiment 29 in the present invention will be described.

The electrode unit is fixed to the main body in the configuration disclosed in Patent Document 1, and the range for attaching both electrodes is a significantly limited area. Therefore, there is a problem that the distance between both electrodes cannot be appropriately adjusted.

The muscle electrostimulation device 1 of Embodiment 29 is configured as follows in view of the problem. The same symbols are provided to the members equivalent to the members of the muscle electrostimulation device 1 in the preceding embodiments, and the description of the members and the description of the usage mode will not be repeated. When the drawings used in the description of this embodiment are the same as the drawings in the preceding embodiments, the drawings in the preceding embodiments will be used.

In the muscle electrostimulation device 1 of Embodiment 29, the electrode unit 30 and the main body 10 are integrally formed, and the joint of the electrode unit 30 and the main body 10 is a bellows structure (what is called bellows structure) although not shown. The controller 40 stored in the main body 10 and the electrode unit 30 are electrically connected through a wire harness (not shown) laid in the main body 10. The wire harness has a length sufficient to allow electrically connecting the electrode unit 30 and the main body 10 even when the bellows structure is extended to the maximum so that the electrode unit 30 and the main body 10 are separated to the maximum extent.

Instead of the wire harness, a conductive ink printed on the inner surface of the electrode support 121 forming the bellows structure may be used to electrically connect the electrode unit 30 and the main body 10. The other components of the muscle electrostimulation device 1 of this embodiment are equivalent to the components of the muscle electrostimulation device 1 of embodiment 1.

The joint of the electrode unit 30 and the main body 10 has a bellows structure in the muscle electrostimulation device 1 of Embodiment 29, and the distance between both electrodes (distance between the first electrode group 31 and the second electrode group) can be easily and appropriately adjusted. Accordingly, the electrodes 311 to 323 can be easily arranged at locations suitable for applying the electrostimulation to the muscles. Although the body constitution varies from person to person, the distance between the both electrodes can be appropriately adjusted to easily handle the individual differences.

As described, according to Embodiment 29, the muscle electrostimulation device 1 can be provided, the device capable of attaining the effects equivalent to the effects in Embodiment 1 and capable of easily and appropriately adjusting the distance between the electrodes (distance between the first electrode group 31 and the second electrode group).

Embodiment 30

The muscle electrostimulation device of Embodiment 30 in the present invention will be described.

In the configuration disclosed in Patent Document 1, the lid main body that supports the electrodes has a uniform thickness around the main body. Therefore, when the device is to be attached to a portion, such as the arm and the leg, with curvature larger than the abdomen or the like, the lid main body is not sufficiently curved around the main body, and the adhesion between the muscle electrostimulation device and the skin surface may be reduced.

The muscle electrostimulation device 1 of Embodiment 30 is configured as follows in view of the problem. The same symbols are provided to the members equivalent to the members of the muscle electrostimulation device 1 in the preceding embodiments, and the description of the members and the description of the usage mode will not be repeated. When the drawings used in the description of this embodiment are the same as the drawings in the preceding embodiments, the drawings in the preceding embodiments will be used.

Figure 53:
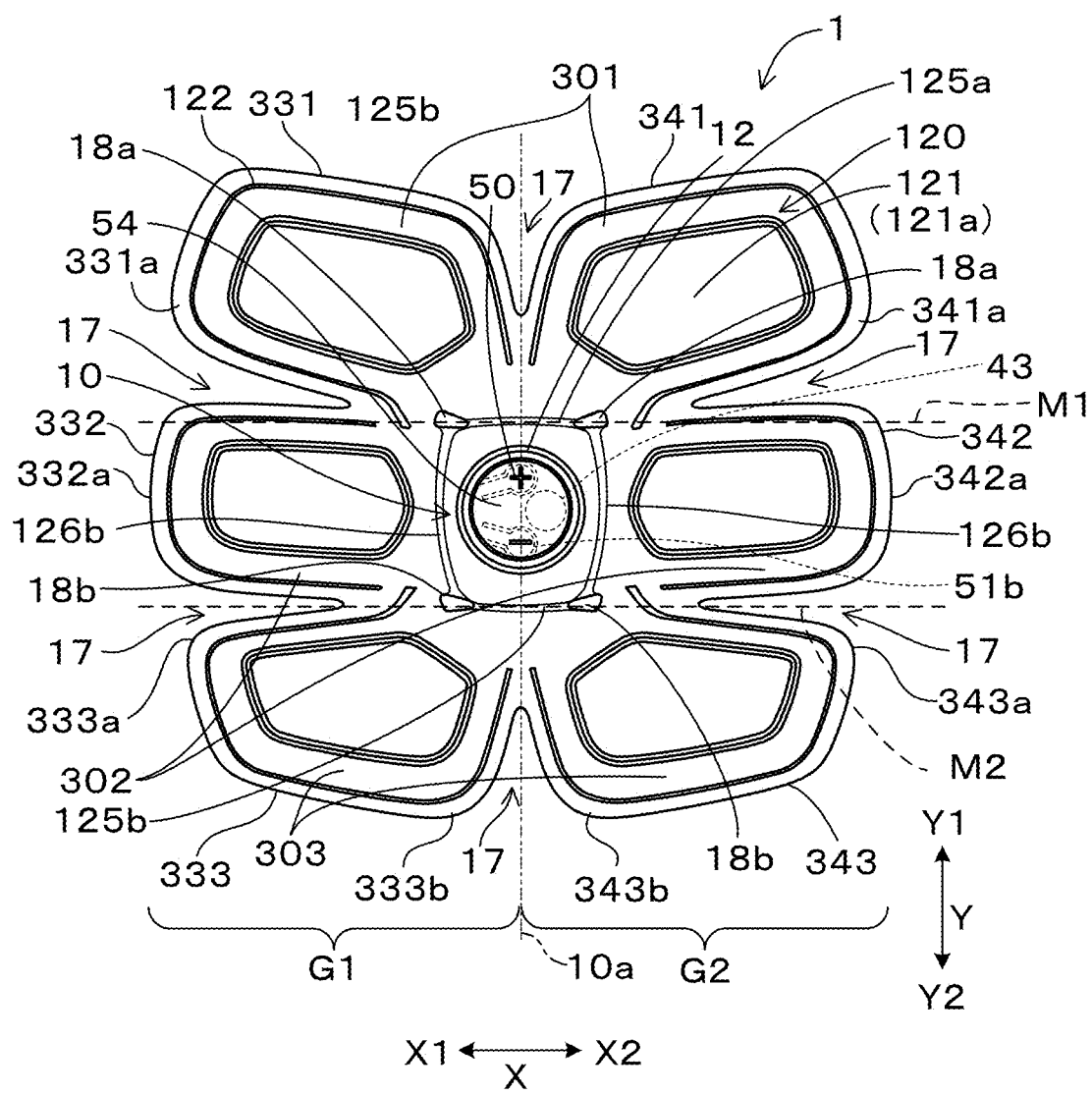
FIG. 53 is a front view of the muscle electrostimulation device in Embodiment 30.

In the muscle electrostimulation device 1 of Embodiment 30, thin bodies 125*a*, 125*b*, 126*a*, and 126*b* formed in a groove shape are provided around the main body 10 on the outer surface 121*a* of the electrode support 121 as shown in FIG. 53. The thin body 125*a* is formed to connect the pair of holes 18*a* on the upper side Y1 along the virtual straight line M1. The thin body 125*b* is formed to connect the pair of holes 18*b* on the lower side Y2 along the virtual straight line M2. On the contrary, the thin body 126*a* is formed to connect one of the holes 18*a* on the upper side and one of the holes 18*b* on the lower side in parallel to the vertical direction (height direction Y). The thin body 126*b* is formed to connect the other of the holes 18*a* on the upper side and the other of the holes 18*b* on the lower side in parallel to the vertical direction (height direction Y).

Accordingly, the thin bodies 125*a*, 125*b*, 126*a*, and 126*b* are formed to surround the main body 10 and connect the four holes 18 formed around the main body 10.

The other components of the muscle electrostimulation device 1 in this embodiment are equivalent to the components of the muscle electrostimulation device 1 in Embodiment 1.

In the muscle electrostimulation device 1 of Embodiment 30, the thin body 125*a* allows the device to easily bend at the position of the virtual straight line M1, and the thin body 125*a* allows the device to easily bend at the position of the virtual straight line M2. Therefore, the muscle electrostimulation device 1 can be bent at the positions to easily attach and wind the device around a part, such as the arm and the leg, with curvature larger than the abdomen 3. As a result, the adhesion between the muscle electrostimulation device 1 and the skin surface increases. For example, to attach the device to the arm, the main body 10 is put on the arm such that the lateral direction X coincides with the extending direction of the arm, the central electrode pair 302 is attached to the arm, and the upper electrode pair 301 and the lower electrode pair 303 are bent along the virtual straight lines M1 and M2 such as to wind the electrode pairs around the arm. In this way, the energization direction (lateral direction X) of the muscle electrostimulation device 1 coincides with the extending direction of the muscles of the arm, and the electrostimulation can be effectively applied to the muscles of the arm.

The muscle electrostimulation device 1 of this embodiment can also be easily bent at the positions of the thin bodies 126a and 126b. Accordingly, since the central electrode pair 302 can be easily bent parallel to the height direction Y, the device can easily follow the curve of the skin surface, and the adhesion between the muscle electrostimulation device 1 and the skin surface increases.

As described, according to Embodiment 30, the muscle electrostimulation device 1 can be provided, the device capable of attaining the effects equivalent to the effects in Embodiment 1, wherein the adhesion between the device and the skin surface, particularly, the skin surface of a part with relatively large curvature such as the arm and the leg, is increased.

The invention claimed is:

1. A muscle electrostimulation device comprising:
   a main body;
   a power source stored in the main body;
   an electrode unit that receives power from the power source;
   a controller that controls supply of power to the electrode unit; and
   an operation unit configured to change a control mode of the controller, the device being configured to bring the electrode unit into contact with an abdomen of a person to apply electrostimulation to the abdomen, wherein:
   the electrode unit comprises:
      a first electrode group extended from the main body so as to be disposed in a right direction with respect to a center line passing through a center of the main body; and
      a second electrode group extended from the main body so as to be disposed in a left direction with respect to—the center line;
   the first electrode group and the second electrode group are configured to apply voltages with different polarities from each other;
   the first electrode group and the second electrode group comprise a pair of upper electrodes, a pair of middle electrodes, and a pair of lower electrodes;
   each of the upper, middle and lower electrodes is configured to be attached to a different one of at least six compartments of rectus abdominis muscles in the abdomen;
   the main body is disposed on an area of the abdomen that is aligned with an umbilicus of the person along a height direction, the pair of upper electrodes are disposed on upper compartments of the rectus abdominis muscles in the abdomen relative to the area in the height direction, and the pair of lower electrodes are disposed on lower compartments of the rectus abdominis muscles in the abdomen relative to the area in the height direction; and
   the upper electrodes extend further than the lower electrodes in a lateral direction orthogonal to the height direction and passing through the umbilicus.

2. The muscle electrostimulation device according to claim 1, wherein
   the first electrode group and the second electrode group comprise the same number of the electrodes.

3. The muscle electrostimulation device according to claim 2, wherein
   the electrodes included in the first electrode group and the electrodes included in the second electrode group are disposed line-symmetrically with respect to the center line.

4. The muscle electrostimulation device according to claim 3, wherein
   the first electrode group comprises a plurality of electrodes arranged in a direction parallel to the center line, and the second electrode group comprises a plurality of electrodes arranged in the direction parallel to the center line.

5. The muscle electrostimulation device according to claim 4, wherein
   each of the first electrode group and the second electrode group comprises three electrodes.

6. The muscle electrostimulation device according to claim 5, wherein:
   in the direction parallel to the center line, the first electrode group and the second electrode group are configured to form:
      an upper electrode pair at uppermost positions, which is the pair of upper electrodes;
      a lower electrode pair at lowermost positions, which is the pair of lower electrodes; and
      a central electrode pair at positions between the upper electrode pair and the lower electrode pair, the central electrode pair being the pair of middle electrodes, and
   the central electrode pair projects in the lateral direction from the main body more than the upper electrode pair and the lower electrode pair.

7. The muscle electrostimulation device according to claim 6, wherein
   the upper electrode pair projects in the lateral direction from the main body more than the lower electrode pair.

8. The muscle electrostimulation device according to claim 7, wherein
   notches cut toward the main body are formed between the electrodes adjacent to each other in the first electrode group and the second electrode group.

9. The muscle electrostimulation device according to claim 3, wherein
   each of the first electrode group and the second electrode group comprises three electrodes.

10. The muscle electrostimulation device according to claim 9, wherein:
    in a direction parallel to the center line, the first electrode group and the second electrode group are configured to form:
       an upper electrode pair at uppermost positions, which is the pair of upper electrodes;
       a lower electrode pair at lowermost positions, which is the pair of lower electrodes; and
       a central electrode pair at positions between the upper electrode pair and the lower electrode pair, the central electrode pair being the pair of middle electrodes, and
    the central electrode pair projects in the lateral direction from the main body more than the upper electrode pair and the lower electrode pair.

11. The muscle electrostimulation device according to claim 10, wherein the upper electrode pair projects in the lateral direction from the main body more than the lower electrode pair.

12. The muscle electrostimulation device according to claim 9, wherein
notches cut toward the main body are formed between the electrodes adjacent to each other in the first electrode group and the second electrode group.

13. The muscle electrostimulation device according to claim 3, wherein
notches cut toward the main body are formed between the electrodes adjacent to each other in the first electrode group and the second electrode group.

14. The muscle electrostimulation device according to claim 1, wherein
each of the first electrode group and the second electrode group comprises three electrodes.

15. The muscle electrostimulation device according to claim 14, wherein:
in a direction parallel to the center line, the first electrode group and the second electrode group are configured to form:
an upper electrode pair at uppermost positions, which is the pair of upper electrodes;
a lower electrode pair at lowermost positions, which is the pair of lower electrodes; and
a central electrode pair at positions between the upper electrode pair and the lower electrode pair, the central electrode pair being the pair of middle electrodes, and
the central electrode pair projects in the lateral direction from the main body more than the upper electrode pair and the lower electrode pair.

16. The muscle electrostimulation device according to claim 15, wherein
the upper electrode pair projects in the lateral direction from the main body more than the lower electrode pair.

17. The muscle electrostimulation device according to claim 16, wherein
notches cut toward the main body are formed between the electrodes adjacent to each other in the first electrode group and the second electrode group.

18. The muscle electrostimulation device according to claim 15, wherein
notches cut toward the main body are formed between the electrodes adjacent to each other in the first electrode group and the second electrode group.

19. The muscle electrostimulation device according to claim 1, wherein
the first electrode group comprises a plurality of electrodes arranged in a direction parallel to the center line, and the second electrode group comprises a plurality of electrodes arranged in the direction parallel to the center line.

20. The muscle electrostimulation device according to claim 1, wherein
notches cut toward the main body are formed between the electrodes adjacent to each other in the first electrode group and the second electrode group.

* * * * *